(12) United States Patent
Branstrom et al.

(10) Patent No.: US 9,650,395 B2
(45) Date of Patent: *May 16, 2017

(54) ANTIBACTERIAL COMPOUNDS AND METHODS FOR USE

(75) Inventors: Arthur Branstrom, East Windsor, NJ (US); Vara Prasad Venkata Nagendra Josyula, Superior Township, MI (US); Michael Andrew Arnold, Flemington, NJ (US); Aleksey I. Gerasyuto, Flemington, NJ (US); Gary Karp, Princeton Junction, NJ (US); Jiashi Wang, Monmouth Junction, NJ (US); Tamil Arasu, Edison, NJ (US); John David Baird, Piscataway, NJ (US); Wu Du, Cranbury, NJ (US); Olya Ginzburg, Bloomfield, NJ (US); Yi Jin Kim Gorske, Brunswick, ME (US); Jana Narasimhan, Scotch Plains, NJ (US); Srinivasa Peddi, Piscataway, NJ (US); Hongyan Qi, Plainsboro, NJ (US); Sean Wesley Smith, Hamilton, NJ (US); Anthony Allan Turpoff, Hillsborough, NJ (US); Richard Gerald Wilde, Somerville, NJ (US); Tianle Yang, Mountainside, NJ (US); Nanjing Zhang, Princeton, NJ (US); Xiaoyan Zhang, Belle Mead, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/241,372

(22) PCT Filed: Aug. 29, 2012

(86) PCT No.: PCT/US2012/052898
§ 371 (c)(1),
(2), (4) Date: Oct. 17, 2014

(87) PCT Pub. No.: WO2013/033240
PCT Pub. Date: Mar. 7, 2013

(65) Prior Publication Data
US 2015/0080362 A1    Mar. 19, 2015

Related U.S. Application Data

(60) Provisional application No. 61/528,576, filed on Aug. 29, 2011.

(51) Int. Cl.
| | | |
|---|---|---|
| A61K 31/4427 | (2006.01) | |
| A61K 31/4412 | (2006.01) | |
| A61K 45/06 | (2006.01) | |
| A61K 31/5383 | (2006.01) | |
| C07D 515/04 | (2006.01) | |
| A61K 31/5377 | (2006.01) | |
| A61K 31/4439 | (2006.01) | |
| C07D 213/80 | (2006.01) | |
| C07D 401/10 | (2006.01) | |
| C07D 487/08 | (2006.01) | |
| A01N 43/40 | (2006.01) | |
| A01N 43/50 | (2006.01) | |
| A01N 43/56 | (2006.01) | |

(Continued)

(52) U.S. Cl.
CPC .......... *C07D 515/04* (2013.01); *A01N 43/40* (2013.01); *A01N 43/50* (2013.01); *A01N 43/56* (2013.01); *A01N 43/60* (2013.01); *A01N 43/647* (2013.01); *A01N 43/84* (2013.01); *A01N 43/90* (2013.01); *A01N 47/38* (2013.01); *A61K 31/4412* (2013.01); *A61K 31/4427* (2013.01); *A61K 31/4439* (2013.01); *A61K 31/496* (2013.01); *A61K 31/5377* (2013.01); *A61K 31/5383* (2013.01); *A61K 45/06* (2013.01); *C07D 213/80* (2013.01); *C07D 401/10* (2013.01); *C07D 487/08* (2013.01)

(58) Field of Classification Search
CPC .. C07D 515/04; C07D 213/80; C07D 401/10; C07D 487/08; A61K 31/5377; A61K 31/4427
USPC ...... 514/210.2, 338, 348, 350, 230.5, 235.5, 514/343; 546/298, 276.7, 296, 268.1, 546/276.4
See application file for complete search history.

(56) References Cited

U.S. PATENT DOCUMENTS

| | | |
|---|---|---|
| 3,703,582 A | 11/1972 | Shen et al. |
| 3,948,903 A | 4/1976 | Doub et al. |
| 3,954,734 A | 5/1976 | Doub et al. |
| 4,331,597 A | 5/1982 | Makabe et al. |
| 4,698,352 A | 10/1987 | Narita et al. |

(Continued)

FOREIGN PATENT DOCUMENTS

| | | |
|---|---|---|
| CN | 1231161 | 10/1999 |
| CN | 1646125 | 7/2005 |

(Continued)

OTHER PUBLICATIONS

Chemical Abstracts STN Database Record for RN 1282753-08-5, database entry date Apr. 20, 2011.*

(Continued)

*Primary Examiner* — Noble Jarrell
*Assistant Examiner* — Daniel Carcanague
(74) *Attorney, Agent, or Firm* — Hoffmann & Baron, LLP

(57) ABSTRACT

The present description relates to compounds and forms and pharmaceutical compositions thereof and methods for use thereof to treat or ameliorate bacterial infections caused by wild-type and multi-drug resistant Gram-negative and Gram-positive pathogens.

19 Claims, No Drawings

(51) Int. Cl.
  *A01N 43/60*    (2006.01)
  *A01N 43/647*   (2006.01)
  *A01N 43/84*    (2006.01)
  *A01N 43/90*    (2006.01)
  *A01N 47/38*    (2006.01)
  *A61K 31/496*   (2006.01)

(56) References Cited

U.S. PATENT DOCUMENTS

| | | | |
|---|---|---|---|
| 6,469,033 | B1 | 10/2002 | Bohn et al. |
| 6,670,380 | B2 | 12/2003 | Sulsky et al. |
| 7,067,540 | B2 | 6/2006 | Devadas et al. |
| 7,629,363 | B2 | 12/2009 | Devadas et al. |
| 9,409,905 | B2 * | 8/2016 | Branstrom ........... A61K 31/437 |
| 2008/0103139 | A1 | 5/2008 | Ishizuka et al. |
| 2009/0202634 | A1 | 8/2009 | Jans et al. |
| 2009/0215764 | A1 | 8/2009 | Das et al. |
| 2010/0056582 | A1 | 3/2010 | Bayne et al. |
| 2015/0038437 | A1* | 2/2015 | Branstrom et al. ............. 514/29 |
| 2015/0038438 | A1* | 2/2015 | Branstrom et al. ............. 514/29 |

FOREIGN PATENT DOCUMENTS

| | | |
|---|---|---|
| CN | 101531631 | 9/2009 |
| EP | 0 308 020 A2 | 3/1989 |
| EP | 0347027 | 12/1989 |
| GB | 2058769 | 4/1981 |
| WO | 91/17987 | 11/1991 |
| WO | 03/068230 | 8/2003 |
| WO | 2005/018557 A2 | 3/2005 |

OTHER PUBLICATIONS

Chemical Abstracts STN Database Record for RN 1283989-97-8, database entry date Apr. 22, 2011.*
Al-Mousawi; Tetrahedron Letters, 2011, 52, 202-204.*
Ito; Journal of Heterocyclic Chemistry, 1992, 29, 1037-1044.*
Cottarel; Trends in Biotechnology, 2007, 25, 547-555.*
Georgopapadakou; Antimicrobial Agents and Chemotherapy, 1987, 31, 616-616.*
Chemical Abstracts STN Database Record for RN 1267146-10-0, database entry date Mar. 9, 2011.*
Chemical Abstracts STN Database Record for RN 1281434-26-1, database entry date Apr. 17, 2011.*
Chemical Abstracts STN Database Record for RN 1283154-73-3, database entry date Apr. 20, 2011.*
Hogberg; Trends in Pharmacological Sciences 2010, 31, 509-515.*
Ito et al., XP-002734962, "Retro-ene . . . ", J. Heterocyclic Chem., vol. 29(5):1037-1044, 1992. (abstract only).
Poschenrieder et al., XP-002734961, "Pyrrolidine-2,4-diones . . . ", Archiv der Pharmazie, vol. 332(9):309-316, 1999. (abstract only).
Stachel et al., XP-002734959, "Reactions of 5-bromoalkylidene-3-pyrrolin-2-ones", Liebigs Annalen der Chemie, vol. 8, 1692-6, 1985. (abstract only).
Stachel et al., XP-002734960, "Derivatives of . . . ", J. Heterocyclic Chemistry, vol. 22(5), 1413-18, 1985. (abstract only).
International Preliminary Report on Patentability of PCT/US2012/052898 mailed on Mar. 4, 2014.
International Preliminary Report on Patentability of PCT/US2012/052922 mailed on Mar. 4, 2014.

International Search Report of PCT/US2012/052922 mailed on Nov. 2, 2012.
Written Opinion of the International Searching Authority of PCT/US2012/052898 mailed on Dec. 21, 2012.
Written Opinion of the International Searching Authority of PCT/US2012/052922 mailed on Nov. 2, 2012.
International Search Report of PCT/US2012/052898 mailed Dec. 21, 2012.
Abdelhamid, "Convenient Synthesis . . . ", J. Heterocyclic Chem., vol. 46(4):680-686; Jul. 1, 2009.
Ciufolin et al., XP-002735063, "Practical Synthesis . . . ", Targets in Heterocyclic Systems, vol. 4, pp. 25-55, 2000. (abstract only).
Farghaly et al., "Synthesis and reactions . . . ", j. chemical research, vol. 3, pp. 152-156, Mar. 1, 2008.
Mabkhot et al., XP-002735064, "Comprehensive and facile . . . ", Int. J. Molecular Sciences, vol. 13, pp. 2263-2275, Feb. 20, 2012. (abstract only).
Zhang, Y. et al., "Carbonarones A and B, New Bioactive gamma Pyrone and alpha Pyridone Derivatives from the Marine-derived Fungus *Aspergillus carbonarius*", J. Antibiot., vol. 60, No. 2, Feb. 7, 2007, pp. 153-157.
Farghaly, Thoraya A., "Synthesis and reactions of 3[3-(dimethylamino)propenoyl]-1,7-diphenyl [1,2,4]truaziki[4,3-a]pyrimidin5(1H)-one", Journal of Chemical Research Mar. 2008 152-156.
Ciufolini, et al., "Practical Synthesis of (20S)-(+)-Camptothecin: The Progenitor of a Promising Group of Anticancer Agents", Targets in heterocyclic systems: chemistry and properties, 1997, pp. 25-55.
Chemical Abstracts STN Database Record for RN 1267392-94-8, dated Mar. 9, 2011.
Chemical Abstracts STN Database Record for RN 1282921-52-1, dated Apr. 20, 2011.
Chemical Abstracts STN Database Record for RN 1284555-52-7, dated Apr. 24, 2011.
Chemical Abstracts STN Database Record for RN 1285231-11-9, dated Apr. 24, 2011.
Chemical Abstracts STN Database Record for RN 1305278-11-8, dated Jun. 3, 2011.
Chemical Abstracts STN Database Record for RN 1268040-15-8, dated Mar. 10, 2011.
Chemical Abstracts STN Database Record for RN 1306268-23-4, dated Jun. 5, 2011.
Chemical Abstracts STN Database Record for RN 1291753-42-8, dated May 8, 2011.
Chemical Abstracts STN Database Record for RN 1225669-93-1, dated May 30, 2010.
Chemical Abstracts STN Database Record for RN 1226083-54-0, dated May 30, 2010.
Chemical Abstracts STN Database Record for RN 1226084-48-5, dated May 30, 2010.
Chemical Abstracts STN Database Record for RN 1266989-99-4, dated Mar. 9, 2011.
Chemical Abstracts STN Database Record for RN 1283181-10-1, dated Apr. 20, 2011.
Chemical Abstracts STN Database Record for RN 1283889-86-0, dated Apr. 22, 2011.
Chemical Abstracts STN Database Record for RN 1284524-20-4, dated Apr. 24, 2011.
Examiner's Search Strategy and Results, Aug. 17, 2015, 365 pages.
Examiner's Search Strategy and Results, Jan. 1, 2016, 62 pages.
Examiner's Search Strategy and Results, May 31, 2016, 24 pages.

* cited by examiner

ANTIBACTERIAL COMPOUNDS AND METHODS FOR USE

CROSS-REFERENCES TO RELATED APPLICATIONS

This application is the National Stage of International Application No. PCT/US2012/052898, filed Aug. 29, 2012, which claims the benefit of U.S. Application No. 61/528,576, filed Aug. 29, 2011, the entire contents of which are incorporated by reference herein.

FIELD OF THE INVENTION

The present description relates to compounds and forms and pharmaceutical compositions thereof and methods of using such compounds, forms or compositions thereof for treating or ameliorating a bacterial infection. More particularly, the present description relates to compounds and forms and pharmaceutical compositions thereof and methods of using such compounds, forms or compositions thereof for treating or ameliorating a bacterial infection, or for treating or ameliorating a multi-drug resistant (MDR) bacterial infection.

BACKGROUND OF THE INVENTION

Currently marketed antimicrobial agents inhibit bacterial DNA synthesis by acting on the two key enzymes of DNA gyrase and topoisomerase IV (see, Mitscher, L. A. Bacterial topoisomerase inhibitors: quinolone and pyridone antibacterial agents, Chem. Rev. 2005, 105, 559-592; Hooper, D. C.; Rubinstein, E. Quinolone antimicrobial agents/edited by David C. Hooper and Ethan Rubinstein; or De Souza, M. V. New fluoroquinolones: a class of potent antibiotics. Mini. Rev. Med. Chem. 2005, 5 (11), 1009-1017).

The DNA gyrase and topoisomerase IV enzymes are both type II topoisomerases, consisting of two protein subunits active as heterodimers ($A_2B_2$). The ATPase domain resides on one polypeptide (GyrB in DNA gyrase, ParE in topoisomerase IV), while the DNA cleavage core lies on a second polypeptide (GyrA in DNA gyrase, ParC in topoisomerase IV). Current therapies, including the aminocoumarin novobiocin, function as competitive inhibitors of energy transduction of DNA gyrase by binding to the ATPase active site in GyrB (see, Maxwell, A. The interaction between coumarin drugs and DNA gyrase. Mol. Microbiol. 1993, 9 (4), 681-686; Flatman, R. H.; Eustaquio, A.; Li, S. M.; Heide, L.; Maxwell, A. Structure-activity relationships of aminocoumarin-type gyrase and topoisomerase IV inhibitors obtained by combinatorial biosynthesis. Antimicrob. Agents Chemother. 2006, 50 (4), 1136-1142).

In contrast, the nalidixic acid, ciprofloxacin and moxifloxacin preferentially bind these enzymes at the cleavage core (GyrA and ParC) and prevent decatenation of replicating DNA (see, Hooper, D. C. Quinolone mode of action. Drugs 1995, 49 Suppl 2, 10-15). Although first site resistance mutations generally occur in gyrA, mutations in gyrB also have been shown to reduce susceptibility to quinolones (see, Yoshida, H.; Bogaki, M.; Nakamura, M.; Yamanaka, L. M.; Nakamura, S. Quinolone resistance-determining region in the DNA gyrase gyrB gene of Escherichia coli. Antimicrob. Agents Chemother. 1991, 35 (8), 1647-1650).

Bacterial DNA synthesis inhibitors (e.g., fluoroquinolones) have been used to treat primarily Gram-negative infections and have historically achieved outstanding clinical outcomes (see, Emmerson, A. M.; Jones, A. M. The quinolones: decades of development and use. J. Antimicrobial Chemotherapy, 2003, 51 (S1), 13-20). A wealth of knowledge exists for the quinolone class of compounds (see, Hooper, D. C.; Rubinstein, E. Quinolone antimicrobial agents/edited by David C. Hooper and Ethan Rubinstein), including bioavailability, tissue distribution, PK/PD relationships and photoxicity. Structurally, quinolone antibiotics possess a bicyclic (ciprofloxacin and moxifloxacin) or tricyclic ring structure (levofloxacin) with an aryl side chain containing an acyclic ring incorporating an amine functionality.

Other ring structures such as the 2-pyridones (monocyclic and bicyclic)(see, Chu, D. T. Recent progress in novel macrolides, quinolones, and 2-pyridones to overcome bacterial resistance. Med. Res. Rev. 1999, 19 (6), 497-520), quinazolinediones (see, Ellsworth, E. L.; Tran, T. P.; Showalter, H. D.; Sanchez, J. P.; Watson, B. M.; Stier, M. A.; Domagala, J. M.; Gracheck, S. J.; Joannides, E. T.; Shapiro, M. A.; Dunham, S. A.; Hanna, D. L.; Huband, M. D.; Gage, J. W.; Bronstein, J. C.; Liu, J. Y.; Nguyen, D. Q.; Singh, R. 3-aminoquinazolinediones as a new class of antibacterial agents demonstrating excellent antibacterial activity against wild-type and multidrug resistant organisms. J. Med. Chem. 2006, 49 (22), 6435-6438; and, Tran, T. P.; Ellsworth, E. L.; Stier, M. A.; Domagala, J. M.; Hollis Showalter, H. D.; Gracheck, S. J.; Shapiro, M. A.; Joannides, T. E.; Singh, R. Synthesis and structural-activity relationships of 3-hydroxyquinazoline-2,4-dione antibacterial agents. Bioorg. Med. Chem. Lett. 2004, 14 (17), 4405-4409) and tricyclic isoquinolones have been described in the literature.

Though some of these molecules, such the 2-pyridone and 4-pyridones (e.g., Ro-13-5478), isoquinolones and quinazolinediones have progressed to the late preclinical stage, none have reached the market. In the 1980s, monocyclic 2-pyridone and 4-pyridones were reported to inhibit DNA gyrase (see, Georgopapadakou, N. H.; Dix, B. A.; Angehrn, P.; Wick, A.; Olson, G. L. Monocyclic and tricyclic analogs of quinolones: mechanism of action. Antimicrob. Agents Chemother. 1987, 31 (4), 614-616).

The monocyclic 4-pyridone class of molecules generally exhibited poor activity against quinolone-resistant ($quin^R$) strains, possessed attendant CNS side effects, and in most cases, had only limited in vivo efficacy. Recent studies on monocyclic-4-pyridone analogs (see, Laursen, J. B.; Nielsen, J.; Haack, T.; Pusuluri, S.; David, S.; Balakrishna, R.; Zeng, Y.; Ma, Z.; Doyle, T. B.; Mitscher, L. A. Further exploration of antimicrobial ketodihydronicotinic acid derivatives by multiple parallel syntheses. Comb. Chem. High Throughput. Screen. 2006, 9 (9), 663-681) demonstrate that these compounds elicit cross-resistance to ciprofloxacin and possess poor antibacterial activity against E. coli.

More recently, antibacterial spiro-tricyclic barbituric acid derivatives (QPT-1) (see, Miller, A. A.; Bundy, G. L.; Mott, J. E.; Skepner, J. E.; Boyle, T. P.; Harris, D. W.; Hromockyj, A. E.; Marrotti, K. R.; Zurenko, G. E.; Munzner, J. B.; Sweeney, M. T.; Bammert, G. F.; Hamel, J. C.; Ford, C. W.; Zhong, W-Z.; Graber, D. R.; Martin, G. E.; Han, F.; Dolak, L. A.; Seest, E. P.; Ruble, J. C.; Kamilar, G. M.; Palmer, J. R.; Banitt, L. S.; Hurd, A. R.; Barbachyn, M. R. Discovery and characterization of QPT-1, the progenitor of a new class of bacterial topoisomerase inhibitors. Antimicrob. Agents Chemother. 2008, 52 (8), 2806-2812; and, Ruble, J. C.; Hurd, A. R.; Johnson, T. A.; Sherry, D. A.; Barbachyn, M. R.; Toogood, P. L.; Bundy, G. L.; Graber, D. R.; Kamilar, G. M. Synthesis of (−)-PNU-286607 by asymmetric cyclization of alkylidene barbiturates. J. Am. Chem. Soc. 2009, 131 (11), 3991-3997), inhibitors possessing a tetrahydroindazole and piperidine motif and a 6-methoxyquinoline moiety (e.g., NXL101 and GSK299423) (see, Black, M. T.; Stachyra, T.; Platel, D.; Girard, A. M.; Claudon, M.; Bruneau, J. M.; Miossec, C. Mechanism of action of the antibiotic NXL101, a novel nonfluoroquinolone inhibitor of bacterial type II topoisomerases. Antimicrob. Agents Chemother. 2008, 52

(9), 3339-3349; Bax, B. D.; Chan, P. F.; Eggleston, D. S.; Fosberry, A.; Gentry, D. R.; Gorrec, F.; Giordano, I.; Hann, M. M.; Hennessy, A.; Hibbs, M.; Huang, J.; Jones, E.; Jones, J.; Brown, K. K.; Lewis, C. J.; May, E. W.; Saunders, M. R.; Singh, O.; Spitzfaden, C. E.; Shen, C.; Shillings, A.; Theobald, A. J.; Wohlkonig, A.; Pearson, N. D.; Gwynn, M. N. Type IIA topoisomerase inhibition by a new class of antibacterial agents. *Nature* 2010, 466 (7309), 935-940; Gomez, L.; Hack, M. D.; Wu, J.; Wiener, J. J.; Venkatesan, H.; Santillan, A., Jr.; Pippel, D. J.; Mani, N.; Morrow, B. J.; Motley, S. T.; Shaw, K. J.; Wolin, R.; Grice, C. A.; Jones, T. K. Novel pyrazole derivatives as potent inhibitors of type II topoisomerases. Part 1: synthesis and preliminary SAR analysis. *Bioorg. Med. Chem. Lett.* 2007, 17 (10), 2723-2727; and, Wiener, J. J.; Gomez, L.; Venkatesan, H.; Santillan, A., Jr.; Allison, B. D.; Schwarz, K. L.; Shinde, S.; Tang, L.; Hack, M. D.; Morrow, B. J.; Motley, S. T.; Goldschmidt, R. M.; Shaw, K. J.; Jones, T. K.; Grice, C. A. Tetrahydroindazole inhibitors of bacterial type II topoisomerases. Part 2: SAR development and potency against multidrug-resistant strains. *Bioorg. Med. Chem. Lett.* 2007, 17 (10), 2718-2722) and isothiazoloquinolones (e.g., ACH-702)(see, Kim, H. Y.; Wiles, J. A.; Wang, Q.; Pais, G. C. G.; Lucien, E.; Hashimoto, A.; Nelson, D. M.; Thanassi, J. A.; Podos, S. D.; Deshpande, M.; Pucci, M. J.; Bradbury, B. J. Exploration of the activity of 7-pyrrolidino-8-methoxyisothiazoloquinolones against methicillin-resistant *Staphylococcus aureus* (MRSA). *J. Med. Chem.*, 2010, 54(9), 3268-3282) have been described as new classes of bacterial topoisomerase inhibitors. The X-ray crystallographic structure of GSK299423 bound to DNA gyrase has also been reported (Bax, B. D., et al., 2010).

Structurally, most of the known inhibitors (with the exception of QPT-1, the tetrahydroindazoles, NXL101, GSK299423 and ACH-702) possess a keto-acid functionality, either a carboxylic acid (ciprofloxacin and moxifloxacin, levofloxacin, the monocyclic and bicyclic 2-pyridone and 4-pyridones), hydroxylamine (quinazolinediones and tricyclic isoquinolones), or a hydrazine (quinazolinediones) group, which relate to DNA gyrase and topoisomerase activity and presumably bind to a divalent cation in the activated complex (see, Laponogov, I.; Sohi, M. K.; Veselkov, D. A.; Pan, X. S.; Sawhney, R.; Thompson, A. W.; McAuley, K. E.; Fisher, L. M.; Sanderson, M. R. Structural insight into the quinolone-DNA cleavage complex of type HA topoisomerases. *Nat. Struct. Mol. Biol.* 2009, 16 (6), 667-669).

Most inhibitors also possess an amine functional group attached to the core heterocycle, making these compounds zwitterionic in nature. Monocyclic 2-pyridone and 4-pyridone (e.g., Ro-13-5478) inhibitors possess this amine functionality attached to a phenyl group (see, Tesfaye, B.; Heck, J. V.; Thorsett, E. D. European Patent Application 0308022 A2, 1987; Narita, H.; Konishi, Y.; Nitta, J.; Misumi, S.; Nagaki, H.; Kitayama, I.; Nagai, Y.; Watanbe, Y.; Matsubare, N.; Minami, S.; Saikawa, I.; UK Patent Application GB2130580, 1983; and, Narita, H.; Konishi, Y.; Nitta, J.; Misumi, S.; Nagaki, H.; Kitayama, I.; Nagai, Y.; Watanbe, Y.; Matsubare, N.; Minami, S.; Saikawa, I. U.S. Pat. No. 4,698,352; 1987).

The zwitterionic nature of these inhibitors relate to the permeation of these compounds into the Gram-negative cell using porin channels (see, Nikaido, H.; Thanassi, D. G. Penetration of lipophilic agents with multiple protonation sites into bacterial cells: tetracyclines and fluoroquinolones as examples. *Antimicrob. Agents Chemother.* 1993, 37 (7), 1393-1399; and, Tieleman, D. P.; Berendsen, H. J. A molecular dynamics study of the pores formed by *Escherichia coli* OmpF porin in a fully hydrated palmitoyloleoylphosphatidylcholine bilayer. *Biophys. J.* 1998, 74 (6), 2786-2801).

Due to increasing resistance of multiple bacteria to marketed antibiotics in hospital as well as in community settings, the discovery of new and especially novel antibiotics is urgently needed (see, Bonhoeffer, S.; Lipsitch, M.; Levin, B. R. Evaluating treatment protocols to prevent antibiotic resistance. *Proc. Natl. Acad. Sci. U.S.A* 1997, 94 (22), 12106-12111; Wang, Y. C.; Lipsitch, M. Upgrading antibiotic use within a class: tradeoff between resistance and treatment success. *Proc. Natl. Acad. Sci. U.S.A* 2006, 103 (25), 9655-9660; and, Payne, D. J.; Gwynn, M. N.; Holmes, D. J.; Pompliano, D. L. Drugs for bad bugs: confronting the challenges of antibacterial discovery. *Nat. Rev. Drug Discov.* 2007, 6 (1), 29-40).

Approximately 70% of bacterial strains causing nosocomial infections are resistant to at least one of the drugs most commonly used to treat such infections, and 25% of bacterial pneumonia cases have been shown to be resistant to penicillin (Todar, K. Todar's Online textbook of Bacteriology, htttp://www.textbookofbacteriology.net/). Recently, there has been a dramatic decrease in the number of new antibiotic approvals, where only two new entities have been approved in the past two years.

There are some antibiotics available that have had success against MRSA (see, Perry, C. M.; Jarvis, B. Linezolid: a review of their use in the management of serious Gram-positive infections. *Drugs* 2001, 61 (4), 525-551; Peterson, L. R. A review of tigecycline—the first glycylcycline. *Int. J. Antimicrob. Agents* 2008, 32 *Suppl* 4, S215-S222; Chu, D. T. Recent developments in macrolides and ketolides. *Curr. Opin. Microbiol.* 1999, 2 (5), 467-474; Kahne, D.; Leimkuhler, C.; Lu, W.; Walsh, C. Glycopeptide and lipoglycopeptide antibiotics. *Chem. Rev.* 2005, 105 (2), 425-448; and, Zhanel, G. G.; Lam, A.; Schweizer, F.; Thomson, K.; Walkty, A.; Rubinstein, E.; Gin, A. S.; Hoban, D. J.; Noreddin, A. M.; Karlowsky, J. A. Ceftobiprole: a review of a broad-spectrum and anti-MRSA cephalosporin. *Am. J. Clin. Dermatol.* 2008, 9 (4), 245-254), but there have been no new clinically approved agents targeting Gram-negative bacteria.

Quinolones have been shown to be highly effective in the clinic, but wide-scale deployment of these current drugs, partly due to generic usage of the effective second generation quinolones (e.g., ciprofloxacin), jeopardizes their future long-term utility. Quinolone resistance is already rising in both hospitals and the community at large. Therefore, new drugs targeting MDR Gram-negative pathogens would be expected to help address this important unmet medical need (see, Talbot, G. H.; Bradley, J.; Edwards, J. E., Jr.; Gilbert, D.; Scheid, M.; Bartlett, J. G. Bad bugs need drugs: an update on the development pipeline from the Antimicrobial Availability Task Force of the Infectious Diseases Society of America. *Clin. Infect. Dis.* 2006, 42 (5), 657-668; and, Rice, L. B. Unmet medical needs in antibacterial therapy. *Biochem. Pharmacol.* 2006, 71 (7), 991-995).

As resistance to marketed antibiotics continues to increase, and new antibacterials have not been readily forthcoming from the pharmaceutical industry, the availability of new antibiotic and antibacterials agents is essential to overcome pre-existing and burgeoning resistance. As an effective monotherapy, novel compounds active against MDR strains of *E. coli* and *A. baumannii* pathogens, as well as other bacterial strains of great interest are needed, including those potentially employable as bioterror agents. New compounds that bind differently than existing DNA synthesis inhibitors and new therapies with combinations of antibacterial and antibiotic agents having additive or synergistic activities, including combinations with current quinolone antibiotics, would enable longer clinical lifetimes for proven antibacterial agents against a mechanistically validated target. Accordingly, the availability of such compounds and therapies would provide a significant current and future human health benefit with a high probability of success on several fronts for the control of difficult bacterial infections for a number of years to come.

6-methoxyquinoline based compounds for use as antibacterial topoisomerase inhibitors possessing Gram-negative activities have been reported by Glaxo-SmithKline, Johnson & Johnson and Novexel. Achillion and Rib-x Pharmaceuticals have also reported isothiazoloquinolones and quinolone (delafloxacin), respectively, that possess activity against resistant Gram-positive strains, including MRSA. Other examples in the literature include AM-1954 (Kyorin), DC-159a and DX-619 (Diaiichi), JNJ-Q2 (Johnson & Johnson), WQ-3813 (Wakunaga). However, all these compounds are derived from a quinolone moiety. Pfizer, Astra Zeneca, Achaogen and Targanta further describe quinolone-based compounds that possess an expanded spectrum of activity, especially against Gram-positive strains. Recently, the literature from 2005 to 2010 has been surveyed for new quinolone antibiotics (see, Wiles, J. A.; Bradbury, B. J.; Pucci, M. J. New quinolone antibiotics: a survey of the literature from 2005 to 2010. *Expert Opin. Ther. Patents*, 2010, 20(10), 1295-1319), including the development of compounds by AstraZeneca, Vertex Pharmaceuticals and Pfizer that act on the gyrase B sub-unit of the enzyme.

Despite the availability of quinolone based agents, the pre-existing and burgeoning resistance to such agents requires the availability of new antibiotic and antibacterials agents. However, the high conservation of sequence identity between DNA gyrase and topoisomerase IV enzymes continues to provide an opportunity for the discovery and development of non-quinolone inhibitors possessing a broad spectrum of activity against these targets. The present description relates to compounds having activity toward wild-type and MDR bacteria. The present description also relates to compounds having activity against quinolone-resistant Gram-negative strains (including MDR strains) as well as antibacterial activity to MDR resistant Gram-positive pathogens (including MRSA strains). The present description also relates to compounds with selectivity between bacterial topoisomerase IV and DNA gyrase enzyme inhibition compared to human topoisomerase II enzyme inhibition. The present description further relates to compounds that may be combined with known antibacterial agents to provide additive or synergistic activity, thus enabling the development of a combination product for the treatment of Gram-negative (especially MDR strains) and Gram-positive infections.

All other documents referred to herein are incorporated by reference into the present application as though fully set forth herein.

SUMMARY

The present description relates to a compound of Formula (I):

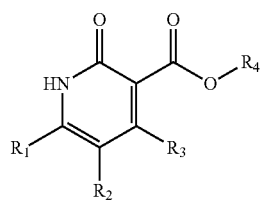

wherein $R_1$, $R_2$, $R_3$ and $R_4$ are as defined herein, and forms and compositions thereof, and also relates to uses of the compound of Formula (I) and methods of treating or ameliorating a bacterial infection, or for treating or ameliorating a multi-drug resistant (MDR) bacterial infection.

The present description further relates to a compound of Formula (I) having activity toward wild-type and MDR bacteria. The present description also relates to a compound of Formula (I) having activity against quinolone-resistant Gram-negative strains (including MDR strains) as well as antibacterial activity to MDR resistant Gram-positive pathogens (including MRSA strains). The present description also relates to a compound of Formula (I) having selectivity between bacterial topoisomerase IV and DNA gyrase enzyme inhibition compared to human topoisomerase II enzyme inhibition. The present description further relates to a compound of Formula (I) that may be combined with known antibacterial agents to provide additive or synergistic activity, thus enabling the development of a combination product for the treatment of Gram-negative (especially MDR strains) and Gram-positive infections.

DETAILED DESCRIPTION

The present description relates to a compound of Formula (I):

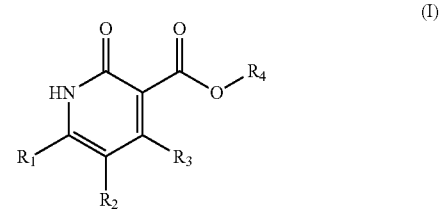

or a form thereof, wherein $R_1$ is phenyl, thienyl, pyrrolyl, pyrazolyl, pyridinyl, pyrimidinyl or pyrazinyl, each optionally substituted with one, two or three substituents each selected from $R_5$ and one additional substituent selected from $R_6$;

$R_2$ is hydrogen, halogen, cyano, $C_{1-8}$alkyl, halo-$C_{1-8}$alkyl, hydroxyl-$C_{1-8}$alkyl, formyl-$C_{1-8}$alkyl, $C_{1-8}$alkoxy-$C_{1-8}$alkyl, $C_{1-8}$alkoxy, $C_{2-8}$alkenyl, $C_{2-8}$alkynl, carboxyl, amino, $C_{1-8}$alkyl-amino, $(C_{1-8}$alkyl$)_2$-amino, amino-$C_{1-8}$alkyl, $C_{1-8}$alkyl-amino-$C_{1-8}$alkyl, $(C_{1-8}$alkyl$)_2$-amino-$C_{1-8}$alkyl, $C_{3-14}$cycloalkyl, $C_{3-8}$cycloalkyl-oxy, aryl or aryl-$C_{1-8}$alkyl, wherein each instance of aryl is optionally substituted with one halogen substituent;

$R_3$ is hydrogen, halogen, hydroxyl, $C_{1-8}$alkyl, $C_{1-8}$alkoxy, carboxyl, amino, $C_{1-8}$alkyl-amino, $(C_{1-8}$alkyl$)_2$-amino or $C_{1-8}$alkyl-$SO_2$-amino;

$R_4$ is hydrogen or $C_{1-8}$alkyl;

$R_5$ is halogen, hydroxyl, oxo, cyano, nitro, $C_{1-8}$alkyl, hydroxyl-$C_{1-8}$alkyl, halo-$C_{1-8}$alkyl, $C_{1-8}$alkoxy, halo-$C_{1-8}$alkoxy, $C_{1-8}$alkyl-thio, carboxyl, $C_{1-8}$alkyl-carbonyl, $C_{1-8}$alkoxy-carbonyl, amino-carbonyl, amino, $C_{1-8}$alkyl-amino, $(C_{1-8}$alkyl$)_2$-amino, $C_{2-8}$alkenyl-amino, $(C_{2-8}$alkenyl$)_2$-amino, $C_{2-8}$alkynyl-amino, $(C_{2-8}$alkynyl$)_2$-amino, amino-$C_{1-8}$alkyl, $C_{1-10}$alkyl-amino-$C_{1-8}$alkyl, $(C_{1-8}$alkyl$)_2$-amino-$C_{1-8}$alkyl, $C_{2-8}$alkenyl-amino-$C_{1-8}$alkyl, $(C_{2-8}$alkenyl$)_2$-amino-$C_{1-8}$alkyl, $C_{2-8}$alkynyl-amino-$C_{1-8}$alkyl, $(C_{2-8}$alkynyl$)_2$-amino-$C_{1-8}$alkyl, halo-$C_{1-8}$alkyl-amino, $(halo$-$C_{1-8}$alkyl$)_2$-amino, halo-$C_{1-8}$alkyl-amino-$C_{1-8}$alkyl, $(halo$-$C_{1-8}$alkyl$)_2$-amino-$C_{1-8}$alkyl, $C_{1-8}$alkoxy-$C_{1-8}$alkyl-amino, $(C_{1-8}$alkoxy-$C_{1-8}$alkyl, $C_{1-8}$alkyl)-amino, $(C_{1-8}$alkoxy-$C_{1-8}$alkyl$)_2$-amino, $C_{1-8}$alkoxy-$C_{1-8}$alkyl-amino-$C_{1-8}$alkyl, ($C_{1-8}$alkoxy-$C_{1-8}$alkyl, $C_{1-8}$alkyl)-amino-$C_{1-8}$alkyl, ($C_{1-8}$alkoxy-$C_{1-8}$alkyl)$_2$-amino-$C_{1-8}$alkyl, amino-$C_{1-8}$alkyl-amino, (amino-$C_{1-8}$alkyl, $C_{1-8}$alkyl)amino, $C_{1-8}$alkyl-amino-$C_{1-8}$alkyl-amino, ($C_{1-8}$alkyl-amino-$C_{1-8}$alkyl, $C_{1-8}$alkyl) amino, ($C_{1-8}$alkyl)$_2$-amino-$C_{1-8}$alkyl-amino, [($C_{1-8}$alkyl)$_2$-amino-$C_{1-8}$alkyl, $C_{1-8}$alkyl]amino, amino-$C_{1-8}$alkyl-amino-$C_{1-8}$alkyl, (amino-$C_{1-8}$alkyl, $C_{1-8}$alkyl) amino-$C_{1-8}$alkyl, $C_{1-8}$alkyl-amino-$C_{1-8}$alkyl-amino-$C_{1-8}$alkyl, ($C_{1-8}$alkyl-amino-$C_{1-8}$alkyl, $C_{1-8}$alkyl)amino-$C_{1-8}$alkyl, ($C_{1-8}$alkyl)$_2$-amino-$C_{1-8}$alkyl-amino-$C_{1-8}$alkyl, [($C_{1-8}$alkyl)$_2$-amino-$C_{1-8}$alkyl, $C_{1-8}$alkyl]amino-$C_{1-8}$alkyl, hydroxyl-amino, hydroxyl-$C_{1-8}$alkyl-amino, (hydroxyl-$C_{1-8}$alkyl, $C_{1-8}$alkyl)amino, (hydroxyl-$C_{1-8}$alkyl)$_2$-amino, hydroxyl-$C_{1-8}$alkyl-amino-$C_{1-8}$alkyl, (hydroxyl-$C_{1-8}$alkyl, $C_{1-8}$alkyl)amino-$C_{1-8}$alkyl, hydroxyl-$C_{1-8}$alkyl-amino-$C_{1-8}$alkyl-amino, (hydroxyl-$C_{1-8}$alkyl-amino-$C_{1-8}$alkyl, $C_{1-8}$alkyl)amino, (hydroxyl-$C_{1-8}$alkyl, $C_{1-8}$alkyl)amino-$C_{1-8}$alkyl-amino, [(hydroxyl-$C_{1-8}$alkyl, $C_{1-8}$alkyl)amino-$C_{1-8}$alkyl, $C_{1-8}$alkyl]amino, ($C_{1-8}$alkyl-carbonyl, $C_{1-8}$alkyl)amino-$C_{1-8}$alkyl, $C_{1-8}$alkyl-amino-carbonyl, ($C_{1-8}$alkyl)$_2$-amino-carbonyl or ($C_{1-8}$alkyl)$_2$-amino-carbonyl-$C_{1-8}$alkyl-amino-$C_{1-8}$alkyl;

$R_6$ is $C_{3-14}$cycloalkyl, $C_{3-14}$cycloalkyl-$C_{1-8}$alkyl, $C_{3-14}$cycloalkyl-oxy, $C_{3-14}$cycloalkyl-$C_{1-8}$alkoxy, $C_{3-14}$cycloalkyl-amino, $C_{3-14}$cycloalkyl-amino-$C_{1-8}$alkyl, ($C_{3-14}$cycloalkyl, $C_{1-8}$alkyl)amino-$C_{1-8}$alkyl, ($C_{3-14}$cycloalkyl)$_2$-amino-$C_{1-8}$alkyl, $C_{3-14}$cycloalkyl-$C_{1-8}$alkyl-amino-$C_{1-8}$alkyl, ($C_{3-14}$cycloalkyl-$C_{1-8}$alkyl, $C_{1-8}$alkyl) amino-$C_{1-8}$alkyl, ($C_{3-14}$cycloalkyl-$C_{1-8}$alkyl)$_2$-amino-$C_{1-8}$alkyl, aryl, aryl-$C_{1-8}$alkyl, aryl-$C_{1-8}$alkoxy, aryl-amino, (aryl, $C_{1-8}$alkyl)amino, (aryl)$_2$-amino, aryl-amino-$C_{1-8}$alkyl, (aryl, $C_{1-8}$alkyl)amino-$C_{1-8}$alkyl, (aryl)$_2$-amino-$C_{1-8}$alkyl, aryl-$C_{1-8}$alkyl-amino, (aryl-$C_{1-8}$alkyl, $C_{1-8}$alkyl)amino, (aryl-$C_{1-8}$alkyl)$_2$-amino, aryl-$C_{1-8}$alkyl-amino-$C_{1-8}$alkyl, (aryl-$C_{1-8}$alkyl, $C_{1-8}$alkyl)amino-$C_{1-8}$alkyl, (aryl-$C_{1-8}$alkyl)$_2$-amino-$C_{1-8}$alkyl, heteroaryl, heteroaryl-$C_{1-8}$alkyl, heteroaryl-amino, heteroaryl-$C_{1-8}$alkyl-amino, (heteroaryl-$C_{1-8}$alkyl, $C_{1-8}$alkyl)amino, (heteroaryl-$C_{1-8}$alkyl)$_2$-amino, heteroaryl-$C_{1-8}$alkyl-amino-$C_{1-8}$alkyl, (heteroaryl-$C_{1-8}$alkyl, $C_{1-8}$alkyl)amino-$C_{1-8}$alkyl, heterocyclyl, heterocyclyl-$C_{1-8}$alkyl, heterocyclyl-oxy, heterocyclyl-$C_{1-8}$alkoxy, heterocyclyl-amino, (heterocyclyl, $C_{1-8}$alkyl)amino, (heterocyclyl)$_2$-amino, heterocyclyl-amino-$C_{1-8}$alkyl, (heterocyclyl, $C_{1-8}$alkyl) amino-$C_{1-8}$alkyl, (heterocyclyl)$_2$-amino-$C_{1-8}$alkyl, (heterocyclyl, $C_{3-14}$cycloalkyl-$C_{1-8}$alkyl)amino-$C_{1-8}$alkyl, heterocyclyl-$C_{1-8}$alkyl-amino-$C_{1-8}$alkyl, (heterocyclyl-$C_{1-8}$alkyl, $C_{1-8}$alkyl)amino-$C_{1-8}$alkyl, (heterocyclyl-$C_{1-8}$alkyl)$_2$-amino-$C_{1-8}$alkyl, heterocyclyl-oxy-amino, (heterocyclyl-oxy, $C_{1-8}$alkyl)amino, (heterocyclyl-oxy)$_2$-amino, (heterocyclyl-oxy-$C_{1-8}$alkyl, $C_{1-8}$alkyl)amino, heterocyclyl-carbonyl or heterocyclyl-carbonyl-oxy;

wherein each instance of heterocyclyl is optionally substituted with one, two or three substituents each selected from $R_7$; and, wherein each instance of $C_{3-14}$cycloalkyl, aryl and heteroaryl is optionally substituted with one, two or three substituents each selected from $R_8$;

$R_7$ is azido, halogen, hydroxyl, oxo, cyano, nitro, $C_{1-8}$alkyl, halo-$C_{1-8}$alkyl, hydroxyl-$C_{1-8}$alkyl, $C_{1-8}$alkoxy-$C_{1-8}$alkyl, $C_{1-8}$alkoxy, halo-$C_{1-8}$alkoxy, hydroxyl-$C_{1-8}$alkoxy, carboxyl, $C_{1-8}$alkyl-carbonyl, $C_{1-8}$alkoxy-carbonyl, amino, $C_{1-8}$alkyl-amino, ($C_{1-8}$alkyl)$_2$-amino, halo-$C_{1-8}$alkyl-amino, (halo-$C_{1-8}$alkyl)$_2$-amino, halo-$C_{1-8}$alkyl-amino-$C_{1-8}$alkyl, (halo-$C_{1-8}$alkyl)$_2$-amino-$C_{1-8}$alkyl, amino-$C_{1-8}$alkyl, $C_{1-8}$alkyl-amino-$C_{1-8}$alkyl, ($C_{1-8}$alkyl)$_2$-amino-$C_{1-8}$alkyl, [($C_{1-8}$alkyl)$_2$-amino-$C_{1-8}$alkyl, $C_{1-8}$alkyl]amino-$C_{1-8}$alkyl $C_{1-8}$alkyl-thio, amino-carbonyl, $C_{1-8}$alkyl-amino-carbonyl, ($C_{1-8}$alkyl)$_2$-amino-carbonyl, $C_{1-8}$alkyl-carbonyl-amino, (carboxyl-$C_{1-8}$alkyl, $C_{1-8}$alkyl)amino-carbonyl-amino, $C_{3-14}$cycloalkyl, $C_{3-14}$cycloalkyl-amino, aryl, aryl-$C_{1-8}$alkyl, aryl-amino, (aryl, $C_{1-8}$alkyl)amino, (aryl)$_2$-amino, aryl-$C_{1-8}$alkyl-amino, (aryl-$C_{1-8}$alkyl, $C_{1-8}$alkyl)amino, (aryl-$C_{1-8}$alkyl)$_2$-amino, aryl-$C_{1-8}$alkyl-amino-$C_{1-8}$alkyl, (aryl-$C_{1-8}$alkyl, $C_{1-8}$alkyl)amino-$C_{1-8}$alkyl, (aryl-$C_{1-8}$alkyl)$_2$-amino-$C_{1-8}$alkyl, aryl-amino-$C_{1-8}$alkyl, (aryl, $C_{1-8}$alkyl)amino-$C_{1-8}$alkyl, (aryl)$_2$-amino-$C_{1-8}$alkyl, aryl-amino-carbonyl, aryl-$C_{1-8}$alkoxy, aryl-$C_{1-8}$alkoxy-carbonyl-amino, heteroaryl, heteroaryl-$C_{1-8}$alkyl, heteroaryl-amino, (heteroaryl)$_2$-amino, heteroaryl-$C_{1-8}$alkyl-amino, (heteroaryl-$C_{1-8}$alkyl, $C_{1-8}$alkyl)amino, (heteroaryl-$C_{1-8}$alkyl)$_2$-amino, heteroaryl-$C_{1-8}$alkyl-amino-$C_{1-8}$alkyl, (heteroaryl-$C_{1-8}$alkyl, $C_{1-8}$alkyl)amino-$C_{1-8}$alkyl, (heteroaryl-$C_{1-8}$alkyl)$_2$-amino-$C_{1-8}$alkyl, heterocyclyl, heterocyclyl-$C_{1-8}$alkyl, heterocyclyl-amino-$C_{1-8}$alkyl or heterocyclyl-oxy;

wherein each instance of $C_{3-14}$cycloalkyl is optionally substituted with one substituent selected from $R_9$;

wherein each instance of aryl is optionally substituted with one substituent selected from $R_{10}$; and, wherein each instance of heterocyclyl and heteroaryl is optionally substituted with one substituent selected from $R_{11}$;

$R_8$ is azido, halogen, hydroxyl, cyano, nitro, $C_{1-8}$alkyl, halo-$C_{1-8}$alkyl, $C_{1-8}$alkoxy, $C_{1-8}$alkoxy-$C_{1-8}$alkyl, halo-$C_{1-8}$alkoxy, carboxyl, $C_{1-8}$alkoxy-carbonyl, amino, $C_{1-8}$alkyl-amino, ($C_{1-8}$alkyl)$_2$-amino, $C_{1-8}$alkyl-thio, aryl, aryl-$C_{1-8}$alkoxy, heteroaryl, heterocyclyl, heterocyclyl-$C_{1-8}$alkyl or heterocyclyl-oxy;

$R_9$ is amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl or aryl-$C_{1-8}$alkyl-amino;

$R_{10}$ is halogen; and, $R_{11}$ is halogen, hydroxyl, $C_{1-8}$alkyl, halo-$C_{1-8}$alkyl, $C_{1-8}$alkoxy, $C_{1-8}$alkoxy-$C_{1-8}$alkyl, halo-$C_{1-8}$alkoxy, amino, $C_{1-8}$alkyl-amino or ($C_{1-8}$alkyl)$_2$-amino.

One embodiment of the present description includes a compound of Formula (I) or a form thereof, wherein $R_1$ is thien-2-yl, pyrrol-2-yl, pyrrol-3-yl, 1H-pyrazol-2-yl, 1H-pyrazol-4-yl, pyrazin-2-yl, pyrimidin-5-yl, pyridin-2-yl or pyridin-3-yl.

One embodiment of the present description includes a compound of Formula (I) or a form thereof, wherein $R_2$, $R_6$, $R_7$ and $R_8$ is $C_{3-14}$cycloalkyl selected in each instance, when present, from cyclopropyl, cyclobutyl, cyclopentyl, cyclohexyl or cycloheptyl;

aryl selected in each instance, when present, from phenyl;

heteroaryl selected in each instance, when present, from pyrrolyl, thiazolyl, 1H-1,2,3-triazolyl, 1H-tetrazolyl, 2H-tetrazolyl, imidazolyl or pyridinyl;

heterocyclyl selected in each instance, when present, from azetidinyl, pyrrolidinyl, tetrahydrofuranyl, piperidinyl, piperazinyl, morpholinyl, 1,4-diazepanyl, 1,3-dioxolanyl, 2,5-dihydro-1H-pyrrolyl, dihydro-1H-imidazolyl, 1,4,5,6-tetrahydropyrimidinyl, 1,2,3,6-tetrahydropyridinyl, tetrahydro-2H-pyranyl, indolinyl, 2,3-dihydrobenzo[d]oxazolyl, 3,4-dihydro-2H-benzo[b][1,4]oxazinyl, 3,4-dihydroisoquinolin-(1H)-yl, 1,2,3,4-tetrahydroisoquinolinyl, 1,2,3,4-tetrahydroquinoxalinyl, hexahydropyrrolo[3,4-b][1,4]oxazin-(2H)-yl, (4aR,7aS)-hexahydropyrrolo[3,4-b][1,4]oxazin-(4aH)-yl, 3,4-dihydro-2H-pyrido[3,2-b][1,4]oxazinyl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, 2,3,4,9-tetrahydro-1H-carbazolyl, 1,2,3,4-tetrahydropyrazino[1,2-a]indolyl, 2,3-dihydro-1H-pyrrolo[1,2-a]indolyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, (1R,5S,6s)-3-azabicyclo[3.1.0]hexanyl, (cis,cis)-3-azabicyclo[3.1.0]hexanyl, 3,6-diazabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl or 2,8-diazaspiro[4.5]decanyl.

One embodiment of the present description includes a compound of Formula (I) or a form thereof, wherein $R_6$, $R_7$ and $R_8$ is heteroaryl selected in each instance, when present, from pyrrol-1-yl, thiazol-2-yl, 1H-1,2,3-triazol-1-yl, 1H-tetrazol-5-yl, 2H-tetrazol-2-yl, imidazol-1-yl, pyridin-2-yl, pyridin-3-yl or pyridin-4-yl;

heterocyclyl selected in each instance, when present, from azetidin-1-yl, pyrrolidin-1-yl, pyrrolidin-2-yl, pyrrolidin-3-yl, tetrahydrofuran-2-yl, piperidin-1-yl, piperidin-2-yl, piperidin-3-yl, piperidin-4-yl, piperazin-1-yl, piperazin-2-yl, morpholin-4-yl, 1,4-diazepan-1-yl, 1,3-dioxolan-2-yl, 2,5-dihydro-1H-pyrrol-1-yl, dihydro-1H-imidazol-2-yl, 1,4,5,6-tetrahydropyrimidin-2-yl, 1,2,3,6-tetrahydropyridin-4-yl, tetrahydro-2H-pyran-2-yl, tetrahydro-2H-pyran-4-yl, 3,4-dihydroisoquinolin-2(1H)-yl, 1,2,3,4-tetrahydroisoquinolin-1-yl, hexahydropyrrolo[3,4-b][1,4]oxazin-6(2H)-yl, (4aR,7aS)-hexahydropyrrolo[3,4-b][1,4]oxazin-4(4aH)-yl, (cis)-octahydrocyclopenta[c]pyrrol-4-yl, hexahydropyrrolo[3,4-b]pyrrol-5(1H)-yl, (3aR,6aR)-hexahydropyrrolo[3,4-b]pyrrol-5(1H)-yl, (3aR,6aS)-hexahydropyrrolo[3,4-c]pyrrol-2(1H)-yl, 5H-pyrrolo[3,4-b]pyridin-6(7H)-yl, 5,7-dihydro-6H-pyrrolo[3,4-b]pyridin-6-yl, tetrahydro-1H-pyrrolo[3,4-b]pyridin-6(2H,7H,7aH)-yl, hexahydro-1H-pyrrolo[3,4-b]pyridin-6(2H)-yl, (4aR,7aR)-hexahydro-1H-pyrrolo[3,4-b]pyridin-6(2H)-yl, octahydro-6H-pyrrolo[3,4-b]pyridin-6-yl, (3aR,6aR)-hexahydrocyclopenta[c]pyrrol-3a(1H)-yl, (3aR,4R,6aS)-hexahydrocyclopenta[c]pyrrol-2(1H)-yl, (3aR,4S,6aS)-hexahydrocyclopenta[c]pyrrol-2(1H)-yl, (3aR,5r,6aS)-hexahydrocyclopenta[c]pyrrol-2(1H)-yl, 1,3-dihydro-2H-isoindol-2-yl, octahydro-2H-isoindol-2-yl, (3aS)-1,3,3a,4,5,6-hexahydro-2H-isoindol-2-yl, (3aR,4R,7aS)-1H-isoindol-2(3H,3aH,4H,5H,6H,7H,7aH)-yl, (3aR,7aS)-octahydro-2H-isoindol-2-yl, (3aR,4R,7aS)-octahydro-2H-isoindol-2-yl, (3aR,4S,7aS)-octahydro-2H-isoindol-2-yl, 2,5-diazabicyclo[2.2.1]heptan-2-yl, 2-azabicyclo[2.2.1]hept-5-en-2-yl, 3-azabicyclo[3.1.0]hexan-3-yl, (1R,5S,6s)-3-azabicyclo[3.1.0]hexan-3-yl, (1R,5S,6s)-3-azabicyclo[3.1.0]hexan-6-yl, (cis,cis)-3-azabicyclo[3.1.0]hexan-3-yl, 3,6-diazabicyclo[3.1.0]hexan-3-yl, (1S,5R,6R)-3-azabicyclo[3.2.0]heptan-3-yl, (1S,5R,6S)-3-azabicyclo[3.2.0]heptan-3-yl, 5-azaspiro[2.4]heptan-5-yl, 2,6-diazaspiro[3.3]heptan-2-yl, 2,5-diazaspiro[3.4]octan-2-yl, 2,6-diazaspiro[3.4]octan-6-yl, 2,7-diazaspiro[3.5]nonan-2-yl, 2,7-diazaspiro[4.4]nonan-2-yl, 2-azaspiro[4.5]decan-2-yl or 2,8-diazaspiro[4.5]decan-2-yl.

One embodiment of the present description includes a compound of Formula (I) or a form thereof, wherein $R_6$, $R_7$ and $R_8$ is heteroaryl selected in each instance, when present, from pyridinyl;

heterocyclyl selected in each instance, when present, from azetidinyl, pyrrolidinyl, tetrahydrofuranyl, piperidinyl, piperazinyl, morpholinyl, 1,4-diazepanyl, 1,3-dioxolanyl, dihydro-1H-imidazolyl, 1,4,5,6-tetrahydropyrimidinyl, 1,2,3,6-tetrahydropyridinyl, tetrahydro-2H-pyranyl, 3,4-dihydroisoquinolin-(1H)-yl, 1,2,3,4-tetrahydroisoquinolinyl, 5H-pyrrolo[3,4-b]pyridin-(7H)-yl, tetrahydro-1H-pyrrolo[3,4-b]pyridin-(2H,7H,7aH)-yl, (3aR,4R,6aS)-hexahydrocyclopenta[c]pyrrol-(1H)-yl, (3aR,4R,7aS)-1H-isoindol-(3H,3aH,4H,5H,6H,7H,7aH)-yl, 2,5-diazabicyclo[2.2.1]heptanyl or (1R,5S,6s)-3-azabicyclo[3.1.0]hexanyl.

One embodiment of the present description includes a compound of Formula (I) or a form thereof, wherein $R_6$, $R_7$ and $R_8$ is heteroaryl selected in each instance, when present, from pyridin-2-yl, pyridin-3-yl or pyridin-4-yl;

heterocyclyl selected in each instance, when present, from azetidin-1-yl, pyrrolidin-1-yl, pyrrolidin-2-yl, pyrrolidin-3-yl, tetrahydrofuran-2-yl, piperidin-1-yl, piperidin-2-yl, piperidin-3-yl, piperidin-4-yl, piperazin-1-yl, piperazin-2-yl, morpholin-4-yl, 1,4-diazepan-1-yl, 1,3-dioxolan-2-yl, dihydro-1H-imidazol-2-yl, 1,4,5,6-tetrahydropyrimidin-2-yl, 1,2,3,6-tetrahydropyridin-4-yl, tetrahydro-2H-pyran-2-yl, tetrahydro-2H-pyran-4-yl, 3,4-dihydroisoquinolin-2(1H)-yl, 1,2,3,4-tetrahydroisoquinolin-1-yl, 5H-pyrrolo[3,4-b]pyridin-6(7H)-yl, tetrahydro-1H-pyrrolo[3,4-b]pyridin-6(2H,7H,7aH)-yl, (3aR,4R,6aS)-hexahydrocyclopenta[c]pyrrol-2(1H)-yl, (3aR,4R,7aS)-1H-isoindol-2(3H,3aH,4H,5H,6H,7H,7aH)-yl, 2,5-diazabicyclo[2.2.1]heptan-2-yl, (1R,5S,6s)-3-azabicyclo[3.1.0]hexan-3-yl or (1R,5S,6s)-3-azabicyclo[3.1.0]hexan-6-yl.

One embodiment of the present description includes a compound of Formula (I) or a form thereof, wherein $R_6$, $R_7$ and $R_8$ is heteroaryl selected in each instance, when present, from pyrrolyl, imidazolyl, 1H-tetrazolyl or 2H-tetrazolyl;

heterocyclyl selected in each instance, when present, from azetidinyl, pyrrolidinyl, tetrahydrofuranyl, piperidinyl, piperazinyl, morpholinyl, 1,4-diazepanyl, 1,3-dioxolanyl, 2,5-dihydro-1H-pyrrolyl, dihydro-1H-imidazolyl, 1,4,5,6-tetrahydropyrimidinyl, 1,2,3,6-tetrahydropyridinyl, tetrahydro-2H-pyranyl, 3,4-dihydroisoquinolin-(1H)-yl, 1,2,3,4-tetrahydroisoquinolinyl, hexahydropyrrolo[3,4-b][1,4]oxazin-(2H)-yl, (4aR,7aS)-hexahydropyrrolo[3,4-b][1,4]oxazin-(4aH)-yl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, 3,6-diazabicyclo[3.1.0]hexanyl, (1R,5S,6s)-3-azabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl or 2,8-diazaspiro[4.5]decanyl.

One embodiment of the present description includes a compound of Formula (I) or a form thereof, wherein $R_6$, $R_7$ and $R_8$ is heteroaryl selected in each instance, when present, from 1H-tetrazol-5-yl, imidazol-1-yl, pyrrol-1-yl or 2H-tetrazol-2-yl;

heterocyclyl selected in each instance, when present, from azetidin-1-yl, pyrrolidin-1-yl, tetrahydrofuran-2-yl, piperidin-1-yl, piperazin-1-yl, morpholin-4-yl, 2,5-dihydro-1H-pyrrol-1-yl, hexahydropyrrolo[3,4-b][1,4]oxazin-6(2H)-yl, (4aR,7aS)-hexahydropyrrolo[3,4-b][1,4]oxazin-4(4aH)-yl, (3aR,6aR)-hexahydropyrrolo[3,4-b]pyrrol-5(1H)-yl, (3aR,6aS)-hexahydropyrrolo[3,4-c]pyrrol-2(1H)-yl, 5,7-dihydro-6H-pyrrolo[3,4-b]pyridin-6-yl, octahydro-6H-pyrrolo[3,4-b]pyridin-6-yl, (3aR,6aR)-hexahydrocyclopenta[c]pyrrol-3a(1H)-yl, (3aR,4R,6aS)-hexahydrocyclopenta[c]pyrrol-2(1H)-yl, (3aR,4S,6aS)-hexahydrocyclopenta[c]pyrrol-2(1H)-yl, (3aR,5r,6aS)-hexahydrocyclopenta[c]pyrrol-2(1H)-yl, 1,3-dihydro-2H-isoindol-2-yl, octahydro-2H-isoindol-2-yl, (3aS)-1,3,3a,4,5,6-hexahydro-2H-isoindol-2-yl, (3aR,7aS)-octahydro-2H-isoindol-2-yl, (3aR,4R,7aS)-octahydro-2H-isoindol-2-yl, (3aR,4S,7aS)-octahydro-2H-isoindol-2-yl, 2,5-diazabicyclo[2.2.1]heptan-2-yl, 2-azabicyclo[2.2.1]hept-5-en-2-yl, 3-azabicyclo[3.1.0]hexan-3-yl, 3,6-diazabicyclo[3.1.0]hexan-3-yl, (1R,5S,6s)-3-azabicyclo[3.1.0]hexan-3-yl, (1R,5S,6s)-3-azabicyclo[3.1.0]hexan-6-yl, (1S,5R,6R)-3-azabicyclo[3.2.0]heptan-3-yl, (1S,5R,6S)-3-azabicyclo[3.2.0]heptan-3-yl, 5-azaspiro[2.4]heptan-5-yl, 2,6-diazaspiro[3.3]heptan-2-yl, 2,5-diazaspiro[3.4]octan-2-yl, 2,6-diazaspiro[3.4]octan-6-yl, 2,7-diazaspiro[3.5]nonan-2-yl, 2,7-diazaspiro[4.4]nonan-2-yl, 2-azaspiro[4.5]decan-2-yl or 2,8-diazaspiro[4.5]decan-2-yl.

One embodiment of the present description includes a compound of Formula (I) or a form thereof, wherein $R_2$ is hydrogen, cyano, $C_{1-8}$alkyl, halo-$C_{1-8}$alkyl, hydroxyl-$C_{1-8}$alkyl, formyl-$C_{1-8}$alkyl, $C_{1-8}$alkoxy-$C_{1-8}$alkyl, $C_{2-8}$alkenyl, $C_{2-8}$alkynyl, carboxyl, $C_{3-14}$cycloalkyl, aryl or aryl-$C_{1-8}$alkyl, wherein each instance of aryl is optionally substituted with one halogen substituent;

$R_3$ is hydrogen, halogen, hydroxyl, $C_{1-8}$alkoxy, carboxyl, amino or $C_{1-8}$alkyl-$SO_2$-amino;

$R_4$ is hydrogen or $C_{1-8}$alkyl;

$R_5$ is halogen, oxo, cyano, $C_{1-8}$alkyl, hydroxyl-$C_{1-8}$alkyl, $C_{1-8}$alkoxy, carboxyl, amino-carbonyl, amino, $C_{1-8}$alkyl-amino, $(C_{1-8}$alkyl$)_2$-amino, $(C_{2-8}$alkenyl$)_2$-amino, amino-$C_{1-8}$alkyl, $C_{1-10}$alkyl-amino-$C_{1-8}$alkyl, $(C_{1-8}$alkyl$)_2$-amino-$C_{1-8}$alkyl, $C_{2-8}$alkenyl-amino-$C_{1-8}$alkyl, $C_{2-8}$alkynyl-amino-$C_{1-8}$alkyl, halo-$C_{1-8}$alkyl-amino, halo-$C_{1-8}$alkyl-amino-$C_{1-8}$alkyl, (hydroxyl-$C_{1-8}$alkyl, $C_{1-8}$alkyl)amino, $(C_{1-8}$alkoxy-$C_{1-8}$alkyl, $C_{1-8}$alkyl)-amino-$C_{1-8}$alkyl, $(C_{1-8}$alkyl$)_2$-amino-$C_{1-8}$alkyl-amino, $[(C_{1-8}$alkyl$)_2$-amino-$C_{1-8}$alkyl, $C_{1-8}$alkyl]amino, amino-$C_{1-8}$alkyl-amino-$C_{1-8}$alkyl, $C_{1-8}$alkyl-amino-$C_{1-8}$alkyl-amino-$C_{1-8}$alkyl, $(C_{1-8}$alkyl$)_2$-amino-$C_{1-8}$alkyl-amino-$C_{1-8}$alkyl, $[(C_{1-8}$alkyl$)_2$-amino-$C_{1-8}$alkyl, $C_{1-8}$alkyl]amino-$C_{1-8}$alkyl, $(C_{1-8}$alkyl-carbonyl, $C_{1-8}$alkyl)amino-$C_{1-8}$alkyl or $(C_{1-8}$alkyl$)_2$-amino-carbonyl-$C_{1-8}$alkyl-amino-$C_{1-8}$alkyl;

$R_6$ is $C_{3-14}$cycloalkyl-amino-$C_{1-8}$alkyl, $(C_{3-14}$cycloalkyl, $C_{1-8}$alkyl)amino-$C_{1-8}$alkyl, $C_{3-14}$cycloalkyl-$C_{1-8}$alkyl-amino-$C_{1-8}$alkyl, aryl, aryl-$C_{1-8}$alkoxy, aryl-amino, (aryl, $C_{1-8}$alkyl)amino, aryl-amino-$C_{1-8}$alkyl, aryl-$C_{1-8}$alkyl-amino-$C_{1-8}$alkyl, (aryl-$C_{1-8}$alkyl, $C_{1-8}$alkyl)amino-$C_{1-8}$alkyl, (aryl-$C_{1-8}$alkyl$)_2$-amino-$C_{1-8}$alkyl, heteroaryl, heteroaryl-$C_{1-8}$alkyl-amino-$C_{1-8}$alkyl, (heteroaryl-$C_{1-8}$alkyl, $C_{1-8}$alkyl)amino-$C_{1-8}$alkyl, heterocyclyl, heterocyclyl-$C_{1-8}$alkyl, heterocyclyl-amino-$C_{1-8}$alkyl, (heterocyclyl, $C_{1-8}$alkyl)amino-$C_{1-8}$alkyl, (heterocyclyl, $C_{3-14}$cycloalkyl-$C_{1-8}$alkyl)amino-$C_{1-8}$alkyl, heterocyclyl-$C_{1-8}$alkyl-amino-$C_{1-8}$alkyl or (heterocyclyl-oxy-$C_{1-8}$alkyl, $C_{1-8}$alkyl)amino;

wherein each instance of heterocyclyl is optionally substituted with one, two or three substituents each selected from $R_7$; and, wherein each instance of heteroaryl is optionally substituted with one, two or three substituents each selected from $R_8$;

$R_7$ is azido, halogen, hydroxyl, oxo, cyano, $C_{1-8}$alkyl, halo-$C_{1-8}$alkyl, hydroxyl-$C_{1-8}$alkyl, $C_{1-8}$alkoxy-$C_{1-8}$alkyl, $C_{1-8}$alkoxy, carboxyl, $C_{1-8}$alkyl-carbonyl, $C_{1-8}$alkoxy-carbonyl, amino, $C_{1-8}$alkyl-amino, $(C_{1-8}$alkyl$)_2$-amino, amino-$C_{1-8}$alkyl, $C_{1-8}$alkyl-amino-$C_{1-8}$alkyl, $(C_{1-8}$alkyl$)_2$-amino-$C_{1-8}$alkyl, $[(C_{1-8}$alkyl$)_2$-amino-$C_{1-8}$alkyl, $C_{1-8}$alkyl]amino-$C_{1-8}$alkyl($C_{1-8}$alkyl$)_2$-amino-carbonyl, $C_{1-8}$alkyl-carbonyl-amino, (carboxyl-$C_{1-8}$alkyl, $C_{1-8}$alkyl)amino-carbonyl-amino, $C_{3-14}$cycloalkyl, $C_{3-14}$cycloalkyl-amino, aryl, aryl-$C_{1-8}$alkyl, aryl-amino, (aryl, $C_{1-8}$alkyl)amino, aryl-$C_{1-8}$alkyl-amino, (aryl-$C_{1-8}$alkyl, $C_{1-8}$alkyl)amino, (aryl-$C_{1-8}$alkyl$)_2$-amino, aryl-$C_{1-8}$alkyl-amino-$C_{1-8}$alkyl, (aryl-$C_{1-8}$alkyl, $C_{1-8}$alkyl)amino-$C_{1-8}$alkyl, (aryl-$C_{1-8}$alkyl$)_2$-amino-$C_{1-8}$alkyl, aryl-amino-$C_{1-8}$alkyl, aryl-$C_{1-8}$alkoxy, aryl-$C_{1-8}$alkoxy-carbonyl-amino, heteroaryl, heteroaryl-$C_{1-8}$alkyl-amino-$C_{1-8}$alkyl, heterocyclyl, heterocyclyl-$C_{1-8}$alkyl, heterocyclyl-amino-$C_{1-8}$alkyl or heterocyclyl-oxy;

wherein each instance of $C_{3-14}$cycloalkyl is optionally substituted with one substituent selected from $R_9$;

wherein each instance of aryl is optionally substituted with one substituent selected from $R_{10}$; and, wherein each instance of heterocyclyl and heteroaryl is optionally substituted with one substituent selected from $R_{11}$;

$R_8$ is $C_{1-8}$alkyl;

$R_9$ is amino, $(C_{1-8}$alkyl$)_2$-amino or aryl-$C_{1-8}$alkyl-amino;

$R_{10}$ is halogen; and, $R_{11}$ is $C_{1-8}$alkyl.

One embodiment of the present description includes a compound of Formula (I) or a form thereof, wherein $R_2$ is $C_{1-8}$alkyl selected from methyl, ethyl, propyl or isopropyl; hydroxyl-$C_{1-8}$alkyl selected from hydroxyl-methyl, hydroxyl-ethyl or hydroxyl-propyl; formyl-$C_{1-8}$alkyl selected from formylmethyl, formylethyl or formylpropyl; $C_{3-14}$cycloalkyl selected from cyclopropyl, cyclobutyl, cyclopentyl or cyclohexyl; aryl selected from phenyl; and, aryl-$C_{1-8}$alkyl selected from benzyl;

$R_3$ is $C_{1-8}$alkoxy selected from methoxy, ethoxy, propoxy or isopropoxy; or, $C_{1-8}$alkyl-$SO_2$-amino selected from methyl-$SO_2$-amino, ethyl-$SO_2$-amino, propyl-$SO_2$-amino or isopropyl-$SO_2$-amino; and, $R_4$ is $C_{1-8}$alkyl selected from methyl, ethyl, propyl or isopropyl.

One embodiment of the present description includes a compound of Formula (I) or a form thereof, wherein $R_2$ is $C_{3-14}$cycloalkyl selected from cyclopropyl or cyclobutyl and aryl selected from phenyl; and $R_3$ is $C_{1-8}$alkoxy selected from methoxy, ethoxy, propoxy or isopropoxy.

One embodiment of the present description includes a compound of Formula (I) or a form thereof, wherein $R_2$ is $C_{1-8}$alkyl selected from methyl, ethyl, propyl or isopropyl; $C_{3-14}$cycloalkyl selected from cyclopropyl, cyclopentyl or cyclohexyl; or, aryl-$C_{1-8}$alkyl selected from benzyl.

One embodiment of the present description includes a compound of Formula (I) or a form thereof, wherein $R_2$ is $C_{3-14}$cycloalkyl selected from cyclopropyl.

One embodiment of the present description includes a compound of Formula (I) or a form thereof, wherein $R_3$ is $C_{1-8}$alkoxy selected from methoxy or ethoxy.

One embodiment of the present description includes a compound of Formula (I) or a form thereof, wherein $R_4$ is $C_{1-8}$alkyl selected from methyl.

One embodiment of the present description includes a compound of Formula (I) or a form thereof, wherein $R_6$ is $C_{3-14}$cycloalkyl-amino-$C_{1-8}$alkyl, wherein $C_{3-14}$cycloalkyl is selected from cyclopropyl, cyclobutyl, cyclopentyl or cyclohexyl;

($C_{3-14}$cycloalkyl, $C_{1-8}$alkyl)amino-$C_{1-8}$alkyl, wherein $C_{3-14}$cycloalkyl is selected from cyclopropyl, cyclobutyl or cyclopentyl;

$C_{3-14}$cycloalkyl-$C_{1-8}$alkyl-amino-$C_{1-8}$alkyl, wherein $C_{3-14}$cycloalkyl is selected from cyclopropyl, cyclobutyl, cyclopentyl, cyclohexyl or cycloheptyl; aryl, wherein aryl is selected from phenyl;

aryl-$C_{1-8}$alkoxy, wherein aryl is selected from phenyl;

aryl-amino, wherein aryl is selected from phenyl;

(aryl, $C_{1-8}$alkyl)amino, wherein aryl is selected from phenyl;

aryl-amino-$C_{1-8}$alkyl, wherein aryl is selected from phenyl;

aryl-$C_{1-8}$alkyl-amino-$C_{1-8}$alkyl, wherein aryl is selected from phenyl;

(aryl-$C_{1-8}$alkyl, $C_{1-8}$alkyl)amino-$C_{1-8}$alkyl, wherein aryl is selected from phenyl;

(aryl-$C_{1-8}$alkyl)$_2$-amino-$C_{1-8}$alkyl, wherein aryl is selected from phenyl;

heteroaryl, wherein heteroaryl is selected from pyrrolyl, thiazolyl, 1H-1,2,3-triazolyl, 1H-tetrazolyl, 2H-tetrazolyl, imidazolyl or pyridinyl;

heteroaryl-$C_{1-8}$alkyl-amino-$C_{1-8}$alkyl, wherein heteroaryl is selected from pyridin-2-yl, pyridin-3-yl or pyridin-4-yl;

(heteroaryl-$C_{1-8}$alkyl, $C_{1-8}$alkyl)amino-$C_{1-8}$alkyl, wherein heteroaryl is selected from pyridin-3-yl or pyridin-4-yl;

heterocyclyl, wherein heterocyclyl is selected from azetidinyl, pyrrolidinyl, tetrahydrofuranyl, piperidinyl, piperazinyl, morpholinyl, 1,4-diazepanyl, 1,3-dioxolanyl, 2,5-dihydro-1H-pyrrolyl, dihydro-1H-imidazolyl, 1,4,5,6-tetrahydropyrimidinyl, 1,2,3,6-tetrahydropyridinyl, tetrahydro-2H-pyranyl, 3,4-dihydroisoquinolin-(1H)-yl, 1,2,3,4-tetrahydroisoquinolinyl, hexahydropyrrolo[3,4-b][1,4]oxazin-(2H)-yl, (4aR,7aS)-hexahydropyrrolo[3,4-b][1,4]oxazin-(4aH)-yl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-2(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, (1R,5S,6s)-3-azabicyclo[3.1.0]hexanyl, (cis,cis)-3-azabicyclo[3.1.0]hexanyl, 3,6-diazabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl or 2,8-diazaspiro[4.5]decanyl;

heterocyclyl-$C_{1-8}$alkyl, wherein heterocyclyl is selected from azetidinyl, pyrrolidinyl, tetrahydrofuranyl, piperidinyl, piperazinyl, morpholinyl, 1,4-diazepanyl, 1,3-dioxolanyl, 2,5-dihydro-1H-pyrrolyl, dihydro-1H-imidazolyl, 1,4,5,6-tetrahydropyrimidinyl, 1,2,3,6-tetrahydropyridinyl, tetrahydro-2H-pyranyl, 3,4-dihydroisoquinolin-(1H)-yl, 1,2,3,4-tetrahydroisoquinolinyl, hexahydropyrrolo[3,4-b][1,4]oxazin-(2H)-yl, (4aR,7aS)-hexahydropyrrolo[3,4-b][1,4]oxazin-(4aH)-yl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-2(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, (1R,5S,6s)-3-azabicyclo[3.1.0]hexanyl, (cis,cis)-3-azabicyclo[3.1.0]hexanyl, 3,6-diazabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl or 2,8-diazaspiro[4.5]decanyl;

heterocyclyl-amino-$C_{1-8}$alkyl, wherein heterocyclyl is selected from azetidin-1-yl or piperidin-4-yl;

(heterocyclyl, $C_{1-8}$alkyl)amino-$C_{1-8}$alkyl, wherein heterocyclyl is selected from piperidin-3-yl or piperidin-4-yl;

(heterocyclyl, $C_{3-14}$cycloalkyl-$C_{1-8}$alkyl)amino-$C_{1-8}$alkyl, wherein heterocyclyl is selected from piperidin-3-yl or piperidin-4-yl;

heterocyclyl-$C_{1-8}$alkyl-amino-$C_{1-8}$alkyl, wherein heterocyclyl is selected from pyrrolidin-2-yl, piperidin-2-yl, piperidin-3-yl, piperidin-4-yl or tetrahydro-2H-pyran-4-yl; and (heterocyclyl-oxy-$C_{1-8}$alkyl, $C_{1-8}$alkyl)amino selected from tetrahydro-2H-pyran-2-yl-oxy-$C_{1-8}$alkyl, $C_{1-8}$alkyl)amino.

One embodiment of the present description includes a compound of Formula (I) or a form thereof, wherein $R_6$ is heteroaryl, wherein heteroaryl is selected from 1H-tetrazolyl, imidazolyl, pyrrolyl or 2H-tetrazolyl; and, heterocyclyl, wherein heterocyclyl is selected from azetidinyl, pyrrolidinyl, tetrahydrofuranyl, piperidinyl, piperazinyl, morpholinyl, 2,5-dihydro-1H-pyrrolyl, 1,2,3,6-tetrahydropyridinyl, hexahydropyrrolo[3,4-b][1,4]oxazin-(2H)-yl, (4aR,7aS)-hexahydropyrrolo[3,4-b][1,4]oxazin-(4aH)-yl, (3aR,6aR)-hexahydropyrrolo[3,4-b]pyrrol-(1H)-yl, (3aR,6aS)-hexahydropyrrolo[3,4-c]pyrrol-(1H)-yl, 5,7-dihydro-6H-pyrrolo[3,4-b]pyridinyl, octahydro-6H-pyrrolo[3,4-b]pyridinyl, (3aR,6aR)-hexahydrocyclopenta[c]pyrrol-3a(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-(1H)-yl, 1,3-dihydro-2H-isoindolyl, octahydro-2H-isoindolyl, (3aS)-1,3,3a,4,5,6-hexahydro-2H-isoindolyl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, 3,6-diazabicyclo[3.1.0]hexanyl, (1R,5S,6s)-3-azabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl or 2,8-diazaspiro[4.5]decanyl.

One embodiment of the present description includes a compound of Formula (I) or a form thereof, wherein $R_6$ is heteroaryl, wherein heteroaryl is selected from 1H-tetrazol-5-yl, imidazol-1-yl, pyrrol-1-yl or 2H-tetrazol-2-yl; and, heterocyclyl, wherein heterocyclyl is selected from azetidin-1-yl, pyrrolidin-1-yl, tetrahydrofuran-2-yl, piperidin-1-yl, piperazin-1-yl, morpholin-4-yl, 2,5-dihydro-1H-pyrrol-1-yl, 1,2,3,6-tetrahydropyridin-4-yl, hexahydropyrrolo[3,4-b][1,4]oxazin-6(2H)-yl, (4aR,7aS)-hexahydropyrrolo[3,4-b][1,4]oxazin-4(4aH)-yl, (3aR,6aR)-hexahydropyrrolo[3,4-b]pyrrol-5(1H)-yl, (3aR,6aS)-hexahydropyrrolo[3,4-c]pyrrol-2(1H)-yl, 5,7-dihydro-6H-pyrrolo[3,4-b]pyridin-6-yl, octahydro-6H-pyrrolo[3,4-b]pyridin-6-yl, (3aR,6aR)-hexahydrocyclopenta[c]pyrrol-3a(1H)-yl, (3aR,4R,6aS)-hexahydrocyclopenta[c]pyrrol-2(1H)-yl, (3aR,4S,6aS)-hexahydrocyclopenta[c]pyrrol-2(1H)-yl, (3aR,5r,6aS)-hexahydrocyclopenta[c]pyrrol-2(1H)-yl, 1,3-dihydro-2H-isoindol-2-yl, octahydro-2H-isoindol-2-yl, (3aS)-1,3,3a,4,5,6-hexahydro-2H-isoindol-2-yl, (3aR,7aS)-octahydro-2H-isoindol-2-yl, (3aR,4R,7aS)-octahydro-2H-isoindol-2-yl, (3aR,4S,7aS)-octahydro-2H-isoindol-2-yl, 2,5-diazabicyclo[2.2.1]heptan-2-yl, 2-azabicyclo[2.2.1]hept-5-en-2-yl, 3-azabicyclo[3.1.0]hexan-3-yl, 3,6-diazabicyclo[3.1.0]hexan-3-yl, (1R,5S,6s)-3-azabicyclo[3.1.0]hexan-3-yl, (1R,5S,6s)-3-azabicyclo[3.1.0]hexan-6-yl, (1S,5R,6R)-3-azabicyclo[3.2.0]heptan-3-yl, (1S,5R,6S)-3-azabicyclo[3.2.0]heptan-3-yl, 5-azaspiro[2.4]heptan-5-yl, 2,6-diazaspiro[3.3]heptan-2-yl, 2,5-diazaspiro[3.4]octan-2-yl, 2,6-diazaspiro[3.4]octan-6-yl, 2,7-diazaspiro[3.5]nonan-2-yl, 2,7-diazaspiro[4.4]nonan-2-yl, 2-azaspiro[4.5]decan-2-yl or 2,8-diazaspiro[4.5]decan-2-yl.

One embodiment of the present description includes a compound of Formula (I) or a form thereof, wherein $R_6$ is heteroaryl, wherein heteroaryl is selected from pyridinyl; and, heterocyclyl, wherein heterocyclyl is selected from azetidinyl, pyrrolidinyl, piperidinyl, piperazinyl, morpholinyl, 1,4-diazepanyl, 1,3-dioxolanyl, dihydro-1H-imidazolyl, 1,4,5,6-tetrahydropyrimidinyl, 1,2,3,6-tetrahydropyridinyl, tetrahydro-2H-pyranyl, 3,4-dihydroisoquinolin-(1H)-yl, 1,2,3,4-tetrahydroisoquinolinyl, 5H-pyrrolo[3,4-b]pyridin-(7H)-yl, tetrahydro-1H-pyrrolo[3,4-b]pyridin-(2H,7H,7aH)-yl, (3aR,4R,6aS)-hexahydrocyclopenta[c]pyrrol-(1H)-yl, (3aR,4R,7aS)-1H-isoindol-(3H,3aH,4H,5H,6H,7H,7aH)-yl, 2,5-diazabicyclo[2.2.1]heptanyl or (1R,5S,6s)-3-azabicyclo[3.1.0]hexanyl.

One embodiment of the present description includes a compound of Formula (I) or a form thereof, wherein $R_6$ is heteroaryl selected in each instance, when present, from pyridin-2-yl, pyridin-3-yl or pyridin-4-yl;

heterocyclyl selected in each instance, when present, from azetidin-1-yl, pyrrolidin-1-yl, pyrrolidin-2-yl, pyrrolidin-3-yl, tetrahydrofuran-2-yl, piperidin-1-yl, piperidin-2-yl, piperidin-3-yl, piperidin-4-yl, piperazin-1-yl, piperazin-2-yl, morpholin-4-yl, 1,4-diazepan-1-yl, 1,3-dioxolan-2-yl, dihydro-1H-imidazol-2-yl, 1,4,5,6-tetrahydropyrimidin-2-yl, 1,2,3,6-tetrahydropyridin-4-yl, tetrahydro-2H-pyran-2-yl, tetrahydro-2H-pyran-4-yl, 3,4-dihydroisoquinolin-2(1H)-yl, 1,2,3,4-tetrahydroisoquinolin-1-yl, 5H-pyrrolo[3,4-b]pyridin-6(7H)-yl, tetrahydro-1H-pyrrolo[3,4-b]pyridin-6(2H,7H,7aH)-yl, (3aR,4R,6aS)-hexahydrocyclopenta[c]pyrrol-2(1H)-yl, (3aR,4R,7aS)-1H-isoindol-2(3H,3aH,4H,5H,6H,7H,7aH)-yl, 2,5-diazabicyclo[2.2.1]heptan-2-yl, (1R,5S,6s)-3-azabicyclo[3.1.0]hexan-3-yl or (1R,5S,6s)-3-azabicyclo[3.1.0]hexan-6-yl.

One embodiment of the present description includes a compound of Formula (I) or a form thereof, wherein $R_7$ is $C_{3-14}$cycloalkyl, wherein $C_{3-14}$cycloalkyl is selected from cyclopropyl or cyclobutyl;

$C_{3-14}$cycloalkyl-amino, wherein $C_{3-14}$cycloalkyl is selected from cyclopropyl;

aryl, wherein aryl is selected from phenyl;

aryl-$C_{1-8}$alkyl, wherein aryl is selected from phenyl;

aryl-amino, wherein aryl is selected from phenyl;

(aryl, $C_{1-8}$alkyl)amino, wherein aryl is selected from phenyl;

aryl-$C_{1-8}$alkyl-amino, wherein aryl is selected from phenyl;

(aryl-$C_{1-8}$alkyl, $C_{1-8}$alkyl)amino, wherein aryl is selected from phenyl;

(aryl-$C_{1-8}$alkyl-amino, wherein aryl is selected from phenyl;

aryl-$C_{1-8}$alkyl-amino-$C_{1-8}$alkyl, wherein aryl is selected from phenyl;

(aryl-$C_{1-8}$alkyl, $C_{1-8}$alkyl)amino-$C_{1-8}$alkyl, wherein aryl is selected from phenyl;

(aryl-$C_{1-8}$alkyl-amino-$C_{1-8}$alkyl, wherein aryl is selected from phenyl;

aryl-$C_{1-8}$alkoxy, wherein aryl is selected from phenyl;

aryl-$C_{1-8}$alkoxy-carbonyl-amino, wherein aryl is selected from phenyl;

heteroaryl, wherein heteroaryl is selected from pyridin-2-yl, pyridin-4-yl, thiazol-2-yl or 1H-1,2,3-triazol-1-yl;
heteroaryl-$C_{1-8}$alkyl-amino-$C_{1-8}$alkyl, wherein heteroaryl is selected from pyridin-2-yl, pyridin-3-yl or pyridin-4-yl;
heterocyclyl, wherein heterocyclyl is selected from pyrrolidin-1-yl or morpholin-4-yl;
heterocyclyl-$C_{1-8}$alkyl, wherein heterocyclyl is selected from pyrrolidin-1-yl; and,
heterocyclyl-oxy, wherein heterocyclyl is selected from tetrahydro-2H-pyran-2-yloxy.

One embodiment of the present description includes a compound of Formula (I) or a form thereof, wherein $R_7$ is aryl, wherein aryl is selected from phenyl;
(aryl-$C_{1-8}$alkyl, $C_{1-8}$alkyl)amino, wherein aryl is selected from phenyl;
(aryl-$C_{1-8}$alkyl-amino, wherein aryl is selected from phenyl;
aryl-amino-$C_{1-8}$alkyl, wherein aryl is selected from phenyl;
heteroaryl, wherein heteroaryl is selected from pyridin-2-yl or pyridin-4-yl;
heterocyclyl, wherein heterocyclyl is selected from piperidin-1-yl; and,
heterocyclyl-amino-$C_{1-8}$alkyl, wherein heterocyclyl is selected from (1R,5S,6s)-3-azabicyclo[3.1.0]hexan-6-yl.

The present description also relates to a compound of Formula (Ia):

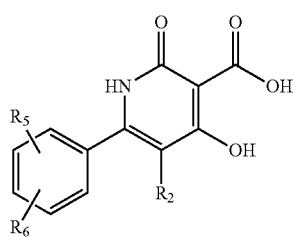

(Ia)

or a form thereof, wherein $R_2$, $R_5$ and $R_6$ are as previously defined herein.

In another embodiment of the present description, a compound or a form thereof is selected from:

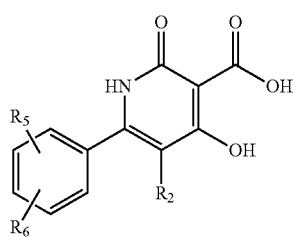

1

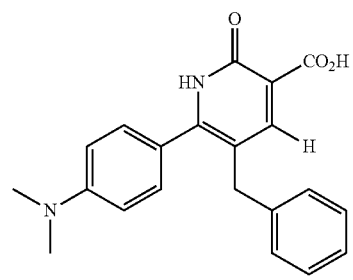

2

-continued

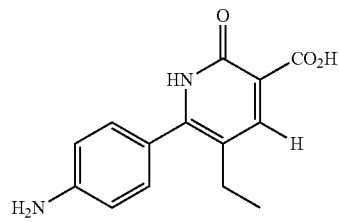

3

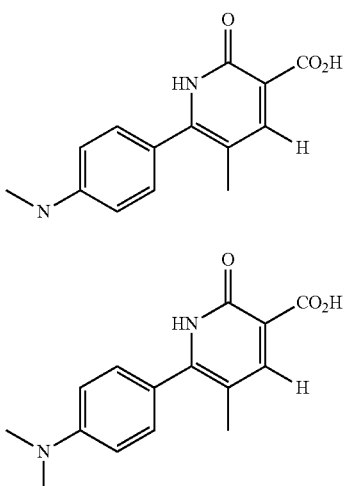

4

5

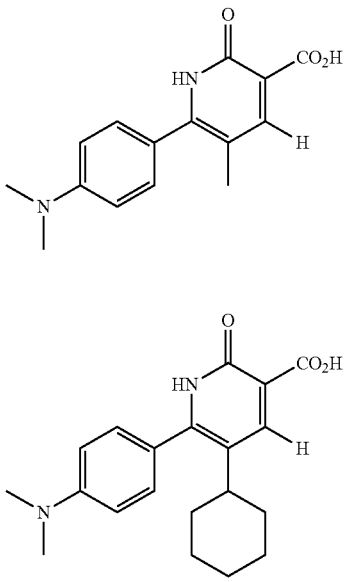

6

7

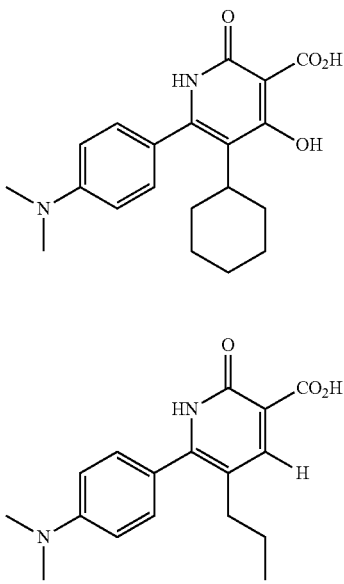

8

-continued
9
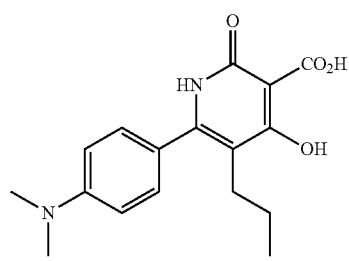
10
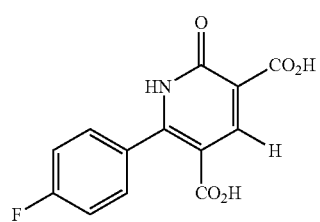
11
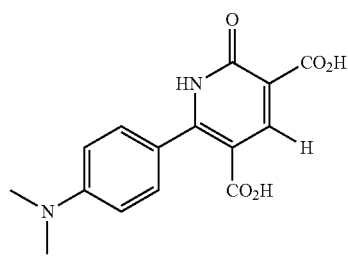
12
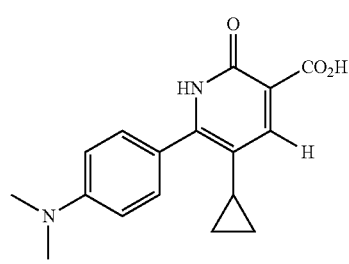
13
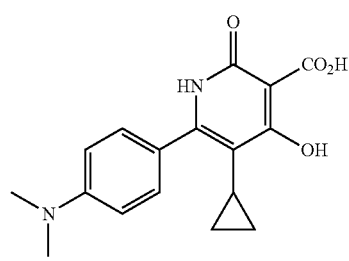
14
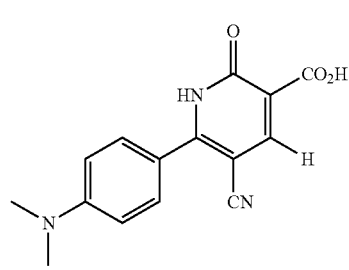
-continued
15
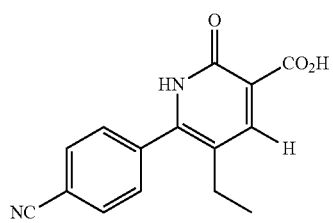
16
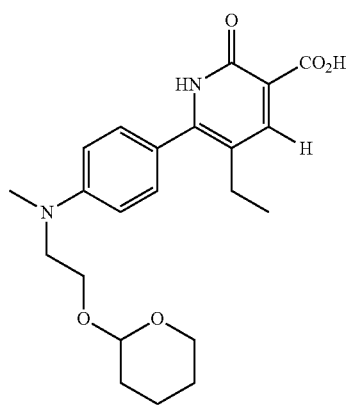
17
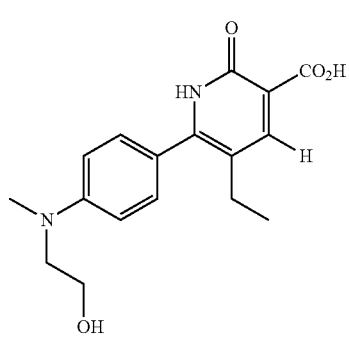
18
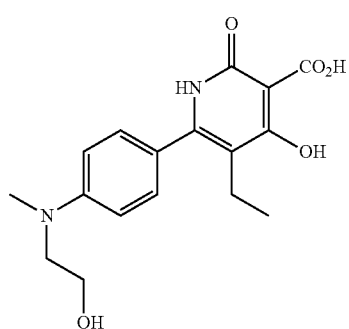
19
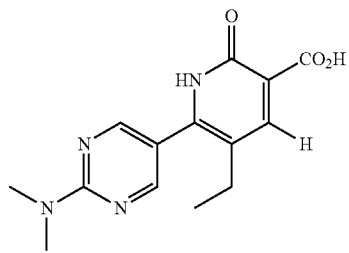

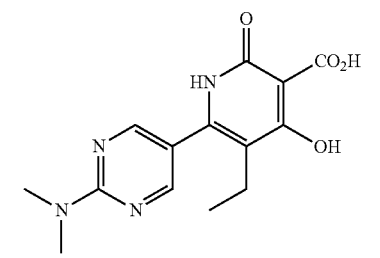
20
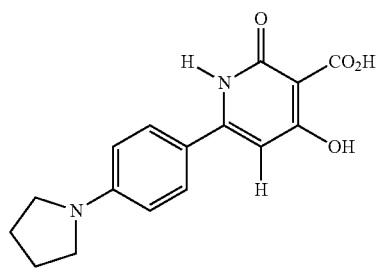
21
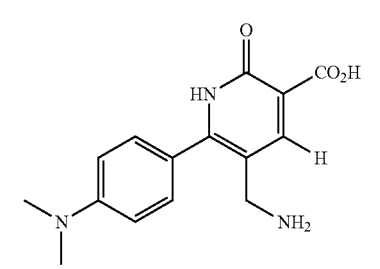
22
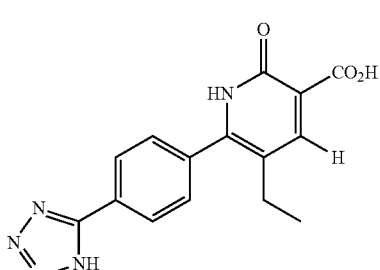
23
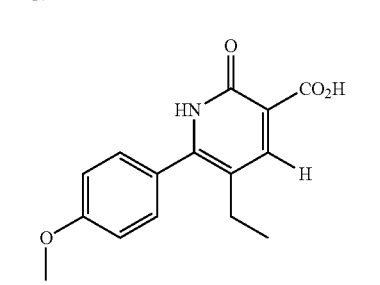
24
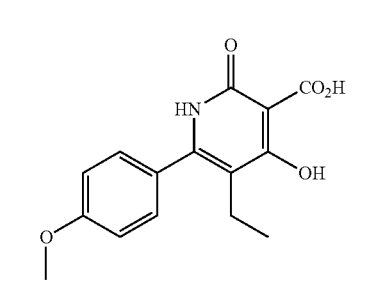
25
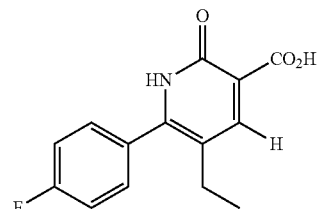
26
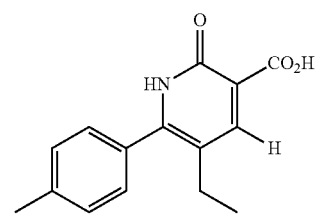
27
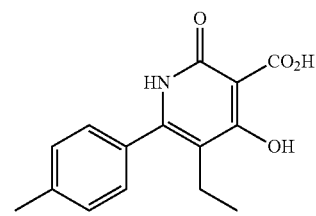
28
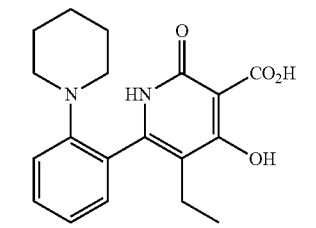
29
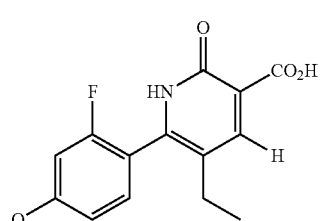
30
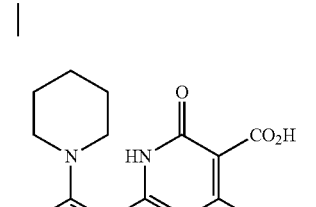
31
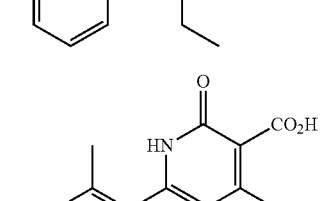
32

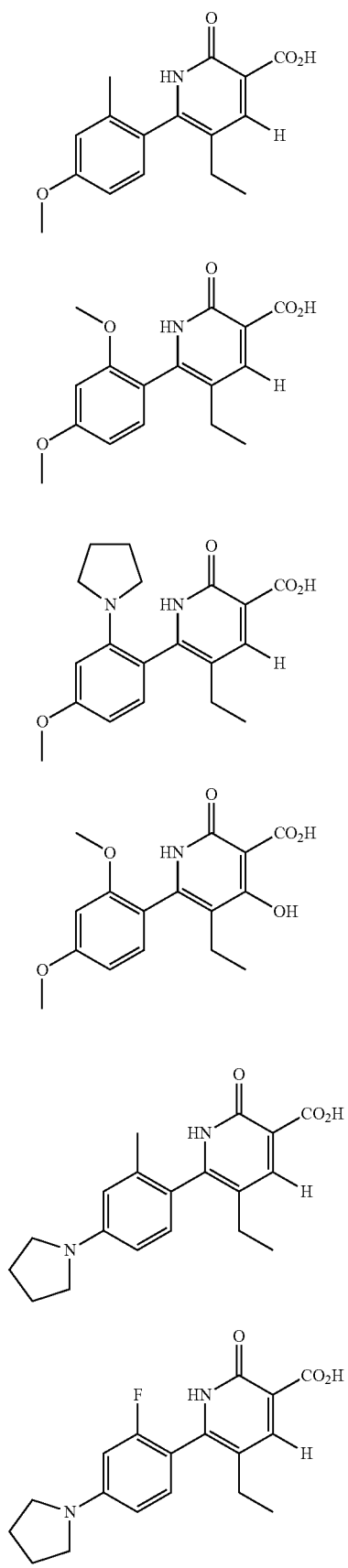
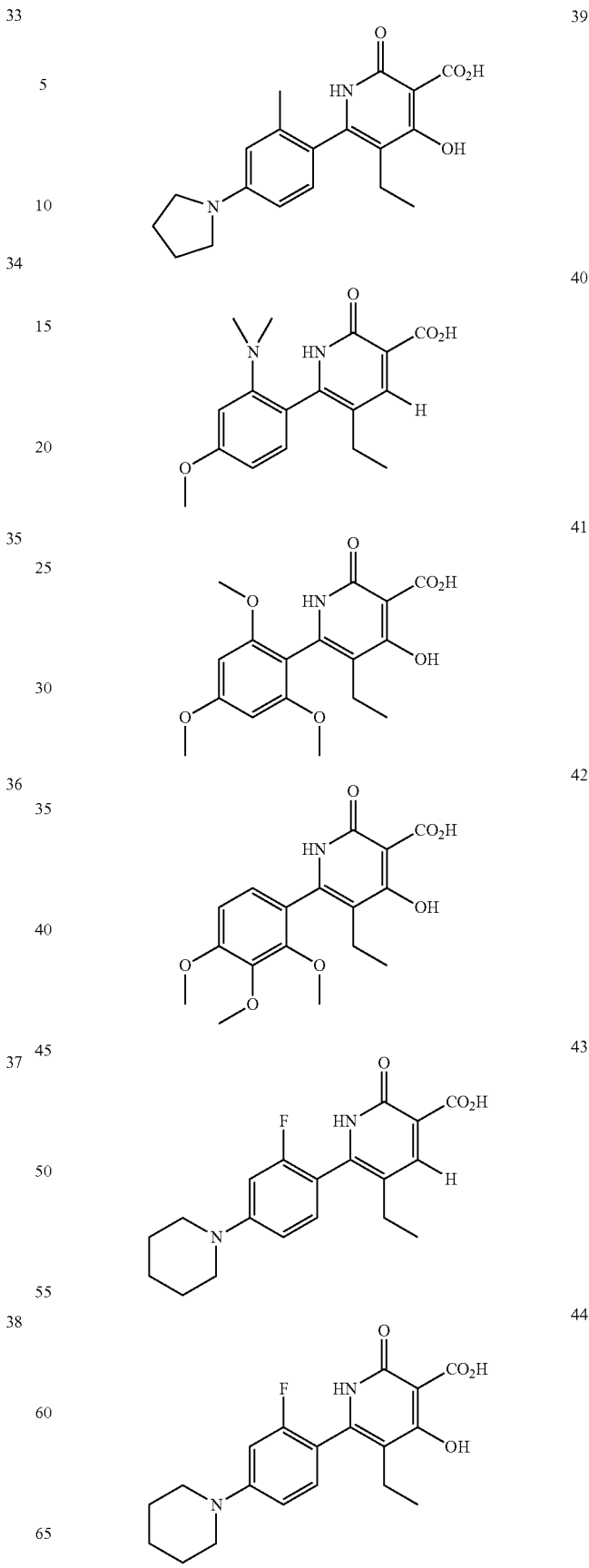

45
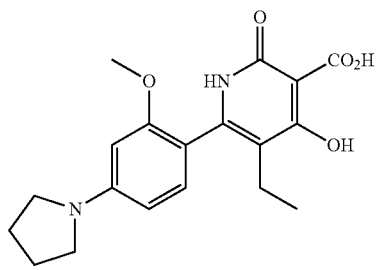
46
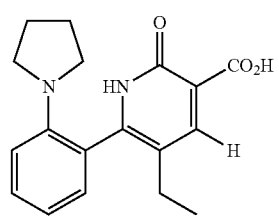
47
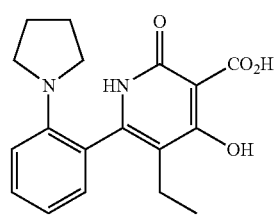
48
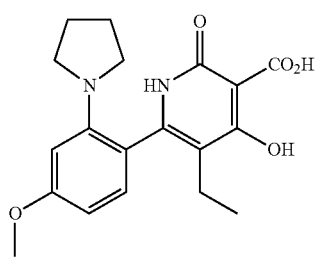
49
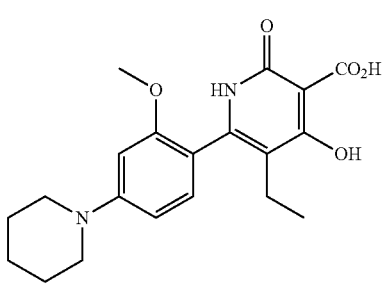
50
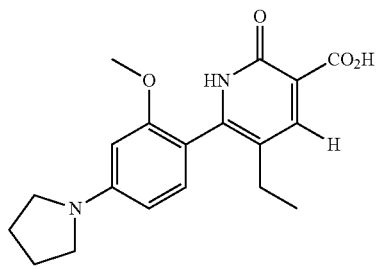
51
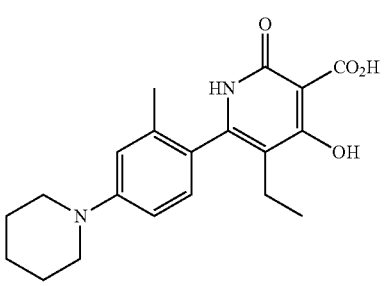
52
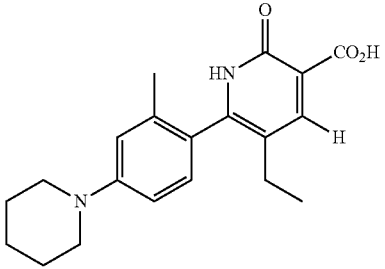
53
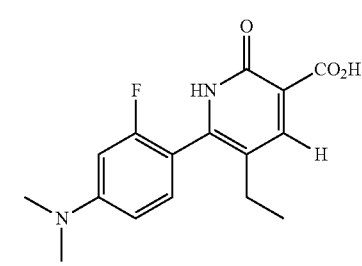
54
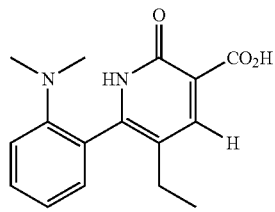
55
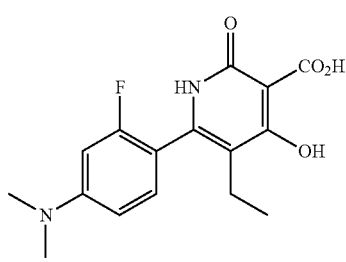
56
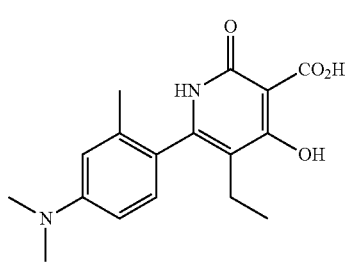

-continued
57
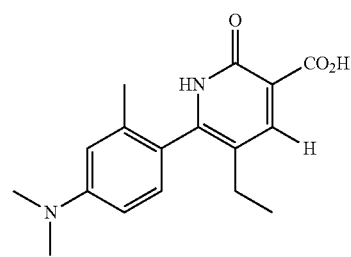
58
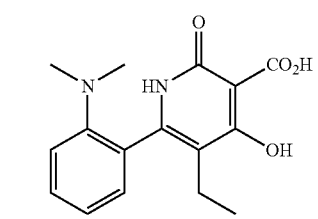
59
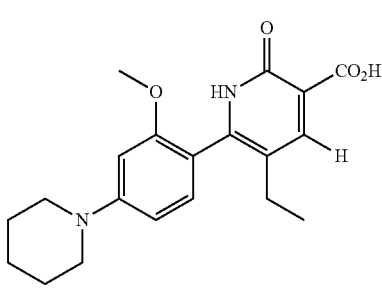
60
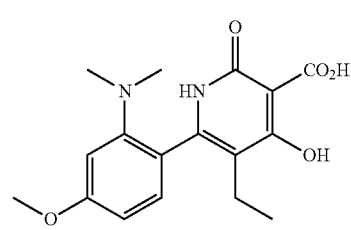
61
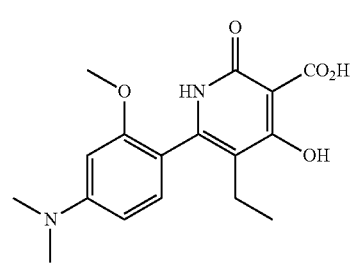
62
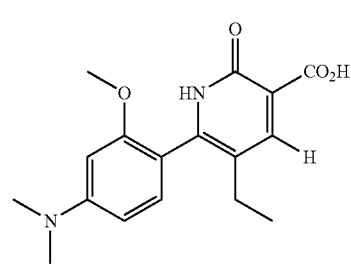
-continued
63
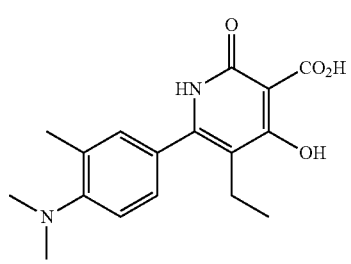
64
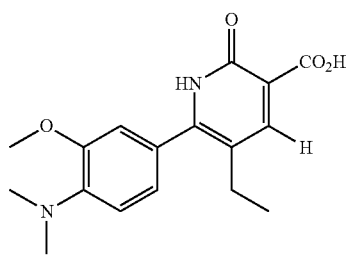
65
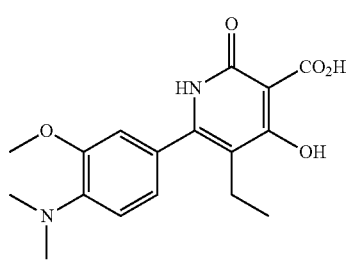
66
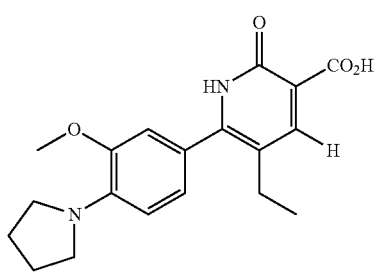
67
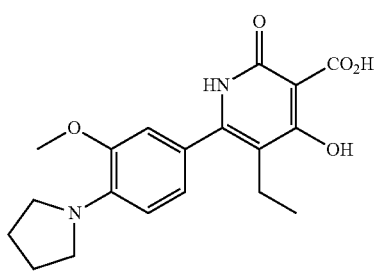
68
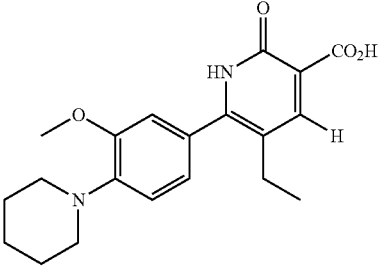

-continued

-continued
82
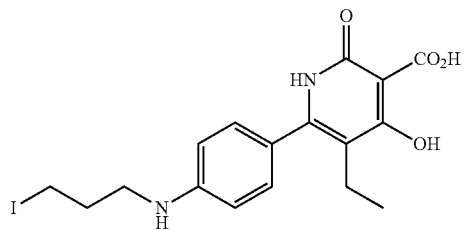
83
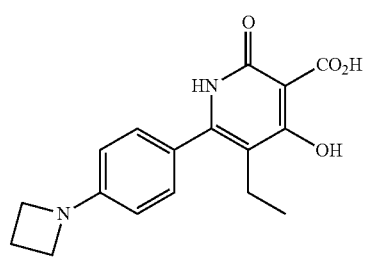
84
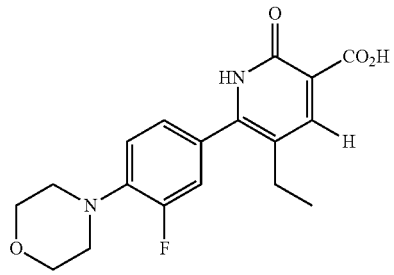
85
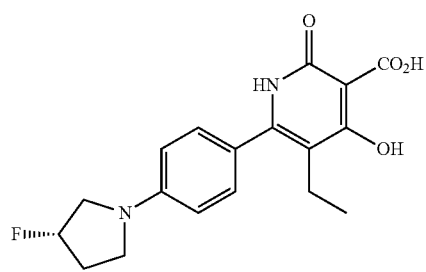
86
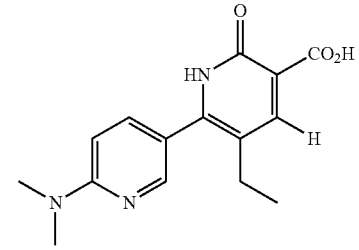
87
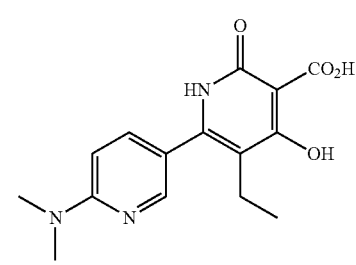
-continued
88
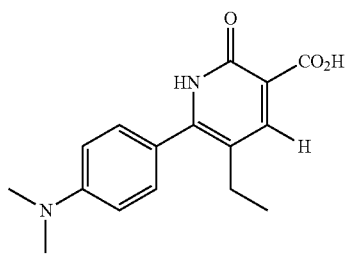
89
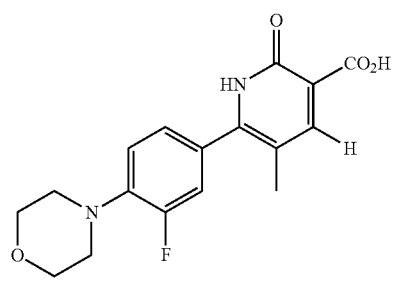
90
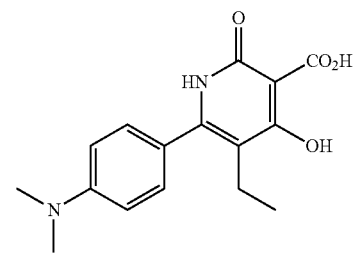
91
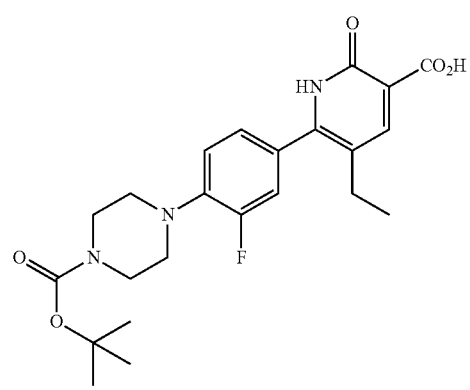
92
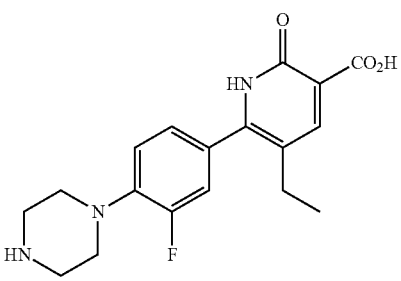

33
-continued
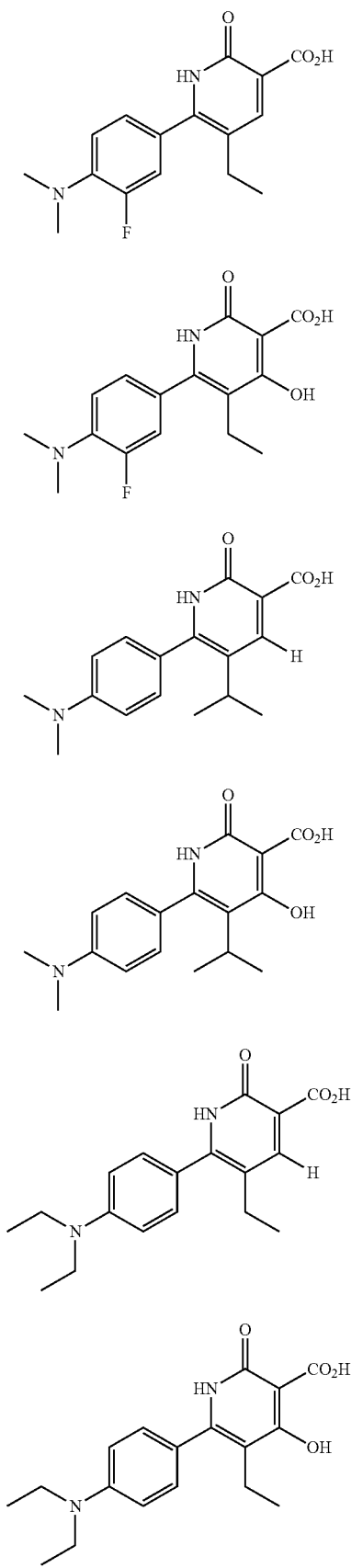
34
-continued
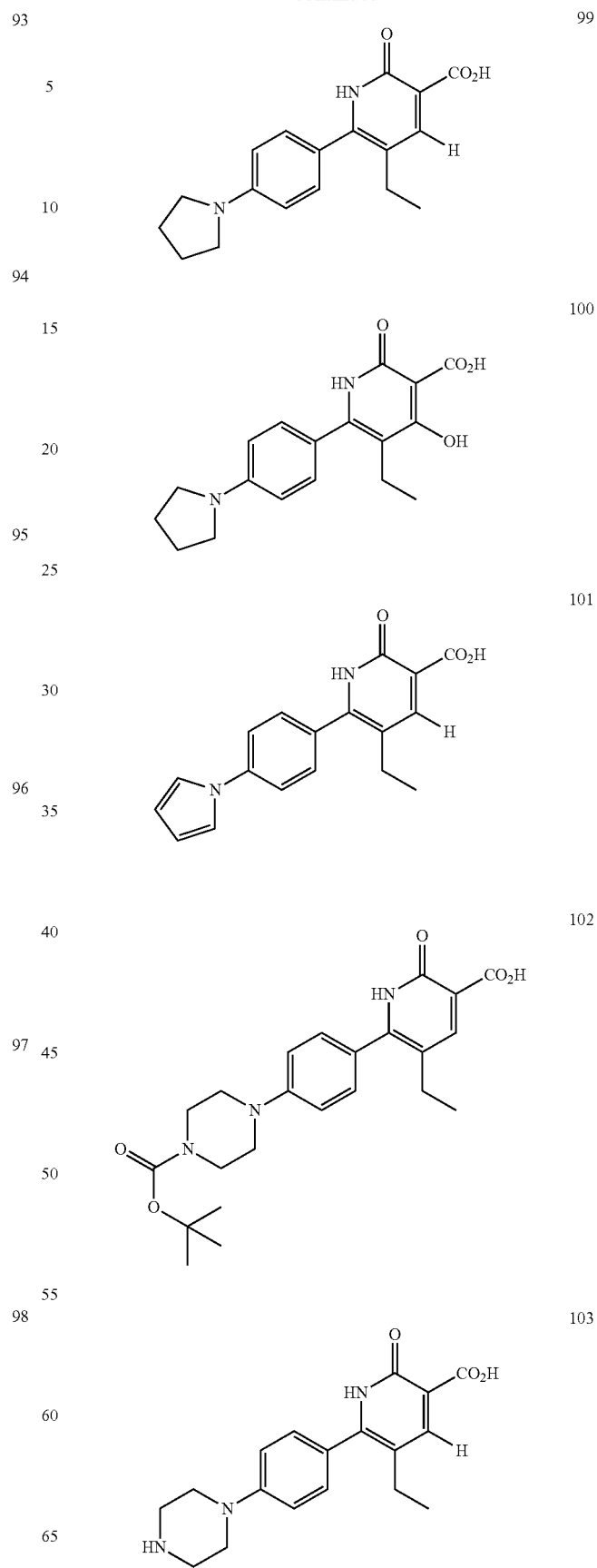

-continued
104
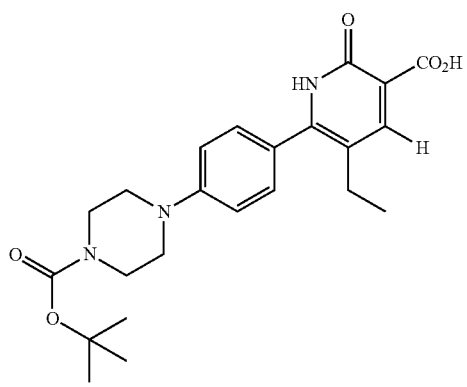
105
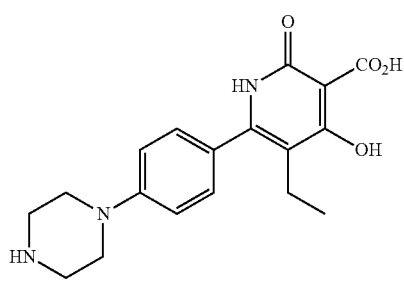
106
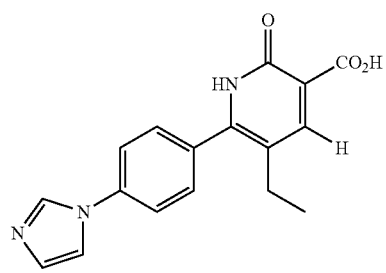
107
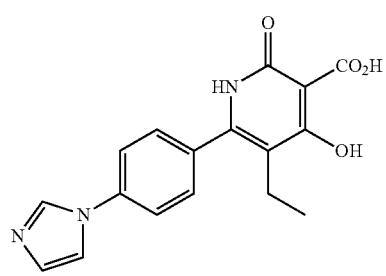
108
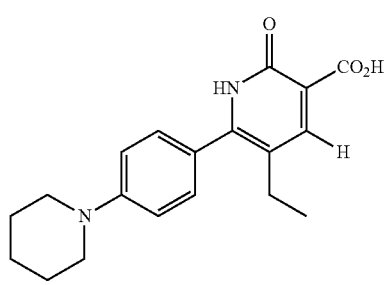
-continued
109
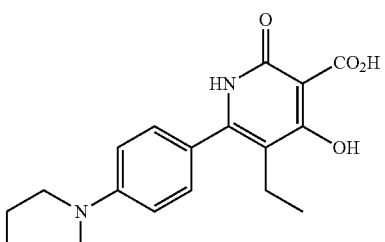
110
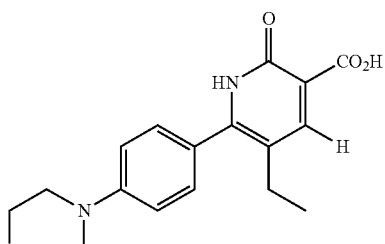
111
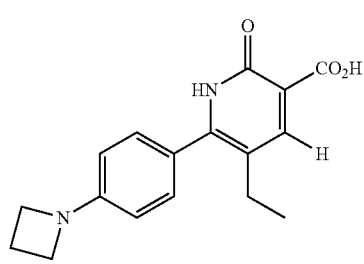
112
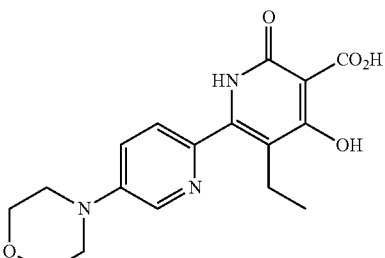
113
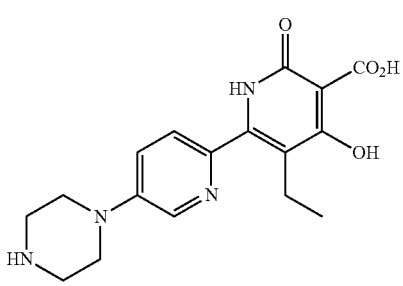
114
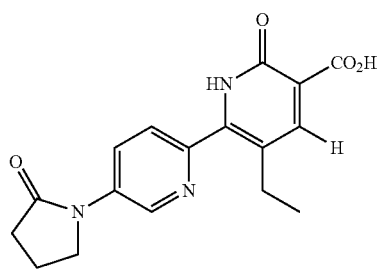

115 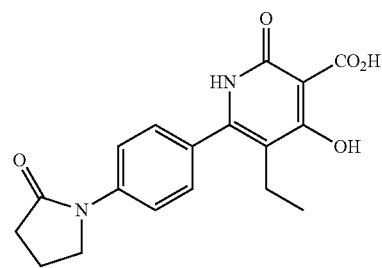
116 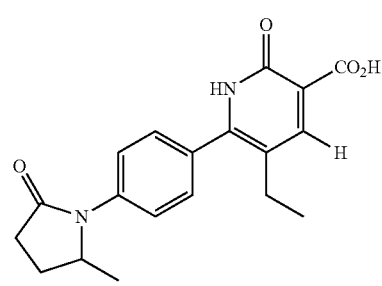
117 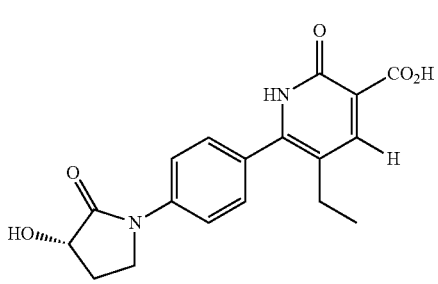
118 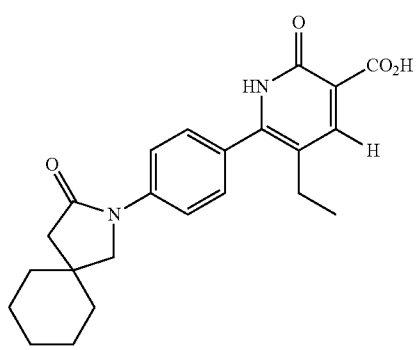
119 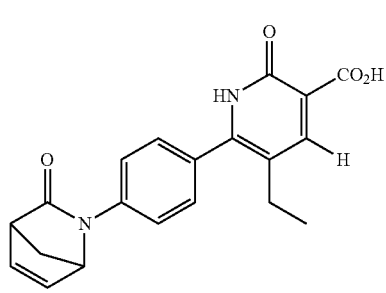
120 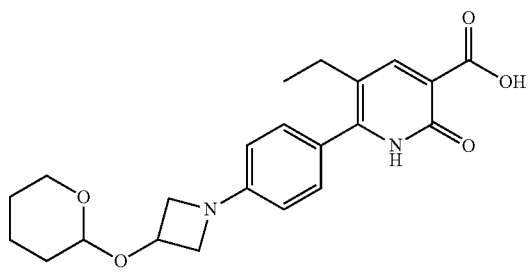
121 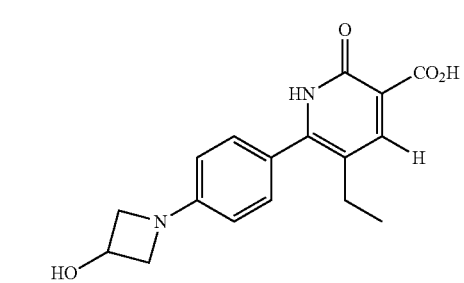
122 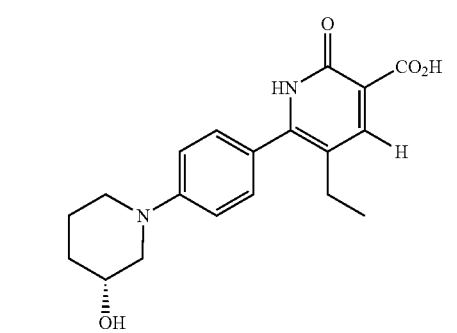
123 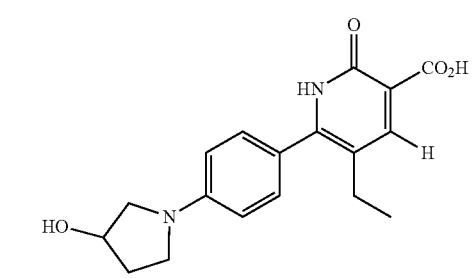
124 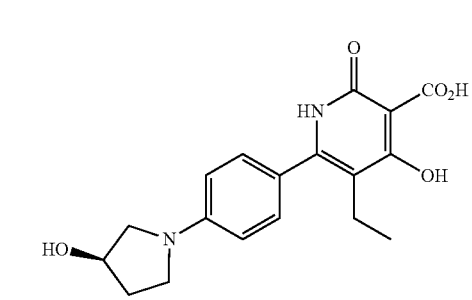

| 125 | 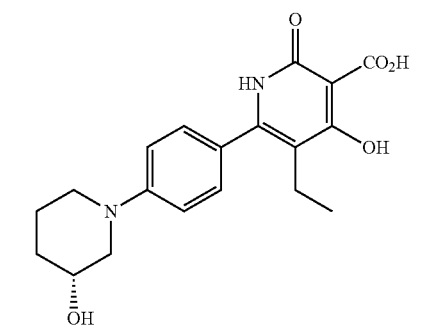 |
| 126 | 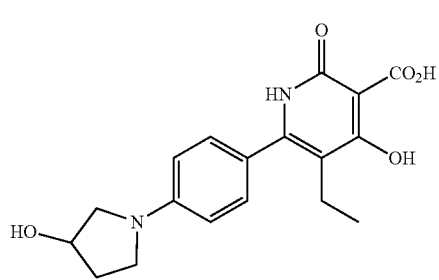 |
| 127 | 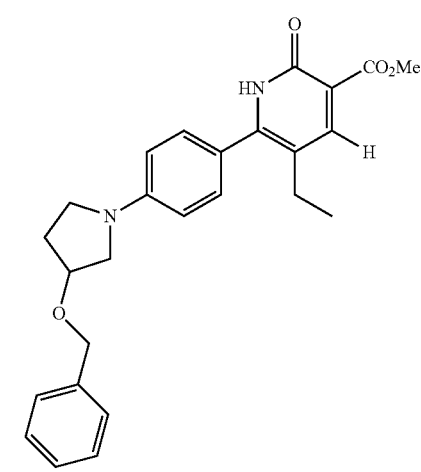 |
| 128 | 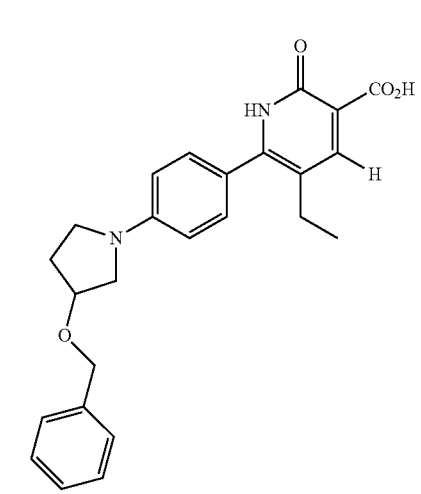 |
| 129 | 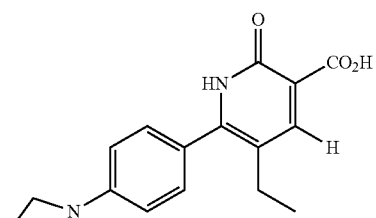 |
| 130 | 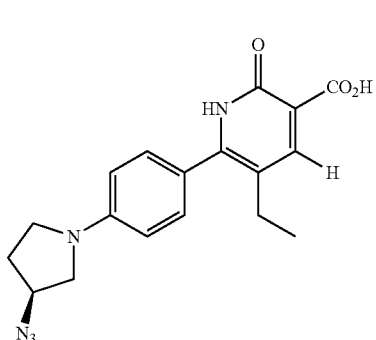 |
| 131 | 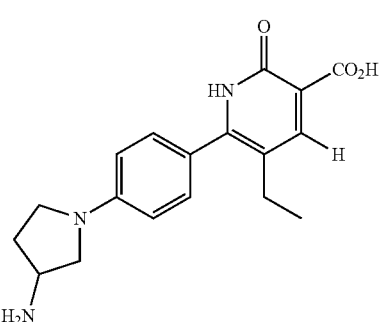 |
| 132 | 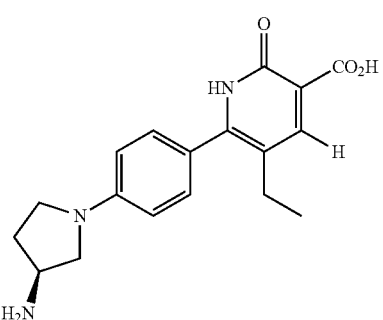 |
| 133 | 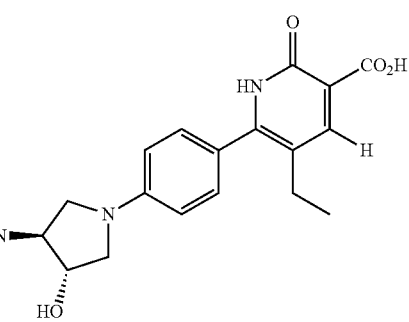 |

134 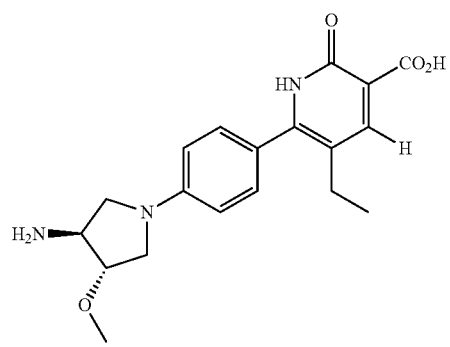
135 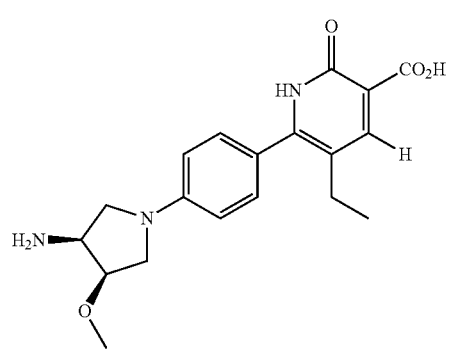
136 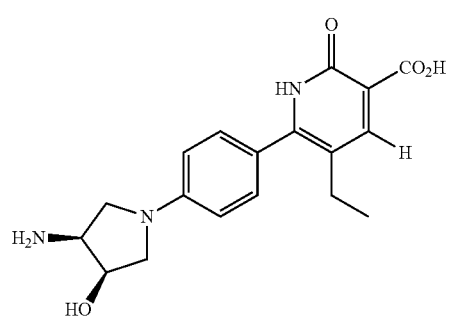
137 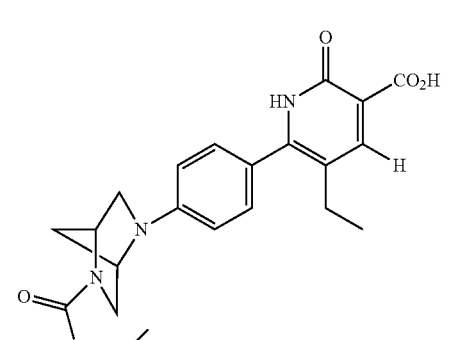
138 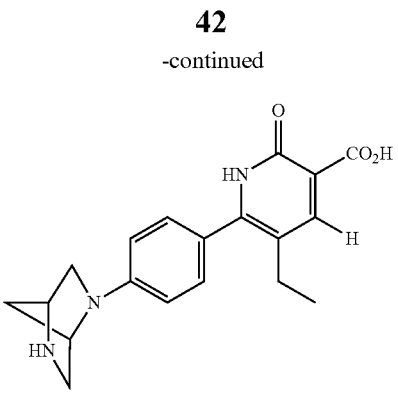
139 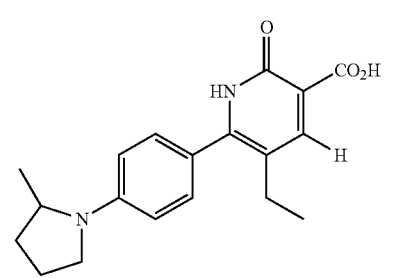
140 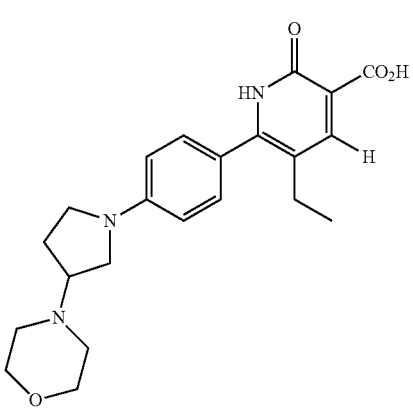
141 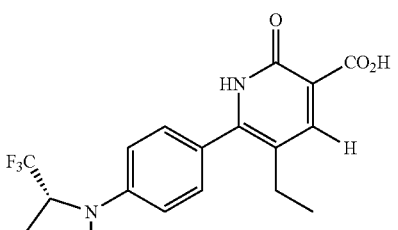
142 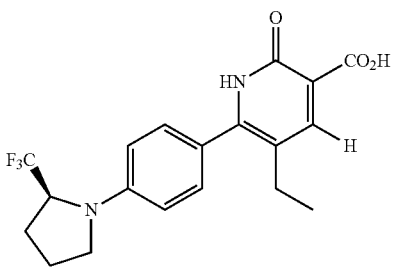

143 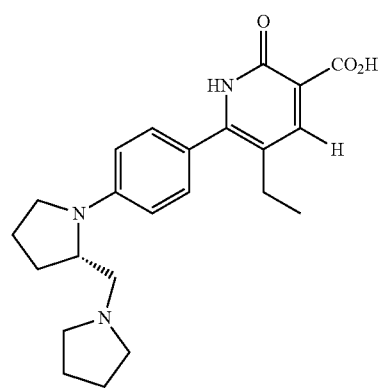
144 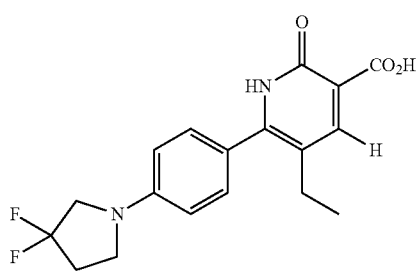
145 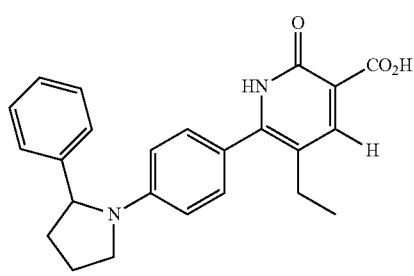
146 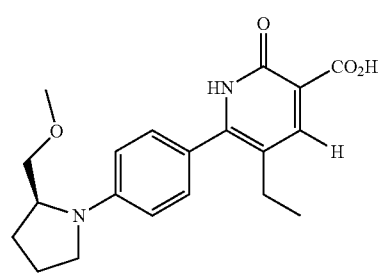
147 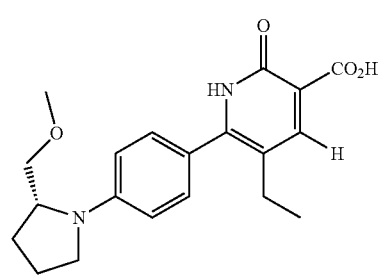
148 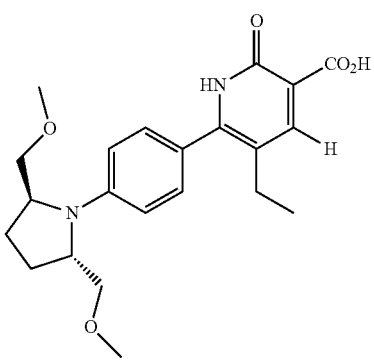
149 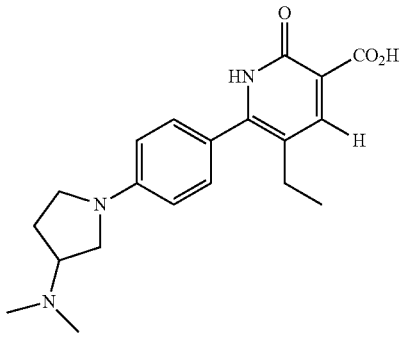
150 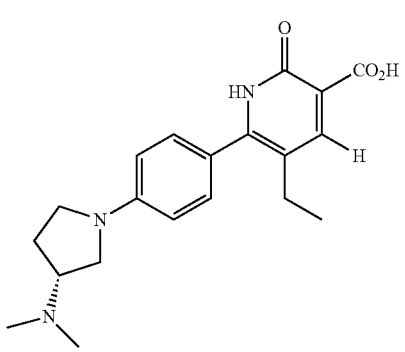
151 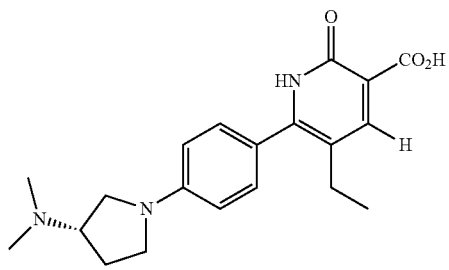
152 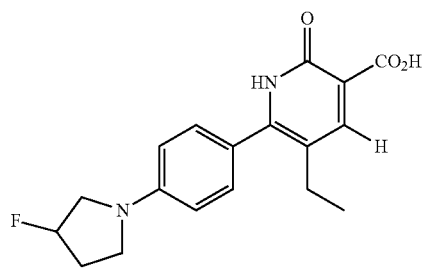

153 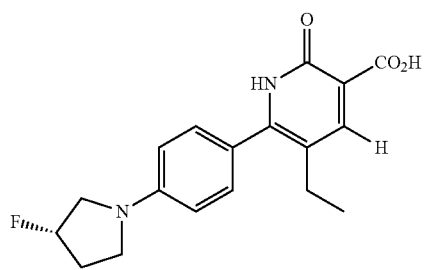
154 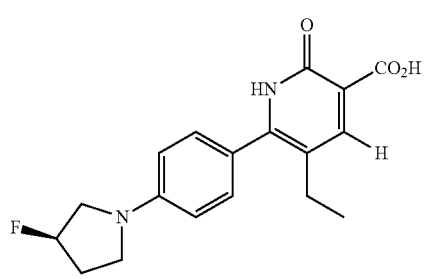
155 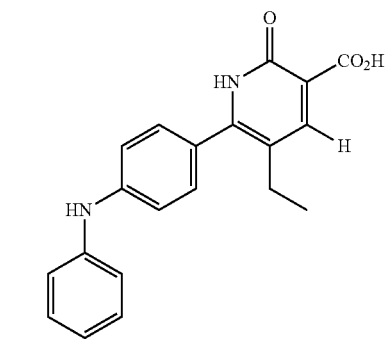
156 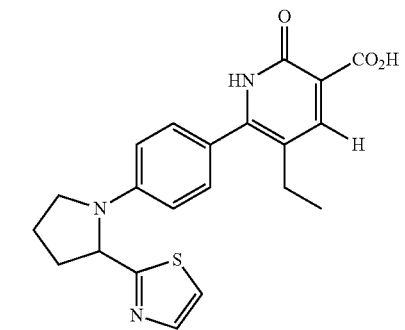
157 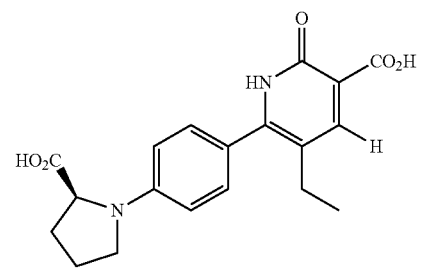
158 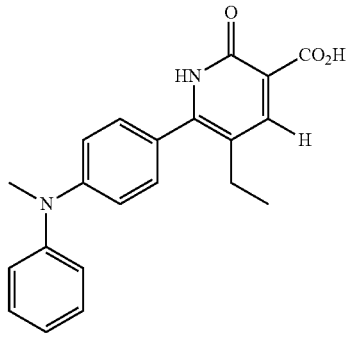
159 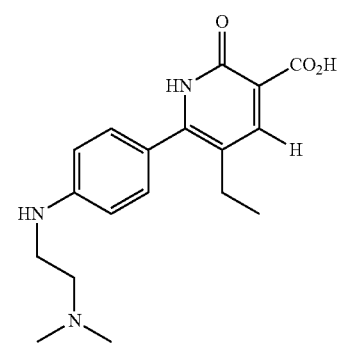
160 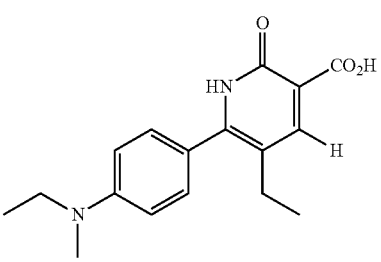
161 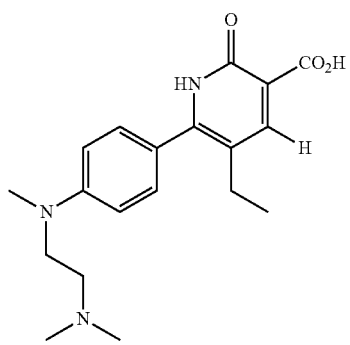
162 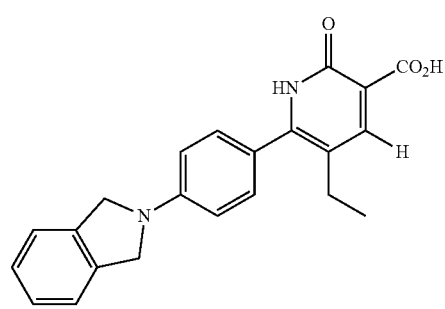

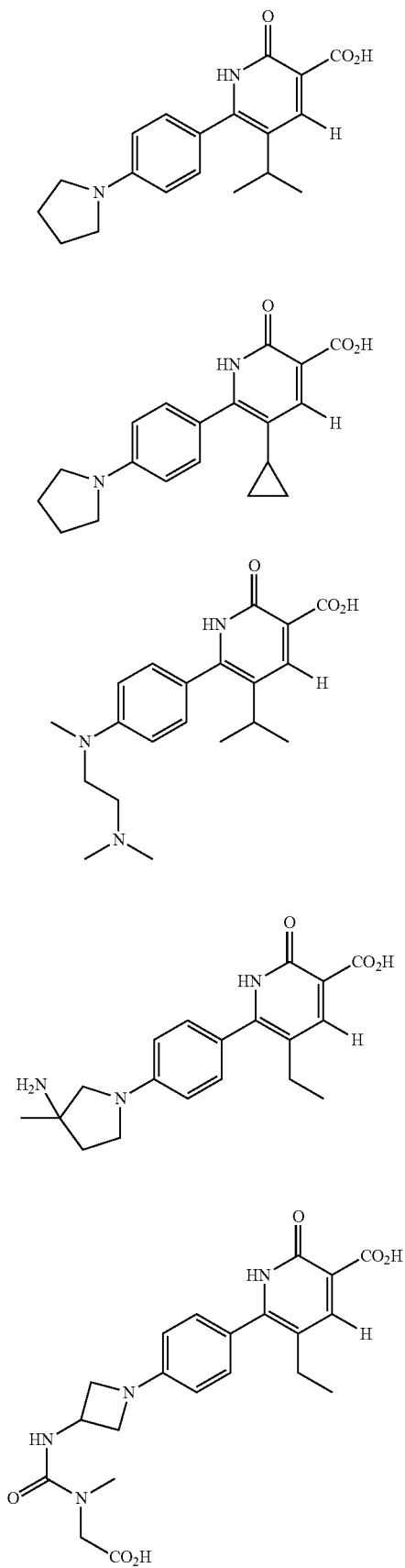
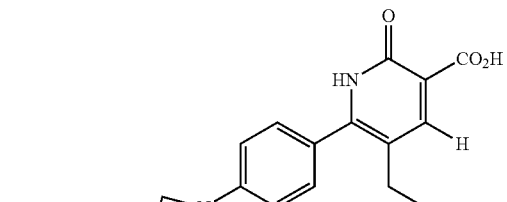
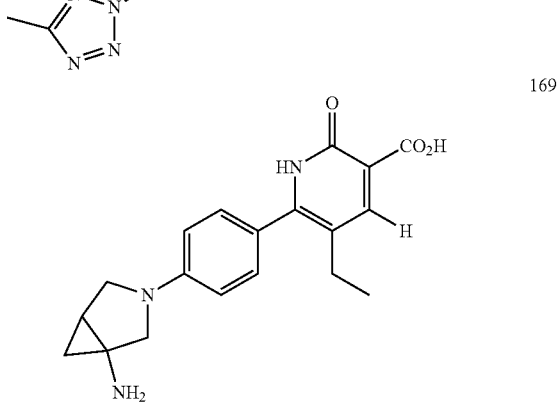
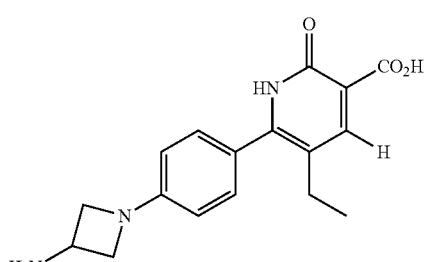
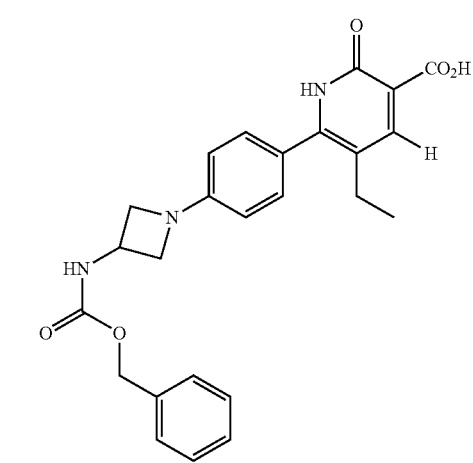
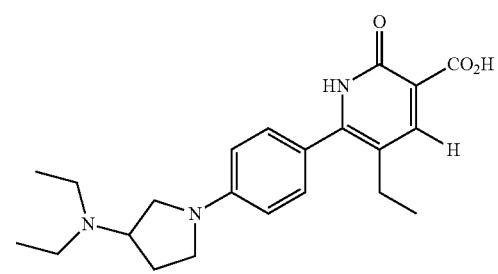

173
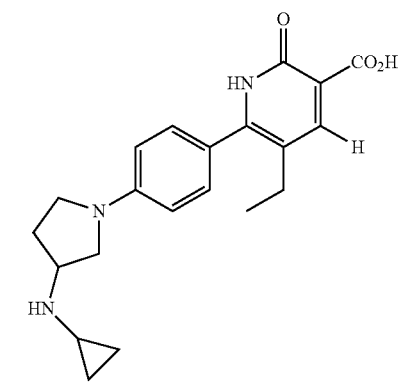
174
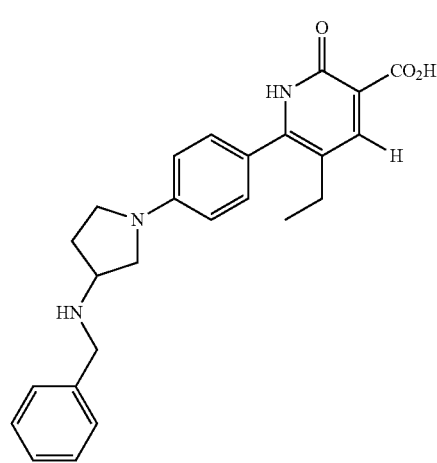
175
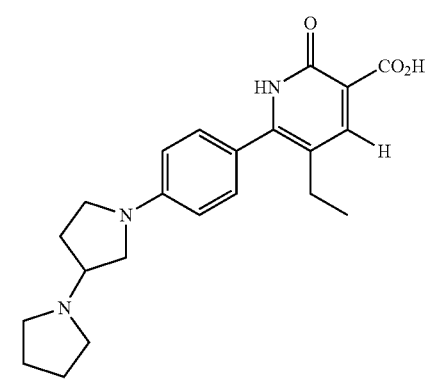
176
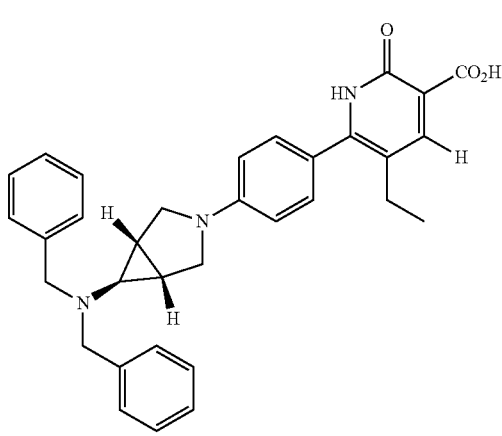
177
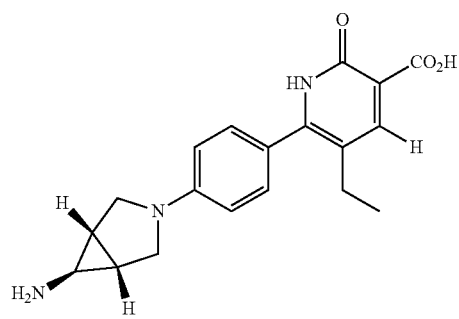
178
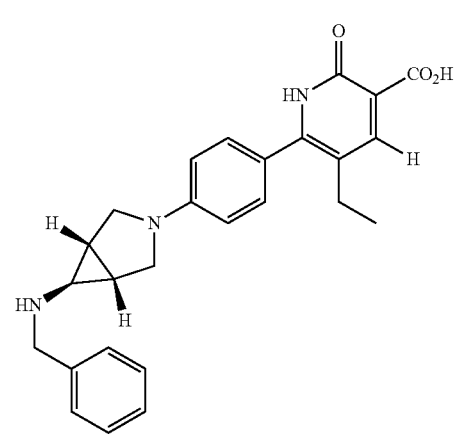
179
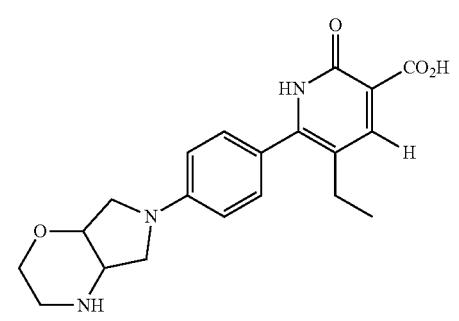
180
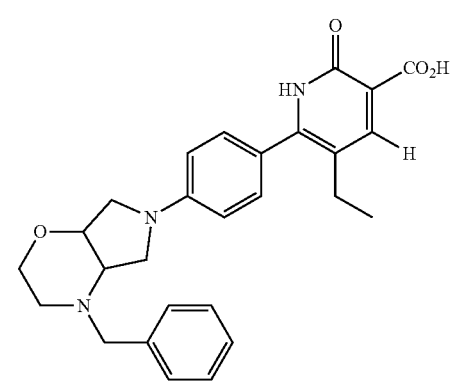

181 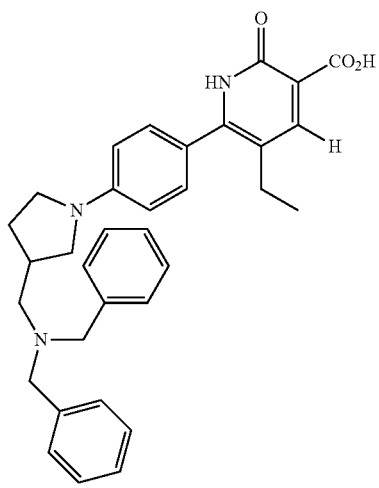
182 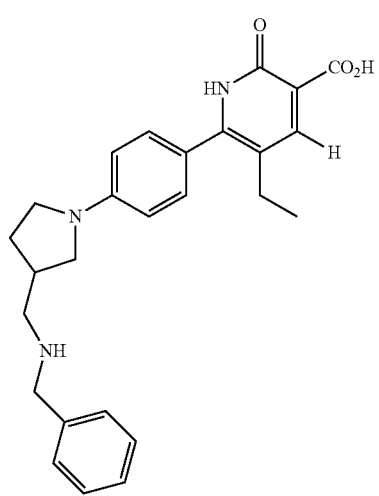
183 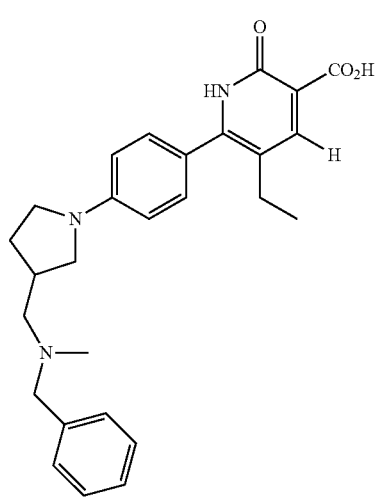
184 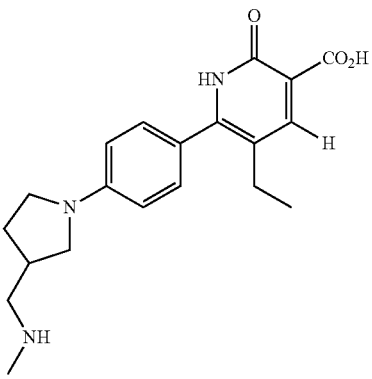
185 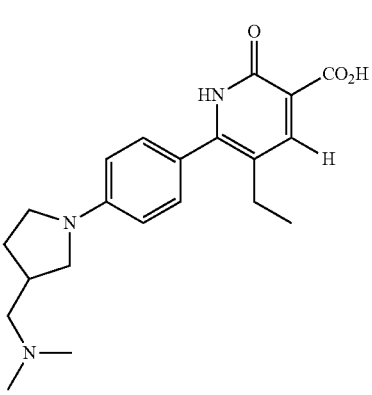
186 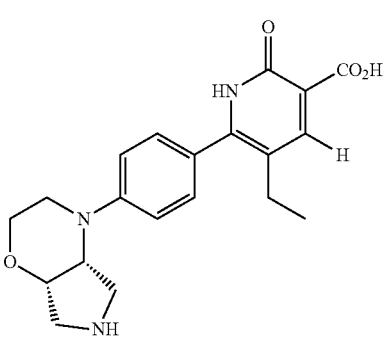
187 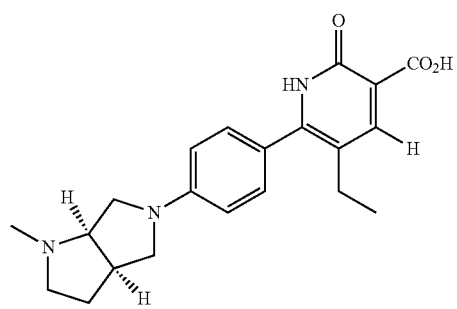

-continued
188 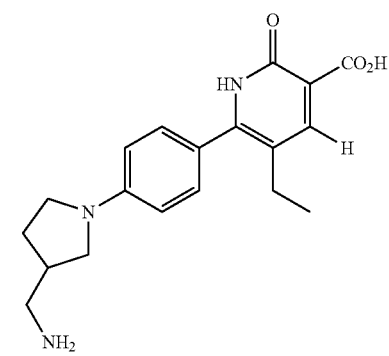
189 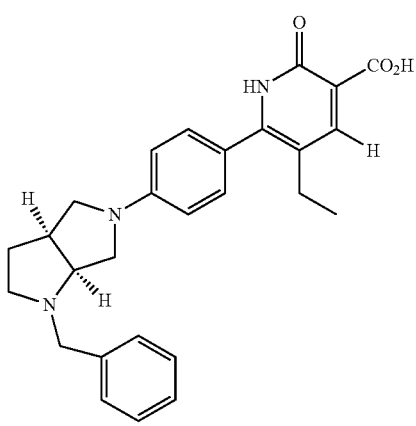
190 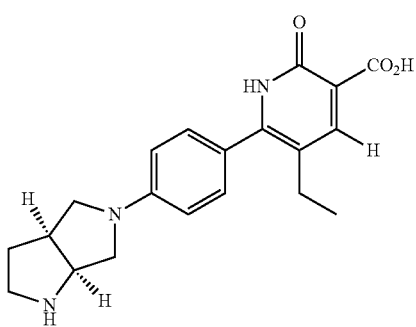
191 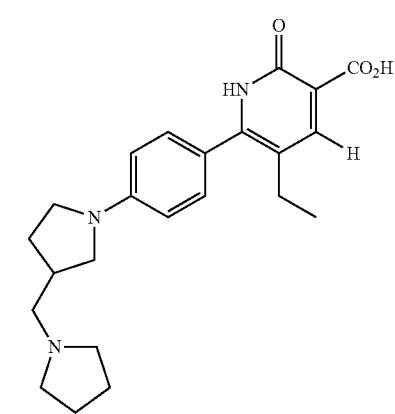
-continued
192 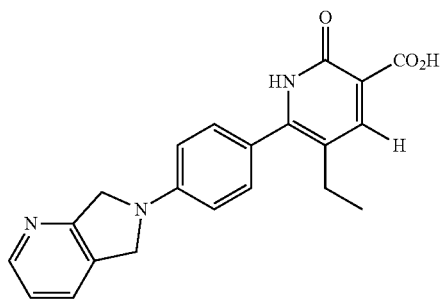
193
194
195
196
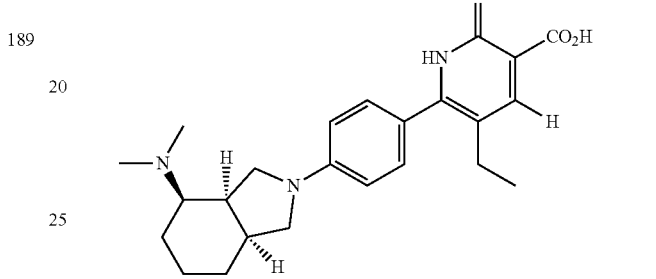
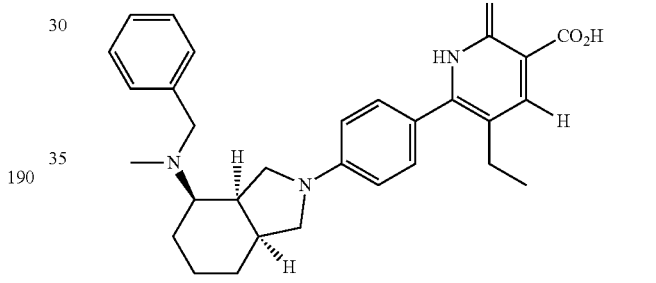
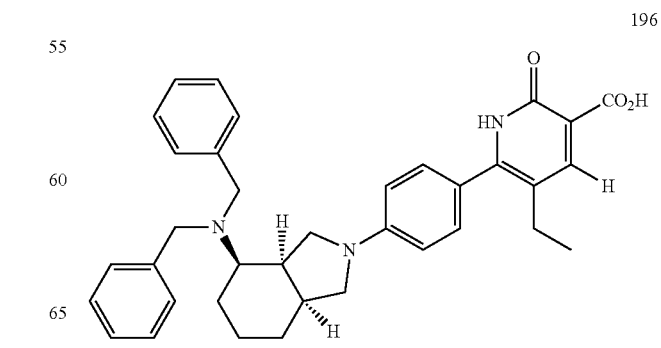

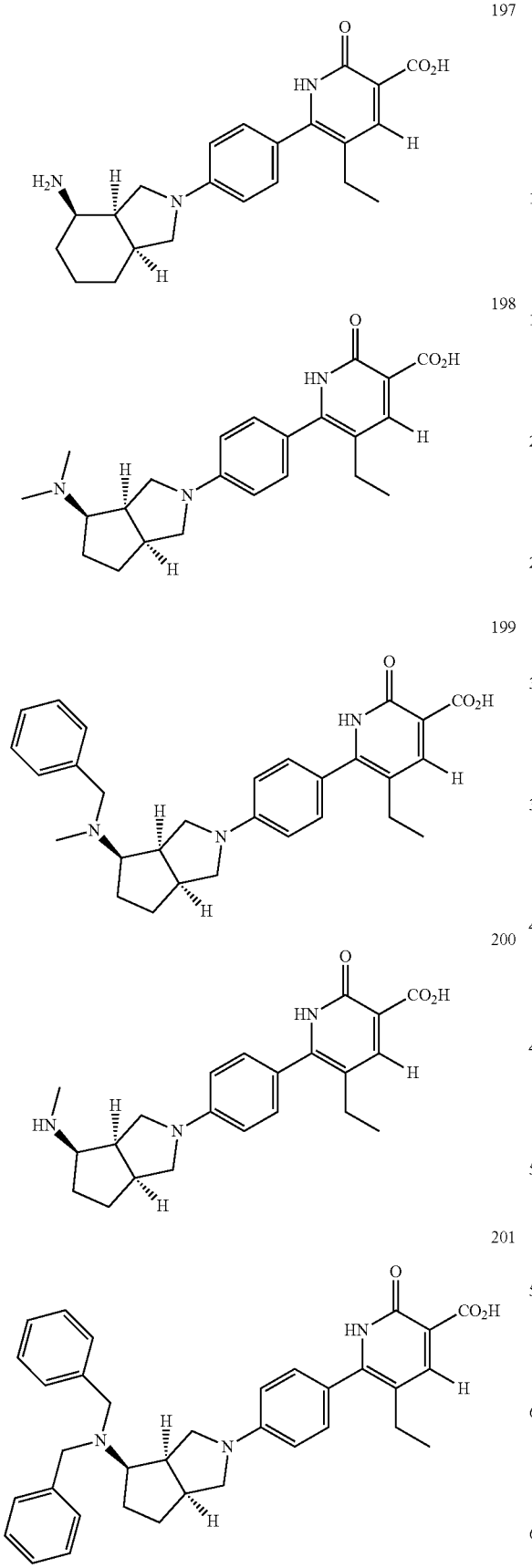
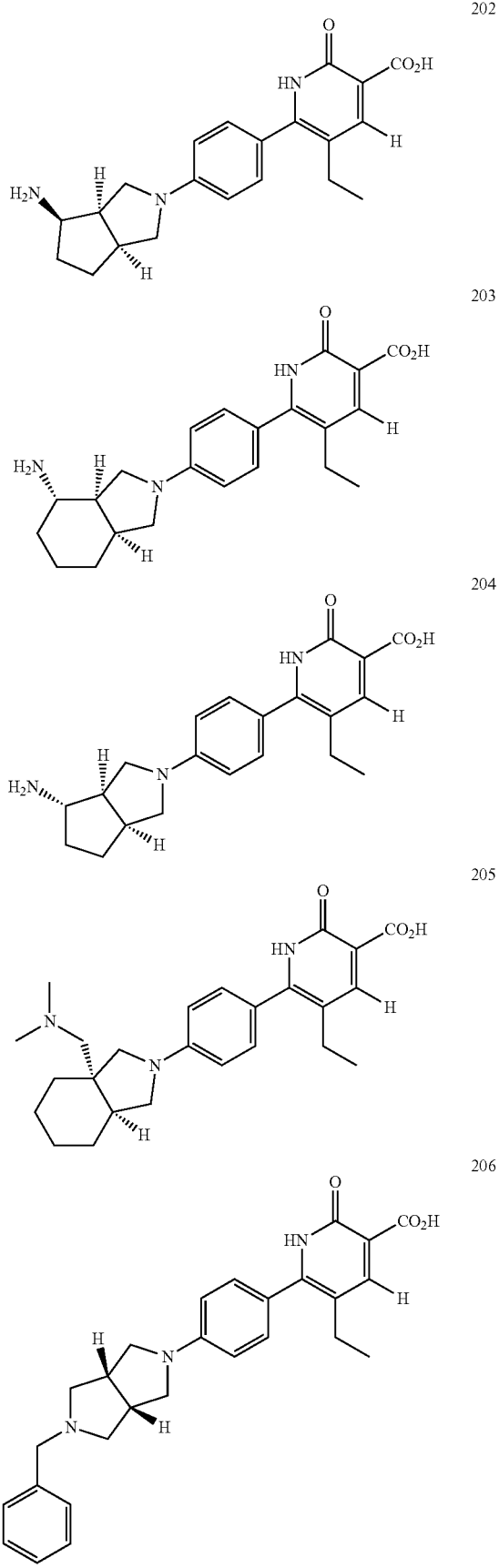

207 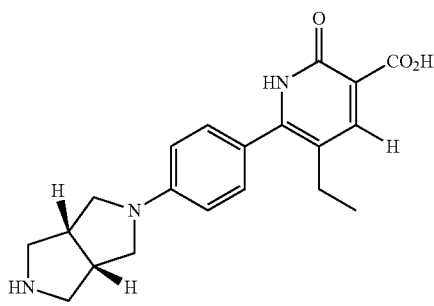
208 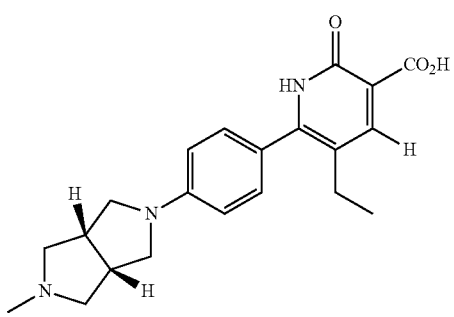
209 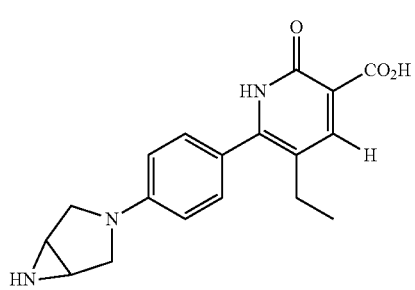
210 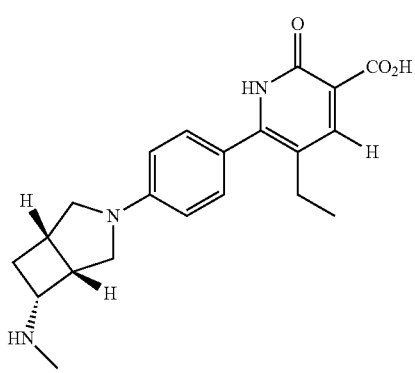
211 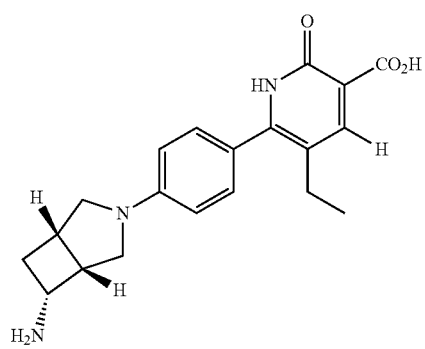
212 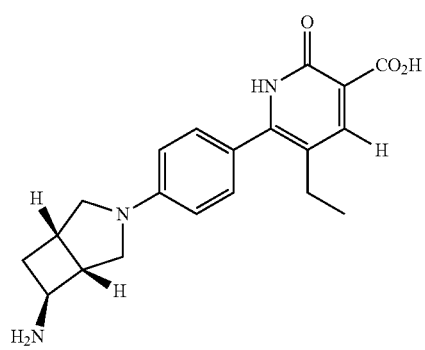
213 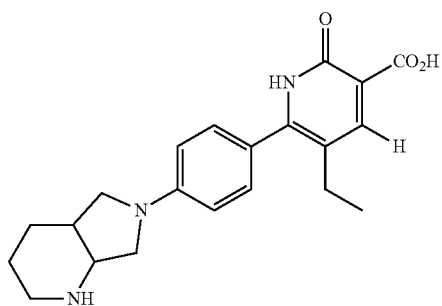
214 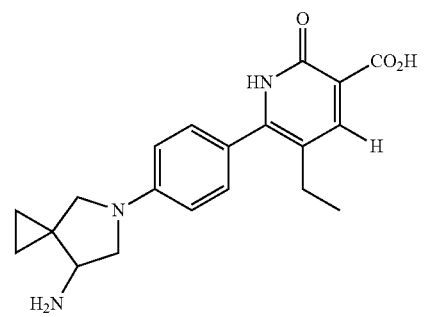

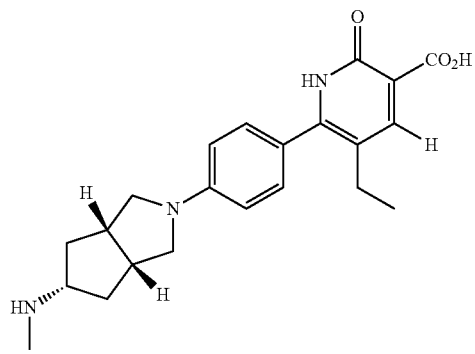
215
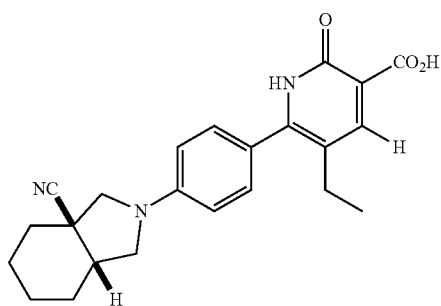
219
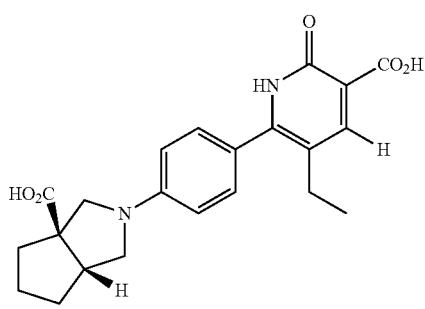
220
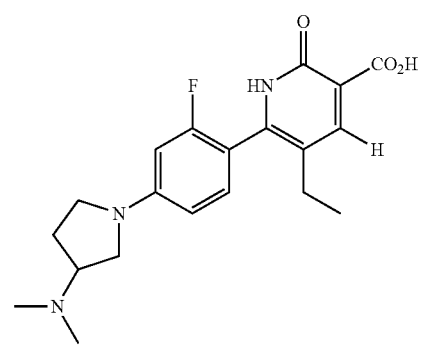
221
216
217
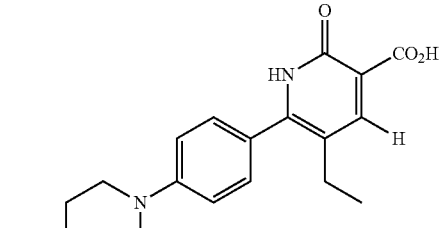
222
218
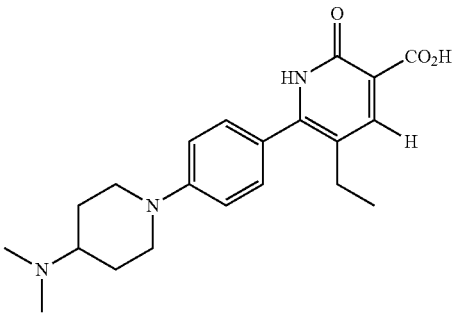
223

| 224 | 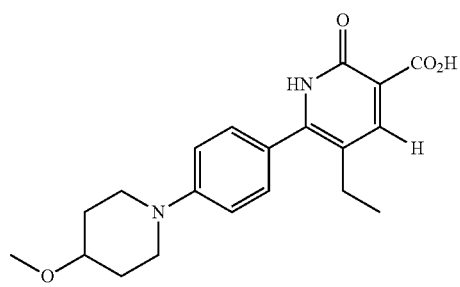 | 228 | 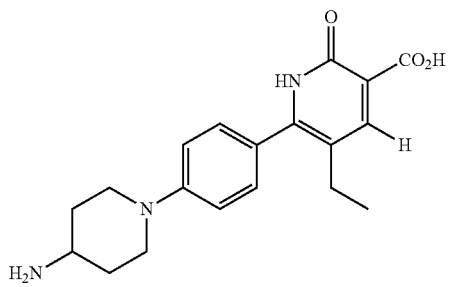 |
| 225 | 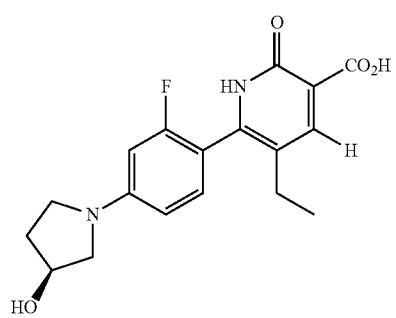 | 230 | 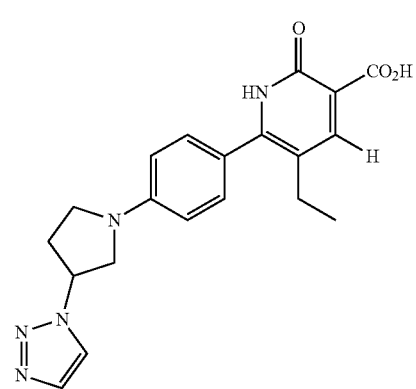 |
| 226 | 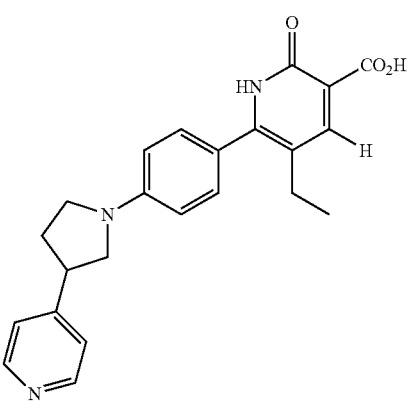 | 231 | 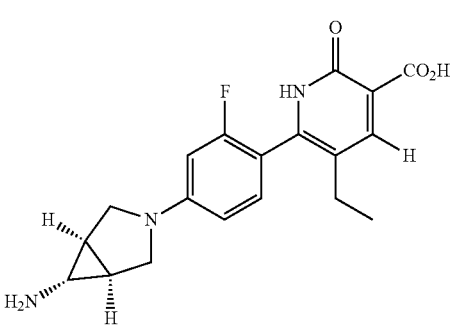 |
| 227 | 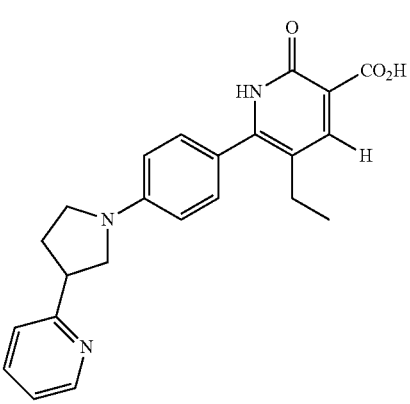 | 232 | 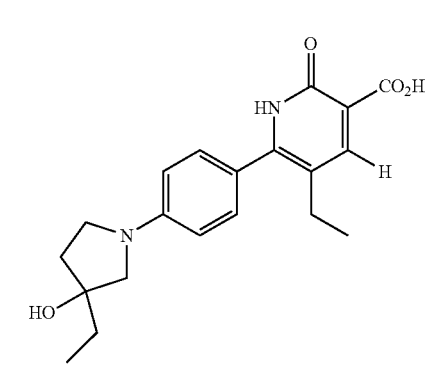 |

233 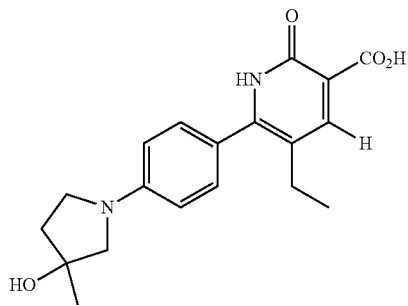
234 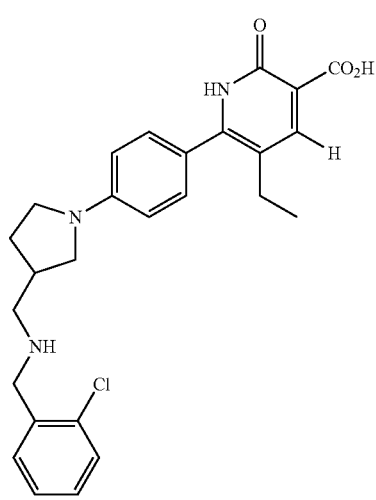
235 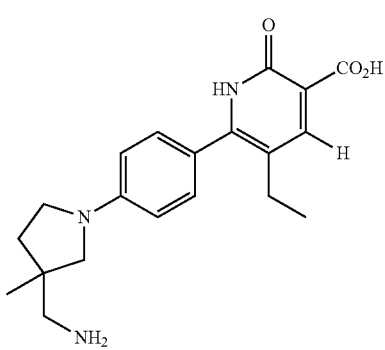
236 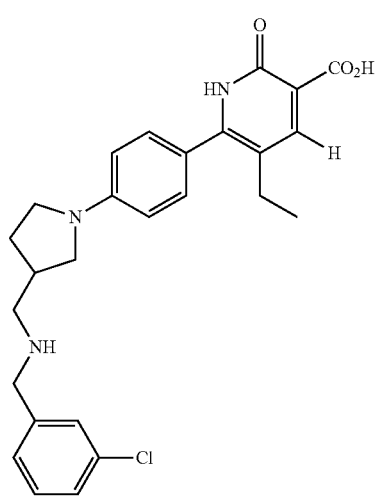
237 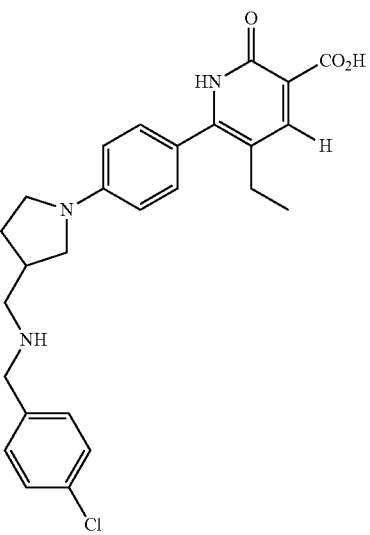
238 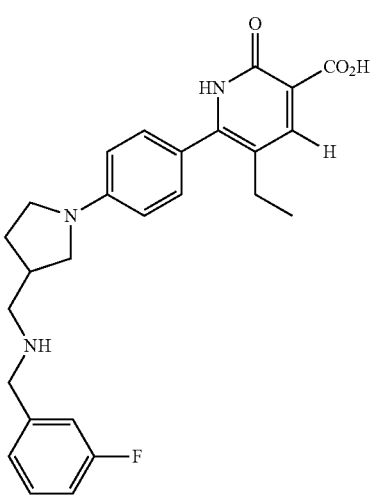
239 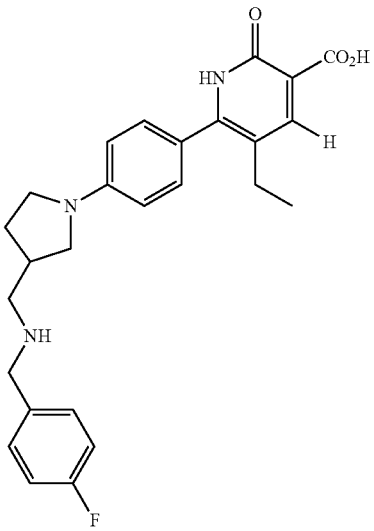

240 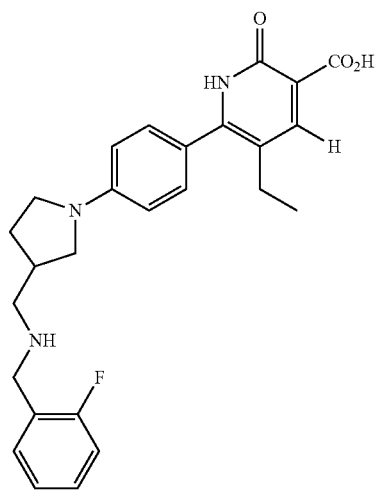
241 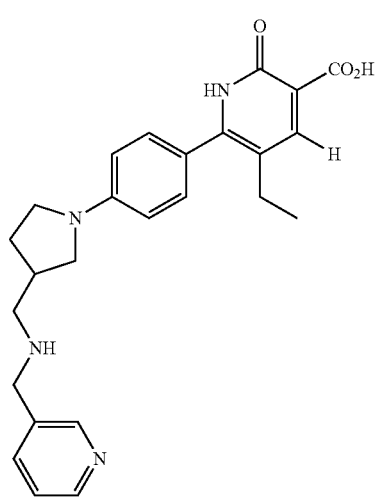
242 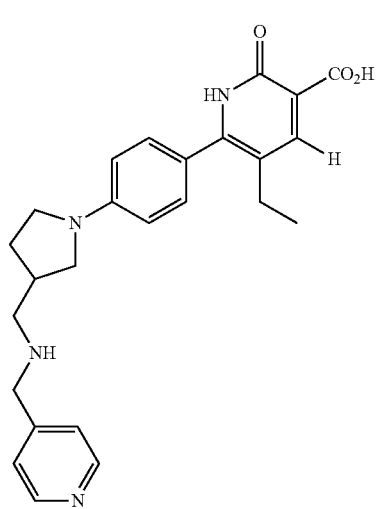
243 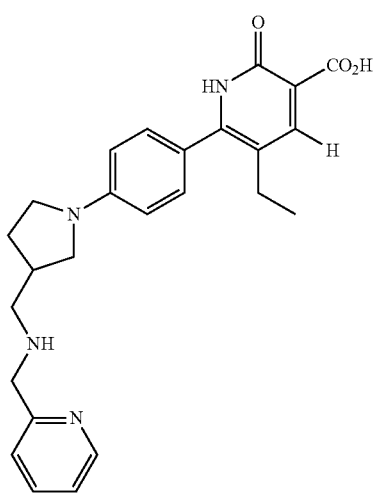
244 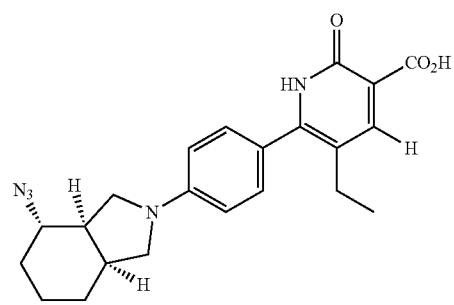
245 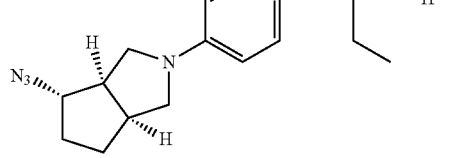
246 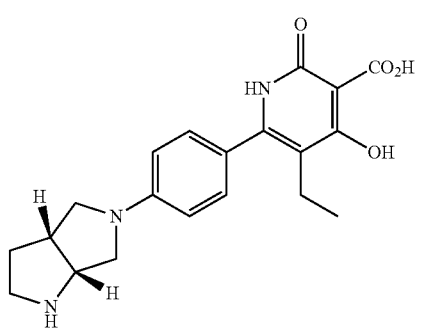

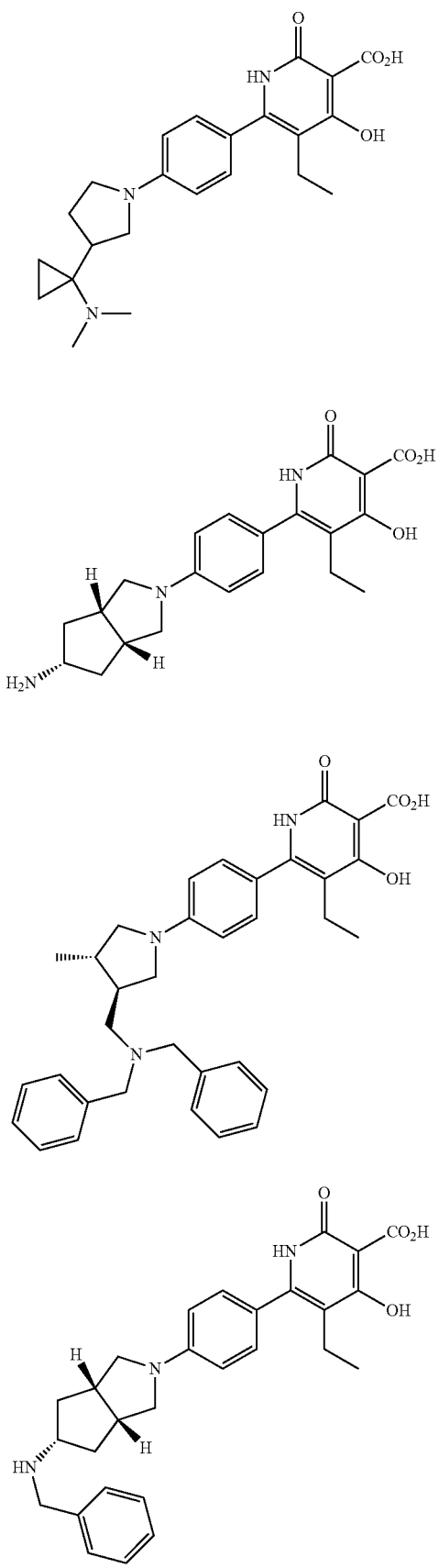
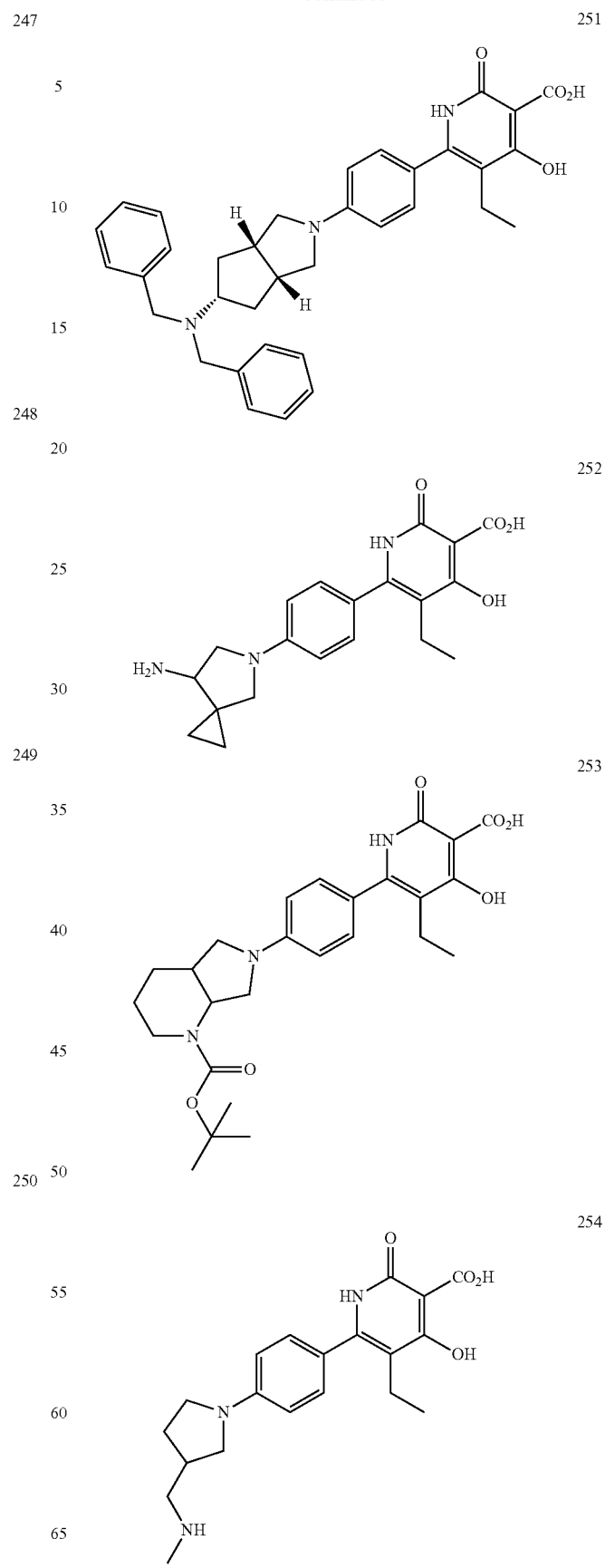

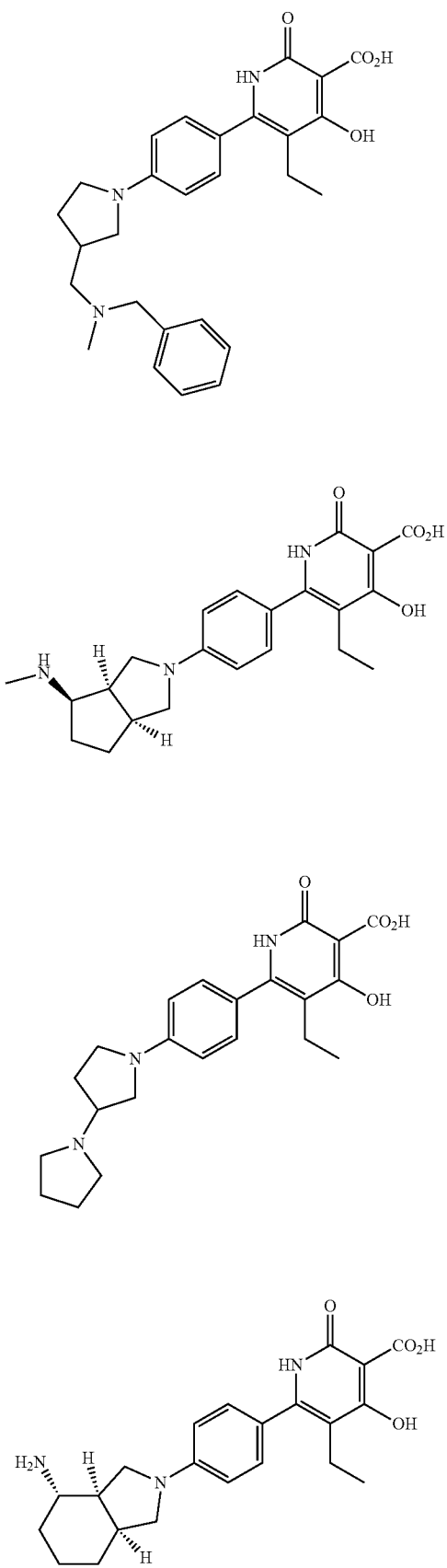
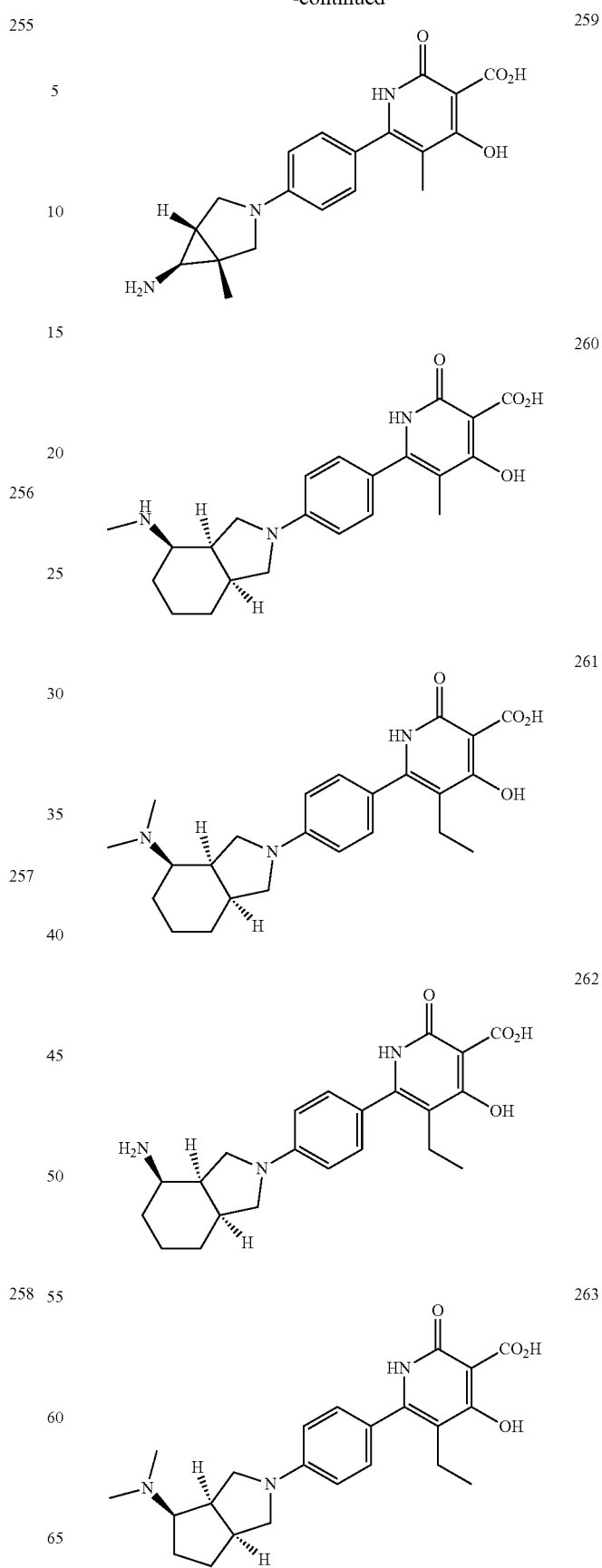

264
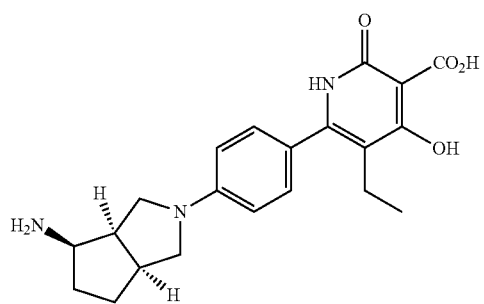
265
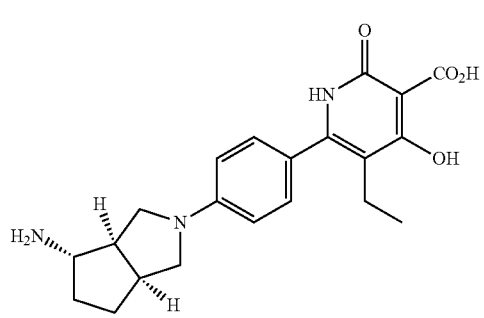
266
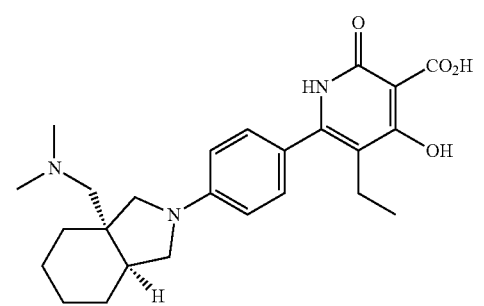
267
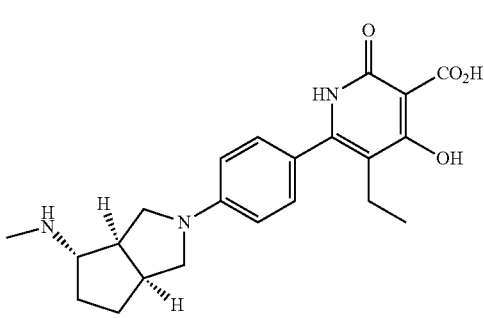
268
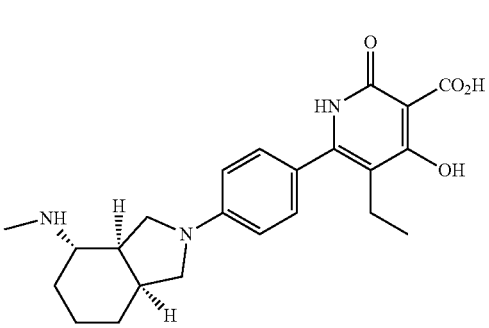
269
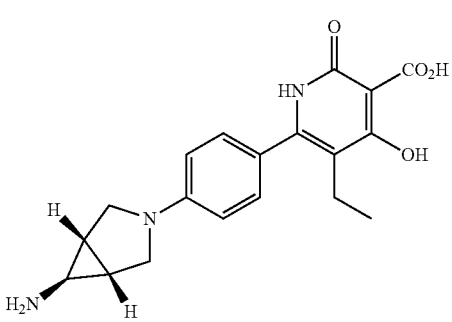
270
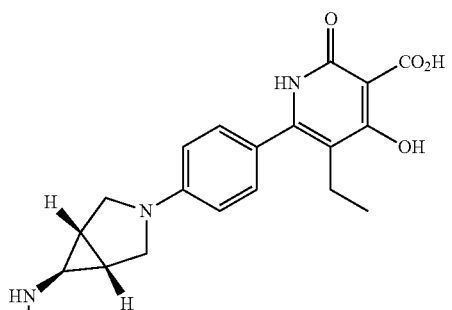
271
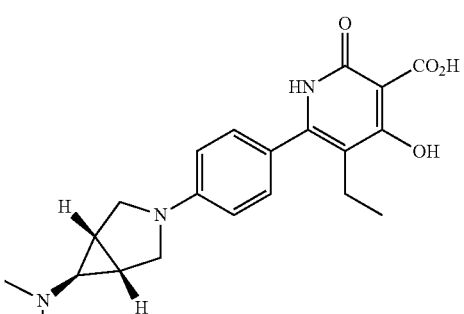
272
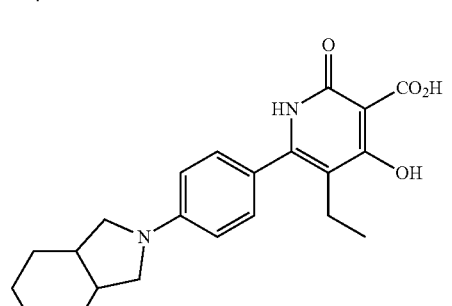
273
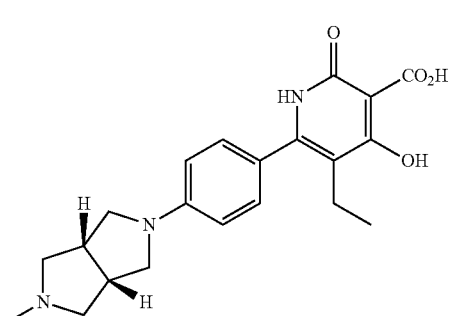

| 274 | 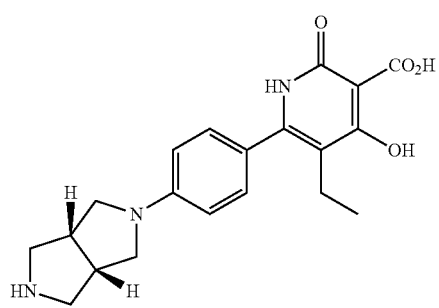 |
| --- | --- |
| 275 | 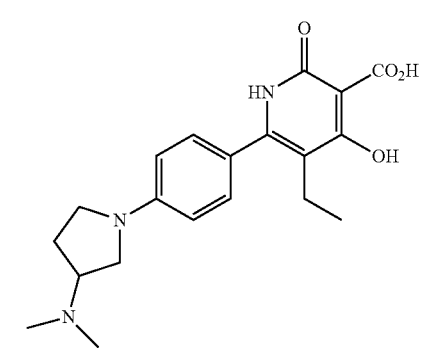 |
| 276 | 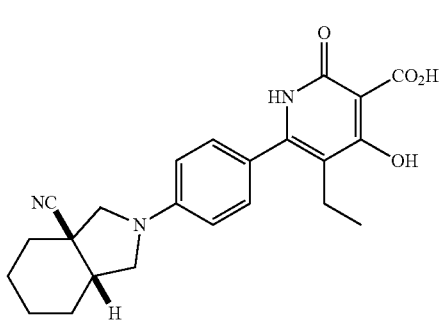 |
| 277 | 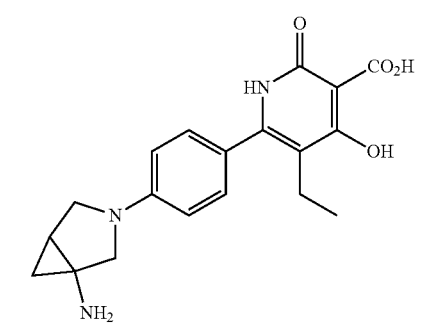 |
| 278 | 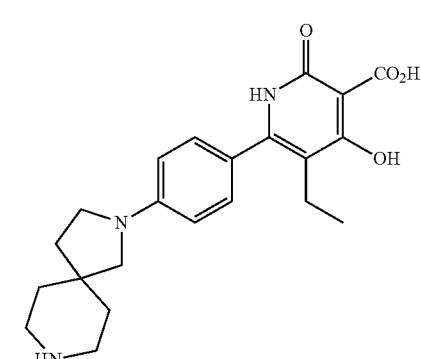 |
| 279 | 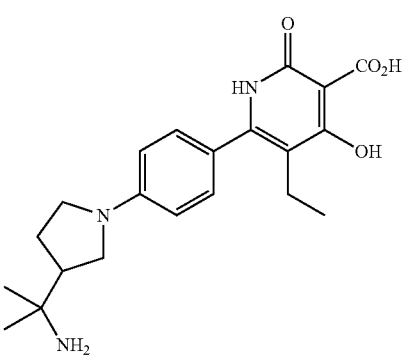 |
| --- | --- |
| 280 | |
| 281 | 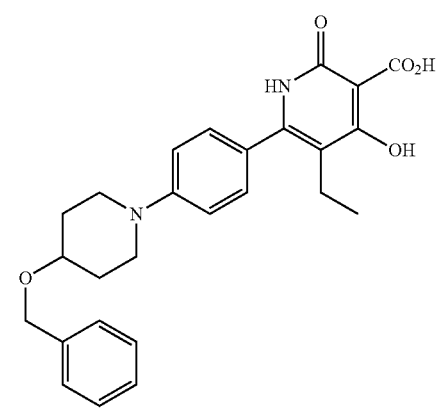 |
| 282 | 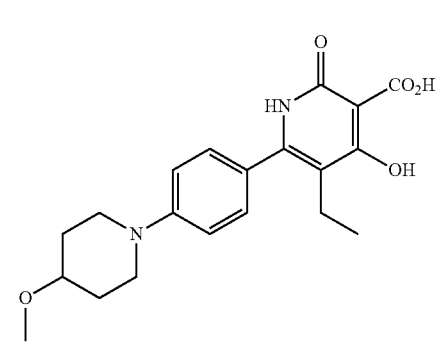 |

| 283 | 287 |
|---|---|
| 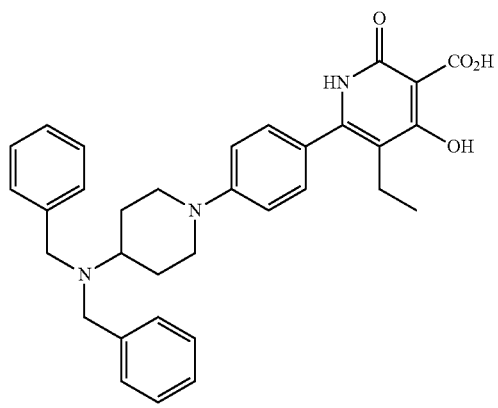 | 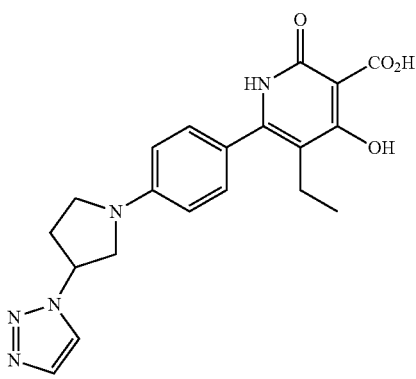 |
| 284 | 288 |
| 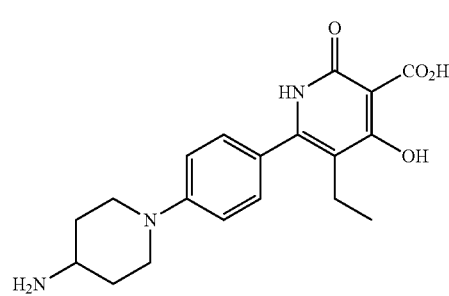 | 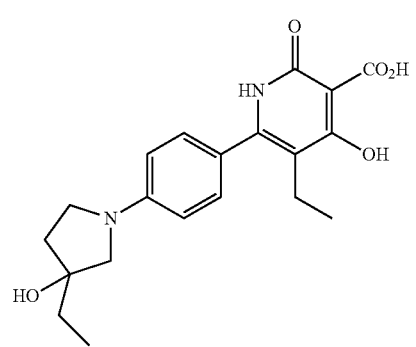 |
| 285 | 289 |
| 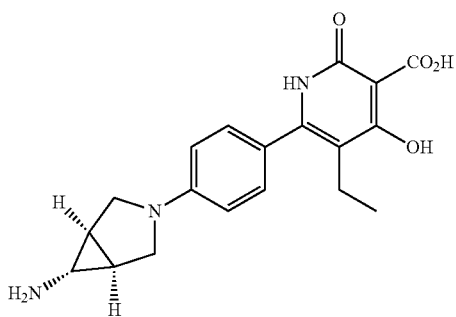 | 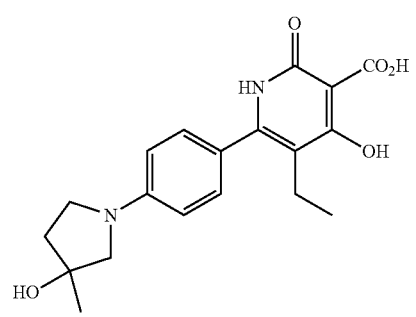 |
| 286 | 290 |
| 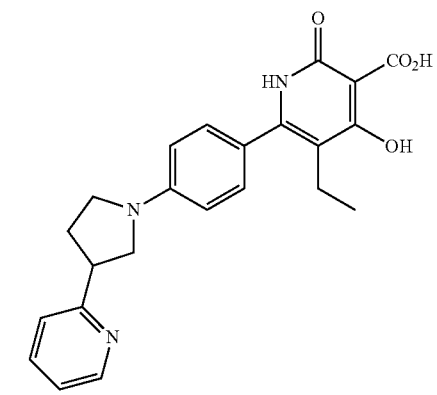 | 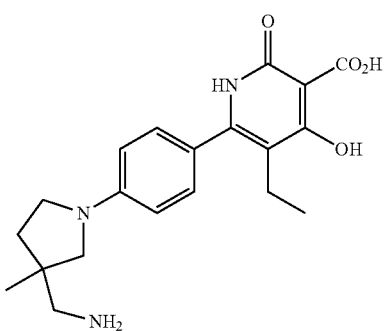 |

291 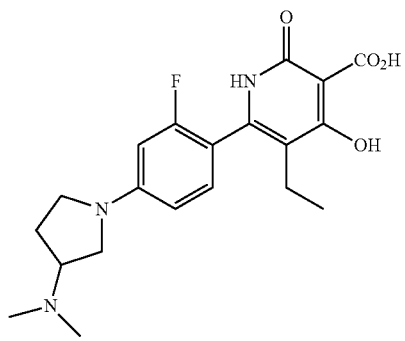
292 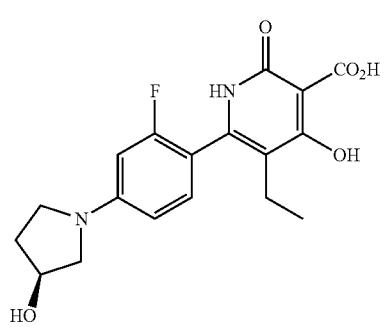
293 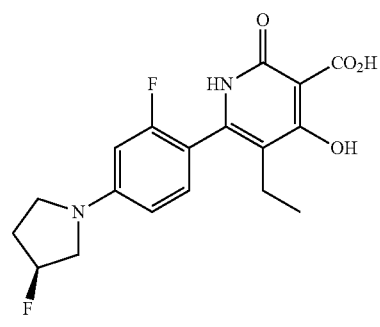
294 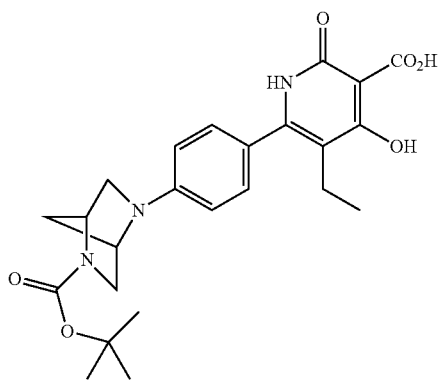
295 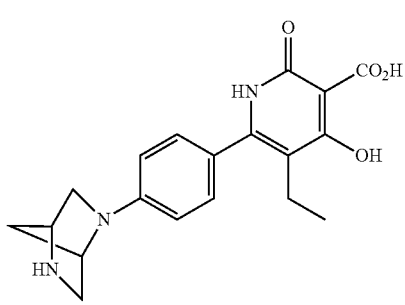
296 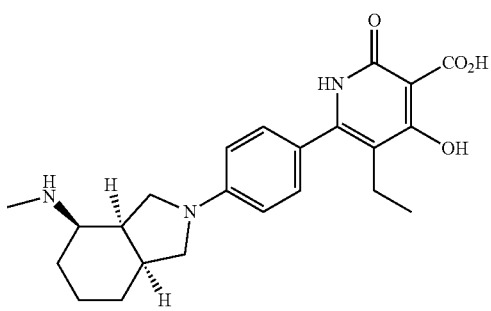
297 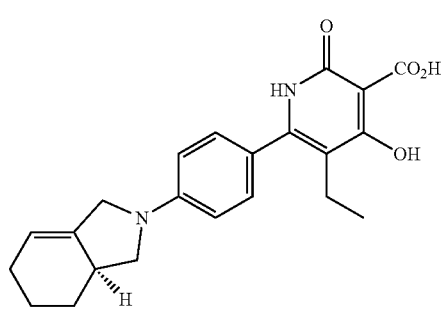
298 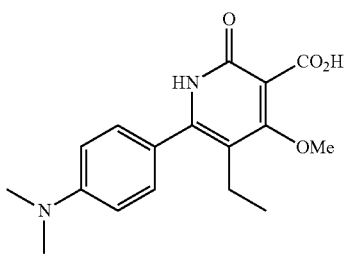
299 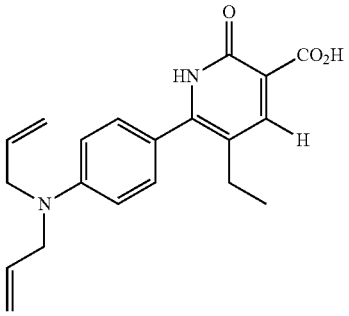
300 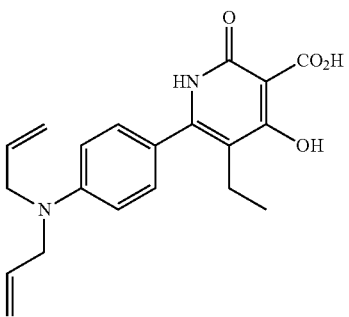

301 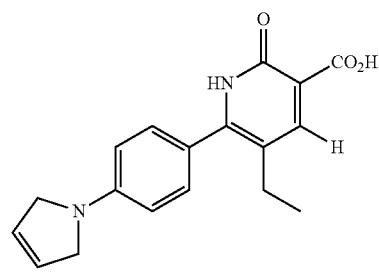
302 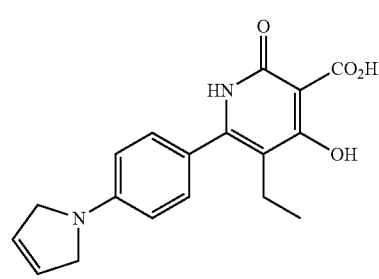
303 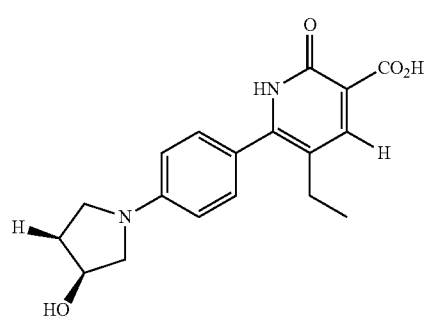
304 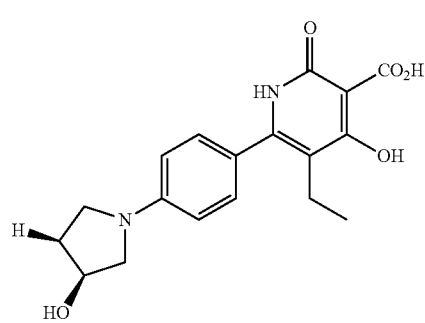
305 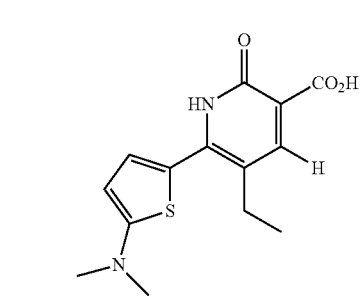
306 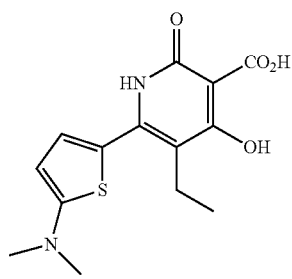
307 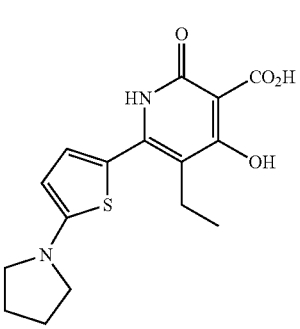
308 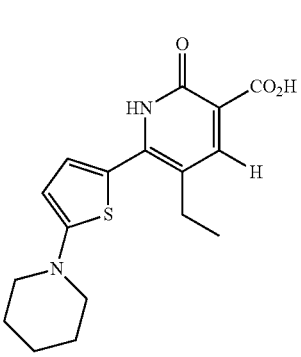
309 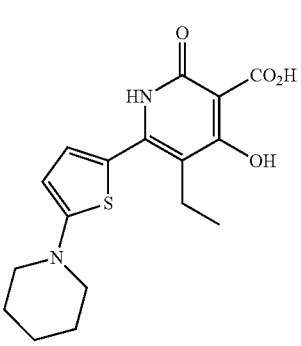
310 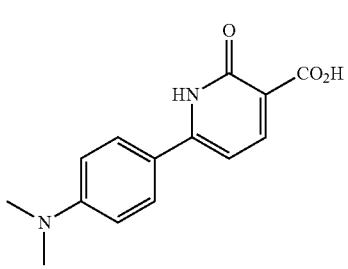

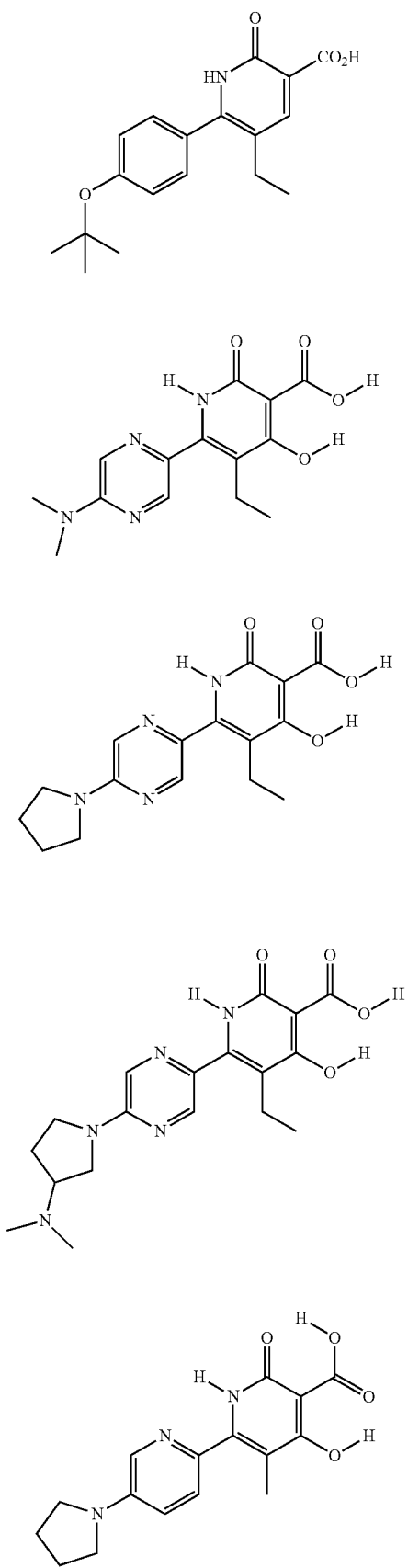
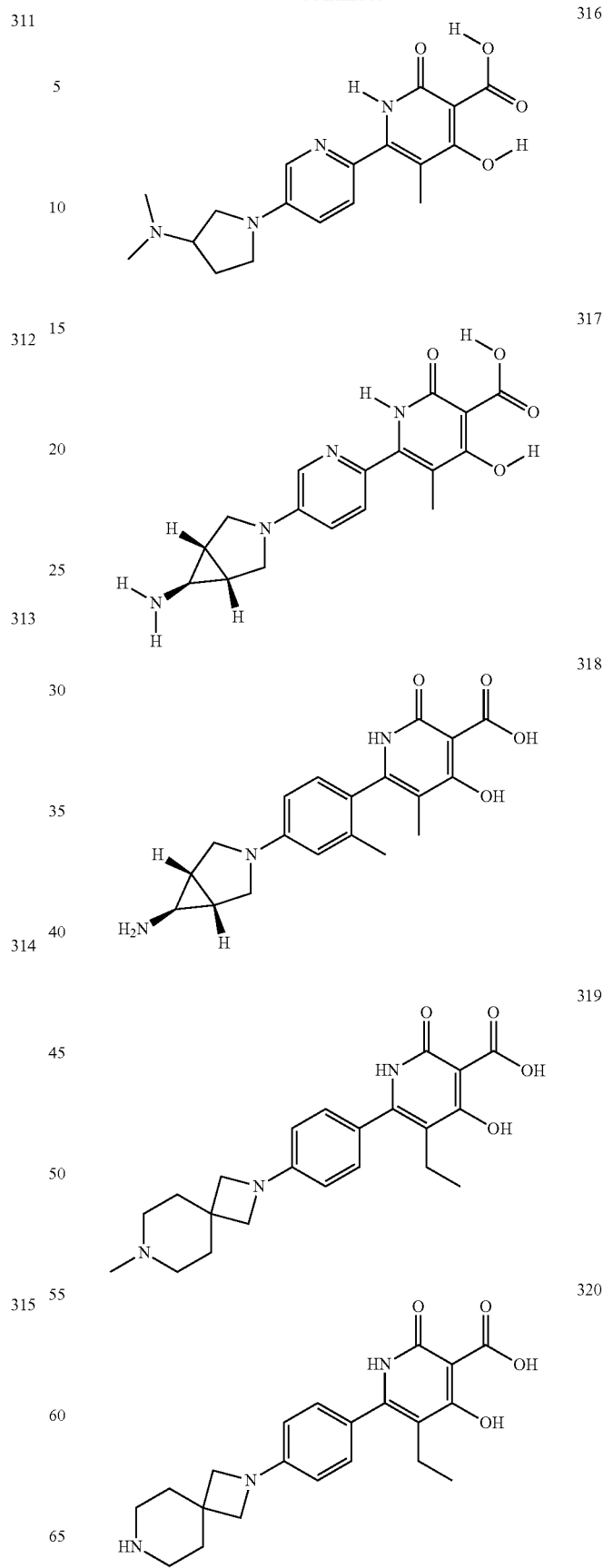

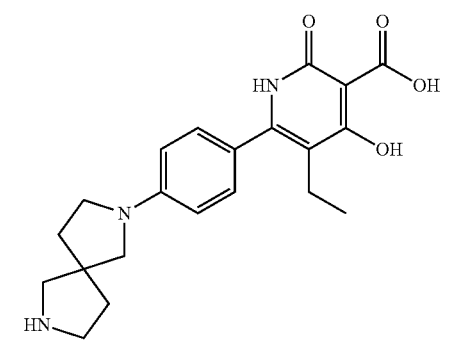
321
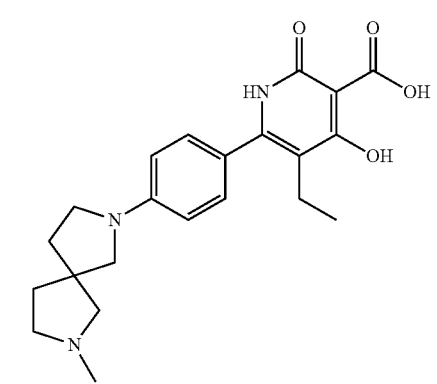
322
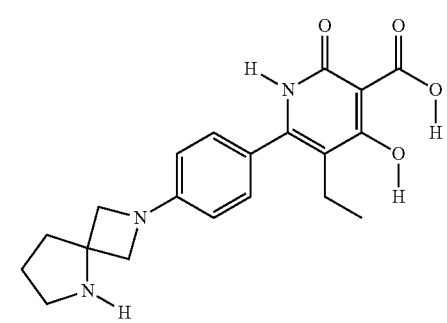
323
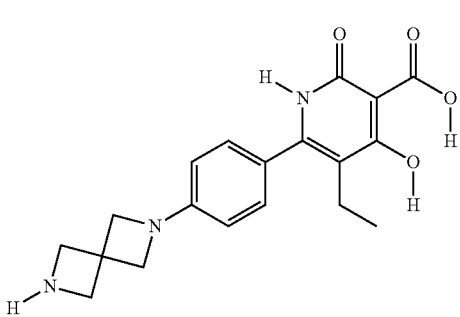
324
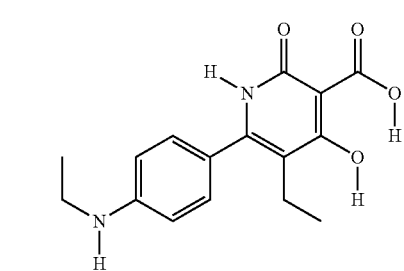
325
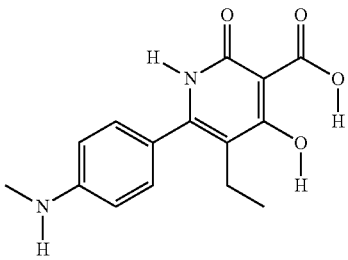
326
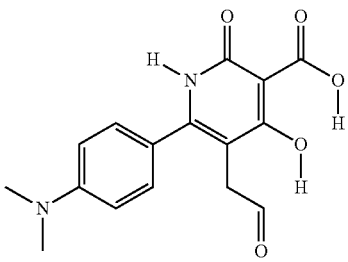
327
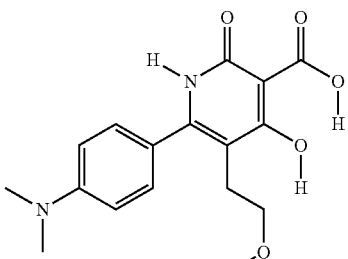
328
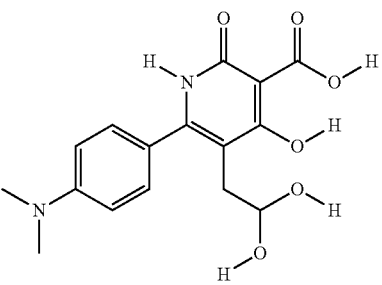
329
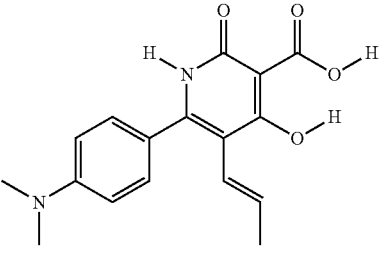
330
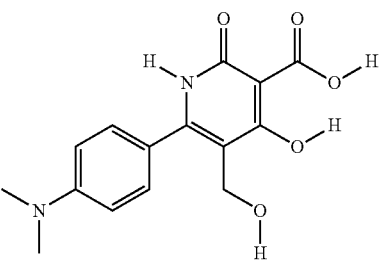
331

332 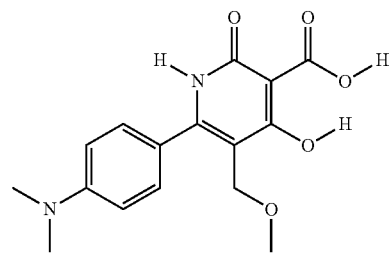
333 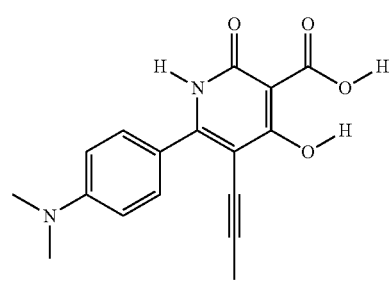
334 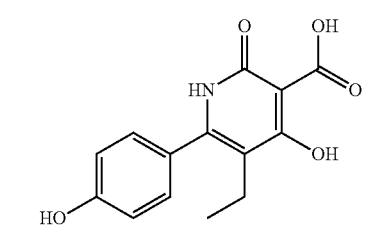
335 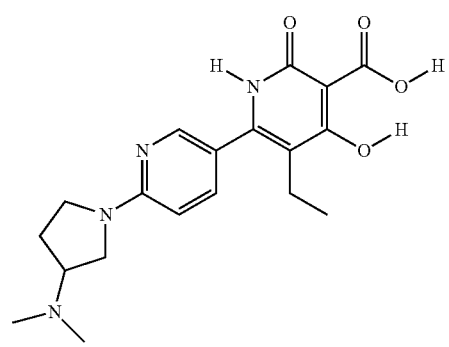
336 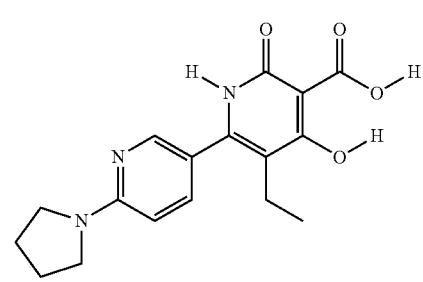
337 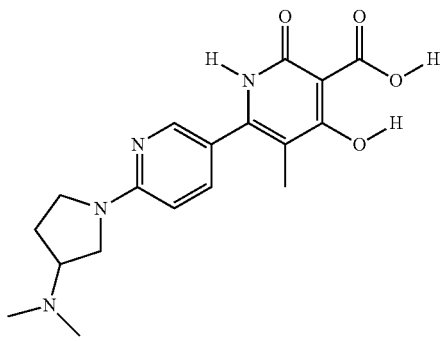
338 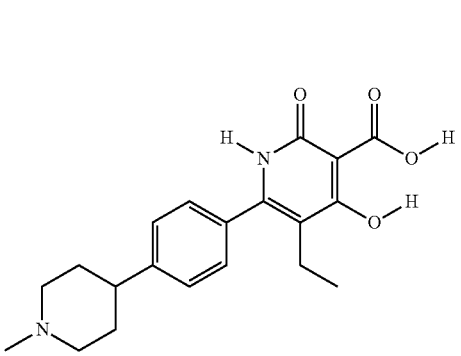
339 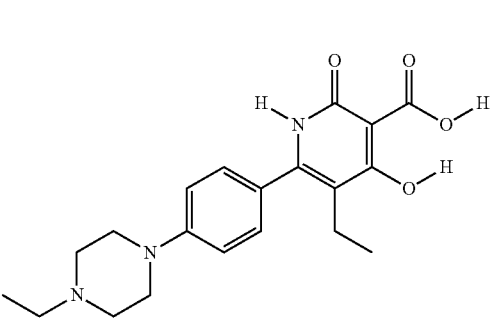
340 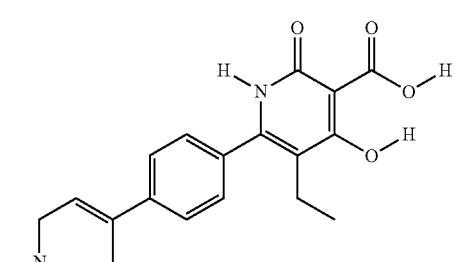
341 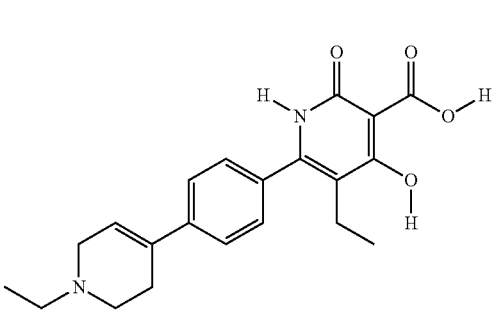

-continued

342
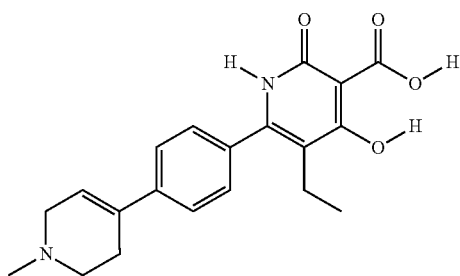

343
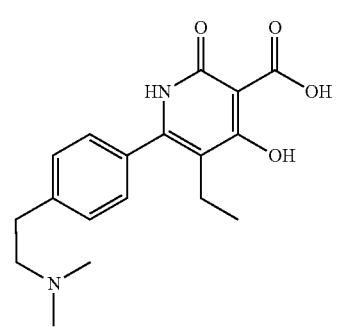

344
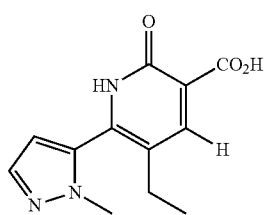

345
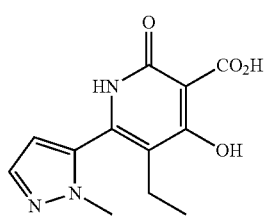

346
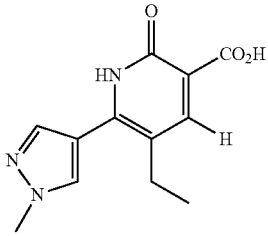

347
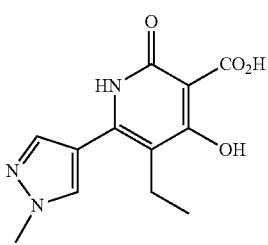

-continued

348
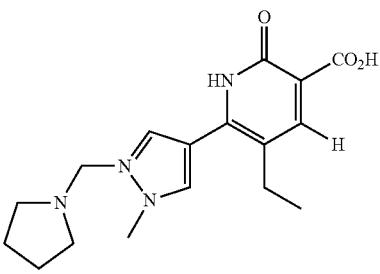

349
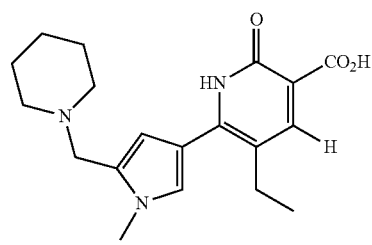

350
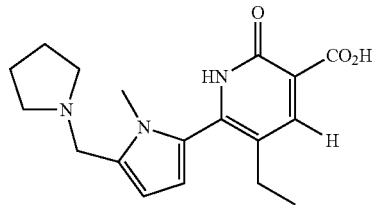

351
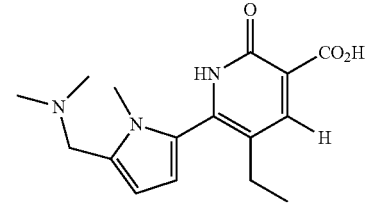

352
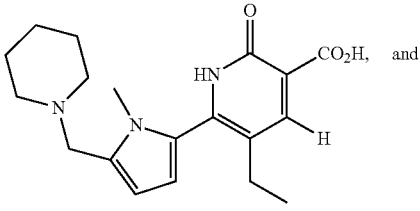
and

353
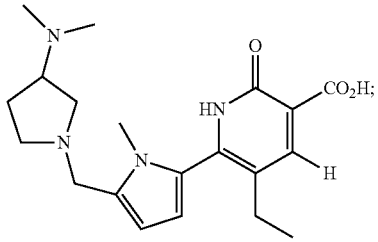
;

wherein the form of the compound is selected from a free acid, free base, salt, hydrate, solvate, clathrate, isotopologue, racemate, enantiomer, diastereomer, stereoisomer, polymorph or tautomer form thereof, and wherein the form is isolated for use.

In another embodiment of the present description, a compound or a form thereof is selected from:

| Cpd | Name |
|---|---|
| 1 | 5-benzyl-6-[4-(dimethylamino)phenyl]-2-oxo-1,2-dihydropyridine-3-carboxylic acid |
| 2 | 5-benzyl-6-[4-(dimethylamino)phenyl]-4-hydroxy-2-oxo-1,2-dihydropyridine-3-carboxylic acid |
| 3 | 6-(4-aminophenyl)-5-ethyl-2-oxo-1,2-dihydropyridine-3-carboxylic acid |
| 4 | 6-[4-(dimethylamino)phenyl]-5-methyl-2-oxo-1,2-dihydropyridine-3-carboxylic acid |
| 5 | 6-[4-(dimethylamino)phenyl]-4-hydroxy-5-methyl-2-oxo-1,2-dihydropyridine-3-carboxylic acid |
| 6 | 5-cyclohexyl-6-[4-(dimethylamino)phenyl]-2-oxo-1,2-dihydropyridine-3-carboxylic acid |
| 7 | 5-cyclohexyl-6-[4-(dimethylamino)phenyl]-4-hydroxy-2-oxo-1,2-dihydropyridine-3-carboxylic acid |
| 8 | 6-[4-(dimethylamino)phenyl]-2-oxo-5-propyl-1,2-dihydropyridine-3-carboxylic acid |
| 9 | 6-[4-(dimethylamino)phenyl]-4-hydroxy-2-oxo-5-propyl-1,2-dihydropyridine-3-carboxylic acid |
| 10 | 6-(4-fluorophenyl)-2-oxo-1,2-dihydropyridine-3,5-dicarboxylic acid |
| 11 | 6-[4-(dimethylamino)phenyl]-2-oxo-1,2-dihydropyridine-3,5-dicarboxylic acid |
| 12 | 5-cyclopropyl-6-[4-(dimethylamino)phenyl]-2-oxo-1,2-dihydropyridine-3-carboxylic acid |
| 13 | 5-cyclopropyl-6-[4-(dimethylamino)phenyl]-4-hydroxy-2-oxo-1,2-dihydropyridine-3-carboxylic acid |
| 14 | 5-cyano-6-[4-(dimethylamino)phenyl]-2-oxo-1,2-dihydropyridine-3-carboxylic acid |
| 15 | 6-(4-cyanophenyl)-5-ethyl-2-oxo-1,2-dihydropyridine-3-carboxylic acid |
| 16 | 5-ethyl-6-(4-{methyl[2-(tetrahydro-2H-pyran-2-yloxy)ethyl]amino}phenyl)-2-oxo-1,2-dihydropyridine-3-carboxylic acid |
| 17 | 5-ethyl-6-{4-[(2-hydroxyethyl)(methyl)amino]phenyl}-2-oxo-1,2-dihydropyridine-3-carboxylic acid |
| 18 | 5-ethyl-4-hydroxy-6-{4-[(2-hydroxyethyl)(methyl)amino]phenyl}-2-oxo-1,2-dihydropyridine-3-carboxylic acid |
| 19 | 6-[2-(dimethylamino)pyrimidin-5-yl]-5-ethyl-2-oxo-1,2-dihydropyridine-3-carboxylic acid |
| 20 | 6-[2-(dimethylamino)pyrimidin-5-yl]-5-ethyl-4-hydroxy-2-oxo-1,2-dihydropyridine-3-carboxylic acid |
| 21 | 4-hydroxy-2-oxo-6-[4-(pyrrolidin-1-yl)phenyl]-1,2-dihydropyridine-3-carboxylic acid |
| 23 | 5-ethyl-2-oxo-6-[4-(1H-tetrazol-5-yl)phenyl]-1,2-dihydropyridine-3-carboxylic acid |
| 24 | 5-ethyl-6-(4-methoxyphenyl)-2-oxo-1,2-dihydropyridine-3-carboxylic acid |
| 25 | 5-ethyl-4-hydroxy-6-(4-methoxyphenyl)-2-oxo-1,2-dihydropyridine-3-carboxylic acid |
| 26 | 5-ethyl-6-(4-fluorophenyl)-2-oxo-1,2-dihydropyridine-3-carboxylic acid |
| 27 | 5-ethyl-6-(4-methylphenyl)-2-oxo-1,2-dihydropyridine-3-carboxylic acid |
| 28 | 5-ethyl-4-hydroxy-6-(4-methylphenyl)-2-oxo-1,2-dihydropyridine-3-carboxylic acid |
| 29 | 5-ethyl-4-hydroxy-2-oxo-6-[2-(piperidin-1-yl)phenyl]-1,2-dihydropyridine-3-carboxylic acid |
| 30 | 5-ethyl-6-(2-fluoro-4-methoxyphenyl)-2-oxo-1,2-dihydropyridine-3-carboxylic acid |
| 31 | 5-ethyl-2-oxo-6-[2-(piperidin-1-yl)phenyl]-1,2-dihydropyridine-3-carboxylic acid |
| 32 | 5-ethyl-4-hydroxy-6-(4-methoxy-2-methylphenyl)-2-oxo-1,2-dihydropyridine-3-carboxylic acid |
| 33 | 5-ethyl-6-(4-methoxy-2-methylphenyl)-2-oxo-1,2-dihydropyridine-3-carboxylic acid |
| 34 | 6-(2,4-dimethoxyphenyl)-5-ethyl-2-oxo-1,2-dihydropyridine-3-carboxylic acid |
| 35 | 5-ethyl-6-[4-methoxy-2-(pyrrolidin-1-yl)phenyl]-2-oxo-1,2-dihydropyridine-3-carboxylic acid |
| 36 | 6-(2,4-dimethoxyphenyl)-5-ethyl-4-hydroxy-2-oxo-1,2-dihydropyridine-3-carboxylic acid |
| 37 | 5-ethyl-6-[2-methyl-4-(pyrrolidin-1-yl)phenyl]-2-oxo-1,2-dihydropyridine-3-carboxylic acid |
| 38 | 5-ethyl-6-[2-fluoro-4-(pyrrolidin-1-yl)phenyl]-2-oxo-1,2-dihydropyridine-3-carboxylic acid |
| 39 | 5-ethyl-4-hydroxy-6-[2-methyl-4-(pyrrolidin-1-yl)phenyl]-2-oxo-1,2-dihydropyridine-3-carboxylic acid |
| 40 | 6-[2-(dimethylamino)-4-methoxyphenyl]-5-ethyl-2-oxo-1,2-dihydropyridine-3-carboxylic acid |
| 41 | 5-ethyl-4-hydroxy-2-oxo-6-(2,4,6-trimethoxyphenyl)-1,2-dihydropyridine-3-carboxylic acid |
| 42 | 5-ethyl-4-hydroxy-2-oxo-6-(2,3,4-trimethoxyphenyl)-1,2-dihydropyridine-3-carboxylic acid |
| 43 | 5-ethyl-6-[2-fluoro-4-(piperidin-1-yl)phenyl]-2-oxo-1,2-dihydropyridine-3-carboxylic acid |
| 44 | 5-ethyl-6-[2-fluoro-4-(piperidin-1-yl)phenyl]-4-hydroxy-2-oxo-1,2-dihydropyridine-3-carboxylic acid |
| 45 | 5-ethyl-4-hydroxy-6-[2-methoxy-4-(pyrrolidin-1-yl)phenyl]-2-oxo-1,2-dihydropyridine-3-carboxylic acid |
| 46 | 5-ethyl-2-oxo-6-[2-(pyrrolidin-1-yl)phenyl]-1,2-dihydropyridine-3-carboxylic acid |
| 47 | 5-ethyl-4-hydroxy-2-oxo-6-[2-(pyrrolidin-1-yl)phenyl]-1,2-dihydropyridine-3-carboxylic acid |
| 48 | 5-ethyl-4-hydroxy-6-[4-methoxy-2-(pyrrolidin-1-yl)phenyl]-2-oxo-1,2-dihydropyridine-3-carboxylic acid |
| 49 | 5-ethyl-4-hydroxy-6-[2-methoxy-4-(piperidin-1-yl)phenyl]-2-oxo-1,2-dihydropyridine-3-carboxylic acid |
| 50 | 5-ethyl-6-[2-methoxy-4-(pyrrolidin-1-yl)phenyl]-2-oxo-1,2-dihydropyridine-3-carboxylic acid |

-continued

| Cpd | Name |
|---|---|
| 51 | 5-ethyl-4-hydroxy-6-[2-methyl-4-(piperidin-1-yl)phenyl]-2-oxo-1,2-dihydropyridine-3-carboxylic acid |
| 52 | 5-ethyl-6-[2-methyl-4-(piperidin-1-yl)phenyl]-2-oxo-1,2-dihydropyridine-3-carboxylic acid |
| 53 | 6-[4-(dimethylamino)-2-fluorophenyl]-5-ethyl-2-oxo-1,2-dihydropyridine-3-carboxylic acid |
| 54 | 6-[2-(dimethylamino)phenyl]-5-ethyl-2-oxo-1,2-dihydropyridine-3-carboxylic acid |
| 55 | 6-[4-(dimethylamino)-2-fluorophenyl]-5-ethyl-4-hydroxy-2-oxo-1,2-dihydropyridine-3-carboxylic acid |
| 56 | 6-[4-(dimethylamino)-2-methylphenyl]-5-ethyl-4-hydroxy-2-oxo-1,2-dihydropyridine-3-carboxylic acid |
| 57 | 6-[4-(dimethylamino)-2-methylphenyl]-5-ethyl-2-oxo-1,2-dihydropyridine-3-carboxylic acid |
| 58 | 6-[2-(dimethylamino)phenyl]-5-ethyl-4-hydroxy-2-oxo-1,2-dihydropyridine-3-carboxylic acid |
| 59 | 5-ethyl-6-[2-methoxy-4-(piperidin-1-yl)phenyl]-2-oxo-1,2-dihydropyridine-3-carboxylic acid |
| 60 | 6-[2-(dimethylamino)-4-methoxyphenyl]-5-ethyl-4-hydroxy-2-oxo-1,2-dihydropyridine-3-carboxylic acid |
| 61 | 6-[4-(dimethylamino)-2-methoxyphenyl]-5-ethyl-4-hydroxy-2-oxo-1,2-dihydropyridine-3-carboxylic acid |
| 62 | 6-[4-(dimethylamino)-2-methoxyphenyl]-5-ethyl-2-oxo-1,2-dihydropyridine-3-carboxylic acid |
| 63 | 6-[4-(dimethylamino)-3-methylphenyl]-5-ethyl-4-hydroxy-2-oxo-1,2-dihydropyridine-3-carboxylic acid |
| 64 | 6-[4-(dimethylamino)-3-methoxyphenyl]-5-ethyl-2-oxo-1,2-dihydropyridine-3-carboxylic acid |
| 65 | 6-[4-(dimethylamino)-3-methoxyphenyl]-5-ethyl-4-hydroxy-2-oxo-1,2-dihydropyridine-3-carboxylic acid |
| 66 | 5-ethyl-6-[3-methoxy-4-(pyrrolidin-1-yl)phenyl]-2-oxo-1,2-dihydropyridine-3-carboxylic acid |
| 67 | 5-ethyl-4-hydroxy-6-[3-methoxy-4-(pyrrolidin-1-yl)phenyl]-2-oxo-1,2-dihydropyridine-3-carboxylic acid |
| 68 | 5-ethyl-6-[3-methoxy-4-(piperidin-1-yl)phenyl]-2-oxo-1,2-dihydropyridine-3-carboxylic acid |
| 69 | 5-ethyl-4-hydroxy-6-[3-methoxy-4-(piperidin-1-yl)phenyl]-2-oxo-1,2-dihydropyridine-3-carboxylic acid |
| 70 | 5-ethyl-6-[3-methyl-4-(pyrrolidin-1-yl)phenyl]-2-oxo-1,2-dihydropyridine-3-carboxylic acid |
| 71 | 5-ethyl-4-hydroxy-6-[3-methyl-4-(pyrrolidin-1-yl)phenyl]-2-oxo-1,2-dihydropyridine-3-carboxylic acid |
| 72 | 5-ethyl-6-[3-methyl-4-(piperidin-1-yl)phenyl]-2-oxo-1,2-dihydropyridine-3-carboxylic acid |
| 73 | 5-ethyl-4-hydroxy-6-[3-methyl-4-(piperidin-1-yl)phenyl]-2-oxo-1,2-dihydropyridine-3-carboxylic acid |
| 74 | 5-ethyl-6-(4-fluorophenyl)-4-hydroxy-2-oxo-1,2-dihydropyridine-3-carboxylic acid |
| 75 | 5-ethyl-2-oxo-6-phenyl-1,2-dihydropyridine-3-carboxylic acid |
| 76 | 6-(4-chlorophenyl)-5-ethyl-2-oxo-1,2-dihydropyridine-3-carboxylic acid |
| 77 | 6-(4-chlorophenyl)-5-ethyl-4-hydroxy-2-oxo-1,2-dihydropyridine-3-carboxylic acid |
| 78 | 6-(4-bromophenyl)-5-ethyl-2-oxo-1,2-dihydropyridine-3-carboxylic acid |
| 79 | 6-(4-bromophenyl)-5-ethyl-4-hydroxy-2-oxo-1,2-dihydropyridine-3-carboxylic acid |
| 80 | 5-ethyl-6-(4-iodophenyl)-2-oxo-1,2-dihydropyridine-3-carboxylic acid |
| 81 | 5-ethyl-4-hydroxy-6-(4-iodophenyl)-2-oxo-1,2-dihydropyridine-3-carboxylic acid |
| 82 | 5-ethyl-4-hydroxy-6-{4-[(3-iodopropyl)amino]phenyl}-2-oxo-1,2-dihydropyridine-3-carboxylic acid |
| 83 | 6-[4-(azetidin-1-yl)phenyl]-5-ethyl-4-hydroxy-2-oxo-1,2-dihydropyridine-3-carboxylic acid |
| 84 | 5-ethyl-6-[3-fluoro-4-(morpholin-4-yl)phenyl]-2-oxo-1,2-dihydropyridine-3-carboxylic acid |
| 85 | 5-ethyl-6-{4-[(3S)-3-fluoropyrrolidin-1-yl]phenyl}-4-hydroxy-2-oxo-1,2-dihydropyridine-3-carboxylic acid |
| 86 | 6-[6-(dimethylamino)pyridin-3-yl]-5-ethyl-2-oxo-1,2-dihydropyridine-3-carboxylic acid |
| 87 | 6-[6-(dimethylamino)pyridin-3-yl]-5-ethyl-4-hydroxy-2-oxo-1,2-dihydropyridine-3-carboxylic acid |
| 88 | 6-[4-(dimethylamino)phenyl]-5-ethyl-2-oxo-1,2-dihydropyridine-3-carboxylic acid |
| 89 | 6-[3-fluoro-4-(morpholin-4-yl)phenyl]-5-methyl-2-oxo-1,2-dihydropyridine-3-carboxylic acid |
| 90 | 6-[4-(dimethylamino)phenyl]-5-ethyl-4-hydroxy-2-oxo-1,2-dihydropyridine-3-carboxylic acid |
| 91 | 6-{4-[4-(tert-butoxycarbonyl)piperazin-1-yl]-3-fluorophenyl}-5-ethyl-2-oxo-1,2-dihydropyridine-3-carboxylic acid |
| 93 | 6-[4-(dimethylamino)-3-fluorophenyl]-5-ethyl-2-oxo-1,2-dihydropyridine-3-carboxylic acid |
| 94 | 6-[4-(dimethylamino)-3-fluorophenyl]-5-ethyl-4-hydroxy-2-oxo-1,2-dihydropyridine-3-carboxylic acid |
| 95 | 6-[4-(dimethylamino)phenyl]-2-oxo-5-(propan-2-yl)-1,2-dihydropyridine-3-carboxylic acid |

-continued

| Cpd | Name |
|---|---|
| 96 | 6-[4-(dimethylamino)phenyl]-4-hydroxy-2-oxo-5-(propan-2-yl)-1,2-dihydropyridine-3-carboxylic acid |
| 97 | 6-[4-(diethylamino)phenyl]-5-ethyl-2-oxo-1,2-dihydropyridine-3-carboxylic acid |
| 98 | 6-[4-(diethylamino)phenyl]-5-ethyl-4-hydroxy-2-oxo-1,2-dihydropyridine-3-carboxylic acid |
| 99 | 5-ethyl-2-oxo-6-[4-(pyrrolidin-1-yl)phenyl]-1,2-dihydropyridine-3-carboxylic acid |
| 100 | 5-ethyl-4-hydroxy-2-oxo-6-[4-(pyrrolidin-1-yl)phenyl]-1,2-dihydropyridine-3-carboxylic acid |
| 101 | 5-ethyl-2-oxo-6-[4-(1H-pyrrol-1-yl)phenyl]-1,2-dihydropyridine-3-carboxylic acid |
| 102 | 6-{4-[4-(tert-butoxycarbonyl)piperazin-1-yl]phenyl}-5-ethyl-2-oxo-1,2-dihydropyridine-3-carboxylic acid |
| 104 | 6-{4-[4-(tert-butoxycarbonyl)piperazin-1-yl]phenyl}-5-ethyl-4-hydroxy-2-oxo-1,2-dihydropyridine-3-carboxylic acid |
| 106 | 5-ethyl-6-[4-(1H-imidazol-1-yl)phenyl]-2-oxo-1,2-dihydropyridine-3-carboxylic acid |
| 107 | 5-ethyl-4-hydroxy-6-[4-(1H-imidazol-1-yl)phenyl]-2-oxo-1,2-dihydropyridine-3-carboxylic acid |
| 108 | 5-ethyl-2-oxo-6-[4-(piperidin-1-yl)phenyl]-1,2-dihydropyridine-3-carboxylic acid |
| 109 | 5-ethyl-4-hydroxy-2-oxo-6-[4-(piperidin-1-yl)phenyl]-1,2-dihydropyridine-3-carboxylic acid |
| 110 | 5-ethyl-6-[4-(morpholin-4-yl)phenyl]-2-oxo-1,2-dihydropyridine-3-carboxylic acid |
| 111 | 6-[4-(azetidin-1-yl)phenyl]-5-ethyl-2-oxo-1,2-dihydropyridine-3-carboxylic acid |
| 112 | 5-ethyl-4-hydroxy-6-(5-morpholinopyridin-2-yl)-2-oxo-1,2-dihydropyridine-3-carboxylic acid |
| 113 | 5-ethyl-4-hydroxy-2-oxo-6-[5-(piperazin-1-yl)pyridin-2-yl]-1,2-dihydropyridine-3-carboxylic acid |
| 114 | 5-ethyl-2-oxo-6-[4-(2-oxopyrrolidin-1-yl)phenyl]-1,2-dihydropyridine-3-carboxylic acid |
| 115 | 5-ethyl-4-hydroxy-2-oxo-6-[4-(2-oxopyrrolidin-1-yl)phenyl]-1,2-dihydropyridine-3-carboxylic acid |
| 116 | 5-ethyl-6-[4-(2-methyl-5-oxopyrrolidin-1-yl)phenyl]-2-oxo-1,2-dihydropyridine-3-carboxylic acid |
| 117 | 5-ethyl-6-{4-[(3S)-3-hydroxy-2-oxopyrrolidin-1-yl]phenyl}-2-oxo-1,2-dihydropyridine-3-carboxylic acid |
| 118 | 5-ethyl-2-oxo-6-[4-(3-oxo-2-azaspiro[4.5]dec-2-yl)phenyl]-1,2-dihydropyridine-3-carboxylic acid |
| 119 | 5-ethyl-2-oxo-6-[4-(3-oxo-2-azabicyclo[2.2.1]hept-5-en-2-yl)phenyl]-1,2-dihydropyridine-3-carboxylic acid |
| 120 | 5-ethyl-2-oxo-6-{4-[3-(tetrahydro-2H-pyran-2-yloxy)azetidin-1-yl]phenyl}-1,2-dihydropyridine-3-carboxylic acid |
| 121 | 5-ethyl-6-[4-(3-hydroxyazetidin-1-yl)phenyl]-2-oxo-1,2-dihydropyridine-3-carboxylic acid |
| 122 | 5-ethyl-6-{4-[(3R)-3-hydroxypiperidin-1-yl]phenyl}-2-oxo-1,2-dihydropyridine-3-carboxylic acid |
| 123 | 5-ethyl-6-[4-(3-hydroxypyrrolidin-1-yl)phenyl]-2-oxo-1,2-dihydropyridine-3-carboxylic acid |
| 124 | 5-ethyl-4-hydroxy-6-{4-[(3R)-3-hydroxypyrrolidin-1-yl]phenyl}-2-oxo-1,2-dihydropyridine-3-carboxylic acid |
| 125 | 5-ethyl-4-hydroxy-6-{4-[(3R)-3-hydroxypiperidin-1-yl]phenyl}-2-oxo-1,2-dihydropyridine-3-carboxylic acid |
| 126 | 5-ethyl-4-hydroxy-6-[4-(3-hydroxypyrrolidin-1-yl)phenyl]-2-oxo-1,2-dihydropyridine-3-carboxylic acid |
| 127 | methyl 6-{4-[3-(benzyloxy)pyrrolidin-1-yl]phenyl}-5-ethyl-2-oxo-1,2-dihydropyridine-3-carboxylate |
| 128 | 6-{4-[3-(benzyloxy)pyrrolidin-1-yl]phenyl}-5-ethyl-2-oxo-1,2-dihydropyridine-3-carboxylic acid |
| 129 | 6-[4-(3-azidopyrrolidin-1-yl)phenyl]-5-ethyl-2-oxo-1,2-dihydropyridine-3-carboxylic acid |
| 130 | 6-{4-[(3S)-3-azidopyrrolidin-1-yl]phenyl}-5-ethyl-2-oxo-1,2-dihydropyridine-3-carboxylic acid |
| 137 | 6-{4-[5-(tert-butoxycarbonyl)-2,5-diazabicyclo[2.2.1]hept-2-yl]phenyl}-5-ethyl-2-oxo-1,2-dihydropyridine-3-carboxylic acid |
| 139 | 5-ethyl-6-[4-(2-methylpyrrolidin-1-yl)phenyl]-2-oxo-1,2-dihydropyridine-3-carboxylic acid |
| 141 | 5-ethyl-2-oxo-6-{4-[(2R)-2-(trifluoromethyl)pyrrolidin-1-yl]phenyl}-1,2-dihydropyridine-3-carboxylic acid |
| 142 | 5-ethyl-2-oxo-6-{4-[(2S)-2-(trifluoromethyl)pyrrolidin-1-yl]phenyl}-1,2-dihydropyridine-3-carboxylic acid |
| 144 | 6-[4-(3,3-difluoropyrrolidin-1-yl)phenyl]-5-ethyl-2-oxo-1,2-dihydropyridine-3-carboxylic acid |
| 145 | 5-ethyl-2-oxo-6-[4-(2-phenylpyrrolidin-1-yl)phenyl]-1,2-dihydropyridine-3-carboxylic acid |
| 146 | 5-ethyl-6-{4-[(2S)-2-(methoxymethyl)pyrrolidin-1-yl]phenyl}-2-oxo-1,2-dihydropyridine-3-carboxylic acid |
| 147 | 5-ethyl-6-{4-[(2R)-2-(methoxymethyl)pyrrolidin-1-yl]phenyl}-2-oxo-1,2-dihydropyridine-3-carboxylic acid |
| 148 | 6-{4-[(2S,5S)-2,5-bis(methoxymethyl)pyrrolidin-1-yl]phenyl}-5-ethyl-2-oxo-1,2-dihydropyridine-3-carboxylic acid |

| Cpd | Name |
|---|---|
| 149 | 6-{4-[3-(dimethylamino)pyrrolidin-1-yl]phenyl}-5-ethyl-2-oxo-1,2-dihydropyridine-3-carboxylic acid |
| 152 | 5-ethyl-6-[4-(3-fluoropyrrolidin-1-yl)phenyl]-2-oxo-1,2-dihydropyridine-3-carboxylic acid |
| 153 | 5-ethyl-6-{4-[(3S)-3-fluoropyrrolidin-1-yl]phenyl}-2-oxo-1,2-dihydropyridine-3-carboxylic acid |
| 154 | 5-ethyl-6-{4-[(3R)-3-fluoropyrrolidin-1-yl]phenyl}-2-oxo-1,2-dihydropyridine-3-carboxylic acid |
| 155 | 5-ethyl-2-oxo-6-[4-(phenylamino)phenyl]-1,2-dihydropyridine-3-carboxylic acid |
| 156 | 5-ethyl-2-oxo-6-{4-[2-(1,3-thiazol-2-yl)pyrrolidin-1-yl]phenyl}-1,2-dihydropyridine-3-carboxylic acid |
| 157 | 6-{4-[(2S)-2-carboxypyrrolidin-1-yl]phenyl}-5-ethyl-2-oxo-1,2-dihydropyridine-3-carboxylic acid |
| 158 | 5-ethyl-6-{4-[methyl(phenyl)amino]phenyl}-2-oxo-1,2-dihydropyridine-3-carboxylic acid |
| 159 | 6-(4-{[2-(dimethylamino)ethyl]amino}phenyl)-5-ethyl-2-oxo-1,2-dihydropyridine-3-carboxylic acid |
| 160 | 5-ethyl-6-{4-[ethyl(methyl)amino]phenyl}-2-oxo-1,2-dihydropyridine-3-carboxylic acid |
| 161 | 6-(4-{[2-(dimethylamino)ethyl](methyl)amino}phenyl)-5-ethyl-2-oxo-1,2-dihydropyridine-3-carboxylic acid |
| 162 | 6-[4-(1,3-dihydro-2H-isoindol-2-yl)phenyl]-5-ethyl-2-oxo-1,2-dihydropyridine-3-carboxylic acid |
| 163 | 5-isopropyl-2-oxo-6-[4-(pyrrolidin-1-yl)phenyl]-1,2-dihydropyridine-3-carboxylic acid |
| 164 | 5-cyclopropyl-2-oxo-6-[4-(pyrrolidin-1-yl)phenyl]-1,2-dihydropyridine-3-carboxylic acid |
| 165 | 6-(4-{[2-(dimethylamino)ethyl](methyl)amino}phenyl)-2-oxo-5-(propan-2-yl)-1,2-dihydropyridine-3-carboxylic acid |
| 167 | 6-[4-(3-{[(carboxymethyl)(methyl)carbamoyl]amino}azetidin-1-yl)phenyl]-5-ethyl-2-oxo-1,2-dihydropyridine-3-carboxylic acid |
| 168 | 5-ethyl-6-{4-[3-(5-methyl-2H-tetrazol-2-yl)azetidin-1-yl]phenyl}-2-oxo-1,2-dihydropyridine-3-carboxylic acid |
| 170 | 6-[4-(3-aminoazetidin-1-yl)phenyl]-5-ethyl-2-oxo-1,2-dihydropyridine-3-carboxylic acid |
| 171 | 6-[4-(3-{[(benzyloxy)carbonyl]amino}azetidin-1-yl)phenyl]-5-ethyl-2-oxo-1,2-dihydropyridine-3-carboxylic acid |
| 173 | 6-{4-[3-(cyclopropylamino)pyrrolidin-1-yl]phenyl}-5-ethyl-2-oxo-1,2-dihydropyridine-3-carboxylic acid |
| 175 | 6-[4-(1,3'-bipyrrolidin-1'-yl)phenyl]-5-ethyl-2-oxo-1,2-dihydropyridine-3-carboxylic acid |
| 177 | 6-{4-[(1R,5S,6s)-6-amino-3-azabicyclo[3.1.0]hex-3-yl]phenyl}-5-ethyl-2-oxo-1,2-dihydropyridine-3-carboxylic acid |
| 178 | 6-{4-[(1R,5S,6s)-6-(benzylamino)-3-azabicyclo[3.1.0]hex-3-yl]phenyl}-5-ethyl-2-oxo-1,2-dihydropyridine-3-carboxylic acid |
| 191 | 5-ethyl-2-oxo-6-{4-[3-(pyrrolidin-1-ylmethyl)pyrrolidin-1-yl]phenyl}-1,2-dihydropyridine-3-carboxylic acid |
| 192 | 6-[4-(5,7-dihydro-6H-pyrrolo[3,4-b]pyridin-6-yl)phenyl]-5-ethyl-2-oxo-1,2-dihydropyridine-3-carboxylic acid |
| 209 | 6-[4-(3,6-diazabicyclo[3.1.0]hex-3-yl)phenyl]-5-ethyl-2-oxo-1,2-dihydropyridine-3-carboxylic acid |
| 211 | 6-{4-[(1S,5R,6R)-6-amino-3-azabicyclo[3.2.0]hept-3-yl]phenyl}-5-ethyl-2-oxo-1,2-dihydropyridine-3-carboxylic acid |
| 216 | 6-{4-[(3S,4R)-3-(aminomethyl)-4-methylpyrrolidin-1-yl]phenyl}-5-ethyl-2-oxo-1,2-dihydropyridine-3-carboxylic acid |
| 219 | 6-[4-(3a-cyanooctahydro-2H-isoindol-2-yl)phenyl]-5-ethyl-2-oxo-1,2-dihydropyridine-3-carboxylic acid |
| 221 | 6-{4-[3-(dimethylamino)pyrrolidin-1-yl]-2-fluorophenyl}-5-ethyl-2-oxo-1,2-dihydropyridine-3-carboxylic acid |
| 222 | 5-ethyl-6-[4-(4-hydroxypiperidin-1-yl)phenyl]-2-oxo-1,2-dihydropyridine-3-carboxylic acid |
| 223 | 6-{4-[4-(dimethylamino)piperidin-1-yl]phenyl}-5-ethyl-2-oxo-1,2-dihydropyridine-3-carboxylic acid |
| 224 | 5-ethyl-6-[4-(4-methoxypiperidin-1-yl)phenyl]-2-oxo-1,2-dihydropyridine-3-carboxylic acid |
| 225 | 5-ethyl-6-{2-fluoro-4-[(3R)-3-hydroxypyrrolidin-1-yl]phenyl}-2-oxo-1,2-dihydropyridine-3-carboxylic acid |
| 226 | 5-ethyl-2-oxo-6-{4-[3-(pyridin-4-yl)pyrrolidin-1-yl]phenyl}-1,2-dihydropyridine-3-carboxylic acid |
| 227 | 5-ethyl-2-oxo-6-{4-[3-(pyridin-2-yl)pyrrolidin-1-yl]phenyl}-1,2-dihydropyridine-3-carboxylic acid |
| 228 | 6-[4-(4-aminopiperidin-1-yl)phenyl]-5-ethyl-2-oxo-1,2-dihydropyridine-3-carboxylic acid |
| 230 | 5-ethyl-2-oxo-6-{4-[3-(1H-1,2,3-triazol-1-yl)pyrrolidin-1-yl]phenyl}-1,2-dihydropyridine-3-carboxylic acid |
| 232 | 5-ethyl-6-[4-(3-ethyl-3-hydroxypyrrolidin-1-yl)phenyl]-2-oxo-1,2-dihydropyridine-3-carboxylic acid |

-continued

| Cpd | Name |
|---|---|
| 233 | 5-ethyl-6-[4-(3-hydroxy-3-methylpyrrolidin-1-yl)phenyl]-2-oxo-1,2-dihydropyridine-3-carboxylic acid |
| 234 | 6-[4-(3-{[(2-chlorobenzyl)amino]methyl}pyrrolidin-1-yl)phenyl]-5-ethyl-2-oxo-1,2-dihydropyridine-3-carboxylic acid |
| 235 | 6-{4-[3-(aminomethyl)-3-methylpyrrolidin-1-yl]phenyl}-5-ethyl-2-oxo-1,2-dihydropyridine-3-carboxylic acid |
| 236 | 6-[4-(3-{[(3-chlorobenzyl)amino]methyl}pyrrolidin-1-yl)phenyl]-5-ethyl-2-oxo-1,2-dihydropyridine-3-carboxylic acid |
| 237 | 6-[4-(3-{[(4-chlorobenzyl)amino]methyl}pyrrolidin-1-yl)phenyl]-5-ethyl-2-oxo-1,2-dihydropyridine-3-carboxylic acid |
| 238 | 5-ethyl-6-[4-(3-{[(3-fluorobenzyl)amino]methyl}pyrrolidin-1-yl)phenyl]-2-oxo-1,2-dihydropyridine-3-carboxylic acid |
| 239 | 5-ethyl-6-[4-(3-{[(4-fluorobenzyl)amino]methyl}pyrrolidin-1-yl)phenyl]-2-oxo-1,2-dihydropyridine-3-carboxylic acid |
| 240 | 5-ethyl-6-[4-(3-{[(2-fluorobenzyl)amino]methyl}pyrrolidin-1-yl)phenyl]-2-oxo-1,2-dihydropyridine-3-carboxylic acid |
| 241 | 5-ethyl-2-oxo-6-[4-(3-{[(pyridin-3-ylmethyl)amino]methyl}pyrrolidin-1-yl)phenyl]-1,2-dihydropyridine-3-carboxylic acid |
| 242 | 5-ethyl-2-oxo-6-[4-(3-{[(pyridin-4-ylmethyl)amino]methyl}pyrrolidin-1-yl)phenyl]-1,2-dihydropyridine-3-carboxylic acid |
| 243 | 5-ethyl-2-oxo-6-[4-(3-{[(pyridin-2-ylmethyl)amino]methyl}pyrrolidin-1-yl)phenyl]-1,2-dihydropyridine-3-carboxylic acid |
| 247 | 6-(4-{3-[1-(dimethylamino)cyclopropyl]pyrrolidin-1-yl}phenyl)-5-ethyl-4-hydroxy-2-oxo-1,2-dihydropyridine-3-carboxylic acid |
| 248 | 6-{4-[(3aR,5r,6aS)-5-aminohexahydrocyclopenta[c]pyrrol-2(1H)-yl]phenyl}-5-ethyl-4-hydroxy-2-oxo-1,2-dihydropyridine-3-carboxylic acid |
| 249 | 6-(4-{(3S,4R)-3-[(dibenzylamino)methyl]-4-methylpyrrolidin-1-yl}phenyl)-5-ethyl-4-hydroxy-2-oxo-1,2-dihydropyridine-3-carboxylic acid |
| 250 | 6-{4-[(3aR,5r,6aS)-5-(benzylamino)hexahydrocyclopenta[c]pyrrol-2(1H)-yl]phenyl}-5-ethyl-4-hydroxy-2-oxo-1,2-dihydropyridine-3-carboxylic acid |
| 251 | 6-{4-[(3aR,5r,6aS)-5-(dibenzylamino)hexahydrocyclopenta[c]pyrrol-2(1H)-yl]phenyl}-5-ethyl-4-hydroxy-2-oxo-1,2-dihydropyridine-3-carboxylic acid |
| 253 | 6-{4-[1-(tert-butoxycarbonyl)octahydro-6H-pyrrolo[3,4-b]pyridin-6-yl]phenyl}-5-ethyl-4-hydroxy-2-oxo-1,2-dihydropyridine-3-carboxylic acid |
| 255 | 6-[4-(3-{[benzyl(methyl)amino]methyl}pyrrolidin-1-yl)phenyl]-5-ethyl-4-hydroxy-2-oxo-1,2-dihydropyridine-3-carboxylic acid |
| 280 | 5-ethyl-4-hydroxy-6-[4-(4-hydroxypiperidin-1-yl)phenyl]-2-oxo-1,2-dihydropyridine-3-carboxylic acid |
| 281 | 6-{4-[4-(benzyloxy)piperidin-1-yl]phenyl}-5-ethyl-4-hydroxy-2-oxo-1,2-dihydropyridine-3-carboxylic acid |
| 282 | 5-ethyl-4-hydroxy-6-[4-(4-methoxypiperidin-1-yl)phenyl]-2-oxo-1,2-dihydropyridine-3-carboxylic acid |
| 283 | 6-{4-[4-(dibenzylamino)piperidin-1-yl]phenyl}-5-ethyl-4-hydroxy-2-oxo-1,2-dihydropyridine-3-carboxylic acid |
| 284 | 6-[4-(4-aminopiperidin-1-yl)phenyl]-5-ethyl-4-hydroxy-2-oxo-1,2-dihydropyridine-3-carboxylic acid |
| 285 | 6-{4-[(1R,5S,6s)-6-amino-3-azabicyclo[3.1.0]hex-3-yl]phenyl}-5-ethyl-4-hydroxy-2-oxo-1,2-dihydropyridine-3-carboxylic acid |
| 286 | 5-ethyl-4-hydroxy-2-oxo-6-{4-[3-(pyridin-2-yl)pyrrolidin-1-yl]phenyl}-1,2-dihydropyridine-3-carboxylic acid |
| 287 | 5-ethyl-4-hydroxy-2-oxo-6-{4-[3-(1H-1,2,3-triazol-1-yl)pyrrolidin-1-yl]phenyl}-1,2-dihydropyridine-3-carboxylic acid |
| 288 | 5-ethyl-6-[4-(3-ethyl-3-hydroxypyrrolidin-1-yl)phenyl]-4-hydroxy-2-oxo-1,2-dihydropyridine-3-carboxylic acid |
| 289 | 5-ethyl-4-hydroxy-6-[4-(3-hydroxy-3-methylpyrrolidin-1-yl)phenyl]-2-oxo-1,2-dihydropyridine-3-carboxylic acid |
| 290 | 6-{4-[3-(aminomethyl)-3-methylpyrrolidin-1-yl]phenyl}-5-ethyl-4-hydroxy-2-oxo-1,2-dihydropyridine-3-carboxylic acid |
| 291 | 6-{4-[3-(dimethylamino)pyrrolidin-1-yl]-2-fluorophenyl}-5-ethyl-4-hydroxy-2-oxo-1,2-dihydropyridine-3-carboxylic acid |
| 292 | 5-ethyl-6-{2-fluoro-4-[(3R)-3-hydroxypyrrolidin-1-yl]phenyl}-4-hydroxy-2-oxo-1,2-dihydropyridine-3-carboxylic acid |
| 293 | 5-ethyl-6-{2-fluoro-4-[(3R)-3-fluoropyrrolidin-1-yl]phenyl}-4-hydroxy-2-oxo-1,2-dihydropyridine-3-carboxylic acid |
| 294 | 6-{4-[5-(tert-butoxycarbonyl)-2,5-diazabicyclo[2.2.1]hept-2-yl]phenyl}-5-ethyl-4-hydroxy-2-oxo-1,2-dihydropyridine-3-carboxylic acid |
| 298 | 6-[4-(dimethylamino)phenyl]-5-ethyl-4-methoxy-2-oxo-1,2-dihydropyridine-3-carboxylic acid |
| 299 | 6-{4-[di(prop-2-en-1-yl)amino]phenyl}-5-ethyl-2-oxo-1,2-dihydropyridine-3-carboxylic acid |
| 300 | 6-{4-[di(prop-2-en-1-yl)amino]phenyl}-5-ethyl-4-hydroxy-2-oxo-1,2-dihydropyridine-3-carboxylic acid |
| 301 | 6-[4-(2,5-dihydro-1H-pyrrol-1-yl)phenyl]-5-ethyl-2-oxo-1,2-dihydropyridine-3-carboxylic acid |
| 302 | 6-[4-(2,5-dihydro-1H-pyrrol-1-yl)phenyl]-5-ethyl-4-hydroxy-2-oxo-1,2-dihydropyridine-3-carboxylic acid |

-continued

| Cpd | Name |
|---|---|
| 303 | 6-{4-[(3R,4S)-3,4-dihydroxypyrrolidin-1-yl]phenyl}-5-ethyl-2-oxo-1,2-dihydropyridine-3-carboxylic acid |
| 304 | 6-{4-[(3R,4S)-3,4-dihydroxypyrrolidin-1-yl]phenyl}-5-ethyl-4-hydroxy-2-oxo-1,2-dihydropyridine-3-carboxylic acid |
| 305 | 6-[5-(dimethylamino)thiophen-2-yl]-5-ethyl-2-oxo-1,2-dihydropyridine-3-carboxylic acid |
| 306 | 6-[5-(dimethylamino)thiophen-2-yl]-5-ethyl-4-hydroxy-2-oxo-1,2-dihydropyridine-3-carboxylic acid |
| 307 | 5-ethyl-4-hydroxy-2-oxo-6-[5-(pyrrolidin-1-yl)thiophen-2-yl]-1,2-dihydropyridine-3-carboxylic acid |
| 308 | 5-ethyl-2-oxo-6-[5-(piperidin-1-yl)thiophen-2-yl]-1,2-dihydropyridine-3-carboxylic acid |
| 309 | 5-ethyl-4-hydroxy-2-oxo-6-[5-(piperidin-1-yl)thiophen-2-yl]-1,2-dihydropyridine-3-carboxylic acid |
| 310 | 6-[4-(dimethylamino)phenyl]-2-oxo-1,2-dihydropyridine-3-carboxylic acid |
| 311 | 6-(4-tert-butoxyphenyl)-5-ethyl-2-oxo-1,2-dihydropyridine-3-carboxylic acid |
| 312 | 6-(5-(dimethylamino)pyrazin-2-yl)-5-ethyl-4-hydroxy-2-oxo-1,2-dihydropyridine-3-carboxylic acid |
| 313 | 5-ethyl-4-hydroxy-2-oxo-6-(5-(pyrrolidin-1-yl)pyrazin-2-yl)-1,2-dihydropyridine-3-carboxylic acid |
| 314 | 6-(5-(3-(dimethylamino)pyrrolidin-1-yl)pyrazin-2-yl)-5-ethyl-4-hydroxy-2-oxo-1,2-dihydropyridine-3-carboxylic acid |
| 315 | 4-hydroxy-5-methyl-2-oxo-6-(5-(pyrrolidin-1-yl)pyridin-2-yl)-1,2-dihydropyridine-3-carboxylic acid |
| 316 | 6-(5-(3-(dimethylamino)pyrrolidin-1-yl)pyridin-2-yl)-4-hydroxy-5-methyl-2-oxo-1,2-dihydropyridine-3-carboxylic acid |
| 317 | 6-(5-((1R,5S,6s)-6-amino-3-azabicyclo[3.1.0]hexan-3-yl)pyridin-2-yl)-4-hydroxy-5-methyl-2-oxo-1,2-dihydropyridine-3-carboxylic acid |
| 318 | 6-(4-((1R,5S,6s)-6-amino-3-azabicyclo[3.1.0]hexan-3-yl)-2-methylphenyl)-4-hydroxy-5-methyl-2-oxo-1,2-dihydropyridine-3-carboxylic acid |
| 319 | 5-ethyl-4-hydroxy-6-(4-(7-methyl-2,7-diazaspiro[3.5]nonan-2-yl)phenyl)-2-oxo-1,2-dihydropyridine-3-carboxylic acid |
| 320 | 6-(4-(2,7-diazaspiro[3.5]nonan-2-yl)phenyl)-5-ethyl-4-hydroxy-2-oxo-1,2-dihydropyridine-3-carboxylic acid |
| 321 | 6-(4-(2,7-diazaspiro[4.4]nonan-2-yl)phenyl)-5-ethyl-4-hydroxy-2-oxo-1,2-dihydropyridine-3-carboxylic acid |
| 322 | 5-ethyl-4-hydroxy-6-(4-(7-methyl-2,7-diazaspiro[4.4]nonan-2-yl)phenyl)-2-oxo-1,2-dihydropyridine-3-carboxylic acid |
| 323 | 6-(4-(2,5-diazaspiro[3.4]octan-2-yl)phenyl)-5-ethyl-4-hydroxy-2-oxo-1,2-dihydropyridine-3-carboxylic acid |
| 324 | 6-(4-(2,6-diazaspiro[3.3]heptan-2-yl)phenyl)-5-ethyl-4-hydroxy-2-oxo-1,2-dihydropyridine-3-carboxylic acid |
| 325 | 5-ethyl-6-(4-(ethylamino)phenyl)-4-hydroxy-2-oxo-1,2-dihydropyridine-3-carboxylic acid |
| 326 | 5-ethyl-4-hydroxy-6-(4-(methylamino)phenyl)-2-oxo-1,2-dihydropyridine-3-carboxylic acid |
| 327 | 6-(4-(dimethylamino)phenyl)-4-hydroxy-2-oxo-5-(2-oxoethyl)-1,2-dihydropyridine-3-carboxylic acid |
| 328 | 6-(4-(dimethylamino)phenyl)-4-hydroxy-5-(2-hydroxyethyl)-2-oxo-1,2-dihydropyridine-3-carboxylic acid |
| 329 | 5-(2,3-dihydroxypropyl)-6-(4-(dimethylamino)phenyl)-4-hydroxy-2-oxo-1,2-dihydropyridine-3-carboxylic acid |
| 330 | (E)-6-(4-(dimethylamino)phenyl)-4-hydroxy-2-oxo-5-(prop-1-enyl)-1,2-dihydropyridine-3-carboxylic acid |
| 331 | 6-(4-(dimethylamino)phenyl)-4-hydroxy-5-(hydroxymethyl)-2-oxo-1,2-dihydropyridine-3-carboxylic acid |
| 332 | 6-(4-(dimethylamino)phenyl)-4-hydroxy-5-(methoxymethyl)-2-oxo-1,2-dihydropyridine-3-carboxylic acid |
| 333 | 6-(4-(dimethylamino)phenyl)-4-hydroxy-2-oxo-5-(prop-1-ynyl)-1,2-dihydropyridine-3-carboxylic acid |
| 334 | 5-ethyl-4-hydroxy-6-(4-hydroxyphenyl)-2-oxo-1,2-dihydropyridine-3-carboxylic acid |
| 335 | 6-(6-(3-(dimethylamino)pyrrolidin-1-yl)pyridin-3-yl)-5-ethyl-4-hydroxy-2-oxo-1,2-dihydropyridine-3-carboxylic acid |
| 336 | 5-ethyl-4-hydroxy-2-oxo-6-(6-(pyrrolidin-1-yl)pyridin-3-yl)-1,2-dihydropyridine-3-carboxylic acid |
| 337 | 6-(6-(3-(dimethylamino)pyrrolidin-1-yl)pyridin-3-yl)-4-hydroxy-5-methyl-2-oxo-1,2-dihydropyridine-3-carboxylic acid |
| 338 | 5-ethyl-4-hydroxy-6-(4-(1-methylpiperidin-4-yl)phenyl)-2-oxo-1,2-dihydropyridine-3-carboxylic acid |
| 339 | 5-ethyl-6-(4-(1-ethylpiperidin-4-yl)phenyl)-4-hydroxy-2-oxo-1,2-dihydropyridine-3-carboxylic acid |
| 340 | 5-ethyl-4-hydroxy-2-oxo-6-(4-(1,2,3,6-tetrahydropyridin-4-yl)phenyl)-1,2-dihydropyridine-3-carboxylic acid |
| 341 | 5-ethyl-6-(4-(1-ethyl-1,2,3,6-tetrahydropyridin-4-yl)phenyl)-4-hydroxy-2-oxo-1,2-dihydropyridine-3-carboxylic acid |
| 342 | 5-ethyl-4-hydroxy-6-(4-(1-methyl-1,2,3,6-tetrahydropyridin-4-yl)phenyl)-2-oxo-1,2-dihydropyridine-3-carboxylic acid |

| Cpd | Name |
|---|---|
| 343 | 6-(4-(2-(dimethylamino)ethyl)phenyl)-5-ethyl-4-hydroxy-2-oxo-1,2-dihydropyridine-3-carboxylic acid |
| 344 | 5-ethyl-6-(1-methyl-1H-pyrazol-5-yl)-2-oxo-1,2-dihydropyridine-3-carboxylic acid |
| 345 | 5-ethyl-4-hydroxy-6-(1-methyl-1H-pyrazol-5-yl)-2-oxo-1,2-dihydropyridine-3-carboxylic acid |
| 346 | 5-ethyl-6-(1-methyl-1H-pyrazol-4-yl)-2-oxo-1,2-dihydropyridine-3-carboxylic acid |
| 347 | 5-ethyl-4-hydroxy-6-(1-methyl-1H-pyrazol-4-yl)-2-oxo-1,2-dihydropyridine-3-carboxylic acid |
| 348 | 5-ethyl-6-(1-methyl-5-(pyrrolidin-1-ylmethyl)-1H-pyrrol-3-yl)-2-oxo-1,2-dihydropyridine-3-carboxylic acid |
| 349 | 5-ethyl-6-(1-methyl-5-(piperidin-1-ylmethyl)-1H-pyrrol-3-yl)-2-oxo-1,2-dihydropyridine-3-carboxylic acid |
| 350 | 5-ethyl-6-(1-methyl-5-(pyrrolidin-1-ylmethyl)-1H-pyrrol-2-yl)-2-oxo-1,2-dihydropyridine-3-carboxylic acid |
| 351 | 6-(5-((dimethylamino)methyl)-1-methyl-1H-pyrrol-2-yl)-5-ethyl-2-oxo-1,2-dihydropyridine-3-carboxylic acid |
| 352 | 5-ethyl-6-(1-methyl-5-(piperidin-1-ylmethyl)-1H-pyrrol-2-yl)-2-oxo-1,2-dihydropyridine-3-carboxylic acid,and |
| 353 | 6-(5-((3-(dimethylamino)pyrrolidin-1-yl)methyl)-1-methyl-1H-pyrrol-2-yl)-5-ethyl-2-oxo-1,2-dihydropyridine-3-carboxylic acid; | wherein the form of the compound is selected from a free acid, free base, salt, hydrate, solvate, clathrate, isotopologue, racemate, enantiomer, diastereomer, stereoisomer, polymorph or tautomer form thereof.

In another embodiment, the compound or a form thereof is isolated for use.

In another embodiment, wherein the compound or a form thereof is selected from:

| Cpd | Name |
|---|---|
| 22 | 5-(aminomethyl)-6-[4-(dimethylamino)phenyl]-2-oxo-1,2-dihydropyridine-3-carboxylic acid hydrochloride |
| 92 | 5-ethyl-6-[3-fluoro-4-(piperazin-1-yl)phenyl]-2-oxo-1,2-dihydropyridine-3-carboxylic acid trifluoroacetate |
| 103 | 5-ethyl-2-oxo-6-[4-(piperazin-1-yl)phenyl]-1,2-dihydropyridine-3-carboxylic acid trifluoroacetate |
| 105 | 5-ethyl-4-hydroxy-2-oxo-6-[4-(piperazin-1-yl)phenyl]-1,2-dihydropyridine-3-carboxylic acid trifluoroacetate |
| 131 | 6-[4-(3-aminopyrrolidin-1-yl)phenyl]-5-ethyl-2-oxo-1,2-dihydropyridine-3-carboxylic acid trifluoroacetate |
| 132 | 6-{4-[(3S)-3-aminopyrrolidin-1-yl]phenyl}-5-ethyl-2-oxo-1,2-dihydropyridine-3-carboxylic acid hydrochloride |
| 133 | 6-{4-[(3R,4R)-3-amino-4-hydroxypyrrolidin-1-yl]phenyl}-5-ethyl-2-oxo-1,2-dihydropyridine-3-carboxylic acid hydrochloride |
| 134 | 6-{4-[(3R,4R)-3-amino-4-methoxypyrrolidin-1-yl]phenyl}-5-ethyl-2-oxo-1,2-dihydropyridine-3-carboxylic acid hydrochloride |
| 135 | 6-{4-[(3R,4S)-3-amino-4-methoxypyrrolidin-1-yl]phenyl}-5-ethyl-2-oxo-1,2-dihydropyridine-3-carboxylic acid hydrochloride |
| 136 | 6-{4-[(3R,4S)-3-amino-4-hydroxypyrrolidin-1-yl]phenyl}-5-ethyl-2-oxo-1,2-dihydropyridine-3-carboxylic acid trifluoroacetate |
| 138 | 6-[4-(2,5-diazabicyclo[2.2.1]hept-2-yl)phenyl]-5-ethyl-2-oxo-1,2-dihydropyridine-3-carboxylic acid trifluoroacetate |
| 140 | 5-ethyl-6-{4-[3-(morpholin-4-yl)pyrrolidin-1-yl]phenyl}-2-oxo-1,2-dihydropyridine-3-carboxylic acid trifluoroacetate |
| 143 | 5-ethyl-2-oxo-6-{4-[(2S)-2-(pyrrolidin-1-ylmethyl)pyrrolidin-1-yl]phenyl}-1,2-dihydropyridine-3-carboxylic acid trifluoroacetate |
| 150 | 6-{4-[(3R)-3-(dimethylamino)pyrrolidin-1-yl]phenyl}-5-ethyl-2-oxo-1,2-dihydropyridine-3-carboxylic acid trifluoroacetate |
| 151 | 6-{4-[(3S)-3-(dimethylamino)pyrrolidin-1-yl]phenyl}-5-ethyl-2-oxo-1,2-dihydropyridine-3-carboxylic acid hydrochloride |
| 166 | 6-[4-(3-amino-3-methylpyrrolidin-1-yl)phenyl]-5-ethyl-2-oxo-1,2-dihydropyridine-3-carboxylic acid trifluoroacetate |
| 169 | 6-[4-(1-amino-3-azabicyclo[3.1.0]hex-3-yl)phenyl]-5-ethyl-2-oxo-1,2-dihydropyridine-3-carboxylic acid hydrochloride |
| 172 | 6-{4-[3-(diethylamino)pyrrolidin-1-yl]phenyl}-5-ethyl-2-oxo-1,2-dihydropyridine-3-carboxylic acid trifluoroacetate |
| 174 | 6-{4-[3-(benzylamino)pyrrolidin-1-yl]phenyl}-5-ethyl-2-oxo-1,2-dihydropyridine-3-carboxylic acid hydrochloride |
| 176 | 6-{4-[(1R,5S,6s)-6-(dibenzylamino)-3-azabicyclo[3.1.0]hex-3-yl]phenyl}-5-ethyl-2-oxo-1,2-dihydropyridine-3-carboxylic acid hydrochloride |
| 179 | 5-ethyl-6-[4-(hexahydropyrrolo[3,4-b][1,4]oxazin-6(2H)-yl)phenyl]-2-oxo-1,2-dihydropyridine-3-carboxylic acid hydrochloride |
| 180 | 6-[4-(4-benzylhexahydropyrrolo[3,4-b][1,4]oxazin-6(2H)-yl)phenyl]-5-ethyl-2-oxo-1,2-dihydropyridine-3-carboxylic acid trifluoroacetate |
| 181 | 6-(4-{3-[(dibenzylamino)methyl]pyrrolidin-1-yl}phenyl)-5-ethyl-2-oxo-1,2-dihydropyridine-3-carboxylic acid trifluoroacetate |

-continued

| Cpd | Name |
|---|---|
| 182 | 6-(4-{3-[(benzylamino)methyl]pyrrolidin-1-yl} phenyl)-5-ethyl-2-oxo-1,2-dihydropyridine-3-carboxylic acid hydrochloride |
| 183 | 6-[4-(3-{[benzyl(methyl)amino]methyl}pyrrolidin-1-yl)phenyl]-5-ethyl-2-oxo-1,2-dihydropyridine-3-carboxylic acid trifluoroacetate |
| 184 | 5-ethyl-6-(4-{3-[(methylamino)methyl]pyrrolidin-1-yl} phenyl)-2-oxo-1,2-dihydropyridine-3-carboxylic acid hydrochloride |
| 185 | 6-(4-{3-[(dimethylamino)methyl]pyrrolidin-1-yl}phenyl)-5-ethyl-2-oxo-1,2-dihydropyridine-3-carboxylic acid trifluoroacetate |
| 186 | 5-ethyl-6-{4-[(4aR,7aS)-hexahydropyrrolo[3,4-b][1,4]oxazin-4(4aH)-yl]phenyl}-2-oxo-1,2-dihydropyridine-3-carboxylic acid trifluoroacetate |
| 187 | 5-ethyl-6-{4-[(3aR,6aR)-1-methylhexahydropyrrolo[3,4-b]pyrrol-5(1H)-yl]phenyl}-2-oxo-1,2-dihydropyridine-3-carboxylic acid trifluoroacetate |
| 188 | 6-{4-[3-(aminomethyl)pyrrolidin-1-yl]phenyl}-5-ethyl-2-oxo-1,2-dihydropyridine-3-carboxylic acid trifluoroacetate |
| 189 | 6-{4-[(3aR,6aR)-1-benzylhexahydropyrrolo[3,4-b]pyrrol-5(1H)-yl]phenyl}-5-ethyl-2-oxo-1,2-dihydropyridine-3-carboxylic acid trifluoroacetate |
| 190 | 5-ethyl-6-{4-[(3aR,6aR)-hexahydropyrrolo[3,4-b]pyrrol-5(1H)-yl]phenyl}-2-oxo-1,2-dihydropyridine-3-carboxylic acid trifluoroacetate |
| 193 | 6-{4-[(3aR,4R,7aS)-4-(dimethylamino)octahydro-2H-isoindol-2-yl]phenyl}-5-ethyl-2-oxo-1,2-dihydropyridine-3-carboxylic acid hydrochloride |
| 194 | 6-(4-{(3aR,4R,7aS)-4-[benzyl(methyl)amino]octahydro-2H-isoindol-2-yl}phenyl)-5-ethyl-2-oxo-1,2-dihydropyridine-3-carboxylic acid trifluoroacetate |
| 195 | 5-ethyl-6-{4-[(3aR,4R,7aS)-4-(methylamino)octahydro-2H-isoiridol-2-yl]phenyl}-2-oxo-1,2-dihydropyridine-3-carboxylic acid trifluoroacetate |
| 196 | 6-{4-[(3aR,4R,7aS)-4-(dibenzylamino)octahydro-2H-isoindol-2-yl]phenyl}-5-ethyl-2-oxo-1,2-dihydropyridine-3-carboxylic acid trifluoroacetate |
| 197 | 6-{4-[(3aR,4R,7aS)-4-aminooctahydro-2H-isoindol-2-yl]phenyl}-5-ethyl-2-oxo-1,2-dihydropyridine-3-carboxylic acid trifluoroacetate |
| 198 | 6-{4-[(3aR,4R,6aS)-4-(dimethylamino)hexahydrocyclopenta[c]pyrrol-2(1H)-yl]phenyl}-5-ethyl-2-oxo-1,2-dihydropyridine-3-carboxylic acid hydrochloride |
| 199 | 6-{4-[(3aR,4R,6aS)-4-[benzyl(methyl)amino]hexahydrocyclopenta[c]pyrrol-2(1H)-yl]phenyl}-5-ethyl-2-oxo-1,2-dihydropyridine-3-carboxylic acid hydrochloride |
| 200 | 5-ethyl-6-{4-[(3aR,4R,6aS)-4-(methylamino)hexahydrocyclopenta[c]pyrrol-2(1H)-yl]phenyl}-2-oxo-1,2-dihydropyridine-3-carboxylic acid hydrochloride |
| 201 | 6-{4-[(3aR,4R,6aS)-4-(dibenzylamino)hexahydrocyclopenta[c]pyrrol-2(1H)-yl]phenyl}-5-ethyl-2-oxo-1,2-dihydropyridine-3-carboxylic acid trifluoroacetate |
| 202 | 6-{4-[(3aR,4R,6aS)-4-aminohexahydrocyclopenta[c]pyrrol-2(1H)-yl]phenyl}-5-ethyl-2-oxo-1,2-dihydropyridine-3-carboxylic acid trifluoroacetate |
| 203 | 6-{4-[(3aR,4S,7aS)-4-aminooctahydro-2H-isoindol-2-yl]phenyl}-5-ethyl-2-oxo-1,2-dihydropyridine-3-carboxylic acid trifluoroacetate |
| 204 | 6-{4-[(3aR,4S,6aS)-4-aminohexahydrocyclopenta[c]pyrrol-2(1H)-yl]phenyl}-5-ethyl-2-oxo-1,2-dihydropyridine-3-carboxylic acid trifluoroacetate |
| 205 | 6-(4-{(3aR,7aS)-3a-[(dimethylamino)methyl]octahydro-2H-isoindol-2-yl}phenyl)-5-ethyl-2-oxo-1,2-dihydropyridine-3-carboxylic acid trifluoroacetate |
| 206 | 6-{4-[(3aR,6aS)-5-benzylhexahydropyrrolo[3,4-c]pyrrol-2(1H)-yl]phenyl}-5-ethyl-2-oxo-1,2-dihydropyridine-3-carboxylic acid hydrochloride |
| 207 | 5-ethyl-6-{4-[(3aR,6aS)-hexahydropyrrolo[3,4-c]pyrrol-2(1H)-yl]phenyl}-2-oxo-1,2-dihydropyridine-3-carboxylic acid hydrochloride |
| 208 | 5-ethyl-6-{4-[(3aR,6aS)-5-methylhexahydropyrrolo[3,4-c]pyrrol-2(1H)-yl]phenyl}-2-oxo-1,2-dihydropyridine-3-carboxylic acid hydrochloride |
| 210 | 5-ethyl-6-{4-[(1S,5R,6R)-6-(methylamino)-3-azabicyclo[3.2.0]hept-3-yl]phenyl}-2-oxo-1,2-dihydropyridine-3-carboxylic acid hydrochloride |
| 212 | 6-{4-[(1S,5R,6S)-6-amino-3-azabicyclo[3.2.0]hept-3-yl]phenyl}-5-ethyl-2-oxo-1,2-dihydropyridine-3-carboxylic acid hydrochloride |
| 213 | 5-ethyl-6-[4-(octahydro-6H-pyrrolo[3,4-b]pyridin-6-yl)phenyl]-2-oxo-1,2-dihydropyridine-3-carboxylic acid hydrochloride |
| 214 | 6-[4-(7-amino-5-azaspiro[2.4]hept-5-yl)phenyl]-5-ethyl-2-oxo-1,2-dihydropyridine-3-carboxylic acid trifluoroacetate |
| 215 | 5-ethyl-6-{4-[(3aR,5r,6aS)-5-(methylamino)hexahydrocyclopenta[c]pyrrol-2(1H)-yl]phenyl}-2-oxo-1,2-dihydropyridine-3-carboxylic acid trifluoroacetate |
| 217 | 6-(4-{3-[1-(benzylamino)cyclopropyl]pyrrolidin-1-yl}phenyl)-5-ethyl-2-oxo-1,2-dihydropyridine-3-carboxylic acid trifluoroacetate |
| 218 | 6-{4-[3-(1-aminocyclobutyl)pyrrolidin-1-yl]phenyl}-5-ethyl-2-oxo-1,2-dihydropyridine-3-carboxylic acid trifluoroacetate |
| 220 | (3aR,6aR)-2-[4-(5-carboxy-3-ethyl-6-oxo-1,6-dihydropyridin-2-yl)phenyl]hexahydrocyclopenta[c]pyrrole-3a(1H)-carboxylic acid trifluoroacetate |
| 231 | 6-{4-[(1R,5S,6s)-6-amino-3-azabicyclo[3.1.0]hex-3-yl]-2-fluorophenyl}-5-ethyl-2-oxo-1,2-dihydropyridine-3-carboxylic acid trifluoroacetate |
| 244 | 6-{4-[(3aR,4S,7aS)-4-azidooctahydro-2H-isoindol-2-yl]phenyl}-5-ethyl-2-oxo-1,2-dihydropyridine-3-carboxylic acid trifluoroacetate |
| 245 | 6-{4-[(3aR,4S,6aS)-4-azidohexahydrocyclopenta[c]pyrrol-2(1H)-yl]phenyl}-5-ethyl-2-oxo-1,2-dihydropyridine-3-carboxylic acid trifluoroacetate |
| 246 | 5-ethyl-6-{4-[(3aR,6aR)-hexahydropyrrolo[3,4-b]pyrrol-5(1H)-yl]phenyl}-4-hydroxy-2-oxo-1,2-dihydropyridine-3-carboxylic acid hydrochloride |
| 252 | 6-[4-(7-amino-5-azaspiro[2.4]hept-5-yl)phenyl]-5-ethyl-4-hydroxy-2-oxo-1,2-dihydropyridine-3-carboxylic acid trifluoroacetate |

| Cpd | Name |
|---|---|
| 254 | 5-ethyl-4-hydroxy-6-(4-{3-[(methylamino)methyl]pyrrolidin-1-yl} phenyl)-2-oxo-1,2-dihydropyridine-3-carboxylic acid hydrochloride |
| 256 | 5-ethyl-4-hydroxy-6-{4-[(3aR,4R,6aS)-4-(methylamino)hexahydrocyclopenta[c]pyrrol-2(1H)-yl]phenyl}-2-oxo-1,2-dihydropyridine-3-carboxylic acid hydrochloride |
| 257 | 6-[4-(1,3'-bipyrrolidin-1'-yl)phenyl]-5-ethyl-4-hydroxy-2-oxo-1,2-dihydropyridine-3-carboxylic acid hydrochloride |
| 258 | 6-{4-[(3aR,4S,7aS)-4-aminooctahydro-2H-isoindol-2-yl]phenyl}-5-ethyl-4-hydroxy-2-oxo-1,2-dihydropyridine-3-carboxylic acid hydrochloride |
| 259 | 6-{4-[(1R,5S,6s)-6-amino-3-azabicyclo[3.1.0]hex-3-yl]phenyl}-4-hydroxy-5-methyl-2-oxo-1,2-dihydropyridine-3-carboxylic acid hydrochloride |
| 260 | 4-hydroxy-5-methyl-6-{4-[(3aR,4R,7aS)-4-(methylamino)octahydro-2H-isoiridol-2-yl]phenyl}-2-oxo-1,2-dihydropyridine-3-carboxylic acid hydrochloride |
| 261 | 6-{4-[(3aR,4R,7aS)-4-(dimethylamino)octahydro-2H-isoindol-2-yl]phenyl}-5-ethyl-4-hydroxy-2-oxo-1,2-dihydropyridine-3-carboxylic acid hydrochloride |
| 262 | 6-{4-[(3aR,4R,7aS)-4-aminooctahydro-2H-isoindol-2-yl]phenyl}-5-ethyl-4-hydroxy-2-oxo-1,2-dihydropyridine-3-carboxylic acid trifluoroacetate |
| 263 | 6-{4-[(3aR,4R,6aS)-4-(dimethylamino)hexahydrocyclopenta[c]pyrrol-2(1H)-yl]phenyl}-5-ethyl-4-hydroxy-2-oxo-1,2-dihydropyridine- carboxylic acid hydrochloride |
| 264 | 6-{4-[(3aR,4R,6aS)-4-aminohexahydrocyclopenta[c]pyrrol-2(1H)-yl]phenyl}-5-ethyl-4-hydroxy-2-oxo-1,2-dihydropyridine-3-carboxylic acid hydrochloride |
| 265 | 6-{4-[(3aR,4S,6aS)-4-aminohexahydrocyclopenta[c]pyrrol-2(1H)-yl]phenyl}-5-ethyl-4-hydroxy-2-oxo-1,2-dihydropyridine-3-carboxylic acid trifluoroacetate |
| 266 | 6-(4-{(3aR,7aS)-3a-[(dimethylamino)methyl]octahydro-2H-isoindol-2-yl}phenyl)-5-ethyl-4-hydroxy-2-oxo-1,2-dihydropyridine-3-carboxylic acid hydrochloride |
| 267 | 5-ethyl-4-hydroxy-6-{4-[(3aR,4S,6aS)-4-(methylamino)hexahydrocyclopenta[c]pyrrol-2(1H)-yl]phenyl}-2-oxo-1,2-dihydropyridine-3-carboxylic acid hydrochloride |
| 268 | 5-ethyl-4-hydroxy-6-{4-[(3aR,4S,7aS)-4-(methylamino)octahydro-2H-isoindol-2-yl]phenyl}-2-oxo-1,2-dihydropyridine-3-carboxylic acid hydrochloride |
| 269 | 6-{4-[(1R,5S,6s)-6-amino-3-azabicyclo[3.1.0]hex-3-yl]phenyl}-5-ethyl-4-hydroxy-2-oxo-1,2-dihydropyridine-3-carboxylic acid hydrochloride |
| 270 | 5-ethyl-4-hydroxy-6-{4-[(1R,5S,6s)-6-(methylamino)-3-azabicyclo[3.1.0]hex-3-yl]phenyl}-2-oxo-1,2-dihydropyridine-3-carboxylic acid hydrochloride |
| 271 | 6-{4-[(1R,5S,6s)-6-(dimethylamino)-3-azabicyclo[3.1.0]hex-3-yl]phenyl}-5-ethyl-4-hydroxy-2-oxo-1,2-dihydropyridine-3-carboxylic acid hydrochloride |
| 272 | 5-ethyl-4-hydroxy-6-[4-(octahydro-6H-pyrrolo[3,4-b]pyridin-6-yl)phenyl]-2-oxo-1,2-dihydropyridine-3-carboxylic acid hydrochloride |
| 273 | 5-ethyl-4-hydroxy-6-{4-[(3aR,6aS)-5-methylhexahydropyrrolo[3,4-c]pyrrol-2(1H)-yl]phenyl}-2-oxo-1,2-dihydropyridine-3-carboxylic acid hydrochloride |
| 274 | 5-ethyl-6-{4-[(3aR,6aS)-hexahydropyrrolo[3,4-c]pyrrol-2(1H)-yl]phenyl}-4-hydroxy-2-oxo-1,2-dihydropyridine-3-carboxylic acid hydrochloride |
| 275 | 6-{4-[3-(dimethylamino)pyrrolidin-1-yl]phenyl}-5-ethyl-4-hydroxy-2-oxo-1,2-dihydropyridine-3-carboxylic acid hydrochloride |
| 276 | 6-[4-(3a-cyanooctahydro-2H-isoindol-2-yl)phenyl]-5-ethyl-4-hydroxy-2-oxo-1,2-dihydropyridine-3-carboxylic acid trifluoroacetate |
| 277 | 6-[4-(1-amino-3-azabicyclo[3.1.0]hex-3-yl)phenyl]-5-ethyl-4-hydroxy-2-oxo-1,2-dihydropyridine-3-carboxylic acid hydrochloride |
| 278 | 6-[4-(2,8-diazaspiro[4.5]dec-2-yl)phenyl]-5-ethyl-4-hydroxy-2-oxo-1,2-dihydropyridine-3-carboxylic acid hydrochloride |
| 279 | 6-{4-[3-(2-aminopropan-2-yl)pyrrolidin-1-yl]phenyl}-5-ethyl-4-hydroxy-2-oxo-1,2-dihydropyridine-3-carboxylic acid hydrochloride |
| 295 | 6-[4-(2,5-diazabicyclo[2.2.1]hept-2-yl)phenyl]-5-ethyl-4-hydroxy-2-oxo-1,2-dihydropyridine-3-carboxylic acid trifluoroacetate |
| 296 | 5-ethyl-4-hydroxy-6-{4-[(3aR,4R,7aS)-4-(methylamino)octahydro-2H-isoindol-2-yl]phenyl}-2-oxo-1,2-dihydropyridine-3-carboxylic acid hydrochloride, and |
| 297 | 5-ethyl-6-{4-[(3aS)-1,3,3a,4,5,6-hexahydro-2H-isoindol-2-yl]phenyl}-4-hydroxy-2-oxo-1,2-dihydropyridine-3-carboxylic acid hydrochloride; | wherein the form of the compound is selected from a free acid, free base, hydrate, solvate, clathrate, isotopologue, racemate, enantiomer, diastereomer, stereoisomer, polymorph or tautomer form thereof.

In another embodiment, the compound or a form thereof is isolated for use.

Chemical Definitions

The chemical terms used above and throughout the description herein, unless specifically defined otherwise, shall be understood by one of ordinary skill in the art to have the following indicated meanings.

As used herein, the term "$C_{1-10}$alkyl" generally refers to saturated hydrocarbon radicals having from one to ten carbon atoms in a straight or branched chain configuration, including, without limitation, methyl, ethyl, n-propyl, isopropyl, n-butyl, isobutyl, sec-butyl, tert-butyl, n-pentyl, n-hexyl, n-heptyl, n-octyl, n-nonyl, n-decyl and the like. In some embodiments, $C_{1-10}$alkyl includes $C_{1-8}$alkyl, $C_{1-6}$alkyl, $C_{1-4}$alkyl and the like. A $C_{1-10}$alkyl radical may be optionally substituted where allowed by available valences.

As used herein, the term "$C_{2-8}$alkenyl" generally refers to partially unsaturated hydrocarbon radicals having from two to eight carbon atoms in a straight or branched chain configuration and one or more carbon-carbon double bonds therein, including, without limitation, ethenyl, allyl, propenyl and the like. In some embodiments, $C_{2-8}$alkenyl includes $C_{2-6}$alkenyl, $C_{2-4}$alkenyl and the like. A $C_{2-8}$alkenyl radical may be optionally substituted where allowed by available valences.

As used herein, the term "$C_{2-8}$alkynyl" generally refers to partially unsaturated hydrocarbon radicals having from two to eight carbon atoms in a straight or branched chain configuration and one or more carbon-carbon triple bonds therein, including, without limitation, ethynyl, propynyl and the like. In some embodiments, $C_{2-8}$alkynyl includes $C_{2-6}$alkynyl, $C_{2-4}$alkynyl and the like. A $C_{2-8}$alkynyl radical may be optionally substituted where allowed by available valences.

As used herein, the term "$C_{1-8}$alkoxy" generally refers to saturated hydrocarbon radicals having from one to eight carbon atoms in a straight or branched chain configuration of the formula: —O—$C_{1-8}$alkyl, including, without limitation, methoxy, ethoxy, n-propoxy, isopropoxy, n-butoxy, isobutoxy, sec-butoxy, tert-butoxy, n-pentoxy, n-hexoxy and the like. In some embodiments, $C_{1-8}$alkoxy includes $C_{1-6}$alkoxy, $C_{1-4}$alkoxy and the like. A $C_{1-8}$alkoxy radical may be optionally substituted where allowed by available valences.

As used herein, the term "$C_{3-14}$cycloalkyl" generally refers to a saturated monocyclic, bicyclic or polycyclic hydrocarbon radical, including, without limitation, cyclopropyl, cyclobutyl, cyclopentyl, cyclohexyl, cycloheptyl, cyclooctyl, 1H-indanyl, indenyl, tetrahydro-naphthalenyl and the like. In some embodiments, $C_{3-14}$cycloalkyl includes $C_{3-8}$cycloalkyl, $C_{5-8}$cycloalkyl, $C_{3-10}$cycloalkyl and the like. A $C_{3-14}$cycloalkyl radical may be optionally substituted where allowed by available valences.

As used herein, the term "$C_{3-14}$cycloalkenyl" generally refers to a partially unsaturated monocyclic, bicyclic or polycyclic hydrocarbon radical having one or more chemically stable carbon-carbon double bonds therein, including, without limitation, cyclopropenyl, cyclobutenyl, cyclopentenyl, cyclohexenyl, cycloheptenyl, cyclooctenyl and the like. In some embodiments, $C_{3-14}$cycloalkenyl includes $C_{3-8}$cycloalkenyl, $C_{5-8}$cycloalkenyl, $C_{3-10}$cycloalkenyl and the like. A $C_{3-14}$cycloalkenyl radical may be optionally substituted where allowed by available valences.

As used herein, the term "aryl" generally refers to a monocyclic, bicyclic or polycyclic aromatic carbon atom ring structure radical, including, without limitation, phenyl, naphthyl, anthracenyl, fluorenyl, azulenyl, phenanthrenyl and the like. An aryl radical may be optionally substituted where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including, without limitation, furanyl, thienyl (also referred to as thiophenyl), pyrrolyl, pyrazolyl, imidazolyl, isoxazolyl, isothiazolyl, oxazolyl, thiazolyl, triazolyl, oxadiazolyl, thiadiazolyl, tetrazolyl, pyranyl, thiopyranyl, pyridinyl, pyrimidinyl, pyrazinyl, pyridazinyl, triazinyl, indolyl, indazolyl, indolizinyl, benzofuranyl, benzothienyl, benzimidazolyl, benzothiazolyl, benzooxazolyl, 9H-purinyl, quinoxalinyl, isoindolyl, quinolinyl, isoquinolinyl, quinazolinyl, acridinyl and the like. A heteroaryl radical may be optionally substituted on a carbon or nitrogen atom ring member where allowed by available valences.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, without limitation, oxiranyl, oxetanyl, azetidinyl, dihydrofuranyl, tetrahydrofuranyl, dihydrothienyl, tetrahydrothienyl, pyrrolinyl, pyrrolidinyl, dihydropyrazolyl, pyrazolinyl, pyrazolidinyl, dihydroimidazolyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, dihydro-2H-pyranyl, dihydro-pyridinyl, tetrahydro-pyridinyl, 1,2,3,6-tetrahydropyridinyl, hexahydro-pyridinyl, dihydro-pyrimidinyl, tetrahydro-pyrimidinyl, 1,4,5,6-tetrahydropyrimidinyl, dihydro-pyrazinyl, tetrahydro-pyrazinyl, dihydro-pyridazinyl, tetrahydro-pyridazinyl, piperazinyl, piperidinyl, morpholinyl, thiomorpholinyl, dihydro-triazinyl, tetrahydro-triazinyl, hexahydro-triazinyl, 1,4-diazepanyl, dihydro-indolyl, indolinyl, tetrahydro-indolyl, dihydro-indazolyl, tetrahydro-indazolyl, dihydro-isoindolyl, dihydro-benzofuranyl, tetrahydro-benzofuranyl, dihydro-benzothienyl, tetrahydro-benzothienyl, dihydro-benzimidazolyl, tetrahydro-benzimidazolyl, dihydro-benzooxazolyl, 2,3-dihydrobenzoldloxazolyl, tetrahydro-benzooxazolyl, dihydro-benzooxazinyl, 3,4-dihydro-2H-benzo[b][1,4]oxazinyl, tetrahydro-benzooxazinyl, benzo[1,3]dioxolyl, benzo[1,4]dioxanyl, dihydro-purinyl, tetrahydro-purinyl, dihydro-quinolinyl, tetrahydro-quinolinyl, 1,2,3,4-tetrahydroquinolinyl, dihydro-isoquinolinyl, 3,4-dihydroisoquinolin-(1H)-yl, tetrahydro-isoquinolinyl, 1,2,3,4-tetrahydroisoquinolinyl, dihydro-quinazolinyl, tetrahydro-quinazolinyl, dihydro-quinoxalinyl, tetrahydro-quinoxalinyl, 1,2,3,4-tetrahydroquinoxalinyl, 1,3-dioxolanyl, 2,5-dihydro-1H-pyrrolyl, dihydro-1H-imidazolyl, tetrahydro-2H-pyranyl, hexahydropyrrolo[3,4-b][1,4]oxazin-(2H)-yl, (4aR,7aS)-hexahydropyrrolo[3,4-b][1,4]oxazin-(4aH)-yl, 3,4-dihydro-2H-pyrido[3,2-b][1,4]oxazinyl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, 2,3,4,9-tetrahydro-1H-carbazolyl, 1,2,3,4-tetrahydropyrazino[1,2-a]indolyl, 2,3-dihydro-1H-pyrrolo[1,2-a]indolyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, 3,6-diazabicyclo[3.1.0]hexanyl, (1R,5S,6s)-3-azabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl, 2,8-diazaspiro[4.5]decanyl and the like. A heterocyclyl radical may be optionally substituted on a carbon or nitrogen atom ring member where allowed by available valences.

As used herein, the term "$C_{2-8}$alkenyl-amino" refers to a radical of the formula: —NH—$C_{2-8}$alkenyl.

As used herein, the term "($C_{2-8}$alkenyl)$_2$-amino" refers to a radical of the formula: —N($C_{2-8}$alkenyl)$_2$.

As used herein, the term "$C_{2-8}$alkenyl-amino-$C_{1-8}$alkyl" refers to a radical of the formula: —$C_{1-8}$alkyl-NH—$C_{2-8}$alkenyl.

As used herein, the term "$(C_{2-8}\text{alkenyl})_2$-amino-$C_{1-8}$alkyl" refers to a radical of the formula: —$C_{1-8}$alkyl-N$(C_{2-8}\text{alkenyl})_2$.

As used herein, the term "$C_{1-8}$alkoxy-$C_{1-8}$alkyl" refers to a radical of the formula: —$C_{1-8}$alkyl-O—$C_{1-8}$alkyl.

As used herein, the term "$C_{1-8}$alkoxy-$C_{1-8}$alkyl-amino" refers to a radical of the formula: —O—$C_{1-8}$alkyl-NH—$C_{1-8}$alkyl-O—$C_{1-8}$alkyl.

As used herein, the term "$(C_{1-8}\text{alkoxy-}C_{1-8}\text{alkyl})_2$-amino" refers to a radical of the formula: —N($C_{1-8}$alkyl-O—$C_{1-8}$alkyl)$_2$.

As used herein, the term "$C_{1-8}$alkoxy-$C_{1-8}$alkyl-amino-$C_{1-8}$alkyl" refers to a radical of the formula: —$C_{1-8}$alkyl-NH—$C_{1-8}$alkyl-O—$C_{1-8}$alkyl.

As used herein, the term "$(C_{1-8}\text{alkoxy-}C_{1-8}\text{alkyl})_2$-amino-$C_{1-8}$alkyl" refers to a radical of the formula: —$C_{1-8}$alkyl-N($C_{1-8}$alkyl-O—$C_{1-8}$alkyl)$_2$.

As used herein, the term "($C_{1-8}$alkoxy-$C_{1-8}$alkyl, $C_{1-8}$alkyl)-amino" refers to a radical of the formula: —N[($C_{1-8}$alkyl)(—$C_{1-8}$alkyl-O—$C_{1-8}$alkyl)].

As used herein, the term "($C_{1-8}$alkoxy-$C_{1-8}$alkyl, $C_{1-8}$alkyl)-amino-$C_{1-8}$alkyl" refers to a radical of the formula: —$C_{1-8}$alkyl-N[($C_{1-8}$alkyl)(—$C_{1-8}$alkyl-O—$C_{1-8}$alkyl)].

As used herein, the term "$C_{1-8}$alkoxy-carbonyl" refers to a radical of the formula: —C(O)—O—$C_{1-8}$alkyl.

As used herein, the term "$C_{1-8}$alkyl-amino" refers to a radical of the formula: —NH—$C_{1-8}$alkyl.

As used herein, the term "$(C_{1-8}\text{alkyl})_2$-amino" refers to a radical of the formula: —N($C_{1-8}$alkyl)$_2$.

As used herein, the term "$C_{1-8}$alkyl-amino-$C_{1-8}$alkyl" refers to a radical of the formula: —$C_{1-8}$alkyl-NH—$C_{1-8}$alkyl.

As used herein, the term "$(C_{1-8}\text{alkyl})_2$-amino-$C_{1-8}$alkyl" refers to a radical of the formula: —$C_{1-8}$alkyl-N($C_{1-8}$alkyl)$_2$.

As used herein, the term "$C_{1-8}$alkyl-amino-$C_{1-8}$alkyl-amino" refers to a radical of the formula: —NH—$C_{1-8}$alkyl-NH—$C_{1-8}$alkyl.

As used herein, the term "$(C_{1-8}\text{alkyl})_2$-amino-$C_{1-8}$alkyl-amino" refers to a radical of the formula: —NH—$C_{1-8}$alkyl-N($C_{1-8}$alkyl)$_2$.

As used herein, the term "$C_{1-8}$alkyl-amino-$C_{1-8}$alkyl-amino-$C_{1-8}$alkyl" refers to a radical of the formula: —$C_{1-8}$alkyl-NH—$C_{1-8}$alkyl-NH—$C_{1-8}$alkyl.

As used herein, the term "$(C_{1-8}\text{alkyl})_2$-amino-$C_{1-8}$alkyl-amino-$C_{1-8}$alkyl" refers to a radical of the formula: —$C_{1-8}$alkyl-NH—$C_{1-8}$alkyl-N($C_{1-8}$alkyl)$_2$.

As used herein, the term "($C_{1-8}$alkyl-amino-$C_{1-8}$alkyl, $C_{1-8}$alkyl)amino" refers to a radical of the formula: —N[($C_{1-8}$alkyl)(—$C_{1-8}$alkyl-NH—$C_{1-8}$alkyl)].

As used herein, the term "[$(C_{1-8}\text{alkyl})_2$-amino-$C_{1-8}$alkyl, $C_{1-8}$alkyl]amino" refers to a radical of the formula: —N[($C_{1-8}$alkyl)(—$C_{1-8}$alkyl-N($C_{1-8}$alkyl)$_2$)].

As used herein, the term "($C_{1-8}$alkyl-amino-$C_{1-8}$alkyl, $C_{1-8}$alkyl)amino-$C_{1-8}$alkyl.

As used herein, the term "[$(C_{1-8}\text{alkyl})_2$-amino-$C_{1-8}$alkyl, $C_{1-8}$alkyl]amino-$C_{1-8}$alkyl" refers to a radical of the formula: —$C_{1-8}$alkyl-N[($C_{1-8}$alkyl)(—$C_{1-8}$alkyl-N($C_{1-8}$alkyl)$_2$)].

As used herein, the term "$C_{1-8}$alkyl-amino-carbonyl" refers to a radical of the formula: —C(O)—NH—$C_{1-8}$alkyl.

As used herein, the term "$(C_{1-8}\text{alkyl})_2$-amino-carbonyl" refers to a radical of the formula: —C(O)—N($C_{1-8}$alkyl)$_2$.

As used herein, the term "$C_{1-8}$alkyl-carbonyl" refers to a radical of the formula: —C(O)—$C_{1-8}$alkyl.

As used herein, the term "$C_{1-8}$alkyl-carbonyl-amino" refers to a radical of the formula: —NH—C(O)—$C_{1-8}$alkyl.

As used herein, the term "($C_{1-8}$alkyl-carbonyl, $C_{1-8}$alkyl)amino-$C_{1-8}$alkyl" refers to a radical of the formula: —$C_{1-8}$alkyl-N[($C_{1-8}$alkyl)(—C(O)—$C_{1-8}$alkyl)].

As used herein, the term "$C_{1-8}$alkyl-thio" refers to a radical of the formula: —S—$C_{1-8}$alkyl.

As used herein, the term "$C_{2-8}$alkynyl-$C_{1-8}$alkyl" refers to a radical of the formula: —$C_{1-8}$alkyl-$C_{2-8}$alkynyl.

As used herein, the term "$C_{2-8}$alkynyl-amino" refers to a radical of the formula: —NH—$C_{2-8}$alkynyl.

As used herein, the term "$(C_{2-8}\text{alkynyl})_2$-amino" refers to a radical of the formula: —N($C_{2-8}$alkynyl)$_2$.

As used herein, the term "$C_{2-8}$alkynyl-amino-$C_{1-8}$alkyl" refers to a radical of the formula: —$C_{1-8}$alkyl-NH—$C_{2-8}$alkynyl.

As used herein, the term "$(C_{2-8}\text{alkynyl})_2$-amino-$C_{1-8}$alkyl" refers to a radical of the formula: —$C_{1-8}$alkyl-N$(C_{2-8}\text{alkynyl})_2$.

As used herein, the term "amino" refers to a radical of the formula: —NH$_2$.

As used herein, the term "amino-$C_{1-8}$alkyl" refers to a radical of the formula: —$C_{1-8}$alkyl-NH$_2$.

As used herein, the term "amino-$C_{1-8}$alkyl-amino" refers to a radical of the formula: —NH—$C_{1-8}$alkyl-NH$_2$.

As used herein, the term "(amino-$C_{1-8}$alkyl)$_2$-amino" refers to a radical of the formula: —N($C_{1-8}$alkyl-NH$_2$)$_2$.

As used herein, the term "amino-$C_{1-8}$alkyl-amino-$C_{1-8}$alkyl" refers to a radical of the formula: —$C_{1-8}$alkyl-NH—$C_{1-8}$alkyl-NH$_2$.

As used herein, the term "(amino-$C_{1-8}$alkyl, $C_{1-8}$alkyl)amino" refers to a radical of the formula: —N[($C_{1-8}$alkyl)(—$C_{1-8}$alkyl-NH$_2$)].

As used herein, the term "(amino-$C_{1-8}$alkyl, $C_{1-8}$alkyl)amino-$C_{1-8}$alkyl" refers to a radical of the formula: —$C_{1-8}$alkyl-N[($C_{1-8}$alkyl)(—$C_{1-8}$alkyl-NH$_2$)].

As used herein, the term "amino-carbonyl" refers to a radical of the formula: —C(O)—NH$_2$.

As used herein, the term "aryl-$C_{1-8}$alkoxy" refers to a radical of the formula: —O—$C_{1-8}$alkyl-aryl.

As used herein, the term "aryl-$C_{1-8}$alkoxy-carbonyl-amino" refers to a radical of the formula: —NH—C(O)—O—$C_{1-8}$alkyl-aryl.

As used herein, the term "aryl-$C_{1-8}$alkyl" refers to a radical of the formula: —$C_{1-8}$alkyl-aryl.

As used herein, the term "aryl-$C_{1-8}$alkyl-amino" refers to a radical of the formula: —NH—$C_{1-8}$alkyl-aryl.

As used herein, the term "(aryl-$C_{1-8}$alkyl)$_2$-amino" refers to a radical of the formula: —N[(—$C_{1-8}$alkyl-aryl)$_2$].

As used herein, the term "aryl-$C_{1-8}$alkyl-amino-$C_{1-8}$alkyl" refers to a radical of the formula: —$C_{1-8}$alkyl-NH—$C_{1-8}$alkyl-aryl.

As used herein, the term "(aryl-$C_{1-8}$alkyl)$_2$-amino-$C_{1-8}$alkyl" refers to a radical of the formula: —$C_{1-8}$alkyl-N[(—$C_{1-8}$alkyl-aryl)$_2$].

As used herein, the term "(aryl, $C_{1-8}$alkyl)amino" refers to a radical of the formula: —N[($C_{1-8}$alkyl)(aryl)].

As used herein, the term "(aryl, $C_{1-8}$alkyl)amino-$C_{1-8}$alkyl" refers to a radical of the formula: —$C_{1-8}$alkyl-N[($C_{1-8}$alkyl)(aryl)].

As used herein, the term "(aryl-$C_{1-8}$alkyl, $C_{1-8}$alkyl)amino" refers to a radical of the formula: —N[($C_{1-8}$alkyl)(—$C_{1-8}$alkyl-aryl)].

As used herein, the term "(aryl-$C_{1-8}$alkyl, $C_{1-8}$alkyl)amino-$C_{1-8}$alkyl" refers to a radical of the formula: —$C_{1-8}$alkyl-N[($C_{1-8}$alkyl)(—$C_{1-8}$alkyl-aryl)].

As used herein, the term "aryl-amino" refers to a radical of the formula: —NH-aryl.

As used herein, the term "(aryl)$_2$-amino" refers to a radical of the formula: —N[(aryl)$_2$].

As used herein, the term "aryl-amino-C$_{1-8}$alkyl" refers to a radical of the formula: —C$_{1-8}$alkyl-NH-aryl.

As used herein, the term "(aryl)$_2$-amino-C$_{1-8}$alkyl" refers to a radical of the formula: —C$_{1-8}$alkyl-N[(aryl)$_2$].

As used herein, the term "aryl-amino-carbonyl" refers to a radical of the formula: —C(O)—NH-aryl.

As used herein, the term "azido" refers to a radical of the formula: —N=N$^+$=N$^-$.

As used herein, the term "carboxyl" refers to a radical of the formula: —COOH, —C(O)OH or —CO$_2$H.

As used herein, the term "(carboxyl-C$_{1-8}$alkyl, C$_{1-8}$alkyl)amino-carbonyl-amino" refers to a radical of the formula: —NH—C(O)—N[(C$_{1-8}$alkyl)(—C$_{1-8}$alkyl-CO$_2$H)].

As used herein, the term "C$_{3-14}$cycloalkyl-C$_{1-8}$alkoxy" refers to a radical of the formula: —O—C$_{1-8}$alkyl-C$_{3-14}$cycloalkyl.

As used herein, the term "C$_{3-14}$cycloalkyl-C$_{1-8}$alkyl" refers to a radical of the formula: —C$_{1-8}$alkyl-C$_{3-14}$cycloalkyl.

As used herein, the term "C$_{3-14}$cycloalkyl-amino" refers to a radical of the formula: —NH—C$_{3-14}$cycloalkyl.

As used herein, the term "C$_{3-14}$cycloalkyl-amino-C$_{1-8}$alkyl" refers to a radical of the formula: —C$_{1-8}$alkyl-NH—C$_{3-14}$cycloalkyl.

As used herein, the term "(C$_{3-14}$cycloalkyl)$_2$-amino-C$_{1-8}$alkyl" refers to a radical of the formula: —C$_{1-8}$alkyl-N[(—C$_{3-14}$cycloalkyl)$_2$].

As used herein, the term "C$_{3-14}$cycloalkyl-C$_{1-8}$alkyl-amino-C$_{1-8}$alkyl" refers to a radical of the formula: —C$_{1-8}$alkyl-NH—C$_{1-8}$alkyl-C$_{3-14}$cycloalkyl.

As used herein, the term "(C$_{3-14}$cycloalkyl-C$_{1-8}$alkyl)$_2$-amino-C$_{1-8}$alkyl" refers to a radical of the formula: —C$_{1-8}$alkyl-N[(—C$_{1-8}$alkyl-C$_{3-14}$cycloalkyl)$_2$].

As used herein, the term "(C$_{3-14}$cycloalkyl, C$_{1-8}$alkyl)amino-C$_{1-8}$alkyl" refers to a radical of the formula: —C$_{1-8}$alkyl-N[(C$_{1-8}$alkyl)(C$_{3-14}$cycloalkyl)].

As used herein, the term "(C$_{3-14}$cycloalkyl-C$_{1-8}$alkyl, C$_{1-8}$alkyl)amino-C$_{1-8}$alkyl" refers to a radical of the formula: —C$_{1-8}$alkyl-N[(C$_{1-8}$alkyl)(—C$_{1-8}$alkyl-C$_{3-14}$cycloalkyl)].

As used herein, the term "C$_{3-14}$cycloalkyl-oxy" refers to a radical of the formula: —O—C$_{3-14}$cycloalkyl.

As used herein, the term "formyl" refers to a radical of the formula: —C(O)—H.

As used herein, the term "formyl-C$_{1-8}$alkyl" refers to a radical of the formula: —C$_{1-8}$alkyl-C(O)—H, including, without limitation, formylmethyl (also referred to as 2-oxoethyl or formylmethyl), 2-formyl-ethyl (also referred to as 3-oxopropyl or formylethyl), 3-formyl-propyl (also referred to as 4-oxobutyl or formylpropyl), 4-formyl-butyl (also referred to as 5-oxopentyl or formylpropyl) and the like.

As used herein, the term "halo" or "halogen" generally refers to a halogen atom radical, including fluoro, chloro, bromo and iodo.

As used herein, the term "halo-C$_{1-8}$alkoxy" refers to a radical of the formula: —O—C$_{1-8}$alkyl-halo, wherein C$_{1-8}$alkyl may be partially or completely substituted where allowed by available valences with one or more halogen atoms, including, without limitation, fluoromethoxy, difluoromethoxy, trifluoromethoxy, fluoroethoxy, difluoroethoxy or trifluoroethoxy and the like. In some embodiments, difluoroethoxy includes 2,2-difluoroethoxy, 1,2-difluoroethoxy or 1,1-difluoroethoxy and the like. In some embodiments, halo-C$_{1-8}$alkoxy includes halo-C$_{1-6}$alkoxy, halo-C$_{1-4}$alkoxy and the like.

As used herein, the term "halo-C$_{1-8}$alkyl" refers to a radical of the formula: —C$_{1-8}$alkyl-halo, wherein C$_{1-8}$alkyl may be partially or completely substituted where allowed by available valences with one or more halogen atoms, including, without limitation, fluoromethyl, difluoromethyl, trifluoromethyl, fluoroethyl, difluoroethyl, trifluoroethyl, fluoroisopropyl, difluoroisopropyl, trifluoroisopropyl, fluoro-tert-butyl, difluoro-tert-butyl, trifluoro-tert-butyl and the like. In some embodiments, difluoroethyl includes 2,2-difluoroethyl, 1,2-difluoroethyl or 1,1-difluoroethyl and the like; difluoroisopropyl includes 1,3-difluoropropan-2-yl and the like; trifluoroisopropyl includes 1,1,1-trifluoropropan-2-yl and the like; trifluoro-tert-butyl includes 1,1,1-trifluoro-2-methylpropan-2-yl and the like. In some embodiments, halo-C$_{1-8}$alkyl includes halo-C$_{1-6}$alkyl, halo-C$_{1-4}$alkyl and the like.

As used herein, the term "halo-C$_{1-8}$alkyl-amino" refers to a radical of the formula: —NH—C$_{1-8}$alkyl-halo.

As used herein, the term "(halo-C$_{1-8}$alkyl-amino" refers to a radical of the formula: —N(C$_{1-8}$alkyl-halo)$_2$.

As used herein, the term "halo-C$_{1-8}$alkyl-amino-C$_{1-8}$alkyl" refers to a radical of the formula: —NH—C$_{1-8}$alkyl-halo.

As used herein, the term "(halo-C$_{1-8}$alkyl-amino-C$_{1-8}$alkyl" refers to a radical of the formula: —C$_{1-8}$alkyl-N(C$_{1-8}$alkyl-halo)$_2$.

As used herein, the term "heteroaryl-C$_{1-8}$alkyl" refers to a radical of the formula: —C$_{1-8}$alkyl-heteroaryl.

As used herein, the term "heteroaryl-amino" refers to a radical of the formula: —NH-heteroaryl.

As used herein, the term "(heteroaryl)$_2$-amino" refers to a radical of the formula: —N[(heteroaryl)$_2$].

As used herein, the term "heteroaryl-C$_{1-8}$alkyl-amino" refers to a radical of the formula: —NH—C$_{1-8}$alkyl-heteroaryl.

As used herein, the term "(heteroaryl-C$_{1-8}$alkyl-amino" refers to a radical of the formula: —N[(—C$_{1-8}$alkyl-heteroaryl)$_2$].

As used herein, the term "heteroaryl-C$_{1-8}$alkyl-amino-C$_{1-8}$alkyl" refers to a radical of the formula: —C$_{1-8}$alkyl-NH—C$_{1-8}$alkyl-heteroaryl.

As used herein, the term "(heteroaryl-C$_{1-8}$alkyl-amino-C$_{1-8}$alkyl" refers to a radical of the formula: —C$_{1-8}$alkyl-N[(—C$_{1-8}$alkyl-heteroaryl)$_2$].

As used herein, the term "(heteroaryl-C$_{1-8}$alkyl, C$_{1-8}$alkyl)amino" refers to a radical of the formula: —N[(—C$_{1-8}$alkyl)(—C$_{1-8}$alkyl-heteroaryl)].

As used herein, the term "(heteroaryl-C$_{1-8}$alkyl, C$_{1-8}$alkyl)amino-C$_{1-8}$alkyl" refers to a radical of the formula: —C$_{1-8}$alkyl-N[(C$_{1-8}$alkyl)(—C$_{1-8}$alkyl-heteroaryl)].

As used herein, the term "heterocyclyl-C$_{1-8}$alkoxy" refers to a radical of the formula: —O—C$_{1-8}$alkyl-heterocyclyl.

As used herein, the term "heterocyclyl-C$_{1-8}$alkyl" refers to a radical of the formula: —C$_{1-8}$alkyl-heterocyclyl.

As used herein, the term "heterocyclyl-amino" refers to a radical of the formula: —NH-heterocyclyl.

As used herein, the term "(heterocyclyl)$_2$-amino" refers to a radical of the formula: —N[(heterocyclyl)$_2$].

As used herein, the term "heterocyclyl-amino-C$_{1-8}$alkyl" refers to a radical of the formula: —C$_{1-8}$alkyl-NH-heterocyclyl.

As used herein, the term "(heterocyclyl)$_2$-amino-C$_{1-8}$alkyl" refers to a radical of the formula: —C$_{1-8}$alkyl-N[(heterocyclyl)$_2$].

As used herein, the term "heterocyclyl-C$_{1-8}$alkyl-amino-C$_{1-8}$alkyl" refers to a radical of the formula: —C$_{1-8}$alkyl-NH—C$_{1-8}$alkyl-heterocyclyl.

As used herein, the term "(heterocyclyl-$C_{1-8}$alkyl)$_2$-amino-$C_{1-8}$alkyl" refers to a radical of the formula: —$C_{1-8}$alkyl-N[(—$C_{1-8}$alkyl-heterocyclyl)$_2$].

As used herein, the term "(heterocyclyl, $C_{1-8}$alkyl)amino" refers to a radical of the formula: —N[($C_{1-8}$alkyl)(heterocyclyl)].

As used herein, the term "(heterocyclyl, $C_{1-8}$alkyl)amino-$C_{1-8}$alkyl" refers to a radical of the formula: —$C_{1-8}$alkyl-N[($C_{1-8}$alkyl)(heterocyclyl)].

As used herein, the term "(heterocyclyl-$C_{1-8}$alkyl, $C_{1-8}$alkyl)amino-$C_{1-8}$alkyl" refers to a radical of the formula: —$C_{1-8}$alkyl-N[($C_{1-8}$alkyl)(—$C_{1-8}$alkyl-heterocyclyl)].

As used herein, the term "(heterocyclyl, $C_{3-14}$cycloalkyl-$C_{1-8}$alkyl)amino-$C_{1-8}$alkyl" refers to a radical of the formula: —$C_{1-8}$alkyl-N[(heterocyclyl)(—$C_{1-8}$alkyl-$C_{3-14}$cycloalkyl)].

As used herein, the term "heterocyclyl-carbonyl" refers to a radical of the formula: —C(O)-heterocyclyl.

As used herein, the term "heterocyclyl-carbonyl-oxy" refers to a radical of the formula: —O—C(O)-heterocyclyl.

As used herein, the term "heterocyclyl-oxy" refers to a radical of the formula: —O-heterocyclyl.

As used herein, the term "heterocyclyl-oxy-amino" refers to a radical of the formula: —NH—O-heterocyclyl.

As used herein, the term "(heterocyclyl-oxy)$_2$-amino" refers to a radical of the formula: —N[(—O-heterocyclyl)$_2$].

As used herein, the term "(heterocyclyl-oxy, $C_{1-8}$alkyl)amino" refers to a radical of the formula: —N[(—$C_{1-8}$alkyl)(—O-heterocyclyl)].

As used herein, the term "(heterocyclyl-oxy-$C_{1-8}$alkyl, $C_{1-8}$alkyl)amino" refers to a radical of the formula: —N[($C_{1-8}$alkyl)(—$C_{1-8}$alkyl-O-heterocyclyl)].

As used herein, the term "hydroxyl-$C_{1-8}$alkoxy" refers to a radical of the formula: —O—$C_{1-8}$alkyl-OH, wherein $C_{1-8}$alkyl may be partially or completely substituted where allowed by available valences with one or more hydroxyl radicals.

As used herein, the term "hydroxyl-$C_{1-8}$alkyl" refers to a radical of the formula: —$C_{1-8}$alkyl-OH, wherein $C_{1-8}$alkyl may be partially or completely substituted where allowed by available valences with one or more hydroxyl radicals.

As used herein, the term "hydroxyl-amino" refers to a radical of the formula: —NH—OH.

As used herein, the term "hydroxyl-$C_{1-8}$alkyl-amino" refers to a radical of the formula: —NH—$C_{1-8}$alkyl-OH, wherein $C_{1-8}$alkyl may be partially or completely substituted where allowed by available valences with one or more hydroxyl radicals.

As used herein, the term "(hydroxyl-$C_{1-8}$alkyl-amino" refers to a radical of the formula: —N($C_{1-8}$alkyl-OH)$_2$, wherein $C_{1-8}$alkyl may be partially or completely substituted where allowed by available valences with one or more hydroxyl radicals.

As used herein, the term "hydroxyl-$C_{1-8}$alkyl-amino-$C_{1-8}$alkyl" refers to a radical of the formula: —$C_{1-8}$alkyl-NH—$C_{1-8}$alkyl-OH, wherein $C_{1-8}$alkyl may be partially or completely substituted where allowed by available valences with one or more hydroxyl radicals.

As used herein, the term "hydroxyl-$C_{1-8}$alkyl-amino-$C_{1-8}$alkyl-amino" refers to a radical of the formula: —NH—$C_{1-8}$alkyl-NH—$C_{1-8}$alkyl-OH, wherein $C_{1-8}$alkyl may be partially or completely substituted where allowed by available valences with one or more hydroxyl radicals.

As used herein, the term "(hydroxyl-$C_{1-8}$alkyl, $C_{1-8}$alkyl)amino" refers to a radical of the formula: —N[($C_{1-8}$alkyl)($C_{1-8}$alkyl-OH)], wherein $C_{1-8}$alkyl may be partially or completely substituted where allowed by available valences with one or more hydroxyl radicals.

As used herein, the term "(hydroxyl-$C_{1-8}$alkyl, $C_{1-8}$alkyl)amino-$C_{1-8}$alkyl" refers to a radical of the formula: —$C_{1-8}$alkyl-N[($C_{1-8}$alkyl)($C_{1-8}$alkyl-OH)], wherein $C_{1-8}$alkyl may be partially or completely substituted where allowed by available valences with one or more hydroxyl radicals.

As used herein, the term "(hydroxyl-$C_{1-8}$alkyl, $C_{1-8}$alkyl)amino-$C_{1-8}$alkyl-amino" refers to a radical of the formula: —NH—$C_{1-8}$alkyl-N[($C_{1-8}$alkyl)($C_{1-8}$alkyl-OH)], wherein $C_{1-8}$alkyl may be partially or completely substituted where allowed by available valences with one or more hydroxyl radicals.

As used herein, the term "Rhydroxyl-$C_{1-8}$alkyl, $C_{1-8}$alkyl)amino-$C_{1-8}$alkyl, $C_{1-8}$alkyl)amino" refers to a radical of the formula: —N[($C_{1-8}$alkyl)(—$C_{1-8}$alkyl-N[(—$C_{1-8}$alkyl)($C_{1-8}$alkyl-OH)])], wherein $C_{1-8}$alkyl may be partially or completely substituted where allowed by available valences with one or more hydroxyl radicals.

As used herein, the term "(hydroxyl-$C_{1-8}$alkyl-amino-$C_{1-8}$alkyl, $C_{1-8}$alkyl)amino" refers to a radical of the formula: —N[($C_{1-8}$alkyl)(—$C_{1-8}$alkyl-NH—$C_{1-8}$alkyl-OH)], wherein $C_{1-8}$alkyl may be partially or completely substituted where allowed by available valences with one or more hydroxyl radicals.

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. A person of ordinary skill in the art should note that any carbon as well as heteroatom with valences that appear to be unsatisfied as described or shown herein is assumed to have a sufficient number of hydrogen atom(s) to satisfy the valences described or shown.

As used herein, the term "and the like," with reference to the definitions of chemical terms provided herein, means that variations in chemical structures that could be expected by one skilled in the art include, without limitation, isomers (including chain, branching or positional structural isomers), hydration of ring systems (including saturation or partial unsaturation of monocyclic, bicyclic or polycyclic ring structures) and all other variations where allowed by available valences which result in a stable compound.

For the purposes of this description, where one or more substituent variables for a compound of Formula (I) encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may occur more than once on the structure of Formula (I), the pattern of substitution at each occurrence is independent of the pattern at any other occurrence. Further, the use of a generic substituent variable on any formula or structure for a compound described herein is understood to include the replacement of the generic substituent with species substituents that are included within the particular genus, e.g., aryl may be replaced with phenyl or naphthalenyl and the like, and that the resulting compound is to be included within the scope of the compounds described herein.

As used herein, the term "each instance of" when used in a phrase such as " . . . aryl, aryl-$C_{1-8}$alkyl, heterocyclyl and heterocyclyl-$C_{1-8}$alkyl, wherein each instance of aryl and heterocyclyl is optionally substituted with one or two substituents . . . " (emphasis added) is intended to optionally include substitution on each appearance of aryl and heterocyclyl, whether the ring is a primary or secondary substituent, that is, where the the aryl and heterocyclyl rings are the primary (first) substituent or where the primary substituent is $C_{1-8}$alkyl and the aryl and heterocyclyl rings are the secondary (second) substituent, as in, for example, aryl-$C_{1-8}$alkyl and heterocyclyl-$C_{1-8}$alkyl.

As used herein, the term "optionally substituted" means optional substitution with the specified substituent variables, groups, radicals or moieties.

As used herein, the terms "stable compound" or "stable structure" mean a compound that is sufficiently robust to survive isolation to a useful degree of purity from a reaction mixture and formulations thereof into an efficacious therapeutic agent.

Compound names used herein were obtained using the ACD Labs Index Name software provided by ACD Labs; and/or, were provided using the Autonom function of ChemDraw Ultra provided by CambridgeSoft. When the compound name disclosed herein conflicts with the structure depicted, the structure shown will supercede the use of the name to define the compound intended.

Compound Forms

As used herein, the term "a compound of Formula (Ia)," as defined previously, refer to a sub-genus of the compound of Formula (I) or a form thereof. Rather than repeat embodiments for a compound of Formula (Ia), in certain embodiments, the term "a compound of Formula (I) or a form thereof" is used to refer to a compound of Formula (Ia) or a form thereof. Thus, embodiments and references to "a compound of Formula (I)" are intended to include compounds of Formula (Ia).

As used herein, the term "form" means a compound of Formula (I) isolated for use selected from a free acid, free base, salt, hydrate, solvate, clathrate, isotopologue, racemate, enantiomer, diastereomer, stereoisomer, polymorph or tautomer form thereof.

In certain embodiments described herein, the form of the compound of Formula (I) is a free acid, free base or salt thereof.

In certain embodiments described herein, the form of the compound of Formula (I) is an isotopologue thereof.

In certain embodiments described herein, the form of the compound of Formula (I) is a stereoisomer, racemate, enantiomer or diastereomer thereof.

In certain embodiments described herein, the form of the compound of Formula (I) is a tautomer thereof.

In certain embodiments described herein, the form of the compound of Formula (I) is a pharmaceutically acceptable form.

In certain embodiments described herein, the compound of Formula (I) or a form thereof is isolated for use.

As used herein, the term "isolated" means the physical state of a compound of Formula (I) after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterizable by standard analytical techniques described herein or well known to the skilled artisan.

As used herein, the term "protected" means that a functional group in a compound of Formula (I) is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

Prodrugs and solvates of the compounds described herein are also contemplated.

As used herein, the term "prodrug" means a form of an instant compound (e.g., a drug precursor) that is transformed in vivo to yield an active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains an alcohol functional group, a prodrug can be formed by the replacement of the hydrogen atom of the alcohol group with a functional group such as alkyl or carbonyloxy and the like. In another example, when a compound of Formula (I) or a form thereof contains an amine functional group, a prodrug can be formed by the replacement of one or more amine hydrogen atoms with a functional group such as alkyl or substituted carbonyl.

One or more compounds described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

One or more compounds described herein may optionally be converted to a solvate. Preparation of solvates is generally known. The preparation of solvates of the antifungal fluconazole in ethyl acetate as well as from water has been described (see, M. Caira et al, *J. Pharmaceutical Sci.*, 93(3), 601-611 (2004)). Similar preparations of solvates, hemisolvate, hydrates and the like have also been described (see, E. C. van Tonder et al, *AAPS PharmSciTech.*, 5(1), article 12 (2004); and A. L. Bingham et al, *Chem. Commun.*, 603-604 (2001)). A typical, non-limiting process involves dissolving a compound in a desired amount of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

As used herein, the term "hydrate" means a solvate wherein the solvent molecule is water.

The compounds of Formula (I) can form salts, which are intended to be included within the scope of this description. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Pharmaceutically acceptable salts include one or more salts of acidic or basic groups present in compounds described herein. Embodiments of acid addition salts include, and are not limited to, acetate, acid phosphate, ascorbate, benzoate, benzenesulfonate, bisulfate, bitartrate, borate, butyrate, chloride, citrate, camphorate, camphorsulfonate, ethanesulfonate, formate, fumarate, gentisinate, gluconate, glucaronate, glutamate, hydrobromide, hydrochloride, dihydrochloride, hydroiodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate salts and the like. Certain embodiments of acid addition salts include chloride, hydrobromide, hydrochloride, dihydrochloride, acetate or trifluoroacetic acid salts.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Suitable basic salts include, but are not limited to, aluminum, ammonium, calcium, lithium, magnesium, potassium, sodium, zinc, and diethanolamine salts. Certain compounds of described herein can also form pharmaceutically acceptable salts with organic bases (for example, organic amines) such as, but not limited to, dicyclohexylamines, t-butyl amines and the like, and with various amino acids such as, but not limited to, arginine, lysine and the like. Basic nitrogen-containing groups may be quarternized with agents such as lower alkyl halides (e.g., methyl, ethyl, and butyl chlorides, bromides and iodides); dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be included within the scope of pharmaceutically acceptable salts as described herein. In addition, all such acid and base salts are considered equivalent to the free forms of the corresponding compounds for purposes of this description.

Pharmaceutically acceptable prodrugs of compounds of Formula (I) or a form thereof include those compounds substituted with one or more of the following groups: carboxylic acid esters, sulfonate esters, amino acid esters phosphonate esters and mono-, di- or triphosphate esters or alkyl substituents, where appropriate. As described herein, it is understood by a person of ordinary skill in the art that one or more of such substituents may be used to provide a compound of Formula (I) or a form thereof as a prodrug.

Compounds of Formula (I), and forms thereof, may further exist in a tautomeric form (for example, as an amide or imino ether). All such tautomeric forms are contemplated and intended to be included within the scope of the compounds of Formula (I) or a form thereof as described herein.

The compounds of Formula (I) may contain asymmetric or chiral centers, and, therefore, exist in different stereoisomeric forms. The present description is intended to include all stereoisomeric forms of the compounds of Formula (I) as well as mixtures thereof, including racemic mixtures.

The compounds described herein may include one or more chiral centers, and as such may exist as racemic mixtures (R/S) or as substantially pure enantiomers and diastereomers.

The compounds may also exist as substantially pure (R) or (S) enantiomers (when one chiral center is present). In one embodiment, the compounds described herein are (S) isomers and may exist as enantiomerically pure compositions substantially comprising only the (S) isomer. In another embodiment, the compounds described herein are (R) isomers and may exist as enantiomerically pure compositions substantially comprising only the (R) isomer. As one of skill in the art will recognize, when more than one chiral center is present, the compounds described herein may also exist as a (R,R), (R,S), (S,R) or (S,S) isomer, as defined by *IUPAC* Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the description, a compound of Formula (I) is a substantially pure (S) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the description, a compound of Formula (I) is a substantially pure (R) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present description embraces all geometric and positional isomers. For example, if a compound of Formula (I) incorporates a double bond or a fused ring, both the cis- and trans-forms, as well as mixtures, are embraced within the scope of the description. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this description.

It is also possible that the compounds of Formula (I) may exist in different tautomeric forms, and all such forms are embraced within the scope of the description. Also, for example, all keto-enol and imine-enamine forms of the compounds are included in the scope of this description.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this description, as are positional isomers (such as, for example, 4-pyridyl and 3-pyridyl). For example, if a compound of Formula (I) incorporates a double bond or a fused ring, both the cis- and trans-forms, as well as mixtures thereof, are embraced herein. Also, for example, all keto-enol and imine-enamine forms of the compounds are included herein. Individual stereoisomers of the compounds described herein may, for example, be substantially free of other isomers, or may be present in a racemic mixture, as described supra.

The use of the terms "salt", "solvate", "ester", "prodrug" and the like, is intended to equally apply to the salt, solvate, ester and prodrug of enantiomers, stereoisomers, rotamers, tautomers, positional isomers, racemates, isotopologues or prodrugs of the instant compounds.

The term "isotopologue" refers to isotopically-enriched compounds described herein which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $H^2$, $H^3$, $C^{13}$, $C^{14}$, $N^{15}$, $O^{18}$, $O^{17}$, $P^{31}$, $P^{32}$, $S^{35}$, $F^{18}$, $Cl^{35}$ and $Cl^{36}$, respectively, each of which are also within the scope of this description.

Certain isotopically-enriched compounds described herein (e.g., those labeled with $H^3$ and $C^{14}$) are useful in compound and/or substrate tissue distribution assays. Tritiated (i.e., $H^3$) and carbon-14 (i.e., $C^{14}$) isotopes are particularly preferred for their ease of preparation and detectability. Further, substitution with heavier isotopes such as deuterium (i.e., $H^2$) may afford certain therapeutic advantages resulting from greater metabolic stability (e.g., increased in vivo half-life or reduced dosage requirements) and hence may be preferred in some circumstances.

Polymorphic crystalline and amorphous forms of the compounds of Formula (I), and of the salts, solvates, hydrates, esters and prodrugs of the compounds of Formula (I), are further intended to be included in the present description.

Use of Compounds

The present description further relates to uses of the compound of Formula (I) and methods of treating or ameliorating a bacterial infection, or of treating or ameliorating a multi-drug resistant (MDR) bacterial infection.

The present description further relates to uses of the compound of Formula (I) having activity toward wild-type and MDR bacteria. The present description also relates to uses of the compound of Formula (I) having activity against quinolone-resistant Gram-negative strains (including MDR strains) as well as antibacterial activity to MDR resistant Gram-positive pathogens (including MRSA strains). The present description also relates to uses of the compound of Formula (I) having selectivity between bacterial topoisomerase IV and DNA gyrase enzyme inhibition compared to human topoisomerase II enzyme inhibition. The present description further relates to uses of the compound of Formula (I) that may be combined with known antibacterial agents to provide additive or synergistic activity, thus enabling the development of a combination product for the treatment of Gram-negative (especially MDR strains) and Gram-positive infections.

The compounds of the present description inhibit the clinically validated bacterial targets DNA gyrase and topoisomerase IV, and, thus, may be used for the treatment of infections caused by Gram-negative and Gram-positive pathogens. The instant compounds possess in vitro antibacterial activity against a wide spectrum of bacteria which have developed resistance to almost all known treatments, including MDR Gram-negative and MDR Gram-positive pathogens and successfully effect the treatment of bacterial infections compared to current antibacterial agents that target the same enzymes. The compounds are also effective in vivo and lack cellular toxicity. In addition to monotherapeutic use, the instant compounds are amenable to combination therapy with current standards of care, having demonstrated additive and synergistic activity with one or more fluoroquinolone based antibacterial agents. The demonstrated additive and synergistic activity of the compounds indicates a mechanistically alternate binding in conjunction with the DNA gyrase and topoisomerase IV targets.

Accordingly, the present description relates to methods of using a compound of Formula (I) for treating or ameliorating a bacterial infection, or for using a compound of Formula (I) for treating or ameliorating a multidrug resistant bacterial infection. In accordance with the present description, compounds that selectively treat or ameliorate a bacterial infection have been identified and methods of using these compounds for treating or ameliorating a bacterial infection or disorders or symptoms associated therewith are provided.

One embodiment of the present description relates to a method of treating or ameliorating a bacterial infection in a subject in need thereof comprising administering an effective amount of a compound of Formula (I) or a form thereof to the subject.

An embodiment of the present description relates to a method of treating or ameliorating a bacterial infection resulting from a bacteria that is a Gram-negative or Gram-positive type in a subject in need thereof comprising administering an effective amount of the compound of Formula (I) or a form thereof to the subject.

An embodiment of the present description relates to a method of treating or ameliorating a bacterial infection resulting from a bacteria that is a resistant Gram-negative or Gram-positive type in a subject in need thereof comprising administering an effective amount of the compound of Formula (I) or a form thereof to the subject.

One embodiment of the present description relates to a use of a compound of Formula (I) or a form thereof for treating or ameliorating a bacterial infection in a subject in need thereof comprising administering an effective amount of the compound to the subject.

An embodiment of the present description relates to a use of a compound of Formula (I) or a form thereof for treating or ameliorating a bacterial infection resulting from a bacteria that is a Gram-negative or Gram-positive type in a subject in need thereof comprising administering an effective amount of the compound to the subject.

An embodiment of the present description relates to a use of a compound of Formula (I) or a form thereof for treating or ameliorating a bacterial infection resulting from a bacteria that is a resistant Gram-negative or Gram-positive type in a subject in need thereof comprising administering an effective amount of the compound to the subject.

An embodiment of the present description relates to a use of a compound of Formula (I) or a form thereof in the manufacture of a medicament for treating or ameliorating a bacterial infection in a subject in need thereof comprising administering an effective amount of the medicament to the subject.

An embodiment of the present description relates to a use of a compound of Formula (I) or a form thereof in the manufacture of a medicament for treating or ameliorating a bacterial infection resulting from a bacteria that is a Gram-negative or Gram-positive type in a subject in need thereof comprising administering an effective amount of the compound to the subject.

An embodiment of the present description relates to a use of a compound of Formula (I) or a form thereof in the manufacture of a medicament for treating or ameliorating a bacterial infection resulting from a bacteria that is a resistant Gram-negative or Gram-positive type in a subject in need thereof comprising administering an effective amount of the compound to the subject.

An embodiment of the present description relates to a use of a compound of Formula (I) or a form thereof in the preparation of a pharmaceutical kit comprising the compound of Formula (I) or a form thereof and instructions for administering the compound for treating or ameliorating a bacterial infection in a subject in need thereof.

Another embodiment of the present description relates to the use of a compound of Formula (I) or a form thereof for treating or ameliorating a bacterial infection by selectively inhibiting DNA gyrase and topoisomerase IV compared to human topoisomerase II.

An embodiment of the present description relates to a method of treating or ameliorating a bacterial infection or disorders or symptoms associated therewith in a subject in need thereof comprising administering an effective amount of a compound of Formula (I) or a form thereof to the subject.

An embodiment of the present description relates to the use of a compound of Formula (I) or a form thereof in the manufacture of a medicament for treating or ameliorating bacterial infection or disorders or symptoms associated therewith in a subject in need thereof comprising administering an effective amount of the medicament to the subject.

An embodiment of the present description relates to the use of a compound of Formula (I) or a form thereof in the preparation of a pharmaceutical kit comprising the compound of Formula (I) or a form thereof and instructions for administering the compound for treating or ameliorating a bacterial infection or disorders or symptoms associated therewith in a subject in need thereof.

In one respect, for each of such embodiments, the subject is treatment naive. In another respect, for each of such embodiments, the subject is not treatment naive.

As used herein, the term "treating" refers to: (i) preventing a disease, disorder or condition from occurring in a subject that may be predisposed to the disease, disorder and/or condition but has not yet been diagnosed as having the disease, disorder and/or condition; (ii) inhibiting a disease, disorder or condition, i.e., arresting the development thereof; and/or (iii) relieving a disease, disorder or condition, i.e., causing regression of the disease, disorder and/or condition.

As used herein, the term "subject" refers to an animal or any living organism having sensation and the power of voluntary movement, and which requires oxygen and organic food. Nonlimiting examples include members of the human, equine, porcine, bovine, murine, canine and feline specie. In some embodiments, the subject is a mammal or a warm-blooded vertebrate animal. In other embodiments, the subject is a human. As used herein, the term "patient" may be used interchangeably with "subject" and "human".

Another aspect of the description relates to a method of treating or ameliorating a bacterial infection resulting from a bacteria that is a Gram-negative or Gram-positive type.

Another aspect of the description relates to a method of treating or ameliorating a bacterial infection resulting from bacteria that is a resistant Gram-negative or Gram-positive type.

Another aspect of the description particularly relates to a method of treating or ameliorating a bacterial infection by a wild type bacteria that is resistant to a currently available antibacterial agent, in a subject in need thereof, comprising administering to the subject an effective amount of a compound of Formula (I) or a form thereof.

Examples of bacterial infections intended to be included within the scope of the description include bacterial infections resulting from a bacteria of the phyla including, but not limited to, Acidobacteria; Actinobacteria; Aquificae; Bacteroidetes; Caldiserica; Chlamydiae; Chlorobi; Chloroflexi; Chrysiogenetes; Cyanobacteria; Deferribacteres; Deinococcus-Thermus; Dictyoglomi; Elusimicrobia; Fibrobacteres; Firmicutes; Fusobacteria; Gemmatimonadetes; Lentisphaerae; Nitrospira; Planctomycetes; Proteobacteria; Spirochaetes; Synergistetes; Tenericutes; Firmicutes; Thermodesulfobacteria; Thermomicrobia; Thermotogae; or Verrucomicrobia. The listing of phyla is obtained from the List of Prokaryotic Names with Standing in Nomenclature (LPSN) (see, http://www.bacterio.cict.fr/index.html)

Another aspect of the description relates to a method of treating or ameliorating a bacterial infection by a bacteria from a phyla that is a Gram-negative or Gram-positive type.

Another aspect of the description relates to a method of treating or ameliorating a bacterial infection by a bacteria from a phyla that is a drug resistant Gram-negative or Gram-positive type.

Another aspect of the description relates to a method of treating or ameliorating a bacterial infection by a bacteria from a phyla that is a multi-drug resistant Gram-negative or Gram-positive type.

Examples of such bacterial infections intended to be included within the scope of the description particularly include bacterial infections that result from a bacteria of the phyla selected from Proteobacteria, Spirochaetes, Bacteriodetes, Chlamydiae, Firmicutes or Actinobacteria.

In a particular example, the bacterial infections include those resulting from a bacterial species selected from *Acinetobacter baumannii, Bacillus anthracis, Bacillus subtilis, Enterobacter* spp., *Enterococcus faecalis, Enterococcus faecalis, Enterococcus faecium, Escherichia coli, Francisella tularensis, Haemophilus influenzae, Klebsiella pneumoniae, Moraxella catarrhalis, Mycobacterium tuberculosis, Neisseria* spp., *Pseudomonas aeruginosa, Shigella* spp., *Staphylococcus aureus, Streptococcus pyogenes, Streptococcus pneumoniae* and *Yersinia pestis*.

In another particular example, the bacteria are selected from *Acinetobacter baumannii* BAA747, *Acinetobacter baumannii* MMX2240 (MDR), *Bacillus anthracis* (wild-type), *Bacillus anthracis* T105-R (Cipro$^R$), *Bacillus subtilis* 23857, *Enterococcus faecalis* 29212, *Enterococcus faecalis* 44841 (quin$^R$), *Enterococcus faecium* 49624, *Escherichia coli* BAS849, *Escherichia coli* 25922, *Escherichia coli* LZ3111, *Escherichia coli* LZ3110, *Escherichia coli* ELZ4251 (MDR), *Escherichia coli* NDM-1, *Francisella tularensis* (wild-type), *Haemophilus influenzae* 49247, *Klebsiella pneumoniae* 35657, *Klebsiella pneumoniae* MMX1232 (MDR), *Moraxella catarrhalis* 25238, *Pseudomonas aeruginosa* 27853, *Staphylococcus aureus* 29213, *Staphylococcus aureus* 43300 (MDR), *Staphylococcus aureus* 700789 (MDR), *Streptococcus pneumoniae* 49150 or *Yersinia pestis* (wild-type).

Another aspect of the description relates to a method of treating or ameliorating treating a bacterial infection by a Gram-negative or Gram-positive bacteria.

Another aspect of the description relates to a method of treating or ameliorating treating a bacterial infection by a resistant Gram-negative or Gram-positive bacteria.

Another aspect of the description relates to a method of treating or ameliorating treating a bacterial infection by a drug resistant Gram-negative or Gram-positive bacteria.

Another aspect of the description relates to a method of treating or ameliorating treating a bacterial infection by a multi-drug resistant Gram-negative or Gram-positive bacteria.

As used herein, the terms "effective amount" or "therapeutically effective amount" mean an amount of compound of Formula (I) or a form, composition or medicament thereof effective in inhibiting the above-noted diseases and thus producing the desired therapeutic, ameliorative, inhibitory or preventative effect in a subject in need thereof.

In general, the effective amount will be in a range of from about 0.001 mg/Kg/day to about 500 mg/Kg/day, or about 0.01 mg/Kg/day to about 500 mg/Kg/day, or about 0.1 mg to about 500 mg/Kg/day, or about 1.0 mg/day to about 500 mg/Kg/day, in single, divided, or a continuous dose for a patient or subject having a weight in a range of between about 40 to about 200 Kg (which dose may be adjusted for patients or subjects above or below this range, particularly children under 40 Kg). The typical adult subject is expected to have a median weight in a range of between about 60 to about 100 Kg.

The dose administered to achieve an effective target plasma concentration may also be administered based upon the weight of the subject or patient. Doses administered on a weight basis may be in the range of about 0.01 mg/kg/day to about 50 mg/kg/day, or about 0.015 mg/kg/day to about 20 mg/kg/day, or about 0.02 mg/kg/day to about 10 mg/kg/day, or about 0.025 mg/kg/day to about 10 mg/kg/day, or about 0.03 mg/kg/day to about 10 mg/kg/day, wherein said amount is orally administered once (once in approximately a 24 hour period), twice (once in approximately a 12 hour period) or thrice (once in approximately an 8 hour period) daily according to subject weight.

In another embodiment, where daily doses are adjusted based upon the weight of the subject or patient, compounds described herein may be formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 5.0, 10, 20 or 50 mg/kg/day. Daily doses adjusted based upon the weight of the subject or patient may be administered as a single, divided, or continuous dose. In embodiments where a dose of compound is given more than once per day, the dose may be administered twice, thrice, or more per day.

Within the scope of the present description, the "effective amount" of a compound of Formula (I) or a form thereof for use and for use in the manufacture of a medicament, the preparation of a pharmaceutical kit or in a method of treating or ameliorating bacterial infection or disorders or symptoms associated therewith in a subject in need thereof, is intended to include an amount in a range of from about 1.0 mg to about 3500 mg administered once daily; 10.0 mg to about 600 mg administered once daily; 0.5 mg to about 2000 mg administered twice daily; or, an amount in a range of from about 5.0 mg to about 300 mg administered twice daily.

For example, the effective amount may be the amount required to treat a bacterial infection, or the amount required to inhibit bacterial replication in a subject or, more specifically, in a human. In some instances, the desired effect can be determined by analyzing the presence of bacterial DNA. The effective amount for a subject will depend upon various factors, including the subject's body weight, size and health. Effective amounts for a given patient can be determined by routine experimentation that is within the skill and judgment of the clinician.

For any compound, the effective amount can be estimated initially either in cell culture assays or in relevant animal models, such as a mouse, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is referred to as the therapeutic index, and can be expressed as the ratio, $LD_{50}/ED_{50}$. In some embodiments, the effective amount is such that a large therapeutic index is achieved. In further embodiments, the dosage is within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to a compound of Formula (I) or a form thereof indicate a target plasma concentration ranging from approximately 0.001 µg/mL to approximately 50 µg/mL, from approximately 0.01 µg/mL to approximately 20 µg/mL, from approximately 0.05 µg/mL to approximately 10 µg/mL, or from approximately 0.1 µg/mL to approximately 5 µg/mL. To achieve such plasma concentrations, the compounds described herein may be administered at doses that vary from 0.1 µg to 100,000 mg, depending upon the route of administration in single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject. Dosage and administration may be adjusted to provide sufficient levels of the active agent(s) or to maintain the desired effect. Factors which may be taken into account include the severity of the disease state, general health of the subject, ethnicity, age, weight, and gender of the subject, diet, time and frequency of administration, drug combination(s), reaction sensitivities, experience with other antibacterial therapies, and tolerance/response to therapy. Long-acting pharmaceutical compositions may be administered every 2, 3 or 4 days, once every week, or once every two weeks depending on half-life and clearance rate of the particular formulation.

The compounds and compositions described herein may be administered to the subject via any drug delivery route known in the art. Nonlimiting examples include oral, ocular, rectal, buccal, topical, nasal, ophthalmic, subcutaneous, intramuscular, intraveneous (bolus and infusion), intracerebral, transdermal, and pulmonary routes of administration.

Metabolites of the Compounds

Also falling within the scope of the present description are the in vivo metabolic products of the compounds described herein. Such products may result, for example, from the oxidation, reduction, hydrolysis, amidation, esterification and the like of the administered compound, primarily due to enzymatic processes. Accordingly, the description includes compounds produced by a process comprising contacting a compound described herein with a mammalian tissue or a mammal for a period of time sufficient to yield a metabolic product thereof.

Such products typically are identified by preparing a radio-labeled isotopologue (e.g., $C^{14}$ or $H^3$) of a compound described herein, administering the radio-labeled compound in a detectable dose (e.g., greater than about 0.5 mg/kg) to a mammal such as a rat, mouse, guinea pig, dog, monkey or human, allowing sufficient time for metabolism to occur (typically about 30 seconds to about 30 hours), and identifying the metabolic conversion products from urine, bile, blood or other biological samples. These products are easily isolated since they are "radiolabeled" by virtue of being isotopically-enriched (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds described herein even if they possess no biological activity of their own.

Pharmaceutical Compositions

Embodiments of the present description include the use of a compound of Formula (I) or a form thereof in a pharmaceutical composition for the prevention or treatment of a bacterial infection comprising an effective amount of a compound of Formula (I) or a form thereof in admixture with a pharmaceutically acceptable excipient.

As used herein, the term "composition" means a product comprising the specified ingredients in the specified amounts, as well as any product which results, directly or indirectly, from combination of the specified ingredients in the specified amounts.

The pharmaceutical composition may be formulated to achieve a physiologically compatible pH, ranging from about pH 3 to about pH 11. In some embodiments, the pharmaceutical composition is formulated to achieve a pH of from about pH 3 to about pH 7. In other embodiments, the pharmaceutical composition is formulated to achieve a pH of from about pH 5 to about pH 8.

The term "pharmaceutically acceptable excipient" refers to an excipient for administration of a pharmaceutical agent, such as the compounds described herein. The term refers to any pharmaceutical excipient that may be administered without undue toxicity. Pharmaceutically acceptable excipients may be determined in part by the particular composition being administered, as well as by the particular mode of administration and/or dosage form. Nonlimiting examples of pharmaceutically acceptable excipients include carriers, solvents, stabilizers, adjuvants, diluents, etc. Accordingly, there exists a wide variety of suitable formulations of pharmaceutical compositions for the instant compoounds described herein (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive antibodies. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended method of administration. Suitable formulations for oral administration include solids, liquid solutions, emulsions and suspensions, while suitable inhaleable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or *acacia*; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In other embodiments, pharmaceutical compositions described herein may be formulated as suspensions comprising a compound of Formula (I) or a form thereof in admixture with at least one pharmaceutically acceptable excipient suitable for the manufacture of a suspension. In yet other embodiments, pharmaceutical compositions described herein may be formulated as dispersible powders and granules suitable for preparation of a suspension by the addition of one or more excipient(s).

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions described herein may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions described herein may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds described herein may be substantially insoluble in water and sparingly soluble in most pharmaceutically acceptable protic solvents and vegetable oils, but generally soluble in medium-chain fatty acids (e.g., caprylic and capric acids) or triglycerides and in propylene glycol esters of medium-chain fatty acids. Thus, contemplated in the description are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compound described herein is formulated for oral administration in a lipid-based composition suitable for low solubility compounds. Lipid-based formulations can generally enhance the oral bioavailability of such compounds. As such, pharmaceutical compositions described herein may comprise a effective amount of a compound of Formula (I) or a form thereof, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polyoxyl 40 hydrogenated castor oil.

In other embodiments, the bioavailability of low solubility compounds may be enhanced using particle size optimization techniques including the preparation of nanoparticles or nanosuspensions using techniques known to those skilled in art. The compound forms present in such preparations include amorphous, partially amorphous, partially crystalline or crystalline forms.

In alternative embodiments, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of α-, β-, and γ-cyclodextrin, and hydroxypropyl-β-cyclodextrin (HPBC). In some embodiments, the pharmaceutical composition further comprises HPBC in a range of from about 0.1% to about 20%, from about 1% to about 15%, or from about 2.5% to about 10%. The amount of solubility enhancer employed may depend on the amount of the compound in the composition.

Preparation of Compounds

General Synthetic Examples

Methods for preparing certain compounds useful for treating or ameliorating bacterial infections or disorders or symptoms associated therewith are available via standard, well-known synthetic methodologies.

As disclosed herein, methods for preparing the compounds described herein are also available via standard, well-known synthetic methodology. Many of the starting materials used herein are commercially available or can be prepared using the routes described below using techniques known to those skilled in the art.

General Schemes

Compounds of Formula (I) can be prepared as described in the Schemes below.

Scheme 1

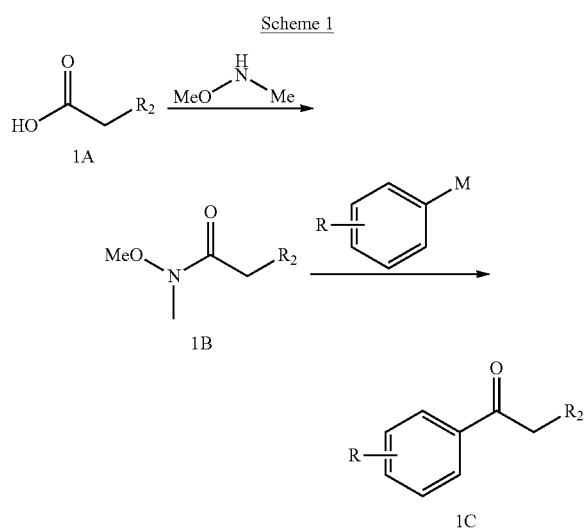

General Procedures for Scheme 1

Ketones of type 1C (wherein R represents one or more optionally present substituents or protecting groups) are prepared from carboxylic acids of type 1A by a two step procedure beginning with treatment of carboxylic acids of type 1A with an appropriate activating agent followed by reaction with N,O-dimethylhydroxylamine in an organic solvent (such as DCM and the like). Ketones of type 1C may then be prepared from amides of type 1B by reaction with an aryl metallated species where the metal is lithium or magnesium and the like.

Scheme 2

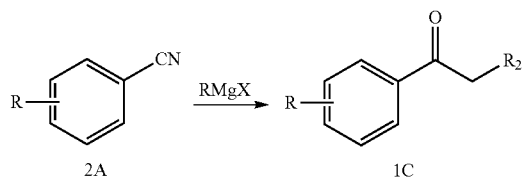

General Procedure for Scheme 2

The ketone moiety starting materials used in Scheme 2 were prepared via the procedures described in Scheme 1. An alternative procedure to prepare ketones of type 1C includes reacting aryl nitriles of type 2A (wherein R represents one or more optionally present substituents or protecting groups) with Grignard reagents in a suitable organic solvent (such as THF and the like) followed by treatment with an aqueous acid.

Scheme 3

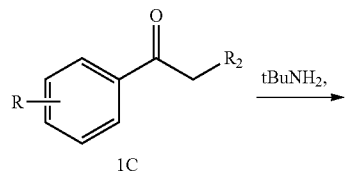

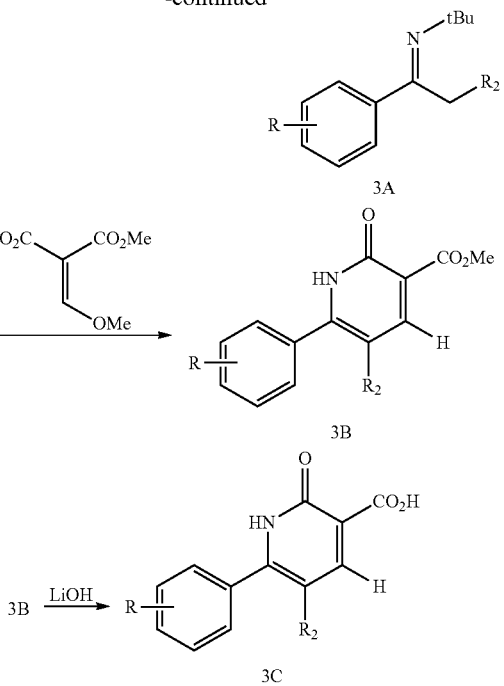

General Procedures for Scheme 3

A ketone of type 1C may be converted into an imine of type 3A (wherein R represents one or more optionally present substituents or protecting groups) by reaction with an excess of tert-butyl amine in the presence of a Lewis acid (such as titanium tetrachloride and the like) or dehydrating agents (such as para-toluene sulfonic acid and the like) in an organic solvent (such as DCM and the like). Imines of type 3A may be used to obtain 2-pyridones of type 3B by reaction with dimethyl 2-(methoxymethylene)malonate in a solvent (such as diphenyl ether and the like) at temperatures ranging from 130° C. to 230° C. The ester moiety on the pyridone of type 3B may be converted to the corresponding carboxylic acid of type 3C by reaction with aqueous lithium hydroxide in an organic solvent (such as THF and the like) at 50° C.

Scheme 4

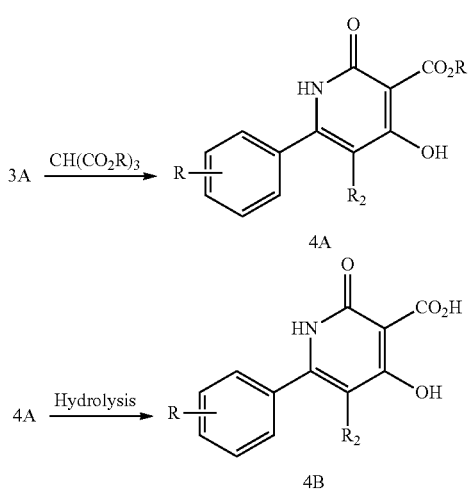

General Procedure for Scheme 4

Imines of type 3A may also be used to obtain hydroxyl 2-pyridones of type 4A by reaction with a trialkyl tricarboxylate in a solvent (such as diphenyl ether and the like) at temperatures ranging from 130° C. to 230° C. Hydrolysis of the ester moiety on the hydroxy 2-pyridone of type 4A is achieved with aqueous hydroxide in a suitable organic solvent (such as THF and the like) or by reaction with iodotrimethyl silane or lithium iodide in an organic solvent (such as EtOAc and the like) at temperatures ranging from 30° C. to 80° C. to provide hydroxyl 2-pyridones of type 4B.

Scheme 5

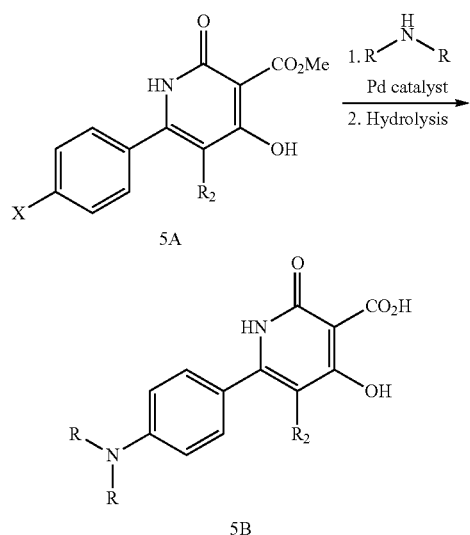

General Procedure for Scheme 5

Anilines of type 5B (wherein R represents one or more optionally present substituents or protecting groups and, wherein the amine R groups can be taken together with the nitrogen of attachment to form a heterocyclyl ring) are prepared from aryl halides of type 5A (wherein X represents one or more optionally present substituents or protecting or leaving groups) by treatment with an amine, a suitable base, and a suitable palladium catalyst in an appropriate organic solvent at temperatures ranging from 80° C. to 110° C. followed by hydrolysis of the ester moiety on the 5B intermediate to provide the corresponding carboxylic acid of type 5B.

Scheme 6

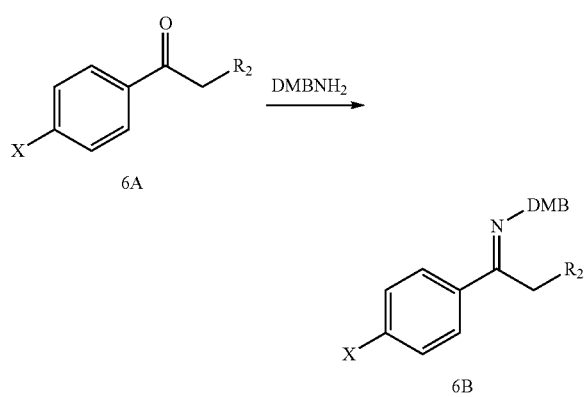

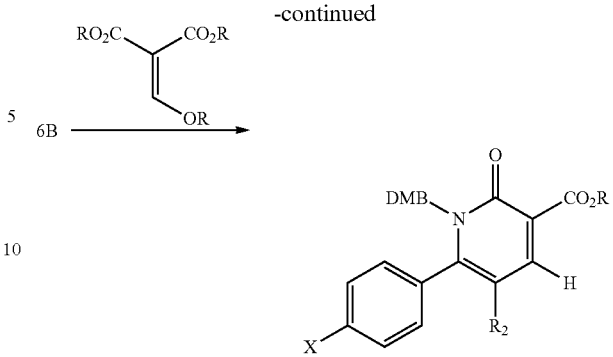

General Procedure for Scheme 6

Ketones of type 6A (wherein X represents one or more optionally present substituents or protecting or leaving groups) may be used to prepare imines of type 6B by reaction with an excess of dimethoxybenzyl amine in the presence of a dehydrating agent (such as para-toluene sulfonic acid and the like) or a Lewis acid (such as titanium tetrachloride and the like) in an organic solvent (such as DCM and the like). Imines of type 6B may be used to obtain 2-pyridones of type 6C (wherein R represents one or more optionally present substituents or protecting groups) by reaction with dialkyl 2-(alkoxymethylene)malonate in an organic solvent (such as diphenyl ether and the like) at temperatures ranging from 130° C. to 230° C.

Scheme 7

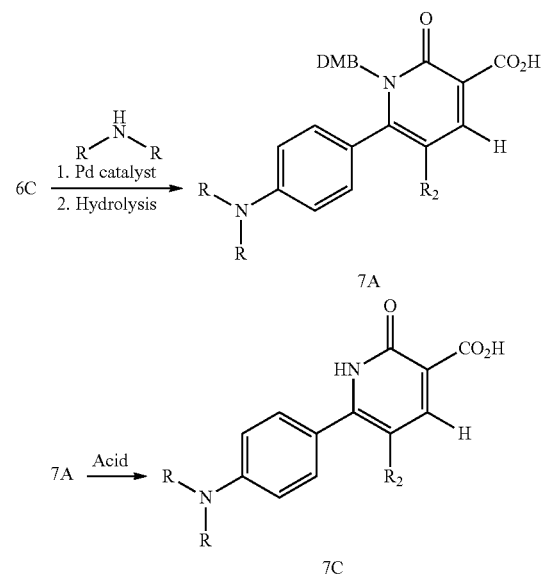

General Procedure for Scheme 7

Aryl halides of type 6C may be used to obtain anilines of type 7A (wherein R represents one or more optionally present substituents or protecting groups and, wherein the amine R groups can be taken together with the nitrogen of attachment to form a heterocyclyl ring) by treatment with an amine, a suitable base, and a suitable palladium catalyst in an appropriate organic solvent at temperatures ranging from 80° C. to 110° C., followed by hydroysis of the ester moiety on the 6C intermediate to provide the corresponding carboxylic acid of type 7A. 2-Pyridones of type 7C are prepared by treatment of the aniline of type 7A with an acid such as trifluoroacetic acid in a suitable organic solvent (such as DCM and the like).

Scheme 8

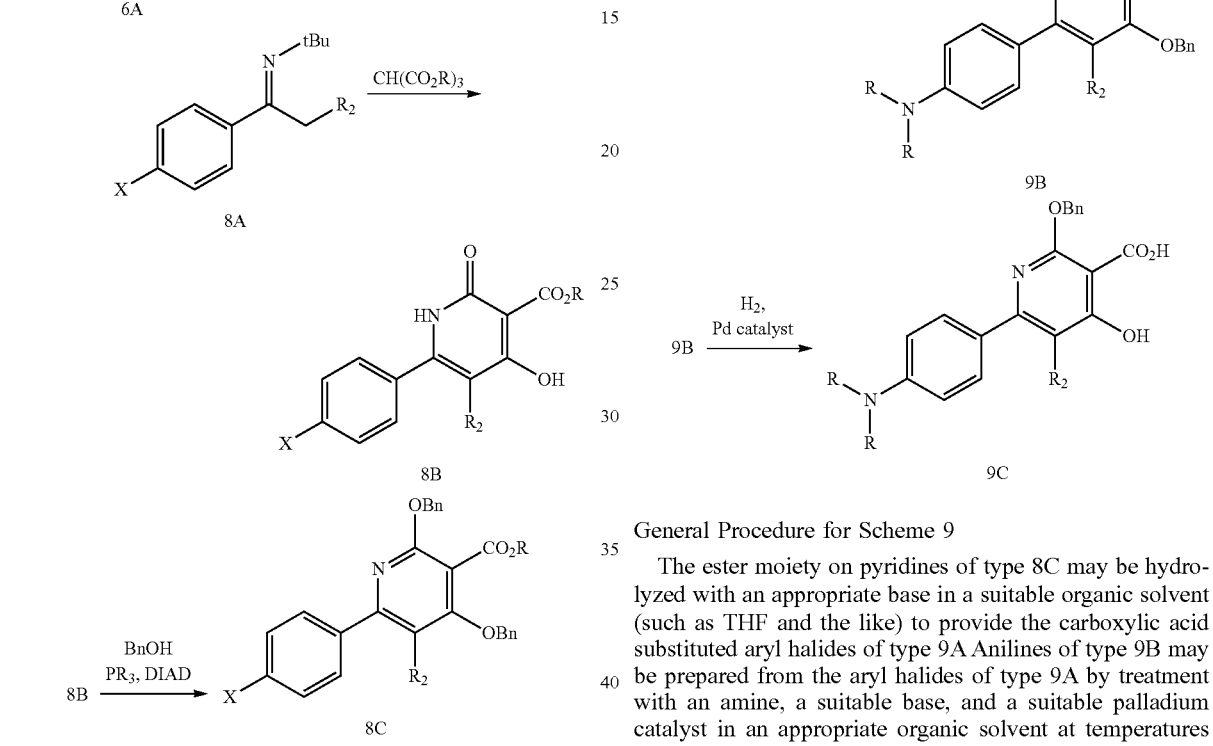

General Procedure for Scheme 8

A ketone of type 6A may be used to obtain an imine of type 8A by reaction with an excess of tertbutyl amine in the presence of a dehydrating agent (such as para-toluene sulfonic acid and the like) or a Lewis acid (such as titanium tetrachloride and the like) in an organic solvent (such as DCM and the like). Imines of type 8A may be used to obtain 2-pyridones of type 8B (wherein R represents one or more optionally present substituents or protecting groups) by reaction with trialkyl methane tricarboxylate in an organic solvent (such as diphenyl ether and the like) at temperatures ranging from 130° C. to 230° C. Pyridines of type 8C are prepared by treatment of the 2-pyridones of type 8B with benzyl alcohol in the presence of a trialkyl phosphine and diisopropyl azodicarboxlate in a suitable organic solvent (such as THF and the like).

Scheme 9

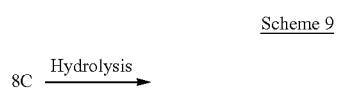

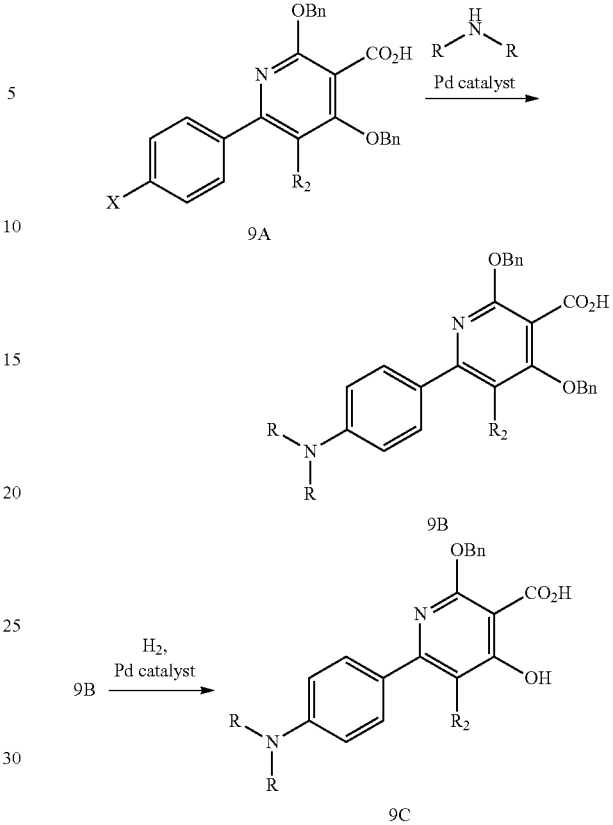

General Procedure for Scheme 9

The ester moiety on pyridines of type 8C may be hydrolyzed with an appropriate base in a suitable organic solvent (such as THF and the like) to provide the carboxylic acid substituted aryl halides of type 9A Anilines of type 9B may be prepared from the aryl halides of type 9A by treatment with an amine, a suitable base, and a suitable palladium catalyst in an appropriate organic solvent at temperatures ranging from 80° C. to 110° C. Finally, 2-pyridones of type 9C may be accessed from pyridines of type 9B by treatment with hydrogen ($H_2$) gas in the presence of a palladium catalyst in an appropriate organic solvent (such as MeOH and the like).

Scheme 10

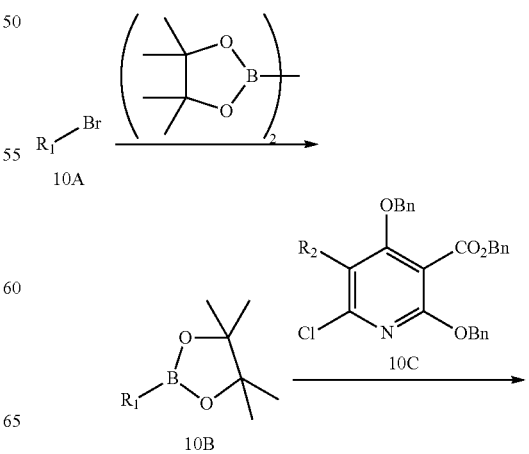

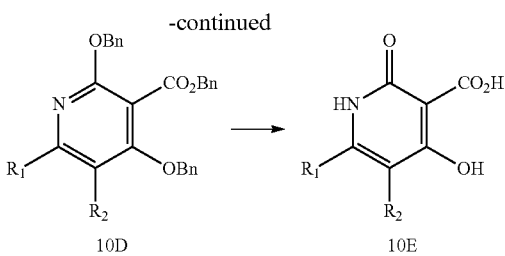

General Procedure for Scheme 10

Aryl and heteroaryl bromides of type 10A may be converted into the corresponding aryl and heteroaryl boronic esters of type 10B in the presence of an excess of bis(pinacolato)diboron, a suitable base (such as potassium acetate and the like) and a suitable palladium catalyst (such as $PdCl_2(dppf)$ and the like) in an organic solvent (such as 1,4-dioxane and the like) at temperatures ranging from 80° C. to 110° C. The 2,4-bisbenzyloxypyridines of type 10D are prepared by Suzuki-coupling between heteroaryl boronic esters of type 10B and 6-chloro-2,4-bisbenzyloxypyridines of type 10C in the presence of a suitable base (such as potassium carbonate and the like), a suitable ligand (such as tri-tert-butylphosphonium tetrafluoroborate and the like) and a suitable palladium catalyst (such as $Pd_2(dba)_3$ and the like) in an organic solvent (such as DMSO and the like) at temperatures ranging from 90° C. to 120° C. The 4-hydroxy-2-pyridones of type 10E are prepared by hydrogenolysis of 2,4-bisbenzyloxypyridines of type 10D with a suitable catalyst (such as palladium on carbon and the like) under hydrogen at room temperature.

Specific Examples

To assist in understanding the present description, the following Examples are included. The experiments relating to this description should not, of course, be construed as specifically limiting the description and such variations of the description, now known or later developed, which would be within the purview of one skilled in the art are considered to fall within the scope of the description as described herein and hereinafter claimed.

Other than in the working examples, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the description are approximations, the numerical values set forth in the working examples are reported as precisely as possible. Any numerical value, however, inherently contains certain errors necessarily resulting from the standard deviation found in their respective testing measurements.

Synthetic Examples

Greater details of the present description are provided with reference to the following non-limiting examples, which are offered to more fully illustrate the description, but are not to be construed as limiting the scope thereof. The examples illustrate the preparation of certain compounds described herein, and the testing of these compounds in vitro and/or in vivo. Those of skill in the art will understand that the techniques described in these examples represent techniques described by persons of ordinary skill in the art to function well in the practice of the description, and as such constitute preferred modes for the practice thereof. However, those of skill in the art should appreciate in light of the present disclosure that many changes can be made to the specific methods that are disclosed and still obtain a like or similar result without departing from the spirit and scope of the description. For example, various conditions were used to obtain LC-MS characterization for the compounds described herein.

As indicated for certain compounds, the 2 Minute Method uses the following column and mobile phase ratios:

Column: Acquity UPLC HSS C18 Column 2.1 × 50 mm, 1.8 μm
Mobile Phase A: $H_2O/0.1\%\ HCO_2H$
Mobile Phase B: Acetonitrile/0.1% $HCO_2H$

| | Time (min) | Flow (mL/min) | % A | % B |
|---|---|---|---|---|
| 1 | 0 | 0.8 | 100 | 0 |
| 2 | 0.2 | 0.8 | 100 | 0 |
| 3 | 1.5 | 0.8 | 0 | 100 |
| 4 | 2.0 | 0.8 | 100 | 0 |

As indicated for certain compounds, the 1 Minute Method uses the following column and mobile phase ratios:

Column: Acquity UPLC HSS C18 Column 2.1 × 50 mm, 1.8 μm
Mobile Phase A: $H_2O/0.1\%\ HCO_2H$
Mobile Phase B: Acetonitrile/0.1% $HCO_2H$

| | Time (min) | Flow (mL/min) | % A | % B |
|---|---|---|---|---|
| 1 | 0 | 0.8 | 90 | 10 |
| 2 | 0.1 | 0.8 | 90 | 10 |
| 3 | 0.8 | 0.8 | 5 | 95 |
| 4 | 1.0 | 0.8 | 90 | 10 |

As indicated for certain compounds, the Polar Method uses the following column and mobile phase ratios:

Column: Acquity UPLC HSS C18 Column 2.1 × 50 mm, 1.8 μm
Mobile Phase A: $H_2O/0.1\%\ HCO_2H$
Mobile Phase B: Acetonitrile/0.1% $HCO_2H$

| | Time (min) | Flow (mL/min) | % A | % B |
|---|---|---|---|---|
| 1 | 0 | 0.8 | 100 | 0 |
| 2 | 0.2 | 0.8 | 100 | 0 |
| 3 | 1.5 | 0.8 | 50 | 50 |
| 4 | 2.0 | 0.8 | 100 | 0 |

As indicated for certain compounds, Method A uses the following column and mobile phase ratios:

| Column: HSS T3 Column 2.1 × 50 mm, 1.8 μm | | | |
|---|---|---|---|
| Mobile Phase A: H₂O/0.1% HCO₂H | | | |
| Mobile Phase B: Acetonitrile/0.1% HCO₂H | | | |
| Time (min) | Flow (ml/min) | % A | % B |
| 1  0 | 0.8 | 80 | 20 |
| 2  0.2 | 0.8 | 80 | 20 |
| 3  1.25 | 0.8 | 5 | 95 |
| 4  2.0 | 0.8 | 80 | 20 |

As indicated for certain compounds, Method B uses the following column and mobile phase ratios:

| Column: HSS T3 Column 2.1 × 50 mm, 1.8 μm | | | |
|---|---|---|---|
| Mobile Phase A: H₂O/0.1% HCO₂H | | | |
| Mobile Phase B: Acetonitrile/0.1% HCO₂H | | | |
| Time (min) | Flow (ml/min) | % A | % B |
| 1  0 | 0.8 | 95 | 5 |
| 2  0.2 | 0.8 | 95 | 5 |
| 3  1.5 | 0.8 | 10 | 90 |
| 4  2.0 | 0.8 | 95 | 5 |

As indicated for certain compounds, Method C uses the following column and mobile phase ratios:

| Column: BEH C18 Column 2.1 × 50 mm, 1.7 μm | | | |
|---|---|---|---|
| Mobile Phase A: NH₄OAc$_{aq}$ 10 mM | | | |
| Mobile Phase B: Acetonitrile | | | |
| Time (min) | Flow (ml/min) | % A | % B |
| 1  0 | 0.8 | 95 | 5 |
| 2  0.2 | 0.8 | 95 | 5 |
| 3  1.5 | 0.8 | 10 | 90 |
| 4  2.0 | 0.8 | 95 | 5 |

As used above, and throughout this description, the following abbreviations, unless otherwise indicated, shall be understood to have the following meanings:

| Abbreviation | Meaning |
|---|---|
| AcOH or HOAc | acetic acid |
| ACN or MeCN | acetonitrile |
| atm | atmosphere |
| Bn | benzyl |
| BnBr | benzyl bromide |
| BnO or OBn | benzyloxy |
| BnOH | benzyl alcohol |
| DCM | dichloromethane (CH₂Cl₂) |
| DIAD | diisopropyl azodicarboxylate |
| DMF | dimethylformamide |
| DMA | dimethylacetamide |
| DMB | dimethoxybenzyl |
| DMSO | dimethylsulfoxide |
| EtOAc | ethyl acetate |
| EtOH | ethanol |
| Et₂O | diethyl ether |
| HPLC | high performance liquid chromatography |
| KF | potassium fluoride |
| KOAc | potassium acetate |
| h/hr/min/s | hour(h or hr)/minute(min)/second(s) |
| LC/MS, LCMS or LC-MS | liquid chromatographic mass spectroscopy |
| LDA | lithium diisopropylamine |
| LiOH | lithium hydroxide |
| MeI | methyl iodide |
| MeOH | methanol |
| Me₂NH | N-methylmethanamine |
| MS | mass spectroscopy |
| NaBH(OAc)₃ | sodium triacetoxyborohydride |

-continued

| Abbreviation | Meaning |
|---|---|
| NMO | N-methylmorpholine-N-oxide |
| n-Bu | n-butyl |
| n-BuLi | n-butyl lithium |
| NMR | nuclear magnetic resonance |
| nPr or n-Pr | n-propyl |
| OSO₄ | osmium tetroxide |
| Pd° | palladium |
| Pd₂(dba)₃ | tris(dibenzylideneacetone)dipalladium(0) |
| PdCl₂(dppf) | [1,1'-bis(diphenylphosphino)ferrocene]dichloropalladium(II) |
| Pd(OAc)₂ | palladium acetate |
| Pd(PPb₃)₄ | tetrakis(triphenylphosphine)palladium |
| Ph₂O | diphenyl ether |
| PPh₃ | triphenylphosphine |
| psi | pounds per square inch pressure |
| PTFE | polytetrafluoroethylene |
| RT | retention time |
| TEA or NEt₃ | triethylamine |
| TPA | trifluoroacetic acid |
| THF | tetrahydrofuran |
| THP | tetrahydro-2H-pyranyl |
| THPO or OTHP | tetrahydro-2H-pyran-2-yloxy |
| TiCl₄ | titanium tetrachloride |
| TMSI | trimethylsilyl iodide |
| TMSOK | potassium trimethylsilanolate |

EXAMPLE 1

5-benzyl-6-(4-(dimethylamino)phenyl)-2-oxo-1,2-dihydropyridine-3-carboxylic acid (Cpd 1)

Step 1: N-methoxy-N-methyl-3-phenylpropanamide

To a solution of 3-phenylpropanoic acid (6.6 g, 43.9 mmol) and oxalyl chloride (4.0 mL, 49 mmol) in CH₂Cl₂ (60 mL) was added DMF (100 μL). The resulting solution was stirred for 1 hr at room temperature and then concentrated. The crude residue was taken up in CH₂Cl₂ (60 mL) then N,O-dimethylhydroxylamine hydrochloride (4.71 g, 49 mmol) and pyridine (5.3 mL, 65 mmol) were added. After stirring at room temperature for 2 hrs, the solution was washed with water (100 mL) and then 1M HCl. The organic phase was dried with Na₂SO₄, then filtered and concentrated to give the title compound as a white solid (7.5 g, 38.6 mmol, 88%).

$^1$H NMR (500 MHz, CDCl₃) δ 2.67 (t, J=7.80 Hz, 2H), 2.86-2.92 (m, 2H), 3.11 (s, 3H), 3.54 (s, 3H), 7.10-7.24 (m, 5H).

Step 2: 1-(4-(dimethylamino)phenyl)-3-phenylpropan-1-one

To a solution of N-methoxy-N-methyl-3-phenylpropanamide (4.7 g, 24.3 mmol) in tetrahydrofuran (100 mL), cooled to −78° C., was added a solution of (4-(dimethylamino)phenyl)magnesium bromide in tetrahydrofuran (50 mL, 0.5M, 25 mmol). After stirring at −78° C. for 30 min, the reaction mixture was allowed to warm to room temperature, then stirred for an additional 1 hr. The reaction was quenched with a saturated solution of ammonium chloride, then poured into water and extracted with ethyl acetate. The combined extracts were dried over Na₂SO₄, then filtered, and concentrated to give the title compound (6.0 g, 23.8 mmol, 98%).

$^1$H NMR (500 MHz, CDCl₃) δ 3.03-3.12 (m, 2H), 3.07 (s, 6H), 3.17-3.26 (m, 2H), 6.71 (m, 2H), 7.25-7.34 (m, 5H), 7.94 (m, 2H).

Step 3: 4-(1-(tert-butylimino)-3-phenylpropyl)-N,N-dimethylaniline

To a solution of 1-(4-(dimethylamino)phenyl)-3-phenylpropan-1-one (2.0 g, 8.0 mmol) and t-butylamine (3.3 mL, 32 mmol) in DCM (15 mL) was added a 1M solution of TiCl$_4$ (5.2 mL, 4.8 mmol) dropwise at 0° C. over 30 min After completion of the addition, the reaction mixture was stirred at room temperature overnight and the reaction was quenched with saturated aqueous sodium bicarbonate. The product was extracted with DCM and the combined organic phases were dried over Na$_2$SO$_4$, then filtered and concentrated to give the title compound as a crude product that was used immediately without further purification.

Step 4: methyl 5-benzyl-6-(4-(dimethylamino)phenyl)-2-oxo-1,2-dihydropyridine-3-carboxylate A solution of 4-(1-(tert-butylimino)-3-phenylpropyl)-N,N-dimethylaniline (0.53 g, 1.7 mmol) and dimethyl 2-(methoxymethylene)malonate (2.55 g. 1.87 mmol) in diglyme (2 mL) was heated at 160° C. for 4 h. The reaction mixture was cooled to room temperature, then the precipitate was filtered and washed with diethyl ether to afford the title compound as a yellow solid (0.22 g, 0.61 mmol, 36%).
$^1$H NMR (500 MHz, DMSO-d$_6$) δ 2.97 (s, 6H), 3.71 (s, 3H), 3.78 (s, 2H), 6.76 (m, 2H), 7.05 (m, 2H), 7.16-7.23 (m, 1H), 7.24-7.32 (m, 4H), 7.88 (s, 1H), 11.90 (br. S., 1H).

Step 5: 5-benzyl-6-[4-(dimethylamino)phenyl]-2-oxo-1,2-dihydropyridine-3-carboxylic acid A solution of methyl 5-benzyl-6-(4-(dimethylamino)phenyl)-2-oxo-1,2-dihydropyridine-3-carboxylate (125 mg, 0.35 mmol) and aqueous LiOH (2 mL, 1M, 2 mmol) in THF (4 mL) was stirred at 50° C. for 3 hrs. The reaction mixture was allowed to cool to room temperature and then acidified with 1M HCl to pH 4. The resulting precipitate was filtered and rinsed with diethyl ether to afford the title compound as a yellow solid (88 mg, 0.25 mmol, 72%).
$^1$H NMR (500 MHz, DMSO-d$_6$) δ 2.93-3.02 (m, 6H), 3.89 (s, 2H), 6.79 (m, 2H), 7.06 (d, 2H), 7.20 (t, 1H), 7.29 (t, 2H), 7.32-7.38 (m, 2H), 8.09 (s, 1H). LC-LC-MS 349.3 [M+H]$^+$, RT 0.77.

EXAMPLE 2

5-benzyl-6-[4-(dimethylamino)phenyl]-4-hydroxy-2-oxo-1,2-dihydropyridine-3-carboxylic acid (Cpd 2)

Step 1: methyl 5-benzyl-6-(4-(dimethylamino)phenyl)-4-hydroxy-2-oxo-1,2-dihydropyridine-3-carboxylate A solution of 4-(1-(tert-butylimino)-3-phenylpropyl)-N,N-dimethylaniline (0.52 g, 1.67 mmol) and triethyl methanetricarboxylate (350 µL. 1.84 mmol) in diglyme (2 mL) was heated at 160° C. for 4 h. The reaction mixture was cooled to room temperature and the resulting precipitate was filtered and washed with diethyl ether to afford the title compound as a yellow solid (0.14 g, 0.36 mmol, 21%).
$^1$H NMR (500 MHz, DMSO-d$_6$) δ 1.30 (t, J=7.09 Hz, 3H), 2.94 (s, 6H), 3.72 (s, 2H), 4.33 (q, J=7.09 Hz, 2H), 6.71 (m, 2H), 7.05 (m, 2H), 7.18 (m, 3H), 7.24 (m, 2H), 11.28-11.35 (s, 1H), 13.58 (s, 1H).

Step 2: 5-benzyl-6-[4-(dimethylamino)phenyl]-4-hydroxy-2-oxo-1,2-dihydropyridine-3-carboxylic acid A solution of methyl 5-benzyl-6-(4-(dimethylamino)phenyl)-4-hydroxy-2-oxo-1,2-dihydropyridine-3-carboxylate (17 mg, 0.04 mmol) and iodotrimethylsilane (20 µL, 0.12 mmol) in a mixture of DCM (500 µL) and acetonitrile (500 µL) was stirred at 80° C. for 1.5 hrs. Additional iodotrimethylsilane (20 µL, 0.12 mmol) was added and the solution was stirred at 80° C. for a further 16 hrs. The reaction mixture was then cooled to room temperature and the reaction was quenched with aqueous HCl (1M). The aqueous phase was extracted with DCM (2×20 mL) and the combined organic extracts were dried over Na$_2$SO$_4$, then filtered and concentrated to give the title compound (10 mg, 0.03 mmol, 69%).
$^1$H NMR (500 MHz, CDCl$_3$) δ 2.96 (s, 6H), 3.88 (s, 2H), 6.65 (m, 2H), 7.00-7.06 (m, 2H), 7.10-7.23 (m, 5H), 10.78 (br. s, 1H), 13.66 (s, 1H), 14.53 (br. s, 1H). LC-MS 365.3 [M+H]$^+$, RT 0.86.

Using the procedure described above, additional compounds described herein may be prepared by substituting the appropriate starting materials, reagents and reaction conditions and include compounds selected from:

| Cpd | Name |
| --- | --- |
| 3 | 6-(4-aminophenyl)-5-ethyl-2-oxo-1,2-dihydropyridine-3-carboxylic acid<br>$^1$H NMR (500 MHz, DMSO-d$_6$) δ ppm 1.06 (t, J = 7.49 Hz, 3H) 2.48 (m, J = 7.50 Hz, 2H) 5.73-5.73 (m, 2H) 6.66 (d, J = 8.51 Hz, 2H) 7.17 (d, J = 8.51 Hz, 2H) 8.30 (s, 1H) 12.84-13.02 (m, 1H) 14.97-15.06 (m, 1H). |
| 4 | 6-[4-(dimethylamino)phenyl]-5-methyl-2-oxo-1,2-dihydropyridine-3-carboxylic acid<br>$^1$H NMR (500 MHz, CDCl$_3$) δ 2.21 (s, 3H), 3.01 (s, 6 H), 6.67-6.78 (m, 2H), 7.27-7.36 (m, 2H), 8.39 (s, 1H). |
| 5 | 6-[4-(dimethylamino)phenyl]-4-hydroxy-5-methyl-2-oxo-1,2-dihydropyridine-3-carboxylic acid<br>$^1$H NMR (500 MHz, DMSO-d$_6$) δ 1.97 (s, 3H), 3.00 (s, 6 H), 6.74-6.81 (m, 2H), 7.29-7.39 (m, 2H). LC-MS 289.2 [M + H]$^+$, RT 0.78. |
| 6 | 5-cyclohexyl-6-[4-(dimethylamino)phenyl]-2-oxo-1,2-dihydropyridine-3-carboxylic acid<br>$^1$H NMR (500 MHz, CDCl$_3$) δ 1.17 (br s, 4H), 1.37-1.49 (m, 2H), 1.60-1.67 (m, 2H), 1.78 (m, 2H), 2.58-2.72 (m, 1H), 3.02 (s, 6 H), 6.77-6.79 (m, 2H), 7.19 (s, 3H), 7.26 (s, 2H), 8.48 (s, 1H), 13.73 (s, 1H). |
| 7 | 5-cyclohexyl-6-[4-(dimethylamino)phenyl]-4-hydroxy-2-oxo-1,2-dihydropyridine-3-carboxylic acid<br>$^1$H NMR (500 MHz, CDCl$_3$) δ 0.92-1.13 (m, 4H), 1.33-1.42 (m, 2H), 1.43-1.51 (m, 1H), 1.55-1.63 (m, 2H), 1.95-2.05 (m, 2H), 2.85-2.91 (m, 2H), 2.91 (s, 6 H), 6.59-6.64 (m, 2H), 7.04-7.12 (m, 2H), 10.35 (s, 1H) 13.85 (s, 1H) 14.67 (s, 1H). |

-continued

| Cpd | Name |
|---|---|
| 8 | 6-[4-(dimethylamino)phenyl]-2-oxo-5-propyl-1,2-dihydropyridine-3-carboxylic acid<br>$^1$H NMR (500 MHz, DMSO-d$_6$) δ 0.79 (t, J = 1.00 Hz, 2H), 1.41-1.49 (m, 2H), 2.43-2.47 (m, 2H), 2.96-3.03 (m, 6 H), 6.75-6.84 (m, 2H), 7.30-7.35 (m, 2H), 8.29 (s, 1H), 13.02 (br. s., 1H), 15.05 (br. s, 1H). LC-MS 301.3 [M + H]$^+$, RT 0.76. |
| 9 | 6-[4-(dimethylamino)phenyl]-4-hydroxy-2-oxo-5-propyl-1,2-dihydropyridine-3-carboxylic acid<br>$^1$H NMR (500 MHz, DMSO-d$_6$) δ 0.71 (t, J = 7.37 Hz, 3H), 1.33-1.42 (m, 2H), 2.23-2.32 (m, 2H), 2.93 (s, 6 H), 6.70-6.77 (m, 2H), 7.19-7.25 (m, 2H), 13.82 (br s, 1H). |
| 10 | 6-(4-fluorophenyl)-2-oxo-1,2-dihydropyridine-3,5-dicarboxylic acid<br>$^1$H NMR (500 MHz, DMSO-d$_6$) δ ppm 7.28-7.36 (m, 2H) 7.53-7.60 (m, 2H) 8.05 (d, J = 0.63 Hz, 1H) 8.73 (d, J = 0.63 Hz, 1H). LC-MS 278.1 [M + H]$^+$, RT 0.48. |
| 11 | 6-[4-(dimethylamino)phenyl]-2-oxo-1,2-dihydropyridine-3,5-dicarboxylic acid<br>$^1$H NMR (500 MHz, DMSO-d$_6$) δ 3.02 (s, 6 H), 6.76 (m, 2H), 7.35 (m, 1H), 8.63 (s, 1H). LC-MS 303.2 [M + H]$^+$, RT 0.52. |
| 12 | 5-cyclopropyl-6-[4-(dimethylamino)phenyl]-2-oxo-1,2-dihydropyridine-3-carboxylic acid<br>$^1$H NMR (500 MHz, DMSO-d$_6$) δ 0.51-0.58 (m, 2H), 0.80-0.86 (m, 2H), 1.78-1.89 (m, 1H), 3.01 (s, 6 H), 6.82-6.87 (m, 2H), 7.46-7.56 (m, 2H), 7.96 (s, 1H), 13.04 (br. s, 1H), 14.99 (br. s., 1H). LC-MS 299.2 [M + H]$^+$, RT 0.72. |
| 13 | 5-cyclopropyl-6-[4-(dimethylamino)phenyl]-4-hydroxy-2-oxo-1,2-dihydropyridine-3-carboxylic acid<br>$^1$H NMR (500 MHz, DMSO-d$_6$) δ 0.45-0.65 (m, 4H), 0.74-0.92 (m, 1H), 3.01 (s, 6 H), 6.83 (d, J = 8.9 Hz, 2H), 7.51 (d, J = 8.9 Hz, 2H), 12.85-13.26 (m, 1H), 14.86-15.17 (m, 1H). LC-MS 313.2 [M − H]$^-$, RT 0.80. |
| 14 | 5-cyano-6-[4-(dimethylamino)phenyl]-2-oxo-1,2-dihydropyridine-3-carboxylic acid<br>$^1$H NMR (500 MHz, DMSO-d$_6$) δ 3.06 (s, 6 H), 6.80-6.94 (m, 2H), 7.58-7.73 (m, 2H), 8.38-8.50 (m, 1H). LC-MS 284.2 [M + H]$^+$, RT 0.63. |
| 15 | 6-(4-cyanophenyl)-5-ethyl-2-oxo-1,2-dihydropyridine-3-carboxylic acid<br>$^1$H NMR (500 MHz, DMSO-d$_6$) δ ppm 1.00 (t, J = 7.53 Hz, 3H) 2.25-2.33 (m, 2H) 7.66 (d, J = 6.78 Hz, 2H) 7.94-8.01 (m, 2H) 8.07 (s, 1H). |
| 16 | 5-ethyl-6-(4-{methyl[2-(tetrahydro-2H-pyran-2-yloxy)ethyl]amino}phenyl)-2-oxo-1,2-dihydropyridine-3-carboxylic acid<br>$^1$H NMR (500 MHz, CHCl$_3$-d) δ ppm 1.12 (t, J = 7.4 Hz, 3H) 1.39-1.54 (m, 4H) 1.60-1.67 (m, 1H) 1.68-1.76 (m, 1H) 2.54 (q, J = 7.49 Hz, 2H) 3.07 (s, 3H) 3.40-3.47 (m, 1H) 3.56-3.67 (m, 3H) 3.74 (ddd, J = 11.23, 8.32, 3.23 Hz, 1H) 3.88-3.95 (m, 1H) 4.52-4.59 (m, 1H) 6.90 (d, J = 8.67 Hz, 2H) 7.32 (d, J = 8.91 Hz, 2H) 8.43 (s, 1H) 12.36 (br. s., 1H) 13.65 (br. s., 1H). |
| 17 | 5-ethyl-6-{4-[(2-hydroxyethyl)(methyl)amino]phenyl}-2-oxo-1,2-dihydropyridine-3-carboxylic acid<br>$^1$H NMR (500 MHz, DMSO-d$_6$) δ ppm 1.09 (t, J = 7.4 Hz 3H) 2.45-2.50 (m, 2H) 3.02 (s, 3H) 3.46-3.52 (m, 2H) 3.56-3.61 (m, 2H) 6.85 (d, J = 8.83 Hz, 2H) 7.33 (d, J = 8.91 Hz, 2H) 8.31 (s, 1H). |
| 18 | 5-ethyl-4-hydroxy-6-{4-[(2-hydroxyethyl)(methyl)amino]phenyl}-2-oxo-1,2-dihydropyridine-3-carboxylic acid<br>$^1$H NMR (500 MHz, DMSO-d$_6$) δ ppm 1.06 (t, J = 7.37 Hz, 3H) 2.39 (d, J = 7.41 Hz, 2H) 3.02 (s, 3H) 3.45-3.51 (m, 2H) 3.56-3.61 (m, 2H) 6.83 (d, J = 8.91 Hz, 2H) 7.29 (d, J = 8.91 Hz, 2H) 12.49-12.57 (m, 1H) 13.82-13.90 (m, 1H). LC-MS 333.3 [M + H]$^+$, RT 0.70. |
| 19 | 6-[2-(dimethylamino)pyrimidin-5-yl]-5-ethyl-2-oxo-1,2-dihydropyridine-3-carboxylic acid<br>$^1$H NMR (500 MHz, CHCl$_3$-d) δ ppm 1.25 (t, J = 7.40 Hz, 3H) 2.61 (q, J = 7.51 Hz, 2H) 3.33 (s, 6 H) 8.50 (s, 2H) 8.57 (s, 1H) 12.60-12.67 (m, 1H) 13.30-13.38 (m, 1H). LC-MS 289.3 [M + H]$^+$, RT 0.70. |
| 20 | 6-[2-(dimethylamino)pyrimidin-5-yl]-5-ethyl-4-hydroxy-2-oxo-1,2-dihydropyridine-3-carboxylic acid<br>$^1$H NMR (500 MHz, CHCl$_3$-d) δ ppm 1.21 (t, J = 7.40 Hz, 3H) 2.55 (q, J = 7.36 Hz, 2H) 3.34 (s, 6 H) 8.50 (br. s., 2H) 11.56 (br. s., 1H) 13.89 (s, 1H) 14.20 (br. s., 1H). LC-MS 305.3 [M + H]$^+$, RT 0.72. |
| 21 | 4-hydroxy-2-oxo-6-[4-(pyrrolidin-1-yl)phenyl]-1,2-dihydropyridine-3-carboxylic acid<br>$^1$H NMR (500 MHz, DMSO-d$_6$) δ ppm 1.95-2.02 (m, 4H) 3.26-3.37 (m, 4H) 6.59 (s, 1H) 6.63 (d, J = 8.91 Hz, 2H) 7.78 (d, J = 8.91 Hz, 2H). LC-MS: 301.1 [M + H]$^+$, RT 1.25. |
| 22 | 5-(aminomethyl)-6-[4-(dimethylamino)phenyl]-2-oxo-1,2-dihydropyridine-3-carboxylic acid hydrochloride (1:1)<br>LC-MS: 288.3 [M + H]$^+$, RT 0.29. |
| 23 | 5-ethyl-2-oxo-6-[4-(1H-tetrazol-5-yl)phenyl]-1,2-dihydropyridine-3-carboxylic acid<br>$^1$H NMR (500 MHz, DMSO-d$_6$) δ ppm 1.05 (t, J = 7.40 Hz, 3H) 2.38-2.45 (m, 2H) 7.73-7.78 (m, 2H) 8.18-8.24 (m, 1H) 8.40-8.45 (m, 1H). |
| 24 | 5-ethyl-6-(4-methoxyphenyl)-2-oxo-1,2-dihydropyridine-3-carboxylic acid<br>LC-MS: 274.3 [M + H]$^+$, RT 0.96 min. |
| 25 | 5-ethyl-4-hydroxy-6-(4-methoxyphenyl)-2-oxo-1,2-dihydropyridine-3-carboxylic acid<br>LC-MS: 290.3 [M + H]$^+$, RT 1.16 min. |
| 26 | 5-ethyl-6-(4-fluorophenyl)-2-oxo-1,2-dihydropyridine-3-carboxylic acid<br>LC-MS: 262.3 [M + H]$^+$, RT 0.96 min. |
| 27 | 5-ethyl-6-(4-methylphenyl)-2-oxo-1,2-dihydropyridine-3-carboxylic acid<br>LC-MS: 259.3 [M + H]$^+$, RT 1.01 min. |
| 28 | 5-ethyl-4-hydroxy-6-(4-methylphenyl)-2-oxo-1,2-dihydropyridine-3-carboxylicacid<br>LC-MS: 274.4 [M + H]$^+$, RT 1.21 min. |

| Cpd | Name |
|---|---|
| 29 | 5-ethyl-4-hydroxy-2-oxo-6-[2-(piperidin-1-yl)phenyl]-1,2-dihydropyridine-3-carboxylic acid<br>LC-MS: 343.3 [M + H]$^+$, RT 1.21 min. |
| 30 | 5-ethyl-6-(2-fluoro-4-methoxyphenyl)-2-oxo-1,2-dihydropyridine-3-carboxylic acid<br>LC-MS: 292.2 [M + H]$^+$, RT 0.95 min. |
| 31 | 5-ethyl-2-oxo-6-[2-(piperidin-1-yl)phenyl]-1,2-dihydropyridine-3-carboxylic acid<br>LC-MS: 327.3 [M + H]$^+$, RT 1.07 min. |
| 32 | 5-ethyl-4-hydroxy-6-(4-methoxy-2-methylphenyl)-2-oxo-1,2-dihydropyridine-3-carboxylic acid<br>LC-MS: 304.2 [M + H]$^+$, RT 1.04 min. |
| 33 | 5-ethyl-6-(4-methoxy-2-methylphenyl)-2-oxo-1,2-dihydropyridine-3-carboxylic acid<br>LC-MS: 288.3 [M + H]$^+$, RT 0.92 min. |
| 34 | 6-(2,4-dimethoxyphenyl)-5-ethyl-2-oxo-1,2-dihydropyridine-3-carboxylic acid<br>LC-MS: 304.3 [M + H]$^+$, RT 1.45 min. |
| 35 | 5-ethyl-6-[4-methoxy-2-(pyrrolidin-1-yl)phenyl]-2-oxo-1,2-dihydropyridine-3-carboxylic acid<br>LC-MS: 343.3 [M + H]$^+$, RT 1.60 min. |
| 36 | 6-(2,4-dimethoxyphenyl)-5-ethyl-4-hydroxy-2-oxo-1,2-dihydropyridine-3-carboxylic acid<br>LC-MS: 320.2 [M + H]$^+$, RT 1.61 min. |
| 37 | 5-ethyl-6-[2-methyl-4-(pyrrolidin-1-yl)phenyl]-2-oxo-1,2-dihydropyridine-3-carboxylic acid<br>LC-MS: 327.4 [M + H]$^+$, RT 1.64 min. |
| 38 | 5-ethyl-6-[2-fluoro-4-(pyrrolidin-1-yl)phenyl]-2-oxo-1,2-dihydropyridine-3-carboxylic acid<br>LC-MS: 331.3 [M + H]$^+$, RT 1.59 min. |
| 39 | 5-ethyl-4-hydroxy-6-[2-methyl-4-(pyrrolidin-1-yl)phenyl]-2-oxo-1,2-dihydropyridine-3-carboxylic acid<br>LC-MS: 343.3 [M + H]$^+$, RT 1.66 min. |
| 40 | 6-[2-(dimethylamino)-4-methoxyphenyl]-5-ethyl-2-oxo-1,2-dihydropyridine-3-carboxylic acid<br>LC-MS: 317.4 [M + H]$^+$, RT 1.83 min. |
| 41 | 5-ethyl-4-hydroxy-2-oxo-6-(2,4,6-trimethoxyphenyl)-1,2-dihydropyridine-3-carboxylic acid<br>LC-MS: 350.3 [M + H]$^+$, RT 1.54 min. |
| 42 | 5-ethyl-4-hydroxy-2-oxo-6-(2,3,4-trimethoxyphenyl)-1,2-dihydropyridine-3-carboxylic acid<br>LC-MS: 350.4 [M + H]$^+$, RT 1.73 min. |
| 43 | 5-ethyl-6-[2-fluoro-4-(piperidin-1-yl)phenyl]-2-oxo-1,2-dihydropyridine-3-carboxylic acid<br>LC-MS: 345.2 [M + H]$^+$, RT 1.67 min. |
| 44 | 5-ethyl-6-[2-fluoro-4-(piperidin-1-yl)phenyl]-4-hydroxy-2-oxo-1,2-dihydropyridine-3-carboxylic acid<br>LC-MS: 361.2 [M + H]$^+$, RT 1.81 min. |
| 45 | 5-ethyl-4-hydroxy-6-[2-methoxy-4-(pyrrolidin-1-yl)phenyl]-2-oxo-1,2-dihydropyridine-3-carboxylic acid<br>LC-MS: 359.4 [M + H]$^+$, RT 1.65 min. |
| 46 | 5-ethyl-2-oxo-6-[2-(pyrrolidin-1-yl)phenyl]-1,2-dihydropyridine-3-carboxylic acid<br>LC-MS: 313.3 [M + H]$^+$, RT 1.55 min. |
| 47 | 5-ethyl-4-hydroxy-2-oxo-6-[2-(pyrrolidin-1-yl)phenyl]-1,2-dihydropyridine-3-carboxylic acid<br>LC-MS: 329.4 [M + H]$^+$, RT 1.73 min. |
| 48 | 5-ethyl-4-hydroxy-6-[4-methoxy-2-(pyrrolidin-1-yl)phenyl]-2-oxo-1,2-dihydropyridine-3-carboxylic acid<br>LC-MS: 359.4 [M + H]$^+$, RT 1.72 min. |
| 49 | 5-ethyl-4-hydroxy-6-[2-methoxy-4-(piperidin-1-yl)phenyl]-2-oxo-1,2-dihydropyridine-3-carboxylic acid<br>LC-MS: 373.4 [M + H]$^+$, RT 1.64 min. |
| 50 | 5-ethyl-6-[2-methoxy-4-(pyrrolidin-1-yl)phenyl]-2-oxo-1,2-dihydropyridine-3-carboxylic acid<br>LC-MS: 343.4 [M + H]$^+$, RT 1.57 min. |
| 51 | 5-ethyl-4-hydroxy-6-[2-methyl-4-(piperidin-1-yl)phenyl]-2-oxo-1,2-dihydropyridine-3-carboxylic acid<br>LC-MS: 357.4 [M + H]$^+$, RT 1.72 min. |
| 52 | 5-ethyl-6-[2-methyl-4-(piperidin-1-yl)phenyl]-2-oxo-1,2-dihydropyridine-3-carboxylic acid<br>LC-MS: 341.4 [M + H]$^+$, RT 1.50 min. |
| 53 | 6-[4-(dimethylamino)-2-fluorophenyl]-5-ethyl-2-oxo-1,2-dihydropyridine-3-carboxylic acid<br>LC-MS: 305.3 [M + H]$^+$, RT 1.46 min. |
| 54 | 6-[2-(dimethylamino)phenyl]-5-ethyl-2-oxo-1,2-dihydropyridine-3-carboxylic acid<br>LC-MS: 287.3 [M + H]$^+$, RT 1.52 min. |
| 55 | 6-[4-(dimethylamino)-2-fluorophenyl]-5-ethyl-4-hydroxy-2-oxo-1,2-dihydropyridine-3-carboxylic acid<br>LC-MS: 321.3 [M + H]$^+$, RT 1.63 min. |

| Cpd | Name |
|---|---|
| 56 | 6-[4-(dimethylamino)-2-methylphenyl]-5-ethyl-4-hydroxy-2-oxo-1,2-dihydropyridine-3-carboxylic acid<br>LC-MS: 317.4 [M + H]$^+$, RT 1.69 min. |
| 57 | 6-[4-(dimethylamino)-2-methylphenyl]-5-ethyl-2-oxo-1,2-dihydropyridine-3-carboxylic acid<br>LC-MS: 301.3 [M + H]$^+$, RT 1.50 min. |
| 58 | 6-[2-(dimethylamino)phenyl]-5-ethyl-4-hydroxy-2-oxo-1,2-dihydropyridine-3-carboxylic acid<br>LC-MS: 303.3 [M + H]$^+$, RT 1.66 min. |
| 59 | 5-ethyl-6-[2-methoxy-4-(piperidin-1-yl)phenyl]-2-oxo-1,2-dihydropyridine-3-carboxylic acid<br>LC-MS: 357.6 [M + H]$^+$, RT 1.57 min. |
| 60 | 6-[2-(dimethylamino)-4-methoxyphenyl]-5-ethyl-4-hydroxy-2-oxo-1,2-dihydropyridine-3-carboxylic acid<br>LC-MS: 333.5 [M + H]$^+$, RT 1.65 min. |
| 61 | 6-[4-(dimethylamino)-2-methoxyphenyl]-5-ethyl-4-hydroxy-2-oxo-1,2-dihydropyridine-3-carboxylic acid<br>LC-MS: 333.5[M + H]$^+$, RT 1.63 min. |
| 62 | 6-[4-(dimethylamino)-2-methoxyphenyl]-5-ethyl-2-oxo-1,2-dihydropyridine-3-carboxylic acid<br>LC-MS: 317.6 [M + H]$^+$, RT 1.45 min. |
| 63 | 6-[4-(dimethylamino)-3-methylphenyl]-5-ethyl-4-hydroxy-2-oxo-1,2-dihydropyridine-3-carboxylic acid<br>LC-MS: 317.4 [M + H]$^+$, RT 1.62 min. |
| 64 | 6-[4-(dimethylamino)-3-methoxyphenyl]-5-ethyl-2-oxo-1,2-dihydropyridine-3-carboxylic acid<br>LC-MS: 317.5 [M + H]$^+$, RT 1.01 min. |
| 65 | 6-[4-(dimethylamino)-3-methoxyphenyl]-5-ethyl-4-hydroxy-2-oxo-1,2-dihydropyridine-3-carboxylic acid<br>LC-MS: 333.3 [M + H]$^+$, RT 1.30 min. |
| 66 | 5-ethyl-6-[3-methoxy-4-(pyrrolidin-1-yl)phenyl]-2-oxo-1,2-dihydropyridine-3-carboxylic acid<br>LC-MS: 343.4 [M + H]$^+$, RT 1.49 min. |
| 67 | 5-ethyl-4-hydroxy-6-[3-methoxy-4-(pyrrolidin-1-yl)phenyl]-2-oxo-1,2-dihydropyridine-3-carboxylic acid<br>LC-MS: 359.3 [M + H]$^+$, RT 1.72 min. |
| 68 | 5-ethyl-6-[3-methoxy-4-(piperidin-1-yl)phenyl]-2-oxo-1,2-dihydropyridine-3-carboxylic acid<br>LC-MS: 357.4 [M + H]$^+$, RT 1.28 min. |
| 69 | 5-ethyl-4-hydroxy-6-[3-methoxy-4-(piperidin-1-yl)phenyl]-2-oxo-1,2-dihydropyridine-3-carboxylic acid<br>LC-MS: 373.4 [M + H]$^+$, RT 1.51 min. |
| 70 | 5-ethyl-6-[3-methyl-4-(pyrrolidin-1-yl)phenyl]-2-oxo-1,2-dihydropyridine-3-carboxylic acid<br>LC-MS: 327.4 [M + H]$^+$, RT 1.59 min. |
| 71 | 5-ethyl-4-hydroxy-6-[3-methyl-4-(pyrrolidin-1-yl)phenyl]-2-oxo-1,2-dihydropyridine-3-carboxylic acid<br>LC-MS: 343.4 [M + H]$^+$, RT 1.76 min. |
| 72 | 5-ethyl-6-[3-methyl-4-(piperidin-1-yl)phenyl]-2-oxo-1,2-dihydropyridine-3-carboxylic acid<br>LC-MS: 341.6 [M + H]$^+$, RT 1.72 min. |
| 73 | 5-ethyl-4-hydroxy-6-[3-methyl-4-(piperidin-1-yl)phenyl]-2-oxo-1,2-dihydropyridine-3-carboxylic acid<br>LC-MS: 357.6 [M + H]$^+$, RT 1.87 min. |
| 74 | 5-ethyl-6-(4-fluorophenyl)-4-hydroxy-2-oxo-1,2-dihydropyridine-3-carboxylic acid<br>LC-MS: 278.3 [M + H]$^+$, RT 1.06 min. |
| 75 | 5-ethyl-2-oxo-6-phenyl-1,2-dihydropyridine-3-carboxylic acid<br>$^1$H NMR (500 MHz, CHCl$_3$-d) δ ppm 1.17 (t, J = 7.6 Hz, 3H) 2.56 (q, J = 7.6 Hz, 2H) 7.48 (dd, J = 7.9, 1.6 Hz, 2H) 7.51-7.63 (m, 3H) 8.56 (s, 1H) 12.77 (br. s., 1H) 13.47 (s, 1H). LC-MS 242.0 [M − H]$^−$, 244.3 [M + H]$^+$, RT 1.01 min. |
| 76 | 6-(4-chlorophenyl)-5-ethyl-2-oxo-1,2-dihydropyridine-3-carboxylic acid<br>$^1$H NMR (500 MHz, DMSO-d$_6$) δ ppm 1.01 (t, J = 7.4 Hz, 3H) 2.36 (q, J = 7.6 Hz, 2H) 7.54 (d, J = 8.8 Hz, 1H) 7.62 (d, J = 8.8 Hz, 2H) 8.38 (s, 1H) 13.31 (br. s., 1H) 14.93 (br. s., 1H). LC-MS 276.2/278.2 [M − H]$^−$, 278.1/280.0 [M + H]$^+$, RT 1.10 min. |
| 77 | 6-(4-chlorophenyl)-5-ethyl-4-hydroxy-2-oxo-1,2-dihydropyridine-3-carboxylic acid<br>$^1$H NMR (500 MHz, DMSO-d$_6$) δ ppm 0.98 (t, J = 7.4 Hz, 3H) 2.26 (q, J = 7.4 Hz, 2H) 7.53 (d, J = 8.5 Hz, 2H) 7.62 (d, J = 8.5 Hz, 2H) 12.82 (br. s., 1H) 13.92 (s, 1H) 16.18 (br. s., 1H). LC-MS 291.7/293.6 [M − H]$^−$, 293.8/295.6 [M + H]$^+$, RT 1.35 min. |
| 78 | 6-(4-bromophenyl)-5-ethyl-2-oxo-1,2-dihydropyridine-3-carboxylic acid<br>$^1$H NMR (500 MHz, CHCl$_3$-d) δ ppm 1.17 (t, J = 7.6 Hz, 3H) 2.53 (q, J = 7.6 Hz, 2H) 7.36 (d, J = 8.5 Hz, 2H) 7.73 (d, J = 8.5 Hz, 2H) 8.57 (s, 1H) 12.65 (br. s., 1H) 13.43 (s, 1H). LC-MS 319.9/321.9 [M − H]$^−$, 322.0/324.0 [M + H]$^+$, RT 1.41 min. |
| 79 | 6-(4-bromophenyl)-5-ethyl-4-hydroxy-2-oxo-1,2-dihydropyridine-3-carboxylic acid<br>$^1$H NMR (500 MHz, DMSO-d$_6$) δ ppm 0.98 (t, J = 7.4 Hz, 3H) 2.26 (q, J = 7.4 Hz, 2H) 7.45 (d, J = 8.5 Hz, 2H) 7.76 (d, J = 8.5 Hz, 2H) 12.84 (br. s., 1H) 13.92 (s, 1H) 16.22 (br. s., 1H). LC-MS 336.0/338.0 [M − H]$^−$, 338.0/340.0 [M + H]$^+$, RT 1.60 min. |

| Cpd | Name |
|---|---|
| 80 | 5-ethyl-6-(4-iodophenyl)-2-oxo-1,2-dihydropyridine-3-carboxylic acid<br>$^1$H NMR (500 MHz, DMSO-$d_6$) δ ppm 1.01 (t, J = 7.4 Hz, 3H) 2.35 (q, J = 7.4 Hz, 2H) 7.30 (d, J = 7.9 Hz, 2H) 7.92 (d, J = 7.9 Hz, 2H) 8.38 (s, 1H) 13.32 (br. s., 1H) 14.95 (br. s., 1H). LC-MS 367.9 [M − H]$^-$, 370.0 [M + H]$^+$, RT 1.18 min. |
| 81 | 5-ethyl-4-hydroxy-6-(4-iodophenyl)-2-oxo-1,2-dihydropyridine-3-carboxylic acid<br>$^1$H NMR (500 MHz, DMSO-$d_6$) δ ppm 0.97 (t, J = 7.3 Hz, 3H) 2.25 (q, J = 7.3 Hz, 2H) 7.29 (d, J = 8.8 Hz, 2H) 7.92 (d, J = 8.8 Hz, 2H) 12.81 (br. s., 1H) 13.91 (br. s., 1H). LC-MS 384.0 [M − H]$^-$, 386.0 [M + H]$^+$, RT 1.36 min. |
| 312 | 6-(5-(dimethylamino)pyrazin-2-yl)-5-ethyl-4-hydroxy-2-oxo-1,2-dihydropyridine-3-carboxylic acid<br>$^1$H NMR (500 MHz, DMSO-$d_6$) δ ppm 1.05 (3 H, t, J = 7.25 Hz), 2.5 (3 H, obscured by DMSO-$d_6$), 3.15 (6 H, s), 8.24 (1 H, d, J = 1.26 Hz), 8.34 (1 H, br. s). LC-MS 305.2 [M + H]$^+$, RT 0.72 min. |
| 313 | 5-ethyl-4-hydroxy-2-oxo-6-(5-(pyrrolidin-1-yl)pyrazin-2-yl)-1,2-dihydropyridine-3-carboxylic acid<br>$^1$H NMR (500 MHz, DMSO-$d_6$) δ ppm 1.07 (3 H, t, J = 7.41 Hz), 1.90-2.05 (4 H, m), 2.48 (2 H, m, J = 7.60 Hz), 3.48-3.58 (4 H, m), 8.10 (1 H, d, J = 1.26 Hz), 8.33 (1 H, d, J = 1.58 Hz), 12.65 (1 H, br. s), 13.91 (1 H, br. s), 16.16-16.31 (1 H, m). LC-MS 331.2 [M + H]$^+$, RT 0.78 min. |
| 314 | 6-(5-(3-(dimethylamino)pyrrolidin-1-yl)pyrazin-2-yl)-5-ethyl-4-hydroxy-2-oxo-1,2-dihydropyridine-3-carboxylic acid<br>$^1$H NMR (500 MHz, MeOH-$d_4$) δ ppm 1.17 (t, J = 7.4 Hz, 3 H), 2.01-2.12 (m, 1 H), 2.38-2.47 (m, 1 H), 2.61 (q, J = 7.5 Hz, 2 H), 2.65 (s, 6 H), 3.20-3.29 (m, 1 H), 3.44-3.50 (m, 1 H), 3.53-3.62 (m, 1 H), 3.82-3.90 (m, 1 H), 3.93-4.01 (m, 1 H), 8.10 (s, 1 H), 8.35 (s, 1 H). LC-MS 374.3 [M + H]$^+$, RT 0.78 min. |
| 344 | 5-ethyl-6-(1-methyl-1H-pyrazol-5-yl)-2-oxo-1,2-dihydropyridine-3-carboxylic acid<br>$^1$H NMR (500 MHz, DMF) δ ppm 1.43 (t, J = 7.53 Hz, 3 H) 2.74 (q, J = 7.54 Hz, 2 H) 4.15 (s, 3 H) 7.01 (d, J = 1.97 Hz, 1 H) 8.02 (d, J = 1.89 Hz, 1 H) 8.84 (s, 1 H). LC-MS 248.2 [M + H]$^+$, RT 0.48 min. |
| 345 | 5-ethyl-4-hydroxy-6-(1-methyl-1H-pyrazol-5-yl)-2-oxo-1,2-dihydropyridine-3-carboxylic acid<br>$^1$H NMR (500 MHz, DMSO-$d_6$) δ ppm 0.97 (t, J = 7.41 Hz, 3 H) 2.52-2.54 (m, 1 H) 3.72-3.75 (m, 3 H) 6.59 (d, J = 1.97 Hz, 1 H) 7.61 (d, J = 1.89 Hz, 1 H). LC-MS 262.2 [M − H]$^-$, RT 0.63 min. |
| 346 | 5-ethyl-6-(1-methyl-1H-pyrazol-4-yl)-2-oxo-1,2-dihydropyridine-3-carboxylic acid<br>$^1$H NMR (500 MHz, DMSO-$d_6$) δ ppm 0.92 (t, J = 7.49 Hz, 3 H) 2.38 (q, J = 7.49 Hz, 2 H) 3.72 (s, 3 H) 7.70 (d, J = 0.79 Hz, 1 H) 8.05 (d, J = 0.24 Hz, 1 H) 8.08 (s, 1 H). LC-MS 248.2 [M + H]$^+$, RT 0.51 min. |
| 347 | 5-ethyl-4-hydroxy-6-(1-methyl-1H-pyrazol-4-yl)-2-oxo-1,2-dihydropyridine-3-carboxylic acid<br>$^1$H NMR (500 MHz, DMSO-$d_6$) δ ppm 1.10-1.13 (m, 3 H) 2.51-2.53 (m, 2 H) 3.94 (s, 3 H) 7.85 (d, J = 0.79 Hz, 1 H) 8.21 (s, 1 H) 12.46-12.52 (m, 1 H) 13.79-13.85 (m, 1 H). LC-MS 264.2 [M + H]$^+$, RT 0.62 min. |

EXAMPLE 3

5-ethyl-4-hydroxy-6-(4-(((3-iodopropyl)amino)phenyl)-2-oxo-1,2-dihydropyridine-3-carboxylic acid (Cpd 82)

A mixture of methyl 6-(4-(azetidin-1-yl)phenyl)-5-ethyl-4-hydroxy-2-oxo-1,2-dihydropyridine-3-carboxylate (0.16 g. 0.47 mmol) and TMSI (0.30 mL, 2.11 mmol) in ACN (1 mL) and DCM (1 mL) was heated in a sealed vial at 60° C. overnight. Additional TMSI (0.30 mL, 2.11 mmol) was added and the heating continued at 60° C. until complete hydrolysis of the ester was observed by LC/MS. The reaction mixture was cooled to room temperature, then diluted with DCM (10 mL) and the reaction was quenched with Na$_2$S$_2$O$_3$ (10% aqueous, 2 mL). The solid was filtered and the DCM layer was separated and dried over Na$_2$SO$_4$. After removal of the solvent, the residue was purified by preparative HPLC to afford the title compound (0.0167 g, 8%) as a pale yellow solid.

$^1$H NMR (500 MHz, DMSO-$d_6$) δ ppm 1.04 (t, J=7.3 Hz, 3H) 2.04 (quin, J=6.8 Hz, 2H) 2.38 (q, J=7.3 Hz, 2H) 2.51-2.53 (m, 2H, solvent overlap) 3.16 (t, J=6.8 Hz, 2H) 6.68 (d, J=8.5 Hz, 2H) 7.21 (d, J=8.5 Hz, 2H) 12.48 (s, 1H) 13.84 (br. s., 1H). LC-MS 441.1 [M−H]$^-$, 443.1 [M+H]$^+$, RT 1.43 min.

EXAMPLE 4

6-(4-(azetidin-1-yl)phenyl)-5-ethyl-4-hydroxy-2-oxo-1,2-dihydropyridine-3-carboxylic acid (Cpd 83)

A mixture of methyl 6-(4-(azetidin-1-yl)phenyl)-5-ethyl-4-hydroxy-2-oxo-1,2-dihydropyridine-3-carboxylate (0.100 g. 0.30 mmol) and TMSOK (0.33 g mL, 2.21 mmol) in DCM (2 mL) was heated in a sealed vial at 50° C. overnight. The reaction mixture was cooled to room temperature, then diluted with Et$_2$O (10 mL) and the reaction was quenched with 1M HCl (2 mL). The solid was filtered off and washed with a DCM/Et$_2$O mixture. The mother liquor was concentrated and the residue was triturated with Et$_2$O. The resulting solid was collected by filtration and washed with Et$_2$O, providing the title compound (0.015 g, 16%) as a pale yellow solid.

¹H NMR (500 MHz, DMSO-d₆) δ ppm 1.03 (t, J=7.3 Hz, 3H) 2.30-2.39 (m, 4H) 3.90 (t, J=7.3 Hz, 4H) 6.51 (d, J=8.5 Hz, 2H) 7.28 (d, J=8.5 Hz, 2H) 12.55 (br. s., 1H) 13.86 (br. s., 1H). LC-MS 312.9 [M−H]⁻, 315.2 [M+H]⁺, RT 1.35 min.

EXAMPLE 5

5-ethyl-6-[3-fluoro-4-(morpholin-4-yl)phenyl]-2-oxo-1,2-dihydropyridine-3-carboxylic acid (Cpd 84)

Step 1: 1-(3-fluoro-4-morpholinophenyl)butan-1-one

To a solution of 3-fluoro-4-morpholinobenzonitrile (4.38 g, 21.24 mmol) in THF (30 mL) was added nPr-MgCl (2 M Et₂O, 16.0 mL, 32 mmol) at 0° C. The reaction mixture was stirred and allowed to warm to room temperature, then heated to reflux for 3 h until the starting material was completely consumed. The reaction was quenched by the addition of NH₄Cl (aqueous saturated, ~50 mL). A solution of HCl (3M aqueous, 20 mL) was added and the mixture was stirred at room temperature for 30 min. The product was extracted with EtOAc (3×70 mL) then the combined organics were washed with NaCl (aqueous saturated) and dried over MgSO₄. The solvents were concentrated and the residue was purified by column chromatography using EtOAc/hexanes (gradient 0-40%) to afford 1-(3-fluoro-4-morpholinophenyl)butan-1-one (2.58 g, 48%).
¹H NMR (500 MHz, CHCl₃-d) δ ppm 1.00 (t, J=7.4 Hz, 3H) 1.76 (sxt, J=7.4 Hz, 2H) 2.87 (t, J=7.4 Hz, 2H) 3.19-3.25 (m, 4H) 3.86-3.91 (m, 4H) 6.92 (t, J=8.5 Hz, 1H) 7.64 (dd, J=14.0, 2.0 Hz, 1H) 7.70 (dd, J=8.5, 2.0 Hz, 1H). LC-MS 252.4 [M+H]⁺, RT 1.32 min.

Step 2: 5-ethyl-6-[3-fluoro-4-(morpholin-4-yl)phenyl]-2-oxo-1,2-dihydropyridine-3-carboxylic acid Using 1-(3-fluoro-4-morpholinophenyl)butan-1-one as prepared above, the title compound was prepared according to the procedure of Example 1.
¹H NMR (500 MHz, DMSO-d₆) δ ppm 1.04 (t, J=7.6 Hz, 3H) 2.41 (d, J=7.6 Hz, 2H) 3.09-3.15 (m, 4H) 3.72-3.82 (m, 4H) 7.16 (t, J=8.8 Hz, 1H) 7.27 (dd, J=8.8, 1.9 Hz, 1H) 7.38 (dd, J=13.6, 1.9 Hz, 1H) 8.36 (s, 1H) 13.18 (br. s., 1H) 14.96 (br. s., 1H). LC-MS 345.0 [M−H]⁻, 347.3 [M+H]⁺, RT 1.12 min.

EXAMPLE 6

5-ethyl-6-{4-[(3S)-3-fluoropyrrolidin-1-yl]phenyl}-4-hydroxy-2-oxo-1,2-dihydropyridine-3-carboxylic acid (Cpd 85)

Step 1: (S)-1-(4-(3-fluoropyrrolidin-1-yl)phenyl)butan-1-one

A mixture of 4-fluorobenzonitrile (1.80 g, 14.86 mmol), (S)-3-fluoropyrrolidine hydrochloride (2.06 g, 16.41 mmol) and K₂CO₃ (5.13 g, 37.11 mmol) in ACN (10 mL) was microwaved at 120° C. for 5 h until the starting materials were completely consumed. The reaction mixture was diluted with EtOAc/DCM and the resulting solids were filtered. The mother liquor was concentrated and the residue was purified by column chromatography using EtOAc/hexanes (gradient 0-40%) to afford (S)-4-(3-fluoropyrrolidin-1-yl)benzonitrile (1.94 g, 69%).
¹H NMR (500 MHz, CHCl₃-d) δ ppm 2.09-2.27 (m, 1H) 2.38-2.50 (m, 1H) 3.50-3.66 (m, 4H) 5.41 (br. d, J=54.9 Hz, 1H) 6.54 (d, J=8.8 Hz, 2H) 7.49 (d, J=8.8 Hz, 2H). LC-MS 191.0 [M+H]⁺, RT 1.13 min.

Step 2: (S)-1-(4-(3-fluoropyrrolidin-1-yl)phenyl)butan-1-one

To a solution of (S)-4-(3-fluoropyrrolidin-1-yl)benzonitrile (2.37 g, 12.45 mmol) in THF (12 mL) was added n-PrMgCl (2 M Et₂O, 10.0 mL, 20 mmol) at 0° C. The reaction mixture was stirred and allowed to warm to room temperature and then heated to reflux overnight. The reaction was quenched by the addition of NH₄Cl (aqueous saturated, ~50 mL) and the product was extracted with EtOAc (3×70 mL). The combined organics were washed with NaCl (aqueous saturated) and dried over Na₂SO₄. The solvent was concentrated to provide an orange oil that was mixed with 6M HCl (20 mL) and stirred at room temperature for 18 h. The mixture was neutralized with NaHCO₃ solution (aqueous saturated) and the product was extracted with DCM (3×70 mL). The combined organics were washed with NaCl (aqueous saturated) and dried over Na₂SO₄. The solvents were concentrated and the resulting residue was purified by column chromatography using EtOAc/hexanes (gradient 0-50%) to afford (S)-1-(4-(3-fluoropyrrolidin-1-yl)phenyl)butan-1-one (2.36 g, 81%).
¹H NMR (500 MHz, CHCl₃-d) δ ppm 1.00 (t, J=7.4 Hz, 3H) 1.76 (sxt, J=7.4 Hz, 2H) 2.06-2.27 (m, 1H) 2.35-2.48 (m, 1H) 2.86 (t, J=7.4 Hz, 2H) 3.49-3.71 (m, 4H) 5.38 (br. d, J=52.0 Hz, 1H) 6.54 (d, J=8.8 Hz, 2H) 7.90 (d, J=8.8 Hz, 2H). LC-MS 236.0 [M+H]⁺, RT 1.24 min.

Step 3: 5-ethyl-6-{4-[(3S)-3-fluoropyrrolidin-1-yl]phenyl}-4-hydroxy-2-oxo-1,2-dihydropyridine-3-carboxylic acid Using (S)-1-(4-(3-fluoropyrrolidin-1-yl)phenyl)butan-1-one prepared above, the title compound was prepared according to the procedure of Example 1, Steps 3-5 or Example 2, Steps 1 and 2. LC-MS 345.9 [M−H]⁻, 347.9 [M+H]⁺, RT 1.31 min.

Using the procedure described above, additional compounds described herein may be prepared by substituting the appropriate starting materials, reagents and reaction conditions and include compounds selected from:

| Cpd | Name |
|---|---|
| 86 | 6-[6-(dimethylamino)pyridin-3-yl]-5-ethyl-2-oxo-1,2-dihydropyridine-3-carboxylic acid<br>¹H NMR (500 MHz, CHCl₃-d) δ ppm 1.22 (t, J = 7.6 Hz, 3H) 2.63 (q, J = 7.6 Hz, 2H) 3.21 (s, 6 H) 6.66 (d, J = 8.5 Hz, 1H) 7.61 (dd, J = 8.5, 2.7 Hz, 2H) 8.32 (d, J = 2.7 Hz, 1H) 8.53 (s, 1H) 12.85 (br. s., 1H) 13.57 (s, 1H). LC-MS 285.8 [M − H]⁻, 287.9 [M + H]⁺ RT 0.81 min. |
| 87 | 6-[6-(dimethylamino)pyridin-3-yl]-5-ethyl-4-hydroxy-2-oxo-1,2-dihydropyridine-3-carboxylic acid<br>¹H NMR (500 MHz, DMSO-d₆) δ ppm 1.04 (t, J = 7.3 Hz, 3H) 2.36 (q, J = 7.3 Hz, 2H) 3.13 (s, 6 H) 6.84 (d, J = 8.2 Hz, 1H) 7.67 (d, J = 8.2 Hz, 1H) 8.19 (d, J = 1.9 Hz, 1H) 12.69 (br. s., 1H) 13.87 (br. s., 1H) 16.23 (br. s., 1H). LC-MS 302.0 [M − H]⁻, 304.0 [M + H]⁺ RT 0.85 min. |

| Cpd | Name |
| --- | --- |
| 88 | 6-[4-(dimethylamino)phenyl]-5-ethyl-2-oxo-1,2-dihydropyridine-3-carboxylic acid<br>$^1$H NMR (500 MHz, CHCl$_3$-d) δ ppm 1.21 (t, J = 7.6 Hz, 3H) 2.64 (q, J = 7.6 Hz, 2H) 3.08 (s, 6 H) 6.80 (d, J = 8.8 Hz, 2H) 7.39 (d, J = 8.8 Hz, 2H) 8.50 (s, 1H) 12.56 (br. s., 1H) 13.79 (s, 1H). LC-MS 285.0 [M − H]$^-$, 287.2 [M + H]$^+$, RT 1.09 min. |
| 89 | 6-[3-fluoro-4-(morpholin-4-yl)phenyl]-5-methyl-2-oxo-1,2-dihydropyridine-3-carboxylic acid<br>$^1$H NMR (500 MHz, DMSO-d$_6$) δ ppm 2.12 (s, 3H) 3.02-3.18 (m, 4H) 3.71-3.81 (m, 4H) 7.15 (t, J = 8.8 Hz, 1H) 7.31 (d, J = 8.8 Hz, 1H) 7.41 (d, J = 13.9 Hz, 1H) 8.32 (s, 1H) 13.18 (br. S., 1H) 15.03 (br. S., 1H). LC-MS 330.9 [M − H]$^-$, 332.9 [M + H]$^+$, RT 0.92 min. |
| 90 | 6-[4-(dimethylamino)phenyl]-5-ethyl-4-hydroxy-2-oxo-1,2-dihydropyridine-3-carboxylic acid<br>$^1$H NMR (500 MHz, DMSO-d$_6$) δ ppm 1.04 (t, J = 7.4 Hz, 3H) 2.38 (q, J = 7.6 Hz, 2H) 2.99 (s, 6 H) 6.81 (d, J = 9.1 Hz, 2H) 7.30 (d, J = 9.1 Hz, 2H) 12.54 (br. s., 1H) 13.87 (br. s., 1H). LC-MS 301.1 [M − H]$^-$, 303.2 [M + H]$^+$, RT 1.52 min. |
| 91 | 6-{4-[4-(tert-butoxycarbonyl)piperazin-1-yl]-3-fluorophenyl}-5-ethyl-2-oxo-1,2-dihydropyridine-3-carboxylic acid<br>$^1$H NMR (500 MHz, CHCl$_3$-d) δ ppm 1.20 (t, J = 7.6 Hz, 3H) 1.51 (s, 9 H) 2.60 (q, J = 7.6 Hz, 2H) 3.14-3.23 (m, 4H) 3.61-3.68 (m, 4H) 7.07 (t, J = 8.5 Hz, 1H) 7.18 (dd, J = 12.8, 2.0 Hz, 1H) 7.23 (dd, J = 8.5, 2.0 Hz, 1H) 8.55 (s, 1H) 12.62 (br. s., 1H) 13.47 (s, 1H). LC-MS 444.0 [M − H]$^-$, 446.2 [M + H]$^+$, RT 1.46 min. |
| 92 | 5-ethyl-6-[3-fluoro-4-(piperazin-1-yl)phenyl]-2-oxo-1,2-dihydropyridine-3-carboxylic acid trifluoroacetate (1:1)<br>$^1$H NMR (500 MHz, DMSO-d$_6$) δ ppm 1.03 (t, J = 7.4 Hz, 3H) 2.41 (q, J = 7.4 Hz, 2H) 3.19-3.33 (m, 8 H) 7.23 (t, J = 8.8 Hz, 1H) 7.29 (dd, J = 8.8, 1.9 Hz, 1H) 7.42 (dd, J = 13.2, 1.9 Hz, 1H) 8.37 (s, 1H) 8.83 (br. s., 2H) 13.21 (br. s., 1H) 14.94 (br. s., 1H). LC-MS 343.9 [M − H]$^-$, 346.2 [M + H]$^+$, RT 0.78 min. |
| 93 | 6-[4-(dimethylamino)-3-fluorophenyl]-5-ethyl-2-oxo-1,2-dihydropyridine-3-carboxylic acid<br>$^1$H NMR (500 MHz, CHCl$_3$-d) δ ppm 1.20 (t, J = 7.6 Hz, 3H) 2.61 (q, J = 7.6 Hz, 2H) 3.03 (d, J = 1.6 Hz, 6 H) 6.95 (t, J = 8.8 Hz, 1H) 7.14 (dd, J = 14.0, 2.0 Hz, 1H) 7.19 (dd, J = 8.8, 2.0 Hz, 1H) 8.53 (s, 1H) 12.64 (br. s., 1H) 13.57 (s, 1H). LC-MS 303.3 [M − H]$^-$, 305.4 [M + H]$^+$, RT 1.15 min. |
| 94 | 6-[4-(dimethylamino)-3-fluorophenyl]-5-ethyl-4-hydroxy-2-oxo-1,2-dihydropyridine-3-carboxylic acid<br>$^1$H NMR (500 MHz, DMSO-d$_6$) δ ppm 1.02 (t, J = 7.4 Hz, 3H) 2.34 (q, J = 7.4 Hz, 2H) 2.89 (d, J = 0.9 Hz, 6 H) 7.04 (t, J = 8.8 Hz, 1H) 7.19 (dd, J = 8.8, 2.0 Hz, 1H) 7.28 (dd, J = 14.3, 2.0 Hz, 1H) 12.66 (br. s., 1H) 13.89 (br. s., 1H). LC-MS 319.1 [M − H]$^-$, 321.3 [M + H]$^+$, RT 1.35 min. |
| 95 | 6-[4-(dimethylamino)phenyl]-2-oxo-5-(propan-2-yl)-1,2-dihydropyridine-3-carboxylic acid<br>$^1$H NMR (500 MHz, CHCl$_3$-d) δ ppm 1.21 (d, J = 6.9 Hz, 6 H) 3.16 (spt, J = 6.9 Hz, 1H) 6.83 (d, J = 8.8 Hz, 2H) 7.35 (d, J = 8.8 Hz, 2H) 8.58 (s, 1H) 12.21 (br. s., 1H) 13.79 (s, 1H). LC-MS 299.2 [M − H]$^-$, 301.2 [M + H]$^+$, RT 1.08 min. |
| 96 | 6-[4-(dimethylamino)phenyl]-4-hydroxy-2-oxo-5-(propan-2-yl)-1,2-dihydropyridine-3-carboxylic acid<br>$^1$H NMR (500 MHz, CHCl$_3$-d) δ ppm 1.32 (d, J = 6.9 Hz, 6 H) 3.08-3.14 (m, 1H) 6.82 (d, J = 8.8 Hz, 2H) 7.28 (d, J = 8.8 Hz, 2H) 10.68 (br. s., 1H) 13.95 (s, 1H) 14.70 (br. s., 1H). LC-MS 315.2 [M − H]$^-$, 317.2 [M + H]$^+$ RT 1.35 min. |
| 97 | 6-[4-(diethylamino)phenyl]-5-ethyl-2-oxo-1,2-dihydropyridine-3-carboxylic acid<br>$^1$H NMR (500 MHz, CHCl$_3$-d) δ ppm 1.22 (t, J = 7.6 Hz, 3H) 1.25 (t, J = 7.3 Hz, 6 H) 2.65 (q, J = 7.6 Hz, 2H) 3.45 (q, J = 7.3 Hz, 4H) 6.78 (br. s., 2H) 7.37 (d, J = 8.8 Hz, 2H) 8.50 (s, 1H) 12.25 (br. s., 1H) 13.84 (s, 1H). LC-MS 313.1 [M − H]$^-$, 315.2 [M + H]$^+$ RT 0.91 min. |
| 98 | 6-[4-(diethylamino)phenyl]-5-ethyl-4-hydroxy-2-oxo-1,2-dihydropyridine-3-carboxylic acid<br>$^1$H NMR (500 MHz, CHCl$_3$-d) δ ppm 1.20 (t, J = 7.5 Hz, 3H) 1.25 (t, J = 7.1 Hz, 6 H) 2.59 (q, J = 7.5 Hz, 2H) 3.44 (q, J = 7.1 Hz, 4H) 6.74 (d, J = 8.2 Hz, 2H) 7.32 (d, J = 8.2 Hz, 2H) 11.05 (br. s., 1H) 13.71 (s, 1H) 14.71 (s, 1H). LC-MS 329.0 [M − H]$^-$, 331.1 [M + H]$^+$, RT 1.34 min. |
| 99 | 5-ethyl-2-oxo-6-[4-(pyrrolidin-1-yl)phenyl]-1,2-dihydropyridine-3-carboxylic acid<br>$^1$H NMR (500 MHz, CHCl$_3$-d) δ ppm 1.21 (t, J = 7.4 Hz, 3H) 2.05-2.10 (m, 4H) 2.64 (q, J = 7.5 Hz, 2H) 3.31-3.44 (m, 4H) 6.67 (d, J = 8.8 Hz, 2H) 7.38 (d, J = 8.8 Hz, 2H) 8.50 (s, 1H) 12.31 (br. s., 1H) 13.84 (s, 1H). LC-MS 310.9 [M − H]$^-$, 312.9 [M + H]$^+$ RT 1.31 min. |
| 100 | 5-ethyl-4-hydroxy-2-oxo-6-[4-(pyrrolidin-1-yl)phenyl]-1,2-dihydropyridine-3-carboxylic acid<br>$^1$H NMR (500 MHz, CHCl$_3$-d) δ ppm 1.18 (t, J = 7.3 Hz, 3H) 2.01-2.13 (m, 4H) 2.58 (q, J = 7.3 Hz, 2H) 3.33-3.44 (m, 4H) 6.65 (d, J = 8.8 Hz, 2H) 7.32 (d, J = 8.8 Hz, 2H) 10.52 (br. s., 1H) 13.72 (s, 1H) 14.76 (s, 1H). LC-MS 327.3 [M − H]$^-$, 329.2 [M + H]$^+$, RT 1.41 min. |
| 101 | 5-ethyl-2-oxo-6-[4-(1H-pyrrol-1-yl)phenyl]-1,2-dihydropyridine-3-carboxylicacid<br>$^1$H NMR (500 MHz, DMSO-d$_6$) δ ppm 1.05 (t, J = 7.6 Hz, 3H) 2.43 (q, J = 7.6 Hz, 2H) 6.32 (t, J = 2.2 Hz, 2H) 7.51 (t, J = 2.2 Hz, 2H) 7.59 (d, J = 8.8 Hz, 2H) 7.77 (d, J = 8.8 Hz, 2H) 8.39 (s, 1H) 13.30 (br. s., 1H) 14.98 (br. s., 1H). LC-MS 306.8 [M − H]$^-$, 309.0 [M + H]$^+$, RT 1.22 min. |

| Cpd | Name |
|---|---|
| 102 | 6-{4-[4-(tert-butoxycarbonyl)piperazin-1-yl]phenyl}-5-ethyl-2-oxo-1,2-dihydropyridine-3-carboxylic acid<br>$^1$H NMR (500 MHz, CHCl$_3$-d) δ ppm 1.20 (t, J = 7.6 Hz, 3H) 1.51 (s, 9 H) 2.62 (d, J = 7.6 Hz, 2H) 3.25-3.37 (m, 4H) 3.59-3.67 (m, 4H) 7.03 (d, J = 9.1 Hz, 2H) 7.41 (d, J = 9.1 Hz, 2H) 8.53 (s, 1H) 12.60 (br. s., 1H) 13.68 (s, 1H). LC-MS 426.3 [M − H]$^-$, 428.3 [M + H]$^+$, RT 1.26 min. |
| 103 | 5-ethyl-2-oxo-6-[4-(piperazin-1-yl)phenyl]-1,2-dihydropyridine-3-carboxylic acid trifluoroacetate (1:1)<br>$^1$H NMR (500 MHz, DMSO-d$_6$) δ ppm 1.04 (t, J = 7.4 Hz, 3H) 2.44 (q, J = 7.4 Hz, 2H) 3.26 (br. s., 4H) 3.44-3.54 (m, 4H) 7.12 (d, J = 8.8 Hz, 2H) 7.40 (d, J = 8.8 Hz, 2H) 8.34 (s, 1H) 8.92 (br. s., 2H) 13.12 (br. s., 1H) 14.97 (br. s., 1H). LC-MS 325.9 [M − H]$^-$, 328.0 [M + H]$^+$, RT 0.59 min. |
| 104 | 6-{4-[4-(tert-butoxycarbonyl)piperazin-1-yl]phenyl}-5-ethyl-4-hydroxy-2-oxo-1,2-dihydropyridine-3-carboxylic acid<br>LC-MS 442.0 [M − H]$^-$, 444.0 [M + H]$^+$ RT 1.40 min. |
| 105 | 5-ethyl-4-hydroxy-2-oxo-6-[4-(piperazin-1-yl)phenyl]-1,2-dihydropyridine-3-carboxylic acid trifluoroacetate (1:1)<br>$^1$H NMR (500 MHz, MeOH-d$_4$) δ ppm 1.08 (t, J = 7.4 Hz, 3H) 2.45 (q, J = 7.4 Hz, 2H) 3.38-3.42 (m, 4H) 3.53-3.57 (m, 4H) 7.18 (d, J = 8.8 Hz, 2H) 7.41 (d, J = 8.8 Hz, 2H). LC-MS 342.1 [M − H]$^-$, 344.4 [M + H]$^+$ RT 0.80 min. |
| 106 | 5-ethyl-6-[4-(1H-imidazol-1-yl)phenyl]-2-oxo-1,2-dihydropyridine-3-carboxylic acid<br>$^1$H NMR (500 MHz, DMSO-d$_6$) δ ppm 1.04 (t, J = 7.4 Hz, 3H) 2.41 (d, J = 7.4 Hz, 2H) 7.28 (s, 1H) 7.68 (d, J = 8.8 Hz, 2H) 7.89 (d, J = 8.8 Hz, 2H) 7.97 (s, 1H) 8.40 (s, 1H) 8.64 (s, 1H) 13.45 (br. s., 1H) 14.95 (br. s., 1H). LC-MS 307.8 [M − H]$^-$, 309.9 [M + H]$^+$, RT 0.59 min. |
| 107 | 5-ethyl-4-hydroxy-6-[4-(1H-imidazol-1-yl)phenyl]-2-oxo-1,2-dihydropyridine-3-carboxylic acid<br>$^1$H NMR (500 MHz, DMSO-d$_6$) δ ppm 1.00 (t, J = 7.3 Hz, 3H) 2.30 (d, J = 7.3 Hz, 2H) 7.73-7.80 (m, 3H) 7.97 (d, J = 8.5 Hz, 2H) 8.27 (s, 1H) 9.44 (br. s., 1H) 12.97 (br. s., 1H) 13.95 (br. s., 1H). LC-MS 323.8 [M − H]$^-$, 326.0 [M + H]$^+$ RT 0.88 min. |
| 108 | 5-ethyl-2-oxo-6-[4-(piperidin-1-yl)phenyl]-1,2-dihydropyridine-3-carboxylic acid<br>Using the 1-minute method: $^1$H NMR (500 MHz, CHCl$_3$-d) δ ppm 1.20 (t, J = 7.6 Hz, 3H) 1.53-1.79 (m, 6 H) 2.62 (q, J = 7.6 Hz, 2H) 3.27-3.40 (m, 4H) 7.01 (d, J = 8.8 Hz, 2H) 7.37 (d, J = 8.8 Hz, 2H) 8.51 (s, 1H) 12.35 (br. s., 1H) 13.76 (s, 1H). LC-MS 325.1 [M − H]$^-$, 327.1 [M + H]$^+$, RT 0.76 min. |
| 109 | 5-ethyl-4-hydroxy-2-oxo-6-[4-(piperidin-1-yl)phenyl]-1,2-dihydropyridine-3-carboxylic acid<br>$^1$H NMR (500 MHz, CHCl$_3$-d) δ ppm 1.16 (t, J = 7.4 Hz, 3H) 1.47-1.91 (m, 6 H) 2.55 (q, J = 7.4 Hz, 2H) 3.35 (br. s., 4H) 7.06 (br. s., 2H) 7.34 (d, J = 7.6 Hz, 2H) 10.80 (br. s., 1H) 13.75 (s, 1H) 14.61 (br. s., 1H). LC-MS 340.9 [M − H]$^-$, 343.0 [M + H]$^+$ RT 1.56 min. |
| 110 | 5-ethyl-6-[4-(morpholin-4-yl)phenyl]-2-oxo-1,2-dihydropyridine-3-carboxylic acid<br>$^1$H NMR (500 MHz, CHCl$_3$-d) δ ppm 1.20 (t, J = 7.6 Hz, 3H) 2.61 (q, J = 7.6 Hz, 2H) 3.32 (t, J = 5.0 Hz, 4H) 3.90 (t, J = 5.0 Hz, 4H) 7.02 (d, J = 8.8 Hz, 2H) 7.41 (d, J = 8.8 Hz, 2H) 8.53 (s, 1H) 12.37 (br. s., 1H) 13.71 (s, 1H). LC-MS 326.8 [M − H]$^-$ 329.1 [M + H]$^+$, RT 1.82 min. |
| 111 | 6-[4-(azetidin-1-yl)phenyl]-5-ethyl-2-oxo-1,2-dihydropyridine-3-carboxylic acid<br>$^1$H NMR (500 MHz, CHCl$_3$-d) δ ppm 1.19 (t, J = 7.4 Hz, 3H) 2.45 (quin, J = 7.3 Hz, 2H) 2.61 (q, J = 7.5 Hz, 2H) 4.02 (t, J = 7.3 Hz, 4H) 6.51 (d, J = 8.5 Hz, 2H) 7.33 (d, J = 8.5 Hz, 2H) 8.50 (s, 1H) 12.44 (br. s., 1H) 13.77 (s, 1H). LC-MS 296.6 [M − H]$^-$ 298.9 [M + H]$^+$, RT 1.45 min. |
| 112 | 5-ethyl-4-hydroxy-6-(5-morpholinopyridin-2-yl)-2-oxo-1,2-dihydropyridine-3-carboxylic acid<br>LC-MS: 346.2 [M + H]$^+$ RT 0.92 min. |
| 113 | 5-ethyl-4-hydroxy-2-oxo-6-[5-(piperazin-1-yl)pyridin-2-yl]-1,2-dihydropyridine-3-carboxylic acid<br>LC-MS: 345.3 [M + H]$^+$ RT 0.73 min. |

EXAMPLE 7

1-(4-butyrylphenyl)pyrrolidin-2-one 1-(4-Iodophenyl)butan-1-one (1.51 g, 5.50 mmol), pyrrolidin-2-one (0.50 mL, 6.52 mmol), CuI (52 mg, 5 mol %), trans-N,N'-dimethylcyclohexane-1,2-diamine (80 mg, 10 mol %) and K$_3$PO$_4$ (2.34 g, 1.10 mmol) were mixed in toluene (6 mL). The reaction mixture was heated at 100° C. for 1 h until complete consumption of the starting material was observed. The mixture was diluted with EtOAc/DCM and the solids were filtered off. The mother liquor was concentrated, the residue was triturated with Et$_2$O and the product (1.09 g, 85%) was collected by filtration.

$^1$H NMR (500 MHz, CHCl$_3$-d) δ ppm 1.01 (t, J=7.4 Hz, 3H) 1.77 (sxt, J=7.4 Hz, 2H) 2.20 (quin, J=7.6 Hz, 2H) 2.65 (t, J=8.1 Hz, 2H) 2.93 (t, J=7.4 Hz, 2H) 3.91 (t, J=7.1 Hz, 2H) 7.75 (d, J=8.8 Hz, 2H) 7.98 (d, J=8.8 Hz, 2H). LC-MS 232.1 [M+H]$^+$, RT 1.10 min.

Using the ketone prepared according to the procedure described above, additional compounds described herein may be prepared by substituting the appropriate starting materials, reagents and reaction conditions and include compounds selected from:

| Cpd | Name |
|---|---|
| 114 | 5-ethyl-2-oxo-6-[4-(2-oxopyrrolidin-1-yl)phenyl]-1,2-dihydropyridine-3-carboxylic acid<br>$^1$H NMR (500 MHz, CHCl$_3$-d) δ ppm 1.18 (t, J = 7.6 Hz, 3H) 2.25 (quin, J = 7.6 Hz, 2H) 2.59 (q, J = 7.6 Hz, 2H) 2.69 (t, J = 7.6 Hz, 2H) 3.98 (t, J = 7.6 Hz, 2H) 7.51 (d, J = 8.8 Hz, 2H) 7.87 (d, J = 8.8 Hz, 2H) 8.55 (s, 1H) 12.94 (br. s., 1H) 13.57 (s, 1H). LC-MS 326.9 [M − H]$^-$, 324.7 [M + H]$^+$, RT 0.94 min. |
| 115 | 5-ethyl-4-hydroxy-2-oxo-6-[4-(2-oxopyrrolidin-1-yl)phenyl]-1,2-dihydropyridine-3-carboxylic acid<br>$^1$H NMR (500 MHz, CHCl$_3$-d) δ ppm 1.13 (t, J = 7.4 Hz, 3H) 2.24 (quin, J = 7.6 Hz, 2H) 2.51 (q, J = 7.4 Hz, 2H) 2.69 (t, J = 7.6 Hz, 2H) 3.96 (t, J = 7.6 Hz, 2H) 7.46 (d, J = 8.8 Hz, 2H) 7.84 (d, J = 8.8 Hz, 2H) 11.33 (br. s., 1H) 13.77 (s, 1H) 14.51 (s, 1H). LC-MS 340.6 [M − H]$^-$, 342.9 [M + H]$^+$, RT 1.09 min. |
| 116 | 5-ethyl-6-[4-(2-methyl-5-oxopyrrolidin-1-yl)phenyl]-2-oxo-1,2-dihydropyridine-3-carboxylic acid<br>LC-MS: 341.3 [M + H]$^+$, RT 0.83 min. |
| 117 | 5-ethyl-6-{4-[(3S)-3-hydroxy-2-oxopyrrolidin-1-yl]phenyl}-2-oxo-1,2-dihydropyridine-3-carboxylic acid<br>LC-MS: 343.3 [M + H]$^+$, RT 0.65 min. |
| 118 | 5-ethyl-2-oxo-6-[4-(3-oxo-2-azaspiro[4.5]dec-2-yl)phenyl]-1,2-dihydropyridine-3-carboxylic acid<br>LC-MS: 395.3 [M + H]$^+$, RT 1.07 min. |
| 119 | 5-ethyl-2-oxo-6-[4-(3-oxo-2-azabicyclo[2.2.1]hept-5-en-2-yl)phenyl]-1,2-dihydropyridine-3-carboxylic acid<br>LC-MS: 349.0 [M − H]$^-$, RT 3.22 min. |

EXAMPLE 8

1-(4-(3-(tetrahydro-2H-pyran-2-yloxy)azetidin-1-yl)phenyl)butan-1-one

A mixture of 1-(4-fluorophenyl)butan-1-one (2.80 g, 16.85 mmol), azetidin-3-ol hydrochloride (2.00 g, 18.26 mmol) and K$_2$CO$_3$ (5.10 g, 36.90 mmol) in DMSO (20 mL) was heated at 110° C. for 24 h and monitored by LC/MS. After the starting material was completely consumed, the reaction mixture was cooled to room temperature and diluted with H$_2$O (~200 mL). The resulting precipitate was collected by filtration and washed with H$_2$O. After drying, the product 1-(4-(3-hydroxyazetidin-1-yl)phenyl)butan-1-one (3.32 g, 15.09 mmol) was dissolved in DCM (40 mL), then TsOH (140 mg, 5 mol %) was added, followed by the addition of 3,4-dihydro-2H-pyran (1.80 mL, 19.66 mmol) dropwise. The reaction mixture was stirred at room temperature for 3 h, then diluted with DCM (150 mL) and washed with NaHCO$_3$ (aqueous saturated). The organic layer was dried over Na$_2$SO$_4$ and the solvents were concentrated. The resulting residue was purified by column chromatography using EtOAc/hexanes (gradient 0-60%) to afford 1-(4-(3-(tetrahydro-2H-pyran-2-yloxy)azetidin-1-yl)phenyl)butan-1-one (3.70 g, 72%).

$^1$H NMR (500 MHz, CHCl$_3$-d) δ ppm 0.99 (t, J=7.4 Hz, 3H) 1.48-1.68 (m, 4H) 1.70-1.80 (m, 3H) 1.81-1.89 (m, 1H) 2.85 (t, J=7.4 Hz, 2H) 3.48-3.61 (m, 1H) 3.82-3.96 (m, 3H) 4.16-4.28 (m, 2H) 4.64-4.75 (m, 1H) 6.40 (d, J=8.5 Hz, 2H) 7.86 (d, J=8.5 Hz, 2H).

Using the ketone prepared according to the procedure described above, additional compounds described herein may be prepared by substituting the appropriate starting materials, reagents and reaction conditions and include compounds selected from:

| Cpd | Name |
|---|---|
| 120 | 5-ethyl-2-oxo-6-{4-[3-(tetrahydro-2H-pyran-2-yloxy)azetidin-1-yl]phenyl}-1,2-dihydropyridine-3-carboxylic acid<br>$^1$H NMR (500 MHz, CHCl$_3$-d) δ ppm 1.19 (t, J = 7.6 Hz, 3H) 1.51-1.70 (m, 4H) 1.73-1.81 (m, 1H) 1.84-1.90 (m, 1H) 2.60 (q, J = 7.6 Hz, 2H) 3.52-3.60 (m, 1H) 3.87-3.94 (m, 2H) 3.96 (dd, J = 8.2, 4.7 Hz, 1H) 4.25 (dt, J = 11.7, 7.1 Hz, 1H) 4.70 (dd, J = 4.7, 3.3 Hz, 1H) 4.74 (tt, J = 6.5, 4.7 Hz, 1H) 6.55 (d, J = 8.8 Hz, 2H) 7.34 (d, J = 8.8 Hz, 2H) 8.50 (s, 1H) 12.28 (br. s., 1H) 13.77 (s, 1H). LC-MS 397.4 [M − H]$^-$, 399.9 [M + H]$^+$, RT 1.27 min. |

EXAMPLE 9

5-ethyl-6-[4-(3-hydroxyazetidin-1-yl)phenyl]-2-oxo-1,2-dihydropyridine-3-carboxylic acid (Cpd 121)

To a solution of 5-ethyl-2-oxo-6-(4-(3-(tetrahydro-2H-pyran-2-yloxy)azetidin-1-yl)phenyl)-1,2-dihydropyridine-3-carboxylic acid (110 mg, 0.28 mmol) in MeOH (1.50 mL) was added concentrated HCl (0.50 mL). The reaction mixture was stirred at room temperature for 20 min and then diluted with H$_2$O (10 mL). The resulting precipitate was collected by filtration, then washed with H$_2$O and dried to afford 5-ethyl-6-(4-(3-hydroxyazetidin-1-yl)phenyl)-2-oxo-1,2-dihydropyridine-3-carboxylic acid (45.7 mg, 53%).

$^1$H NMR (500 MHz, DMSO-d$_6$) δ ppm 1.04 (t, J=7.6 Hz, 3H) 2.45 (q, J=7.6 Hz, 2H) 3.61 (dd, J=8.5, 4.9 Hz, 2H) 4.15 (dd, J=8.5, 6.6 Hz, 2H) 4.56-4.67 (m, 1H) 6.52 (d, J=8.5 Hz, 2H) 7.30 (d, J=8.5 Hz, 2H) 8.31 (s, 1H) 13.02 (br. s., 1H) 15.00 (br. s., 1H). LC-MS 312.6 [M−H]$^-$, 315.1 [M+H]$^+$, RT 0.90 min.

Using the procedure described above, additional compounds described herein may be prepared by substituting the appropriate starting materials, reagents and reaction conditions and include compounds selected from:

| Cpd | Name |
|---|---|
| 122 | 5-ethyl-6-{4-[(3R)-3-hydroxypiperidin-1-yl]phenyl}-2-oxo-1,2-dihydropyridine-3-carboxylic acid<br>$^1$H NMR (500 MHz, DMSO-d$_6$) δ ppm 1.05 (t, J = 7.4 Hz, 3H) 1.30-1.40 (m, 1H) 1.45-1.57 (m, 1H) 1.71-1.81 (m, 1H) 1.87-1.95 (m, 1H) 2.46 (q, J = 7.4 Hz, 2H) 2.70 (dd, J = 12.3, 9.1 Hz, 1H) 2.81-2.88 (m, 1H) 3.53-3.66 (m, 2H) 3.71 (dd, J = 12.3, 4.7 Hz, 1H) 4.85 (d, J = 4.7 Hz, 1H) 7.01 (d, J = 8.8 Hz, 2H) 7.32 (d, J = 8.8 Hz, 2H) 8.30 (s, 1H) 13.02 (br. s., 1H) 15.06 (br. s., 1H). LC-MS 341.3 [M − H]$^-$, 343.6 [M + H]$^+$, RT 0.94 min. |

| Cpd | Name |
|---|---|
| 123 | 5-ethyl-6-[4-(3-hydroxypyrrolidin-1-yl)phenyl]-2-oxo-1,2-dihydropyridine-3-carboxylic acid<br>$^1$H NMR (500 MHz, DMSO-$d_6$) δ ppm 1.05 (t, J = 7.6 Hz, 3H) 1.88-1.97 (m, 1H) 2.00-2.11 (m, 1H) 2.48 (q, J = 7.6 Hz, 2H) 3.15 (br. d, J = 10.4 Hz, 1H) 3.32-3.44 (m, 2H) 3.46 (dd, J = 10.4, 4.7 Hz, 1H) 4.43 (br. s., 1H) 4.99 (br. s., 1H) 6.62 (d, J = 8.8 Hz, 2H) 7.31 (d, J = 8.8 Hz, 2H) 8.30 (s, 1H) 13.01 (br. s., 1H) 15.01 (s, 1H). LC-MS 327.0 [M − H]$^-$, 329.0 [M + H]$^+$, RT 0.91 min. |

EXAMPLE 10

5-ethyl-4-hydroxy-6-{4-[(3R)-3-hydroxypyrrolidin-1-yl]phenyl}-2-oxo-1,2-dihydropyridine-3-carboxylic acid (Cpd 124)

To a suspension of methyl 5-ethyl-4-hydroxy-2-oxo-6-(4-((3R)-3-(tetrahydro-2H-pyran-2-yloxy)pyrrolidin-1-yl)phenyl)-1,2-dihydropyridine-3-carboxylate (0.200 g, 0.45 mmol) in EtOAc (2.5 mL) was added LiI (0.15 g, 1.12 mmol). The reaction mixture was heated at 65° C. for 1.5 h until complete ester hydrolysis was observed. The reaction was diluted with Et$_2$O (15 mL) and a solution of HCl (1M, 4.0 mL) was added. The mixture was stirred vigorously for 2 h until complete cleavage of the THP-protecting group was observed by LC/MS. The solid was then collected by filtration, then washed with H$_2$O and Et$_2$O and dried to provide the title compound (0.110 g, 69%) as a yellow solid.

$^1$H NMR (500 MHz, DMSO-$d_6$) δ ppm 1.04 (t, J=7.3 Hz, 3H) 1.88-1.98 (m, 1H) 2.01-2.10 (m, 1H) 2.39 (q, J=7.3 Hz, 2H) 3.15 (d, J=10.4 Hz, 1H) 3.31-3.42 (m, 2H) 3.46 (dd, J=10.4, 4.7 Hz, 1H) 4.34-4.48 (m, 1H) 6.62 (d, J=8.5 Hz, 2H) 7.28 (d, J=8.5 Hz, 2H) 12.54 (s, 1H) 13.84 (br. s., 1H). LC-MS 343.0 [M−H]$^-$, 345.5 [M+H]$^+$, RT 1.14 min.

Using the procedure described above, additional compounds described herein may be prepared by substituting the appropriate starting materials, reagents and reaction conditions and include compounds selected from:

| Cpd | Name |
|---|---|
| 125 | 5-ethyl-4-hydroxy-6-{4-[(3R)-3-hydroxypiperidin-1-yl]phenyl}-2-oxo-1,2-dihydropyridine-3-carboxylic acid<br>$^1$H NMR (500 MHz, DMSO-$d_6$) δ ppm 1.03 (t, J = 7.4 Hz, 3H) 1.33-1.44 (m, 1H) 1.53-1.65 (m, 1H) 1.76-1.86 (m, 1H) 1.86-1.95 (m, 1H) 2.34 (q, J = 7.4 Hz, 2H) 2.80 (t, J = 10.7 Hz, 1H) 2.94 (t, J = 10.7 Hz, 1H) 3.54-3.73 (m, 3H) 7.17 (br. s., 2H) 7.36 (d, J = 8.8 Hz, 2H) 12.60 (br. s., 1H) 13.87 (br. s., 1H). LC-MS 357.2 [M − H]$^-$, 359.5 [M + H]$^+$, RT 1.13 min. |
| 126 | 5-ethyl-4-hydroxy-6-[4-(3-hydroxypyrrolidin-1-yl)phenyl]-2-oxo-1,2-dihydropyridine-3-carboxylic acid<br>$^1$H NMR (500 MHz, CHCl$_3$-d) δ ppm 1.17 (t, J = 7.4 Hz, 3H) 2.12-2.26 (m, 2H) 2.55 (q, J = 7.4 Hz, 2H) 3.37 (d, J = 10.7 Hz, 1H) 3.46 (td, J = 8.9, 3.0 Hz, 1H) 3.54-3.63 (m, 2H) 4.68 (br. s., 1H) 6.64 (d, J = 8.5 Hz, 2H) 7.31 (d, J = 8.5 Hz, 2H) 10.38 (br. s., 1H) 13.71 (s, 1H) 14.79 (br. s., 1H). LC-MS 343.1 [M − H]$^-$, 345.2 [M + H]$^+$, RT 1.11 min. |

EXAMPLE 11

Step 1: 1-(4-(3-(benzyloxy)pyrrolidin-1-yl)phenyl)butan-1-one

To a suspension of NaH (60% oil, 1.59 g, 39.75 mmol) in THF (30 mL) was added a solution of ethyl 4-(3-hydroxypyrrolidin-1-yl)benzoate (6.20 g, 26.35 mmol) in THF (30 mL) at 0° C. The reaction was allowed to stir for 10 min at this temperature, then a solution of BnBr (4.60 mL, 38.72 mmol) in THF (30 mL) was added. The mixture was allowed to warm to room temperature and then heated to 50° C. for 3 h. After cooling the mixture, the reaction was quenched with NH$_4$Cl (aqueous saturated) and the product was extracted with EtOAc (4×90 mL). The organic phase was washed with NaCl (aqueous saturated), dried over Na$_2$SO$_4$ and the solvents were concentrated. The residue was purified by column chromatography using EtOAc/hexanes (gradient 20-50%) to afford ethyl 4-(3-(benzyloxy)pyrrolidin-1-yl) benzoate (6.25 g, 73%).

$^1$H NMR (500 MHz, CHCl$_3$-d) δ ppm 1.38 (t, J=7.1 Hz, 3H) 2.10-2.19 (m, 1H) 2.21-2.29 (m, 1H) 3.40-3.49 (m, 2H) 3.50-3.57 (m, 2H) 4.33 (q, J=7.1 Hz, 2H) 4.32-4.33 (m, 1H) 4.58 (d, J=12.0 Hz, 1H) 4.60 (d, J=12.0 Hz, 1H) 6.52 (d, J=9.1 Hz, 2H) 7.28-7.38 (m, 5H) 7.92 (d, J=8.1 Hz, 2H). LC-MS 326.1 [M+H]$^+$, RT 1.61 min.

Step 2

To a solution of the ethyl 4-(3-(benzyloxy)pyrrolidin-1-yl)benzoate obtained above (6.25 g, 19.20 mmol) in THF (100 mL) and EtOH (30 mL), a solution of LiOH (1M aqueous, 60.0 mL, 60.00 mmol) and NaOH (1M aqueous, 20.0 mL, 20.00 mmol) was added. The mixture was heated at 65° C. overnight, then the solvents were concentrated and the residue was treated with 3M HCl to pH~2. The resulting solid was then collected by filtration and washed with H$_2$O. After drying, the product 4-(3-(benzyloxy)pyrrolidin-1-yl) benzoic acid (5.15 g, 90%) was obtained.

$^1$H NMR (500 MHz, DMSO-$d_6$) δ ppm 2.02-2.23 (m, 2H) 3.34-3.43 (m, 3H) 3.50 (dd, J=11.0, 4.7 Hz, 1H) 4.27-4.35 (m, 1H) 4.53 (d, J=12.0 Hz, 1H) 4.56 (d, J=12.0 Hz, 1H) 6.55 (d, J=8.8 Hz, 2H) 7.13-7.41 (m, 5H) 7.75 (d, J=8.8 Hz, 2H) 12.05 (br. s., 1H). LC-MS 298.0 [M+H]$^+$, RT 1.36 min.

Step 3

To a suspension of 4-(3-(benzyloxy)pyrrolidin-1-yl)benzoic acid (5.15 g, 17.32 mmol) in DCM (50 mL) at 0° C., oxalyl chloride (1.90 mL, 21.78 mmol) was added dropwise followed by 1 drop of DMF. The reaction mixture was stirred at 0° C. for 15 min, then was slowly allowed to warm to room temperature and stirred for an additional 45 min. The solvent and excess oxalyl chloride were removed by vacuum, then the resulting orange solid was redissolved in fresh DCM (50 mL) and N,O-dimethylhydroxylamine hydrochloride (2.11 g, 21.63 mmol) was added. The mixture was cooled to 0° C. and NEt$_3$ (6.20 mL, 44.48 mmol) was added dropwise. The reaction mixture was allowed to warm to room temperature, stirred for 30 min, then diluted with DCM (200 mL) and washed with H$_2$O (2×50 mL). The organic phase was dried over Na$_2$SO$_4$, then filtered and concentrated to afford a yellowish oil (5.54 g) which was used directly in the next step.

Step 4

The product obtained above (5.54 g, 16.27 mmol) was dissolved in THF and the mixture was cooled to –45° C. A solution of n-PrMgCl (2M Et$_2$O, 10.5 mL, 10.5 mmol) was added dropwise. The reaction mixture was stirred at –45° C. and slowly allowed to warm to room temperature, then stirred for an additional 30 min After complete consumption of the starting material, the reaction was quenched with an NH$_4$Cl solution (aqueous saturated) at 0° C. and the product was extracted with EtOAc (3×100 mL). The organic phase was washed with NaCl (aqueous saturated), dried over Na$_2$SO$_4$ and the solvents were concentrated. The residue was purified by column chromatography using EtOAc/hexanes (gradient 0-25%) to afford 1-(4-(3-(benzyloxy)pyrrolidin-1-yl)phenyl)butan-1-one (3.80 g, 68%).

$^1$H NMR (500 MHz, CHCl$_3$-d) δ ppm 1.00 (t, J=7.4 Hz, 3H) 1.76 (sxt, J=7.4 Hz, 2H) 2.10-2.19 (m, 1H) 2.22-2.30 (m, 1H) 2.86 (t, J=7.4 Hz, 2H) 3.35-3.66 (m, 4H) 4.33 (tt, J=5.1, 2.8 Hz, 1H) 4.58 (d, J=12.0 Hz, 1H) 4.60 (d, J=12.0 Hz, 1H) 6.53 (d, J=8.8 Hz, 2H) 7.27-7.40 (m, 5H) 7.89 (d, J=8.8 Hz, 2H). LC-MS 324.1 [M+H]$^+$, RT 1.46 min.

Using the procedure described above, additional compounds described herein may be prepared by substituting the appropriate starting materials, reagents and reaction conditions and include compounds selected from:

EXAMPLE 12

6-(4-(3-azidopyrrolidin-1-yl)phenyl)-5-ethyl-2-oxo-1,2-dihydropyridine-3-carboxylic acid (Cpd 129)

Step 1

A solution of methyl 6-(4-(3-(benzyloxy)pyrrolidin-1-yl)phenyl)-5-ethyl-2-oxo-1,2-dihydropyridine-3-carboxylate (0.225 g, 0.52 mmol) in MeOH/AcOH (2:1 mixture) was hydrogenated over Pd/C (10%, 100 mg) in a Paar shaker at 60 psi of H$_2$ for 4 days and monitored by LC/MS. After complete consumption of starting material, the catalyst was filtered off and the mixture was washed with DCM. The mother liquor was then concentrated and the residue was treated with H$_2$O. The resulting solid was collected by filtration, then dried in an N$_2$-flow and washed with Et$_2$O to provide methyl 5-ethyl-6-(4-(3-hydroxypyrrolidin-1-yl)phenyl)-2-oxo-1,2-dihydropyridine-3-carboxylate (0.124 g, 69%). LC-MS 343.0 [M+H]$^+$, RT 0.94 min.

Step 2

To a solution of the methyl 5-ethyl-6-(4-(3-hydroxypyrrolidin-1-yl)phenyl)-2-oxo-1,2-dihydropyridine-3-carboxylate (44 mg, 0.13 mmol) obtained above was added NEt$_3$ (60 μL, 0.43 mmol), followed by a mesyl anhydride solution (2M DCM, 0.20 mL, 0.40 mmol) at 0° C. The reaction mixture was stirred for 5 min until complete consumption of the starting material was observed by LC/MS. A mixture of mono- and di-mesylated products was observed. The reaction mixture was diluted with DCM, then washed with H$_2$O, dried over Na$_2$SO$_4$ and the solvents were removed. The residue was dissolved in DMSO (1 mL) and NaN$_3$ (60 mg, 0.92 mmol) was added. The mixture was heated overnight at 50° C. and then diluted with H$_2$O. The resulting product was extracted with DCM. The organic phase was dried over Na$_2$SO$_4$ and the solvents were removed. The obtained material was dissolved in THF (0.80 mL) and treated with LiOH (1 M aqueous, 0.40 mL, 0.40 mmol). The reaction mixture was heated at 50° C. for 3 h, then cooled to room temperature and acidified with 1M HCl to pH~2. The product was extracted with DCM and the organic phase was dried over Na$_2$SO$_4$. The solvents were removed and the crude product (40 mg) was purified by prep HPLC to afford 6-(4-(3-azidopyrrolidin-1-yl)phenyl)-5-ethyl-2-oxo-1,2-dihydropyridine-3-carboxylic acid (6.0 mg, 13%) over 3 steps.

$^1$H NMR (500 MHz, CHCl$_3$-d) δ ppm 1.21 (t, J=7.4 Hz, 3H) 2.21-2.28 (m, 1H) 2.29-2.37 (m, 1H) 2.63 (q, J=7.4 Hz, 2H) 3.43 (dd, J=10.4, 2.2 Hz, 1H) 3.47-3.60 (m, 2H) 3.65 (dd, J=10.4, 5.5 Hz, 1H) 4.28-4.48 (m, 1H) 6.67 (d, J=8.8 Hz, 2H) 7.38 (d, J=8.8 Hz, 2H) 8.51 (s, 1H) 11.99 (br. s., 1H) 13.81 (br. s., 1H). LC-MS 352.1 [M–H]$^-$, 354.1 [M+H]$^+$, RT 1.21 min.

| Cpd | Name |
|---|---|
| 127 | methyl 6-{4-[3-(benzyloxy)pyrrolidin-1-yl]phenyl}-5-ethyl-2-oxo-1,2-dihydropyridine-3-carboxylate<br>$^1$H NMR (500 MHz, CHCl$_3$-d) δ ppm 1.16 (t, J = 7.6 Hz, 3H) 2.10-2.22 (m, 1H) 2.24-2.31 (m, 1H) 2.54 (q, J = 7.6 Hz, 2H) 3.29-3.64 (m, 4H) 3.93 (s, 3H) 4.31-4.38 (m, 1H) 4.57 (s, 1H) 4.61 (d, J = 12.0 Hz, 1H) 6.62 (d, J = 8.8 Hz, 2H) 7.28-7.40 (m, 7 H) 8.23 (s, 1H). LC-MS 433.3 [M + H]$^+$, RT 1.51 min. |
| 128 | 6-{4-[3-(benzyloxy)pyrrolidin-1-yl]phenyl}-5-ethyl-2-oxo-1,2-dihydropyridine-3-carboxylic acid<br>$^1$H NMR (500 MHz, CHCl$_3$-d) δ ppm 1.21 (t, J = 7.5 Hz, 3H) 2.07-2.25 (m, 1H) 2.24-2.33 (m, 1H) 2.64 (q, J = 7.5 Hz, 2H) 3.43-3.53 (m, 2H) 3.53-3.63 (m, 2H) 4.31-4.39 (m, 1H) 4.61 (s, 2H) 6.66 (d, J = 8.5 Hz, 2H) 7.28-7.34 (m, 1H) 7.34-7.41 (m, 6 H) 8.50 (s, 1H) 12.32 (br. s., 1H) 13.84 (s, 1H). LC-MS 417.2 [M – H]$^-$, 419.2 [M + H]$^+$, RT 1.35 min. |

Using the procedure described above, additional compounds described herein may be prepared by substituting the appropriate starting materials, reagents and reaction conditions and include compounds selected from:

| Cpd | Name |
|---|---|
| 132 | 6-{4-[(3S)-3-aminopyrrolidin-1-yl]phenyl}-5-ethyl-2-oxo-1,2-dihydropyridine-3-carboxylic acid hydrochloride (1:1)<br>$^1$H NMR (500 MHz, DMSO-$d_6$) δ ppm 1.04 (t, J = 7.6 Hz, 3H) 2.08-2.18 (m, 1H) 2.29-2.38 (m, 1H) 2.47 (q, J = 7.6 Hz, 2H) 3.36-3.44 (m, 2H) 3.50-3.58 (m, 1H) 3.61 (dd, J = 11.0, 6.3 Hz, 1H) 3.97 (br. s., 1H) 6.68 (d, J = 8.8 Hz, 2H) 7.35 (d, J = 8.8 Hz, 2H) 8.32 (s, 1H) 8.34 (br. s., 3H) 13.10 (s, 1H) 15.02 (br. s., 1H). LC-MS 326.1 [M − H]$^-$, 328.0 [M + H]$^+$, RT 0.69 min. |
| 133 | 6-{4-[(3R,4R)-3-amino-4-hydroxypyrrolidin-1-yl]phenyl}-5-ethyl-2-oxo-1,2-dihydropyridine-3-carboxylic acid hydrochloride (1:1)<br>$^1$H NMR (500 MHz, DMSO-$d_6$) δ ppm 1.04 (t, J = 7.6 Hz, 3H) 2.47 (q, J = 7.6 Hz, 2H) 3.23 (dd, J = 10.7, 2.8 Hz, 4H) 3.41 (dd, J = 10.7, 2.2 Hz, 4H) 3.62-3.78 (m, 2H) 4.41 (br. s., 1H) 5.83 (d, J = 3.8 Hz, 1H) 6.67 (d, J = 8.8 Hz, 2H) 7.35 (d, J = 8.8 Hz, 2H) 8.32 (s, 1H) 8.41 (br. s., 3H) 13.11 (br. s., 1H) 15.02 (br. s., 1H). LC-MS 342.2 [M − H]$^-$, 344.2 [M + H]$^+$, RT 0.65 min. |
| 134 | 6-{4-[(3R,4R)-3-amino-4-methoxypyrrolidin-1-yl]phenyl}-5-ethyl-2-oxo-1,2-dihydropyridine-3-carboxylic acid hydrochloride (1:1)<br>$^1$H NMR (500 MHz, DMSO-$d_6$) δ ppm 1.04 (t, J = 7.4 Hz, 3H) 2.46 (q, J = 7.4 Hz, 2H) 3.35-3.39 (m, 1H) 3.38 (s, 3H) 3.44 (dd, J = 11.5, 2.7 Hz, 1H) 3.65 (dd, J = 11.3, 6.1 Hz, 1H) 3.79 (dd, J = 11.3, 5.4 Hz, 1H) 3.91 (br. s., 1H) 4.11-4.18 (m, 1H) 6.70 (d, J = 8.8 Hz, 2H) 7.36 (d, J = 8.8 Hz, 2H) 8.32 (s, 1H) 8.44 (br. s., 3H) 13.08 (br. s., 1H) 15.00 (br. s., 1H). LC-MS 356.2 [M − H]$^-$, 358.5 [M + H]$^+$, RT 0.73 min. |
| 135 | 6-{4-[(3R,4S)-3-amino-4-methoxypyrrolidin-1-yl]phenyl}-5-ethyl-2-oxo-1,2-dihydropyridine-3-carboxylic acid hydrochloride (1:1)<br>LC-MS 356.2 [M − H]$^-$, 358.2 [M + H]$^+$, RT 0.73 min. |
| 136 | 6-{4-[(3R,4S)-3-amino-4-hydroxypyrrolidin-1-yl]phenyl}-5-ethyl-2-oxo-1,2-dihydropyridine-3-carboxylic acid trifluoroacetate (1:1)<br>$^1$H NMR (500 MHz, DMSO-$d_6$) δ ppm 1.04 (t, J = 7.4 Hz, 3H) 2.47 (q, J = 7.4 Hz, 2H) 3.29-3.39 (m, 2H) 3.60 (dd, J = 10.7, 5.4 Hz, 1H) 3.65 (dd, J = 10.1, 7.3 Hz, 1H) 3.85 (br. s., 1H) 4.45-4.54 (m, 1H) 6.66 (d, J = 8.8 Hz, 2H) 7.35 (d, J = 8.8 Hz, 2H) 8.17 (br. s., 3H) 8.32 (s, 1H) 13.07 (br. s., 1H) 15.00 (br. s., 1H). LC-MS 342.3 [M − H]$^-$, 344.7 [M + H]$^+$, RT 0.64 min. | appropriate starting materials, reagents and reaction conditions and include compounds selected from:

| Cpd | Name |
|---|---|
| 130 | 6-{4-[(3S)-3-azidopyrrolidin-1-yl]phenyl}-5-ethyl-2-oxo-1,2-dihydropyridine-3-carboxylic acid<br>$^1$H NMR (500 MHz, CHCl$_3$-d) δ ppm 1.21 (t, J = 7.4 Hz, 3H) 2.21-2.28 (m, 1H) 2.29-2.37 (m, 1H) 2.63 (q, J = 7.4 Hz, 2H) 3.43 (dd, J = 10.4, 2.2 Hz, 1H) 3.47-3.60 (m, 2H) 3.65 (dd, J = 10.4, 5.5 Hz, 1H) 4.28-4.48 (m, 1H) 6.67 (d, J = 8.8 Hz, 2H) 7.38 (d, J = 8.8 Hz, 2H) 8.51 (s, 1H) 11.99 (br. s., 1H) 13.81 (br. s., 1H). LC-MS 352.1 [M − H]$^-$, 354.1 [M + H]$^+$, RT 1.21 min. |

EXAMPLE 13

6-(4-(3-aminopyrrolidin-1-yl)phenyl)-5-ethyl-2-oxo-1,2-dihydropyridine-3-carboxylic acid trifluoroacetate (Cpd 131)

A solution of 6-(4-(3-azidopyrrolidin-1-yl)phenyl)-5-ethyl-2-oxo-1,2-dihydropyridine-3-carboxylic acid (5.0 mg) in MeOH (1 mL) and TFA (0.5 mL) was hydrogenated over Pd/C (5 mg) under H$_2$. After 30 min, complete conversion to the product was observed. The catalyst was filtered off and the mother liquor was concentrated to afford 6-(4-(3-aminopyrrolidin-1-yl)phenyl)-5-ethyl-2-oxo-1,2-dihydropyridine-3-carboxylic acid (6.0 mg) as a trifluoroacetate salt.

$^1$H NMR (500 MHz, DMSO-$d_6$) δ ppm 1.04 (t, J=7.6 Hz, 3H) 2.08-2.18 (m, 1H) 2.29-2.38 (m, 1H) 2.47 (q, J=7.6 Hz, 2H) 3.36-3.44 (m, 2H) 3.50-3.58 (m, 1H) 3.61 (dd, J=11.0, 6.3 Hz, 1H) 3.97 (br. s., 1H) 6.68 (d, J=8.8 Hz, 2H) 7.35 (d, J=8.8 Hz, 2H) 8.32 (s, 1H) 8.34 (br. s., 3H) 13.10 (s, 1H) 15.02 (br. s., 1H). LC-MS 326.0 [M−H]$^-$, 328.1 [M+H]$^+$, RT 0.70 min.

Using the procedure described above, additional compounds described herein may be prepared by substituting the appropriate starting materials, reagents and reaction conditions and include compounds selected from:

EXAMPLE 14

6-{4-[5-(tert-butoxycarbonyl)-2,5-diazabicyclo[2.2.1]hept-2-yl]phenyl}-5-ethyl-2-oxo-1,2-dihydropyridine-3-carboxylic acid (Cpd 137)

Methyl 6-(4-bromophenyl)-5-ethyl-2-oxo-1,2-dihydropyridine-3-carboxylate (0.106 mg, 0.31 mmol), Pd-catalyst (7.3 mg, 5 mol %) and t-BuONa (0.072 g, 0.75 mmol) were mixed under Argon in a heat-gun dried vial. Anhydrous toluene (1.0 mL) was added to the mixture followed by tert-butyl 2,5-diazabicyclo[2.2.1]heptane-2-carboxylate (0.19 g, 0.95 mmol). The reaction was heated under Argon at 80° C. for 1 hr until complete consumption of the starting material was observed. The mixture was cooled to room temperature and the reaction was quenched with HCl (1M, 5 mL). The product was extracted with DCM (3×7 mL), followed by drying of the organic phase over Na$_2$SO$_4$. The solvents were concentrated and the resulting residue (0.166 g) was taken used in the step without further purification.

The residue obtained above (0.166 g) was heated in THF (2 mL) with a LiOH solution (1M aqueous, 1.0 mL, 1.0 mmol) at 50° C. for 4 h. The reaction mixture was cooled to room temperature and acidified with 1 M HCl to pH~2. The product was extracted with DCM, then the organic phase was dried over Na$_2$SO$_4$ and the solvent concentrated. The resulting residue was purified by preparative HPLC to provide (S,S)-6-(4-(5-(tert-butoxycarbonyl)-2,5-diazabicyclo[2.2.1]hept-2-yl)phenyl)-5-ethyl-2-oxo-1,2-dihydropyridine-3-carboxylic acid (0.0444 g, 32%) as a yellow solid.

$^1$H NMR (500 MHz, CHCl$_3$-d) δ ppm 1.22 (t, J=7.6 Hz, 3H) 1.37-1.51 (m, 9H) 1.90-2.09 (m, 2H) 2.64 (q, J=7.6 Hz, 2H) 3.17-3.38 (m, 1H) 3.39-3.56 (m, 2H) 3.62 (dd, J=15.9, 8.7 Hz, 1H) 4.47-4.76 (m, 2H) 6.66 (d, J=8.2 Hz, 2H) 7.37

(d, J=8.6 Hz, 2H) 8.51 (s, 1H) 12.50 (br. s., 1H) 13.81 (br. s., 1H). LC-MS 437.7 [M−H]⁻, 440.0 [M+H]⁺, RT 1.27 min.

EXAMPLE 15

6-[4-(2,5-diazabicyclo[2.2.1]hept-2-yl)phenyl]-5-ethyl-2-oxo-1,2-dihydropyridine-3-carboxylic acid trifluoroacetate (1:1) (Cpd 138)

A solution of (S,S)-6-(4-(5-(tert-butoxycarbonyl)-2,5-diazabicyclo[2.2.1]hept-2-yl)phenyl)-5-ethyl-2-oxo-1,2-dihydropyridine-3-carboxylic acid (42.1 mg, 0.096 mmol) in DCM (2 mL) was stirred with TFA (0.5 mL) at room temperature for 30 min. The solvents were removed and Et₂O was added to the residue. A yellow solid was filtered off, then washed with Et₂O and dried to afford (S,S)-6-(4-(2,5-diazabicyclo[2.2.1]hept-2-yl)phenyl)-5-ethyl-2-oxo-1,2-dihydropyridine-3-carboxylic acid (40.0 mg, 90%) as a trifluoroacetate salt.

¹H NMR (500 MHz, DMSO-d₆) δ ppm 1.05 (t, J=7.6 Hz, 3H) 1.96 (d, J=10.7 Hz, 1H) 2.16 (d, J=10.7 Hz, 1H) 2.46 (q, J=7.6 Hz, 2H) 3.13-3.21 (m, 1H) 3.28 (t, J=9.0 Hz, 1H) 3.35 (d, J=10.4 Hz, 1H) 3.65 (d, J=10.4 Hz, 1H) 4.51 (br. s., 1H) 4.74 (br. s, 1H) 6.79 (d, J=8.8 Hz, 2H) 7.37 (d, J=8.8 Hz, 2H) 8.33 (s, 1H) 8.61 (br. s., 1H) 9.05 (br. s., 1H) 13.08 (br. s., 1H) 15.01 (br. s., 1H). LC-MS 337.7 [M−H]⁻, 340.0 [M+H]⁺, RT 0.72 min.

Using the procedure described above, additional compounds described herein may be prepared by substituting the appropriate starting materials, reagents and reaction conditions and include compounds selected from:

| Cpd | Name |
|---|---|
| 139 | 5-ethyl-6-[4-(2-methylpyrrolidin-1-yl)phenyl]-2-oxo-1,2-dihydropyridine-3-carboxylic acid<br>¹H NMR (500 MHz, CHCl₃-d) δ ppm 1.22 (t, J = 7.6 Hz, 3H) 1.25 (d, J = 6.0 Hz, 3H) 1.98-2.22 (m, 4H) 2.64 (q, J = 7.6 Hz, 2H) 3.23-3.33 (m, 1H) 3.48-3.53 (m, 1H) 3.95-4.05 (m, 1H) 6.68 (d, J = 8.8 Hz, 2H) 7.35 (d, J = 8.8 Hz, 2H) 8.50 (s, 1H) 11.54 (br. s., 1H) 13.86 (br. s., 1H). LC-MS 325.0 [M − H]⁻, 327.2 [M + H]⁺, RT 1.51 min. |
| 140 | 5-ethyl-6-{4-[3-(morpholin-4-yl)pyrrolidin-1-yl]phenyl}-2-oxo-1,2-dihydropyridine-3-carboxylic acid trifluoroacetate (1:1)<br>LC-MS 396.2 [M − H]⁻, 398.3 [M + H]⁺, RT 1.16 min. |
| 141 | 5-ethyl-2-oxo-6-{4-[(2R)-2-(trifluoromethyl)pyrrolidin-1-yl]phenyl}-1,2-dihydropyridine-3-carboxylic acid<br>¹H NMR (500 MHz, CHCl₃-d) δ ppm 1.21 (t, J = 7.4 Hz, 3H) 2.09-2.22 (m, 2H) 2.23-2.36 (m, 2H) 2.63 (q, J = 7.5 Hz, 2H) 3.34-3.41 (m, 1H) 3.72 (t, J = 8.7 Hz, 1H) 4.35 (quin, J = 7.3 Hz, 1H) 6.90 (d, J = 8.8 Hz, 2H) 7.40 (d, J = 8.8 Hz, 2H) 8.53 (s, 1H) 12.48 (br. s., 1H) 13.71 (br. s., 1H). LC-MS 379.1 [M − H]⁻, 381.2 [M + H]⁺, RT 1.57 min. |
| 142 | 5-ethyl-2-oxo-6-{4-[(2S)-2-(trifluoromethyl)pyrrolidin-1-yl]phenyl}-1,2-dihydropyridine-3-carboxylic acid<br>¹H NMR (500 MHz, CHCl₃-d) δ ppm 1.21 (t, J = 7.4 Hz, 3H) 2.09-2.22 (m, 2H) 2.23-2.36 (m, 2H) 2.63 (q, J = 7.5 Hz, 2H) 3.34-3.41 (m, 1H) 3.72 (t, J = 8.7 Hz, 1H) 4.35 (quin, J = 7.3 Hz, 1H) 6.90 (d, J = 8.8 Hz, 2H) 7.40 (d, J = 8.8 Hz, 2H) 8.53 (s, 1H) 12.48 (br. s., 1H) 13.71 (br. s., 1H). LC-MS 378.6 [M − H]⁻, 380.9 [M + H]⁺, RT 1.28 min. |
| 143 | 5-ethyl-2-oxo-6-{4-[(2S)-2-(pyrrolidin-1-ylmethyl)pyrrolidin-1-yl]phenyl}-1,2-dihydropyridine-3-carboxylic acid trifluoroacetate (1:1)<br>¹H NMR (500 MHz, CHCl₃-d) δ ppm 1.24 (t, J = 7.6 Hz, 3H) 2.01-2.46 (m, 8H) 2.61-2.77 (m, 2H) 3.19 (dd, J = 12.9, 11.0 Hz, 1H) 3.23-3.33 (m, 3H) 3.39 (d, J = 12.9 Hz, 9H) 3.50-3.61 (m, 1H) 3.92 (br. s., 1H) 4.11 (br. s., 1H) 4.33 (t, J = 8.2 Hz, 1H) 6.73 (d, J = 8.8 Hz, 2H) 7.45 (d, J = 8.8 Hz, 2H) 8.47 (s, 1H) 11.99 (br. s., 1H) 13.29 (br. s., 1H) 14.13 (br. s., 1H). LC-MS 394.2 [M − H]⁻, 396.3 [M + H]⁺, RT 1.15 min. |
| 144 | 6-[4-(3,3-difluoropyrrolidin-1-yl)phenyl]-5-ethyl-2-oxo-1,2-dihydropyridine-3-carboxylic acid<br>¹H NMR (500 MHz, CHCl₃-d) δ ppm 1.20 (t, J = 7.6 Hz, 3H) 2.51-2.65 (m, 4H) 3.65 (t, J = 7.1 Hz, 2H) 3.77 (t, J = 12.9 Hz, 2H) 6.67 (d, J = 8.8 Hz, 2H) 7.40 (d, J = 8.8 Hz, 2H) 8.53 (s, 1H) 12.07 (br. s., 1H) 13.73 (br. s., 1H). LC-MS 347.0 [M − H]⁻, 349.2 [M + H]⁺, RT 1.50 min. |
| 145 | 5-ethyl-2-oxo-6-[4-(2-phenylpyrrolidin-1-yl)phenyl]-1,2-dihydropyridine-3-carboxylic acid<br>¹H NMR (500 MHz, CHCl₃-d) δ ppm 1.18 (t, J = 7.6 Hz, 3H) 1.96-2.16 (m, 3H) 2.47 (tt, J = 11.3, 7.6 Hz, 1H) 2.58 (q, J = 7.6 Hz, 2H) 3.54 (td, J = 9.3, 7.6 Hz, 1H) 3.76-3.82 (m, 1H) 4.86 (dd, J = 8.0, 1.7 Hz, 1H) 6.59 (d, J = 8.8 Hz, 2H) 7.22 (d, J = 8.8 Hz, 2H) 7.24-7.28 (m, 3H) 7.34 (t, J = 7.6 Hz, 2H) 8.48 (s, 1H) 11.86 (br. s., 1H) 13.78 (br. s., 1H). LC-MS 386.7 [M − H]⁻, 389.0 [M + H]⁺, RT 1.42 min. |
| 146 | 5-ethyl-6-{4-[(2S)-2-(methoxymethyl)pyrrolidin-1-yl]phenyl}-2-oxo-1,2-dihydropyridine-3-carboxylic acid<br>¹H NMR (500 MHz, CHCl₃-d) δ ppm 1.21 (t, J = 7.6 Hz, 3H) 1.99-2.18 (m, 4H) 2.64 (q, J = 7.6 Hz, 2H) 3.19-3.33 (m, 2H) 3.43 (s, 3H) 3.52 (t, J = 7.7 Hz, 1H) 3.57 (dd, J = 9.5, 3.8 Hz, 1H) 4.00 (dt, J = 7.6, 3.8 Hz, 1H) 6.76 (d, J = 8.8 Hz, 2H) 7.37 (d, J = 8.8 Hz, 2H) 8.50 (s, 1H) 12.30 (br. s., 1H) 13.82 (br. s., 1H). LC-MS 355.2 [M − H]⁻, 357.2 [M + H]⁺, RT 1.50 min. |
| 147 | 5-ethyl-6-{4-[(2R)-2-(methoxymethyl)pyrrolidin-1-yl]phenyl}-2-oxo-1,2-dihydropyridine-3-carboxylic acid<br>¹H NMR (500 MHz, CHCl₃-d) δ ppm 1.21 (t, J = 7.6 Hz, 3H) 1.99-2.18 (m, 4H) 2.64 (q, J = 7.6 Hz, 2H) 3.19-3.33 (m, 2H) 3.43 (s, 3H) 3.52 (t, J = 7.7 Hz, 1H) 3.57 (dd, J = 9.5, 3.8 Hz, 1H) 4.00 (dt, J = 7.6, 3.8 Hz, 1H) 6.76 (d, J = 8.8 Hz, 2H) 7.37 (d, J = 8.8 Hz, 2H) 8.50 (s, 1H) 12.30 (br. s., 1H) 13.82 (br. s., 1H). LC-MS 355.1 [M − H]⁻, 357.2 [M + H]⁺, RT 1.14 min. |
| 148 | 6-{4-[(2S,5S)-2,5-bis(methoxymethyl)pyrrolidin-1-yl]phenyl}-5-ethyl-2-oxo-1,2-dihydropyridine-3-carboxylic acid<br>LC-MS 399.2 [M − H]⁻, 401.3 [M + H]⁺, RT 1.48 min. |

| Cpd | Name |
|---|---|
| 149 | 6-{4-[3-(dimethylamino)pyrrolidin-1-yl]phenyl}-5-ethyl-2-oxo-1,2-dihydropyridine-3-carboxylic acid<br>$^1$H NMR (500 MHz, DMSO-d$_6$) δ ppm 1.05 (t, J = 7.6 Hz, 3H) 1.76-1.93 (m, 1H) 2.16-2.24 (m, 1H) 2.27 (s, 6 H) 2.48 (q, J = 7.6 Hz, 2H) 2.85-2.97 (m, 1H) 3.13 (t, J = 8.7 Hz, 1H) 3.22-3.35 (m, 1H) 3.46 (t, J = 8.4 Hz, 1H) 3.53 (t, J = 8.4 Hz, 1H) 6.64 (d, J = 8.5 Hz, 2H) 7.32 (d, J = 8.5 Hz, 2H) 8.25 (s, 1H) 12.73 (br. s., 1H) 15.26 (br. s., 1H). LC-MS 354.1 [M − H]$^-$, 356.2 [M + H]$^+$, RT 1.12 min. |
| 150 | 6-{4-[(3R)-3-(dimethylamino)pyrrolidin-1-yl]phenyl}-5-ethyl-2-oxo-1,2-dihydropyridine-3-carboxylic acid trifluoroacetate (1:1)<br>$^1$H NMR (500 MHz, DMSO-d$_6$) δ ppm 1.05 (t, J = 7.6 Hz, 3H) 1.76-1.93 (m, 1H) 2.16-2.24 (m, 1H) 2.27 (s, 6 H) 2.48 (q, J = 7.6 Hz, 2H) 2.85-2.97 (m, 1H) 3.13 (t, J = 8.7 Hz, 1H) 3.22-3.35 (m, 1H) 3.46 (t, J = 8.4 Hz, 1H) 3.53 (t, J = 8.4 Hz, 1H) 6.64 (d, J = 8.5 Hz, 2H) 7.32 (d, J = 8.5 Hz, 2H) 8.25 (s, 1H) 12.73 (br. s., 1H) 15.26 (br. s., 1H). LC-MS 354.1 [M − H]$^-$, 356.2 [M + H]$^+$, RT 0.70 min. |
| 151 | 6-{4-[(3S)-3-(dimethylamino)pyrrolidin-1-yl]phenyl}-5-ethyl-2-oxo-1,2-dihydropyridine-3-carboxylic acid hydrochloride (1:1)<br>$^1$H NMR (500 MHz, DMSO-d$_6$) δ ppm 1.05 (t, J = 7.6 Hz, 3H) 1.76-1.93 (m, 1H) 2.16-2.24 (m, 1H) 2.27 (s, 6 H) 2.48 (q, J = 7.6 Hz, 2H) 2.85-2.97 (m, 1H) 3.13 (t, J = 8.7 Hz, 1H) 3.22-3.35 (m, 1H) 3.46 (t, J = 8.4 Hz, 1H) 3.53 (t, J = 8.4 Hz, 1H) 6.64 (d, J = 8.5 Hz, 2H) 7.32 (d, J = 8.5 Hz, 2H) 8.25 (s, 1H) 12.73 (br. s., 1H) 15.26 (br. s., 1H). LC-MS 354.1 [M − H]$^-$, 356.2 [M + H]$^+$, RT 0.70 min. |
| 152 | 5-ethyl-6-[4-(3-fluoropyrrolidin-1-yl)phenyl]-2-oxo-1,2-dihydropyridine-3-carboxylic acid<br>$^1$H NMR (500 MHz, CHCl$_3$-d) δ ppm 1.21 (t, J = 7.4 Hz, 3H) 2.13-2.31 (m, 1H) 2.45 (ddt, J = 18.4, 14.3, 4.0, 4.0 Hz, 1H) 2.64 (q, J = 7.4 Hz, 2H) 3.58 (d, J = 4.1 Hz, 1H) 3.60 (d, J = 4.1 Hz, 1H) 3.62-3.71 (m, 2H) 5.45 (br. d, J = 52.6 Hz, 1H) 6.69 (d, J = 8.8 Hz, 2H) 7.40 (d, J = 8.8 Hz, 2H) 8.51 (s, 1H) 12.29 (br. s., 1H) 13.81 (br. s., 1H). LC-MS 328.8 [M − H]$^-$, 331.0 [M + H]$^+$, RT 1.28 min. |
| 153 | 5-ethyl-6-{4-[(3S)-3-fluoropyrrolidin-1-yl]phenyl}-2-oxo-1,2-dihydropyridine-3-carboxylic acid<br>$^1$H NMR (500 MHz, CHCl$_3$-d) δ ppm 1.21 (t, J = 7.4 Hz, 3H) 2.13-2.31 (m, 1H) 2.45 (ddt, J = 18.4, 14.3, 4.0, 4.0 Hz, 1H) 2.64 (q, J = 7.4 Hz, 2H) 3.58 (d, J = 4.1 Hz, 1H) 3.60 (d, J = 4.1 Hz, 1H) 3.62-3.71 (m, 2H) 5.45 (br. d, J = 52.6 Hz, 1H) 6.69 (d, J = 8.8 Hz, 2H) 7.40 (d, J = 8.8 Hz, 2H) 8.51 (s, 1H) 12.29 (br. s., 1H) 13.81 (br. s., 1H). LC-MS 329.1 [M − H]$^-$, 331.2 [M + H]$^+$, RT 1.43 min. |
| 154 | 5-ethyl-6-{4-[(3R)-3-fluoropyrrolidin-1-yl]phenyl}-2-oxo-1,2-dihydropyridine-3-carboxylic acid<br>$^1$H NMR (500 MHz, CHCl$_3$-d) δ ppm 1.21 (t, J = 7.4 Hz, 3H) 2.13-2.31 (m, 1H) 2.45 (ddt, J = 18.4, 14.3, 4.0, 4.0 Hz, 1H) 2.64 (q, J = 7.4 Hz, 2H) 3.58 (d, J = 4.1 Hz, 1H) 3.60 (d, J = 4.1 Hz, 1H) 3.62-3.71 (m, 2H) 5.45 (br. d, J = 52.6 Hz, 1H) 6.69 (d, J = 8.8 Hz, 2H) 7.40 (d, J = 8.8 Hz, 2H) 8.51 (s, 1H) 12.29 (br. s., 1H) 13.81 (br. s., 1H). LC-MS 329.1 [M − H]$^-$, 331.2 [M + H]$^+$, RT 1.14 min. |
| 155 | 5-ethyl-2-oxo-6-[4-(phenylamino)phenyl]-1,2-dihydropyridine-3-carboxylic acid<br>$^1$H NMR (500 MHz, DMSO-d$_6$) δ ppm 1.07 (t, J = 7.4 Hz, 3H) 2.47 (q, J = 7.4 Hz, 2H) 6.94 (t, J = 7.3 Hz, 1H) 7.13-7.19 (m, 4H) 7.28-7.33 (m, 2H) 7.36 (d, J = 8.5 Hz, 2H) 8.34 (s, 1H) 8.63 (s, 1H) 13.11 (br. s., 1H) 15.02 (s, 1H). LC-MS 332.6 [M − H]$^-$, 334.9 [M + H]$^+$, RT 1.21 min. |
| 156 | 5-ethyl-2-oxo-6-{4-[2-(1,3-thiazol-2-yl)pyrrolidin-1-yl]phenyl}-1,2-dihydropyridine-3-carboxylic acid<br>$^1$H NMR (500 MHz, CHCl$_3$-d) δ ppm 1.18 (t, J = 7.4 Hz, 3H) 2.05-2.33 (m, 3H) 2.44-2.55 (m, 1H) 2.58 (q, J = 7.4 Hz, 2H) 3.46 (dd, J = 9.5, 7.2 Hz, 0 H) 3.83 (t, J = 9.5 Hz, 0 H)<br>5.18 (d, J = 7.2 Hz, 1H) 6.72 (d, J = 8.8 Hz, 2H) 7.26 (d, J = 3.5 Hz, 1H) 7.33 (d, J = 8.8 Hz, 2H) 7.80 (d, J = 3.5 Hz, 1H) 8.49 (s, 1H) 12.29 (br. s., 1H) 13.74 (s, 1H). LC-MS 394.2 [M − H]$^-$, 396.2 [M + H]$^+$, RT 1.16 min. |
| 157 | 6-{4-[(2S)-2-carboxypyrrolidin-1-yl]phenyl}-5-ethyl-2-oxo-1,2-dihydropyridine-3-carboxylic acid<br>LC-MS 355.9 [M − H]$^-$, 357.9 [M + H]$^+$, RT 0.99 min. |
| 158 | 5-ethyl-6-{4-[methyl(phenyl)amino]phenyl}-2-oxo-1,2-dihydropyridine-3-carboxylic acid<br>$^1$H NMR (500 MHz, CHCl$_3$-d) δ ppm 1.20 (t, J = 7.5 Hz, 3H) 2.61 (q, J = 7.5 Hz, 2H) 3.42 (s, 3H) 6.92 (d, J = 8.8 Hz, 2H) 7.24 (t, J = 7.3 Hz, 1H) 7.28-7.33 (m, 4H) 7.45 (t, J = 7.3 Hz, 2H) 8.51 (s, 1H) 11.92 (br. s., 1H) 13.81 (br. s., 1H). LC-MS 346.8 [M − H]$^-$, 349.1 [M + H]$^+$, RT 1.39 min. |
| 159 | 6-(4-{[2-(dimethylamino)ethyl]amino}phenyl)-5-ethyl-2-oxo-1,2-dihydropyridine-3-carboxylic acid<br>$^1$H NMR (500 MHz, DMSO-d$_6$) δ ppm 1.13 (t, J = 7.01 Hz, 3H) 2.48-2.53 (m, 2H) 2.86 (br. s., 6 H) 3.25-3.33 (m, 2H) 3.56 (t, J = 6.46 Hz, 2H) 6.81 (d, J = 8.75 Hz, 2H) 7.32 (d, J = 8.67 Hz, 2H) 8.35 (s, 1H). |
| 160 | 5-ethyl-6-{4-[ethyl(methyl)amino]phenyl}-2-oxo-1,2-dihydropyridine-3-carboxylic acid<br>$^1$H NMR (500 MHz, DMSO-d$_6$) δ ppm 1.08-1.12 (m, 3H) 1.15-1.20 (m, 2H) 2.53-2.57 (m, 2H) 2.93 (s, 3H) 3.46 (d, J = 7.01 Hz, 2H) 6.77 (d, J = 8.91 Hz, 2H) 7.31 (d, J = 8.83 Hz, 2H) 8.13 (s, 1H). |

-continued

| Cpd | Name |
|---|---|
| 161 | 6-(4-{[2-(dimethylamino)ethyl](methyl)amino}phenyl)-5-ethyl-2-oxo-1,2-dihydropyridine-3-carboxylic acid<br>$^1$H NMR (500 MHz, DMSO-d$_6$) δ ppm 1.07 (t, J = 7.40 Hz, 3H) 2.54-2.59 (m, 2H) 3.30-3.37 (m, 11H) 3.51-3.57 (m, 2H) 6.78-6.82 (m, 2H) 7.30-7.36 (m, 2H) 8.21-8.27 (m, 1H). LC-MS 344.3 [M + H]$^+$, RT 0.47. |
| 162 | 6-[4-(1,3-dihydro-2H-isoindol-2-yl)phenyl]-5-ethyl-2-oxo-1,2-dihydropyridine-3-carboxylic acid<br>$^1$H NMR (500 MHz, DMSO-d$_6$) δ ppm 1.08 (t, J = 7.49 Hz, 3H) 2.52-2.54 (m, 2H) 4.72 (s, 4H) 6.81 (d, J = 8.75 Hz, 2H) 7.36 (s, 2H) 7.40-7.46 (m, 4H) 8.33 (s, 1H). |
| 163 | 5-isopropyl-2-oxo-6-[4-(pyrrolidin-1-yl)phenyl]-1,2-dihydropyridine-3-carboxylic acid<br>$^1$H NMR (500 MHz, CHCl$_3$-d) δ ppm 1.14 (d, J = 7.40 Hz, 6H) 1.59-1.70 (m, 2H) 1.74-1.85 (m, 2H) 2.80-2.95 (m, 1H) 3.46-3.63 (m, 4H) 7.23 (d, J = 8.59 Hz, 2H) 7.64 (d, J = 8.59 Hz, 2H) 8.55 (s, 1H). LC-MS 325.3 [M − H]$^−$, RT 0.83. |
| 164 | 5-cyclopropyl-2-oxo-6-[4-(pyrrolidin-1-yl)phenyl]-1,2-dihydropyridine-3-carboxylic acid<br>$^1$H NMR (500 MHz, DMSO-d$_6$) δ ppm 0.55 (br. s., 4H) 0.75-0.84 (m, 1H) 1.66-1.73 (m, 1H) 1.80-1.87 (m, 1H) 2.16-2.24 (m, 1H) 2.25-2.34 (m, 1H) 3.41 (s, 1H) 3.49-3.67 (m, 3H) 6.70 (d, J = 8.91 Hz, 2H) 7.52 (d, J = 8.83 Hz, 2H) 7.98 (s, 1H). LC-MS 325.3 [M + H]$^+$, RT 0.80. |
| 165 | 6-(4-{[2-(dimethylamino)ethyl](methyl)amino}phenyl)-2-oxo-5-(propan-2-yl)-1,2-dihydropyridine-3-carboxylic acid<br>$^1$H NMR (500 MHz, DMSO-d$_6$) δ ppm 1.03 (d, J = 6.94 Hz, 6H) 2.78-2.88 (m, 1H) 3.23 (s, 9H) 3.25-3.34 (m, 4H) 6.53-6.59 (m, 2H) 7.16-7.23 (m, 2H) 8.24-8.28 (m, 1H) 14.94-15.00 (m, 1H). LC-MS 358.3 [M + H]$^+$, RT 0.48. |
| 166 | 6-[4-(3-amino-3-methylpyrrolidin-1-yl)phenyl]-5-ethyl-2-oxo-1,2-dihydropyridine-3-carboxylic acid trifluoroacetate (1:1)<br>$^1$H NMR (500 MHz, DMSO-d$_6$): d 15.01 (1H, br), 13.11 (1H, br), 8.33 (1H, s), 8.15 (3H, br s), 7.36 (2H, d, J = 8.8 Hz), 6.68 (2H, d, J = 8.8 Hz), 3.60-3.35 (4H, obscured), 2.47 (2H, q, J = 7.5 Hz), 2.38-2.34 (1H, m), 2.22-2.16 (1H, m), 1.49 (3H, s), 1.05 (3H, t, J = 7.5 Hz). |
| 167 | 6-[4-(3-{[(carboxymethyl)(methyl)carbamoyl]amino}azetidin-1-yl)phenyl]-5-ethyl-2-oxo-1,2-dihydropyridine-3-carboxylic acid<br>$^1$H NMR (500 MHz, CDCl$_3$): d 8.45 (1H, s), 7.16 (2H, d, J = 8.6 Hz), 6.45 (2H, d, J = 8.6 Hz), 5.12 (1H, m), 4.25-4.15 (4H, m), 3.83 (2H, s), 2.94 (3H, s), 2.50 (2H, q, J = 7.5 Hz), 0.93 (3H, t, J = 7.5 Hz). |
| 168 | 5-ethyl-6-{4-[3-(5-methyl-2H-tetrazol-2-yl)azetidin-1-yl]phenyl}-2-oxo-1,2-dihydropyridine-3-carboxylic acid<br>$^1$H NMR (500 MHz, CDCl$_3$): d 13.75 (1H, s), 12.47 (1H, s), 8.55 (1H, s), 7.41 (2H, d, J = 8.6 Hz), 6.66 (2H, d, J = 8.6 Hz), 5.86 (1H, m), 4.64-4.60 (2H, m), 4.56-4.53 (2H, m), 2.63 (2H, q, J = 7.3 Hz), 2.62 (3H, s), 1.22 (3H, t, J = 7.3 Hz). |
| 169 | 6-[4-(1-amino-3-azabicyclo[3.1.0]hex-3-yl)phenyl]-5-ethyl-2-oxo-1,2-dihydropyridine-3-carboxylic acid hydrochloride (1:1)<br>$^1$H NMR (500 MHz, DMSO-d$_6$): d 14.99 (1H, br), 13.06 (1H, br), 8.98 (2H, br), 8.32 (1H, s), 7.33 (2H, d, J = 8.7 Hz), 6.69 (2H, d, J = 8.7 Hz), 3.86-3.39 (4H, m), 2.48 (2H, obscured), 2.14 (2H, m), 1.39 (1H, m), 1.05 (3H, dt, J = 7.0, 6.8 Hz). |
| 170 | 6-[4-(3-aminoazetidin-1-yl)phenyl]-5-ethyl-2-oxo-1,2-dihydropyridine-3-carboxylic acid<br>$^1$H NMR (500 MHz, CDCl$_3$): δ 8.02 (1H, s), 6.80 (2H, d, J = 8 Hz), 6.74 (2H, d, J = 8 Hz), 2.60-2.40 (7H, m), 0.87 (3H, t, J = 7.5 Hz). |
| 171 | 6-[4-(3-{[(benzyloxy)carbonyl]amino}azetidin-1-yl)phenyl]-5-ethyl-2-oxo-1,2-dihydropyridine-3-carboxylic acid<br>$^1$H NMR (500 MHz, CDCl$_3$): δ 8.46 (1H, s), 7.35-7.20 (7H, m), 6.55 (2H, d, J = 8.6 Hz), 5.06 (2H, s), 4.39-4.36 (2H, m), 3.90-3.70 (3H, m), 2.53 (2H, q, J = 7.5 Hz), 1.10 (3H, t, J = 7.5 Hz). |
| 172 | 6-{4-[3-(diethylamino)pyrrolidin-1-yl]phenyl}-5-ethyl-2-oxo-1,2-dihydropyridine-3-carboxylic acid trifluoroacetate (1:1)<br>$^1$H NMR (500 MHz, DMSO-d$_6$): d 13.07 (1H, br), 9.60 (1H, br), 8.33 (1H, s), 7.37 (2H, d, J = 8.8 Hz), 6.75 (2H, d, J = 8.8 Hz), 3.80-3.20 (9H, m), 2.47 (2H, q, J = 7.5 Hz), 2.24-2.18 (2H, m), 1.26 (6H, t, J = 7.2 Hz), 1.06 (3H, t, J = 7.5 Hz). |
| 173 | 6-{4-[3-(cyclopropylamino)pyrrolidin-1-yl]phenyl}-5-ethyl-2-oxo-1,2-dihydropyridine-3-carboxylic acid<br>$^1$H NMR (500 MHz, DMSO-d$_6$) δ ppm 0.27-0.34 (m, 1H) 0.41-0.48 (m, 1H) 1.06 (t, J = 7.53 Hz, 4H) 1.42 (d, J = 17.10 Hz, 1H) 1.87-1.99 (m, 1H) 2.18 (d, J = 3.39 Hz, 1H) 3.11-3.20 (m, 1H) 3.51 (d, J = 9.38 Hz, 2H) 6.62 (d, J = 8.83 Hz, 2H) 7.32 (d, J = 8.83 Hz, 2H) 8.15 (s, 2H) 8.26 (s, 1H). LC-MS: 368.6 [M + H]$^+$, RT 0.76 min. |
| 174 | 6-{4-[3-(benzylamino)pyrrolidin-1-yl]phenyl}-5-ethyl-2-oxo-1,2-dihydropyridine-3-carboxylic acid hydrochloride (1:1)<br>$^1$H NMR (500 MHz, DMSO-d$_6$) δ ppm 1.03-1.09 (m, 4H) 2.40 (dd, J = 13.99, 6.90 Hz, 2H) 2.44-2.50 (m, 2H) 3.37 (d, J = 9.22 Hz, 1H) 3.58 (d, J = 6.86 Hz, 1H) 3.61-3.67 (m, 1H) 3.68-3.74 (m, 1H) 3.90-4.01 (m, 1H) 4.27 (br. s., 2H) 6.70 (d, J = 8.91 Hz, 2H) 7.33-7.40 (m, 2H) 7.42-7.51 (m, 3H) 7.62-7.70 (m, 2H) 8.33 (s, 1H) 9.70-9.90 (m, 1H) 13.10 (br. s., 1H). LC-MS: 418.8 [M + H]$^+$, RT 0.83 min. |
| 175 | 6-[4-(1,3'-bipyrrolidin-1'-yl)phenyl]-5-ethyl-2-oxo-1,2-dihydropyridine-3-carboxylic acid<br>$^1$H NMR (500 MHz, CHCl$_3$-d) δ ppm 1.19 (t, J = 7.49 Hz, 3H) 2.16 (br. s., 2H) 2.23-2.38 (m, 2H) 2.44-2.66 (m, 3H) 2.70-2.86 (m, 1H) 3.02 (br. s., 2H) 3.41-3.54 (m, 1H) 3.62-3.72 (m, 1H) 3.74-3.99 (m, 4H) 6.64 (d, J = 8.35 Hz, 2H) 7.34 (d, J = 8.43 Hz, 2H) 8.45 (s, 1H). LC-MS: 382.5 [M + H]$^+$, RT 0.76 min. |

| Cpd | Name |
|---|---|
| 176 | 6-{4-[(1R,5S,6s)-6-(dibenzylamino)-3-azabicyclo[3.1.0]hex-3-yl]phenyl}-5-ethyl-2-oxo-1,2-dihydropyridine-3-carboxylic acid hydrochloride (1:1)<br>$^1$H NMR (500 MHz, DMSO-$d_6$) δ ppm 1.03 (t, J = 7.41 Hz, 3H) 1.50-1.85 (m, 3H) 2.44 (q, J = 7.57 Hz, 2H) 3.14 (br. s., 2H) 3.35-3.41 (m, 2H) 4.38 (br. s., 2H) 4.60 (br. s., 2H) 6.59 (d, J = 8.51 Hz, 2H) 7.29 (d, J = 8.51 Hz, 2H) 7.30-7.70 (m, 10 H) 8.31 (s, 1H) 10.55 (br. s., 1H) 13.02 (br. s., 1H) 14.99 (br. s., 1H). LC-MS: 518.3 [M − H]$^-$, 520.3 [M + H]$^+$, RT 1.62 min. |
| 177 | 6-{4-[(1R,5S,6s)-6-amino-3-azabicyclo[3.1.0]hex-3-yl]phenyl}-5-ethyl-2-oxo-1,2-dihydropyridine-3-carboxylic acid<br>$^1$H NMR (500 MHz, MeOH-$d_4$) δ ppm 1.12 (t, J = 7.41 Hz, 3H) 2.07 (br. s., 2H) 2.43 (t, J = 2.21 Hz, 1H) 2.55 (q, J = 7.57 Hz, 2H) 3.35-3.40 (m, 2H) 3.72 (d, J = 9.77 Hz, 2H) 6.72 (d, J = 8.83 Hz, 2H) 7.33 (d, J = 8.83 Hz, 2H) 8.37 (s, 1H) 8.48 (s, 1H). LC-MS: 338.1 [M − H]$^-$, 340.5 [M + H]$^+$, RT 0.71 min. |
| 178 | 6-{4-[(1R,5S,6s)-6-(benzylamino)-3-azabicyclo[3.1.0]hex-3-yl]phenyl}-5-ethyl-2-oxo-1,2-dihydropyridine-3-carboxylic acid<br>$^1$H NMR (500 MHz, MeOH-$d_4$) δ ppm 1.12 (t, J = 7.41 Hz, 3H) 1.85 (br. s., 2H) 2.03 (s, 1H) 2.56 (q, J = 7.57 Hz, 2H) 3.30-3.36 (m, 2H) 3.55 (d, J = 9.46 Hz, 2H) 3.89 (s, 2H) 4.62 (s, 1H) 6.65 (d, J = 8.83 Hz, 2H) 7.24-7.33 (m, 3H) 7.33-7.41 (m, 4H) 7.41-7.48 (m, 1H) 8.36 (s, 1H) 8.52 (s, 1H). LC-MS: 428.2 [M − H]$^-$, 430.6 [M + H]$^+$, RT 0.90 min. |

EXAMPLE 16

5-ethyl-6-[4-(hexahydropyrrolo[3,4-b][1,4]oxazin-6(2H)-yl)phenyl]-2-oxo-1,2-dihydropyridine-3-carboxylic acid hydrochloride (1:1) (Cpd 179)

Step 1: N-(1-(4-bromophenyl)butylidene)-2-methylpropan-2-amine

To a solution of 1-(4-bromophenyl)butan-1-one (6.0 g, 26.4 mmol) and t-butylamine (11 mL, 106 mmol) in DCM (100 mL) was added a 1M solution of TiCl$_4$ (16 mL, 16 mmol) dropwise at 0° C. over 30 min. After completion of the addition, the mixture was stirred at room temperature overnight, then the reaction was quenched with saturated aqueous NaHCO$_3$. The product was extracted with DCM and the combined organic phases were dried over Na$_2$SO$_4$, then filtered and concentrated to give the title compound as a crude product that was used immediately in the next step without further purification.

Step 2: (N-(1-(4-bromophenyl)butylidene)-1-(2,4-dimethoxyphenyl)methanamine

To a solution of 1-(4-bromophenyl)butan-1-one (10.4 g, 45.6 mmol) and dimethoxybenzylamine (7.6 mL, 50.4 mmol) in CH$_2$Cl$_2$ (150 mL) was added a 1M solution of TiCl$_4$ (27.4 mL, 27.4 mmol) in CH$_2$Cl$_2$ dropwise at 0° C. over 30 min After completion of the addition, the mixture was stirred at room temperature overnight, then the reaction was quenched with saturated aqueous sodium bicarbonate. The product was extracted with CH$_2$Cl$_2$ and the combined organic phases were dried over Na$_2$SO$_4$, then filtered and concentrated to give the title compound as a crude product that was used immediately in the next step without further purification.

Step 3: methyl-6-(4-bromophenyl)-1-(2,4-dimethoxybenzyl)-5-ethyl-2-oxo-1,2-dihydropyridine-3-carboxylate To a solution of crude (N-(1-(4-bromophenyl)butylidene)-1-(2,4-dimethoxyphenyl)methanamine (15.4 g, 41 mmol) in Ph$_2$O (20 mL), was added dimethyl 2-(methoxymethylene)malonate (7.9 g, 45.4 mmol). The mixture was heated at 180° C. for 1 hr, and the solution was allowed to cool to room temperature. The crude residue was purified on silica gel (EtOAc/hexanes, 0-100% gradient) to afford the title compound as a light yellow foam (6.0 g, 30%).

$^1$H NMR (500 MHz, CHCl$_3$-d) δ ppm 0.97 (t, J=7.40 Hz, 3H) 2.06 (q, J=7.51 Hz, 2H) 3.50 (s, 3H) 3.78 (s, 3H) 3.97 (s, 3H) 5.04 (s, 2H) 6.24 (d, J=2.44 Hz, 1H) 6.37 (dd, J=8.43, 2.44 Hz, 1H) 6.75-6.81 (m, 2H) 6.83 (d, J=8.43 Hz, 1H) 7.45 (d, J=8.59 Hz, 2H) 8.18 (s, 1H).

Step 4: 6-(4-bromophenyl)-1-(2,4-dimethoxybenzyl)-5-ethyl-2-oxo-1,2-dihydropyridine-3-carboxylic acid To a suspension of methyl-6-(4-bromophenyl)-1-(2,4-dimethoxybenzyl)-5-ethyl-2-oxo-1,2-dihydropyridine-3-carboxylate (1.6 g, 3.28 mmol) in THF (5.0 mL) was added LiOH (5.0 mL, 1M solution). The mixture was heated at 50° C. for 3 hrs, then cooled to 0° C. and neutralized with 1M HCl. The precipitate was filtered, then rinsed with Et$_2$O and dried over an N$_2$ stream to afford the title compound as a white solid (1.3 g, 85%).

Step 5: 6-(4-(4-benzylhexahydropyrrolo[3,4-b][1,4]oxazin-6(2H)-yl)phenyl)-1-(2,4-dimethoxybenzyl)-5-ethyl-2-oxo-1,2-dihydropyridine-3-carboxylic acid 6-(4-bromophenyl)-1-(2,4-dimethoxybenzyl)-5-ethyl-2-oxo-1,2-dihydropyridine-3-carboxylic acid (0.4 g, 0.82 mmol), (4aS,7aR)-4-benzyloctahydropyrrolo[3,4-b][1,4]oxazine (0.34 g, 1.0 mmol), NaOtBu (0.4 g, 1.2 mmol), and 2-(2'-di-tert-butylphosphine)biphenylpalladium(II) acetate (3 mg) were weighed into a vial. The vial was evacuated and then back filled with Argon. Toluene (3 mL) was added and the vial was sealed and heated to 100° C. for 16 hrs. The reaction mixture was cooled to room temperature, then poured into 1M HCl (10 mL) and extracted with DCM. The combined organic phase was dried over Na$_2$SO$_4$, then filtered and concentrated.

Step 6: 5-ethyl-6-[4-(hexahydropyrrolo[3,4-b][1,4]oxazin-6(2H)-yl)phenyl]-2-oxo-1,2-dihydropyridine-3-carboxylic acid hydrochloride (1:1)

To a solution of crude 6-(4-(4-benzylhexahydropyrrolo[3,4-b][1,4]oxazin-6(2H)-yl)phenyl)-1-(2,4-dimethoxybenzyl)-5-ethyl-2-oxo-1,2-dihydropyridine-3-carboxylic acid (0.17 g, 0.3 mmol) in CH$_2$Cl$_2$ (1mL) was added TFA (1 mL). The reaction mixture was stirred at room temperature for 1 hr, then concentrated and the residue was dissolved in EtOH (5 mL). A solution of concentrated HCl (0.5 mL) and 10% Pd/C (0.1 g) was added. The flask was evacuated and then back filled with H$_2$. After stirring at room temperature for 16 hrs, the reaction mixture was filtered through Celite and concentrated in vacuo. The crude residue was dissolved in CH$_2$Cl$_2$ (2 mL) and triturated with Et$_2$O to afford the title compound as a yellow powder (41 mg, 43%).

$^1$H NMR (500 MHz, DMSO-d$_6$) δ ppm 1.07-1.13 (m, 3H) 2.44-2.49 (m, 2H) 3.09-3.18 (m, 1H) 3.25-3.35 (m, 1H) 3.54-3.71 (m, 4H) 3.76-3.83 (m, 1H) 3.90-3.99 (m, 1H) 4.02-4.12 (m, 1H) 4.41-4.48 (m, 1H) 6.62-6.68 (m, 2H) 7.35-7.41 (m, 2H) 8.31-8.35 (m, 1H). LC-MS 370.3 [M+H]$^+$, RT 0.47.

Using the procedure described above, additional compounds described herein may be prepared by substituting the appropriate starting materials, reagents and reaction conditions and include compounds selected from:

| Cpd | Name |
|---|---|
| 180 | 6-[4-(4-benzylhexahydropyrrolo[3,4-b][1,4]oxazin-6(2H)-yl)phenyl]-5-ethyl-2-oxo-1,2-dihydropyridine-3-carboxylic acid trifluoroacetate (1:1)<br>$^1$H NMR (500 MHz, DMSO-d$_6$) δ ppm 0.96 (t, J = 6.98 Hz, 3H) 2.27-2.37 (m, 6 H) 2.47-2.47 (m, 4H) 3.25 (m, , 2H) 3.60 (s, 2H) 6.53-6.62 (m, 2H) 7.20-7.28 (m, 2H) 7.28-7.56 (m, 5H) 8.19 (s, 1H). LC-MS 460.4 [M + H]$^+$, RT 0.64. |
| 181 | 6-(4-{3-[(dibenzylamino)methyl]pyrrolidin-1-yl}phenyl)-5-ethyl-2-oxo-1,2-dihydropyridine-3-carboxylic acid trifluoroacetate (1:1)<br>$^1$H NMR (500 MHz, DMSO-d$_6$) δ ppm 1.06 (t, J = 7.49 Hz, 3H) 1.54-1.67 (m, 1H) 2.11-2.20 (m, 1H) 2.44-2.50 (m, 2H) 2.74-2.82 (m, 1H) 2.83-2.90 (m, 1H) 3.12 (br. s., 1H) 3.17-3.29 (m, 2H) 3.53-3.64 (m, 1H) 4.13-4.20 (m, 1H) 4.32-4.42 (m, 2H) 4.43-4.53 (m, 2H) 6.56 (d, J = 8.75 Hz, 2H) 7.31 (d, J = 8.67 Hz, 2H) 7.40-7.57 (m, 6 H) 7.72 (br. s., 4H) 8.31 (s, 1H) 12.96-13.07 (m, 1H). LC-MS 522.3 [M + H]$^+$, RT 0.74. |
| 182 | 6-(4-{3-[(benzylamino)methyl]pyrrolidin-1-yl}phenyl)-5-ethyl-2-oxo-1,2-dihydropyridine-3-carboxylic acid hydrochloride (1:1)<br>$^1$H NMR (500 MHz, DMSO-d$_6$) δ ppm 1.06 (t, J = 7.53 Hz, 3H) 1.81-1.90 (m, 1H) 2.19-2.29 (m, 1H) 2.45-2.49 (m, 2H) 2.77-2.86 (m, 1H) 3.00-3.09 (m, 2H) 3.15-3.22 (m, 1H) 3.28-3.36 (m, 1H) 3.37-3.46 (m, 1H) 3.52-3.60 (m, 1H) 4.19 (s, 3H) 6.62 (d, J = 8.75 Hz, 2H) 7.34 (d, J = 8.75 Hz, 2H) 7.40-7.50 (m, 3H) 7.64 (dd, J = 7.61, 1.54 Hz, 2H) 8.31 (s, 1H) 9.49-9.59 (m, 1H). LC-MS 433.4 [M + H]$^+$, RT 0.92. |
| 183 | 6-[4-(3-{[benzyl(methyl)amino]methyl}pyrrolidin-1-yl)phenyl]-5-ethyl-2-oxo-1,2-dihydropyridine-3-carboxylic acid trifluoroacetate (1:1)<br>$^1$H NMR (500 MHz, DMSO-d$_6$) δ ppm 1.06 (t, J = 7.49 Hz, 3H) 1.74-1.86 (m, 1H) 2.22-2.32 (m, 1H) 2.48 (br. s., 2H) 2.76 (br. s., 3H) 2.83-2.93 (m, 1H) 3.03-3.14 (m, 1H) 3.16-3.35 (m, 2H) 3.38-3.54 (m, 2H) 3.60-3.69 (m, 1H) 4.28-4.36 (m, 2H) 4.41-4.51 (m, 1H) 6.64 (br. s., 3H) 7.34 (d, J = 8.59 Hz, 3H) 7.49 (br. s., 4H) 7.57-7.65 (m, 3H) 8.32 (s, 1H). LC-MS 446.4 [M + H]$^+$, RT 0.54. |
| 184 | 5-ethyl-6-(4-{3-[(methylamino)methyl]pyrrolidin-1-yl}phenyl)-2-oxo-1,2-dihydropyridine-3-carboxylic acid hydrochloride (1:1)<br>$^1$H NMR (500 MHz, DMSO-d$_6$) δ ppm 1.06 (t, J = 7.49 Hz, 3H) 1.81-1.90 (m, 1H) 2.16-2.27 (m, 1H) 2.45-2.49 (m, 2H) 2.58 (t, J = 5.40 Hz, 3H) 2.68-2.77 (m, 1H) 2.99-3.07 (m, 2H) 3.15-3.22 (m, 1H) 3.29-3.36 (m, 1H) 3.42-3.48 (m, 1H) 3.51-3.58 (m, 1H) 6.63 (d, J = 8.91 Hz, 2H) 7.34 (d, J = 8.83 Hz, 2H) 8.32 (s, 1H). LC-MS 356.3 [M + H]$^+$, RT 0.47. |
| 185 | 6-(4-{3-[(dimethylamino)methyl]pyrrolidin-1-yl}phenyl)-5-ethyl-2-oxo-1,2-dihydropyridine-3-carboxylic acid trifluoroacetate (1:1)<br>$^1$H NMR (500 MHz, DMSO-d$_6$) δ ppm 1.06 (t, J = 7.49 Hz, 3H) 1.82 (dd, J = 11.94, 8.63 Hz, 1H) 2.25 (d, J = 6.23 Hz, 1H) 2.44-2.49 (m, 2H) 2.84 (br. s., 6 H) 3.13 (t, J = 8.71 Hz, 1H) 3.25 (br. s., 2H) 3.28-3.36 (m, 1H) 3.39 (q, J = 6.96 Hz, 1H) 3.42-3.48 (m, 1H) 3.57-3.63 (m, 1H) 6.65 (d, J = 8.59 Hz, 2H) 7.34 (d, J = 8.51 Hz, 2H) 8.32 (s, 1H) 9.94-10.04 (m, 1H) 13.03 (br. s., 1H). LC-MS 370.3 [M + H]$^+$, RT 0.49. |
| 186 | 5-ethyl-6-{4-[(4aR,7aS)-hexahydropyrrolo[3,4-b][1,4]oxazin-4(4aH)-yl]phenyl}-2-oxo-1,2-dihydropyridine-3-carboxylic acid trifluoroacetate (1:1)<br>$^1$H NMR (500 MHz, DMSO-d$_6$) δ ppm 0.85 (t, J = 7.49 Hz, 3H) 2.22-2.28 (m, 3H) 2.88 (br. s., 2H) 3.05-3.12 (m, 2H) 3.33-3.41 (m, 1H) 3.43-3.51 (m, 1H) 3.82-3.88 (m, 1H) 4.03 (br. s., 1H) 4.44-4.52 (m, 1H) 6.87 (d, J = 8.83 Hz, 2H) 7.21 (d, J = 8.75 Hz, 2H) 8.14 (s, 1H). LC-MS 370.3 [M + H]$^+$, RT 0.46. |
| 187 | 5-ethyl-6-{4-[(3aR,6aR)-1-methylhexahydropyrrolo[3,4-b]pyrrol-5(1H)-yl]phenyl}-2-oxo-1,2-dihydropyridine-3-carboxylic acid trifluoroacetate (1:1)<br>$^1$H NMR (500 MHz, DMSO-d$_6$) δ ppm 1.05 (t, J = 7.49 Hz, 3H) 1.79-1.89 (m, 1H) 1.89-1.97 (m, 1H) 2.46 (q, J = 7.46 Hz, 2H) 2.90 (br. s., 3H) 3.13-3.22 (m, 1H) 3.24-3.31 (m, 1H) 3.41-3.47 (m, 4H) 4.01 (d, J = 11.98 Hz, 1H) 4.13-4.20 (m, 1H) 6.80 (d, J = 8.67 Hz, 2H) 7.37 (d, J = 8.83 Hz, 2H) 8.33 (s, 1H) 13.06-13.16 (m, 1H). LC-MS 368.3 [M + H]$^+$, RT 0.47. |
| 188 | 6-{4-[3-(aminomethyl)pyrrolidin-1-yl]phenyl}-5-ethyl-2-oxo-1,2-dihydropyridine-3-carboxylic acid trifluoroacetate (1:1)<br>$^1$H NMR (500 MHz, DMSO-d$_6$) δ ppm 0.92 (t, J = 7.40 Hz, 3H) 2.34-2.35 (m, 2H) 2.41-2.49 (m, 3H) 2.77-2.84 (m, 1H) 3.12-3.18 (m, 2H) 3.26-3.32 (m, 1H) 3.32-3.39 (m, 1H) 3.93-4.01 (m, 1H) 6.46-6.50 (m, 1H) 7.18-7.23 (m, 2H) 8.11-8.20 (m, 1H). LC-MS 342.4 [M + H]$^+$, RT 0.47. |
| 189 | 6-{4-[(3aR,6aR)-1-benzylhexahydropyrrolo[3,4-b]pyrrol-5(1H)-yl]phenyl}-5-ethyl-2-oxo-1,2-dihydropyridine-3-carboxylic acid trifluoroacetate (1:1)<br>$^1$H NMR (500 MHz, DMSO-d$_6$) δ ppm 1.04 (t, J = 7.49 Hz, 3H) 1.80-1.92 (m, 1H) 2.45 (q, J = 7.46 Hz, 3H) 3.20 (dd, J = 11.94, 7.21 Hz, 1H) 3.27 (d, J = 9.46 Hz, 2H) 3.47-3.53 (m, 3H) 3.67 (d, J = 11.82 Hz, 1H) 4.34 (d, J = 6.78 Hz, 1H) 4.46 (d, J = 4.49 Hz, 2H) 6.65 (d, J = 8.59 Hz, 2H) 7.34 (d, J = 8.59 Hz, 2H) 7.47-7.53 (m, 3H) 7.67-7.73 (m, 2H) 8.32 (s, 1H) 11.06-11.18 (m, 1H) 13.08 (br. s., 1H). LC-MS 444.7 [M + H]$^+$, RT 0.59. |

-continued

| Cpd | Name |
|---|---|
| 190 | 5-ethyl-6-{4-[(3aR,6aR)-hexahydropyrrolo[3,4-b]pyrrol-5(1H)-yl]phenyl}-2-oxo-1,2-dihydropyridine-3-carboxylic acid trifluoroacetate (1:1)<br>$^1$H NMR (500 MHz, DMSO-$d_6$) δ ppm 1.05 (t, J = 7.53 Hz, 3H) 1.88-1.97 (m, 1H) 2.12-2.24 (m, 1H) 2.46 (d, J = 7.49 Hz, 2H) 3.13-3.30 (m, 3H) 3.37-3.40 (m, 1H) 3.40-3.54 (m, 2H) 3.81-3.90 (m, 1H) 4.30-4.39 (m, 1H) 6.77 (d, J = 8.59 Hz, 2H) 7.34-7.41 (m, 2H) 8.33 (s, 1H) 14.97-15.08 (m, 1H). LC-MS 354.3 [M + H]$^+$, RT 0.46. |
| 191 | 5-ethyl-2-oxo-6-{4-[3-(pyrrolidin-1-ylmethyl)pyrrolidin-1-yl]phenyl}-1,2-dihydropyridine-3-carboxylic acid<br>$^1$H NMR (500 MHz, CHCl$_3$-d) δ ppm 1.10-1.15 (m, 3H) 1.88-1.97 (m, 3H) 2.04 (br. s., 4H) 2.55 (q, J = 7.43 Hz, 3H) 2.72-2.84 (m, 2H) 2.89-3.03 (m, 2H) 3.19-3.27 (m, 1H) 3.36 (s, 2H) 3.40-3.49 (m, 2H) 3.61-3.69 (m, 1H) 6.59 (d, J = 8.35 Hz, 2H) 7.28 (d, J = 8.51 Hz, 2H) 8.39 (s, 1H). LC-MS 396.4 [M + H]$^+$, RT 0.50. |
| 192 | 6-[4-(5,7-dihydro-6H-pyrrolo[3,4-b]pyridin-6-yl)phenyl]-5-ethyl-2-oxo-1,2-dihydropyridine-3-carboxylic acid<br>$^1$H NMR (500 MHz, DMSO-$d_6$) δ ppm 1.09 (t, J = 7.40 Hz, 3H) 3.39 (q, J = 7.01 Hz, 2H) 4.70 (br. s., 2H) 4.75 (br. s., 2H) 6.85 (d, J = 8.75 Hz, 2H) 7.36 (dd, J = 7.57, 4.97 Hz, 1H) 7.43 (d, J = 8.67 Hz, 2H) 7.87 (d, J = 7.41 Hz, 1H) 8.31 (s, 1H) 8.52 (d, J = 4.57 Hz, 1H) 13.09-13.17 (m, 1H) 15.16-15.25 (m, 1H). LC-MS 362.2 [M + H]$^+$, RT 0.66. |
| 193 | 6-{4-[(3aR,4R,7aS)-4-(dimethylamino)octahydro-2H-isoindol-2-yl]phenyl}-5-ethyl-2-oxo-1,2-dihydropyridine-3-carboxylic acid hydrochloride (1:1)<br>$^1$H NMR (500 MHz, CHCl$_3$-d) δ ppm 8.42-8.51 (m, 1H) 7.35 (d, J = 8.43 Hz, 2H) 6.69 (d, J = 7.41 Hz, 2H) 3.74-3.80 (m, 1H) 3.64 (s, 1H) 3.51-3.51 (m, 1H) 3.46-3.55 (m, 2H) 3.23 (d, J = 9.14 Hz, 1H) 2.95-2.95 (m, 1H) 2.90-2.90 (m, 1H) 2.88-2.88 (m, 1H) 2.91 (dd, J = 16.83, 4.30 Hz, 6 H) 2.81-2.82 (m, 1H) 2.54-2.66 (m, 2H) 2.45 (dd, J = 11.78, 5.48 Hz, 1H) 2.17 (d, J = 10.33 Hz, 1H) 2.04 (d, J = 13.56 Hz, 1H) 1.93 (d, J = 11.90 Hz, 1H) 1.40-1.48 (m, 1H) 1.13-1.36 (m, 6 H). LC-MS 410.6 [M + H]$^+$, RT 0.85. |
| 194 | 6-(4-{(3aR,4R,7aS)-4-[benzyl(methyl)amino]octahydro-2H-isoindol-2-yl}phenyl)-5-ethyl-2-oxo-1,2-dihydropyridine-3-carboxylic acid trifluoroacetate (1:1)<br>$^1$H NMR (500 MHz, CHCl$_3$-d) δ ppm 8.47 (s, 1H) 7.54 (br. s., 2H) 7.43-7.51 (m, 3H) 7.36 (d, J = 8.59 Hz, 2H) 6.67 (d, J = 8.59 Hz, 2H) 3.63-3.81 (m, 4H) 3.51-3.61 (m, 2H) 3.48 (t, J = 7.01 Hz, 2H) 3.21 (d, J = 9.22 Hz, 2H) 2.76 (br. s., 3H) 2.63 (q, J = 7.51 Hz, 2H) 1.24-1.32 (m, 2H) 1.13-1.21 (m, 3H). LC-MS 486.8 [M + H]$^+$, RT 1.02. |
| 195 | 5-ethyl-6-{4-[(3aR,4R,7aS)-4-(methylamino)octahydro-2H-isoindol-2-yl]phenyl}-2-oxo-1,2-dihydropyridine-3-carboxylic acid trifluoroacetate (1:1)<br>LC-MS 396.6 [M + H]$^+$, RT 0.85. |
| 196 | 6-{4-[(3aR,4R,7aS)-4-(dibenzylamino)octahydro-2H-isoindol-2-yl]phenyl}-5-ethyl-2-oxo-1,2-dihydropyridine-3-carboxylic acid trifluoroacetate (1:1)<br>$^1$H NMR (500 MHz, CHCl$_3$-d) δ ppm 8.48 (s, 1H) 7.59 (br. s., 3H) 7.40-7.50 (m, 7 H) 7.36 (d, J = 8.59 Hz, 2H) 6.67 (d, J = 8.59 Hz, 2H) 4.24 (br. s., 4H) 3.63-3.81 (m, 3H) 3.46-3.52 (m, 1H) 3.39-3.46 (m, 1H) 3.15 (d, J = 9.46 Hz, 1H) 2.63 (d, J = 7.41 Hz, 2H) 2.26-2.37 (m, 1H) 2.16-2.23 (m, 1H) 1.93-2.04 (m, 1H) 1.65-1.73 (m, 1H) 1.46-1.55 (m, 1H) 1.30 (br. s., 2H) 1.13-1.23 (m, 3H). LC-MS 562.6 [M + H]$^+$, RT 1.27. |
| 197 | 6-{4-[(3aR,4R,7aS)-4-aminooctahydro-2H-isoindol-2-yl]phenyl}-5-ethyl-2-oxo-1,2-dihydropyridine-3-carboxylic acid trifluoroacetate (1:1)<br>$^1$H NMR (500 MHz, DMSO-$d_6$) δ ppm 8.31 (s, 1H) 8.06 (br. s., 1H) 7.35 (d, J = 8.28 Hz, 2H) 6.57 (d, J = 8.43 Hz, 2H) 3.21-3.28 (m, 1H) 3.11-3.19 (m, 2H) 2.16-2.20 (m, 1H) 1.71-1.77 (m, 2H) 1.49-1.56 (m, 1H) 1.37-1.44 (m, 1H) 1.35 (s, 3H) 1.20-1.25 (m, 1H) 1.05 (t, J = 7.25 Hz, 5H). LC-MS 382.5 [M + H]$^+$, RT 0.83. |
| 198 | 6-{4-[(3aR,4R,6aS)-4-(dimethylamino)hexahydrocyclopenta[c]pyrrol-2(1H)-yl]phenyl}-5-ethyl-2-oxo-1,2-dihydropyridine-3-carboxylic acid hydrochloride (1:1)<br>LC-MS 396.4 [M + H]$^+$, RT 0.79. |
| 199 | 6-{4-[(3aR,4R,6aS)-4-[benzyl(methyl)amino]hexahydrocyclopenta[c]pyrrol-2(1H)-yl]phenyl}-5-ethyl-2-oxo-1,2-dihydropyridine-3-carboxylic acid hydrochloride (1:1)<br>$^1$H NMR (500 MHz, CHCl$_3$-d) δ ppm 8.48 (s, 1H) 7.48-7.56 (m, 3H) 7.36 (d, J = 8.28 Hz, 2H) 3.79 (s, 3H) 3.49 (d, J = 7.01 Hz, 7 H) 3.37 (d, J = 9.85 Hz, 4H) 2.73-2.81 (m, 2H) 2.61 (d, J = 7.57 Hz, 2H) 1.15-1.23 (m, 3H). LC-MS 472.6 [M + H]$^+$, RT 0.97. |
| 200 | 5-ethyl-6-{4-[(3aR,4R,6aS)-4-(methylamino)hexahydrocyclopenta[c]pyrrol-2(1H)-yl]phenyl}-2-oxo-1,2-dihydropyridine-3-carboxylic acid hydrochloride (1:1)<br>LC-MS 382.3 [M + H]$^+$, RT 0.81. |
| 201 | 6-{4-[(3aR,4R,6aS)-4-(dibenzylamino)hexahydrocyclopenta[c]pyrrol-2(1H)-yl]phenyl}-5-ethyl-2-oxo-1,2-dihydropyridine-3-carboxylic acid trifluoroacetate (1:1)<br>$^1$H NMR (500 MHz, DMSO-$d_6$) δ ppm 8.26-8.31 (m, 1H) 7.28-7.39 (m, 11H) 7.17-7.25 (m, 2H) 6.64-6.72 (m, 2H) 3.73-3.82 (m, 2H) 3.64-3.72 (m, 1H) 3.43-3.59 (m, 3H) 3.11-3.21 (m, 2H) 2.99-3.11 (m, 2H) 2.74-2.84 (m, 1H) 1.81-1.90 (m, 1H) 1.64-1.72 (m, 1H) 1.32-1.44 (m, 2H) 1.07 (s, 3H). LC-MS 548.5 [M + H]$^+$, RT 1.40. |
| 202 | 6-{4-[(3aR,4R,6aS)-4-aminohexahydrocyclopenta[c]pyrrol-2(1H)-yl]phenyl}-5-ethyl-2-oxo-1,2-dihydropyridine-3-carboxylic acid trifluoroacetate (1:1)<br>LC-MS 368.3 [M + H]$^+$, RT 0.86. |
| 203 | 6-{4-[(3aR,4S,7aS)-4-aminooctahydro-2H-isoindol-2-yl]phenyl}-5-ethyl-2-oxo-1,2-dihydropyridine-3-carboxylic acid trifluoroacetate (1:1)<br>$^1$H NMR (500 MHz, DMSO-$d_6$) δ ppm 8.23-8.29 (m, 1H) 7.92 (s, 1H) 7.25-7.34 (m, 2H) 6.48-6.58 (m, 2H) 3.13-3.33 (m, 1H) 1.81-1.97 (m, 1H) 1.52-1.52 (m, 1H) 1.46-1.71 (m, 5H) 1.13-1.44 (m, 7 H) 1.05 (t, J = 7.45 Hz, 3H). LC-MS 382.3 [M + H]$^+$, RT 0.92. |

| Cpd | Name |
|---|---|
| 204 | 6-{4-[(3aR,4S,6aS)-4-aminohexahydrocyclopenta[c]pyrrol-2(1H)-yl]phenyl}-5-ethyl-2-oxo-1,2-dihydropyridine-3-carboxylic acid trifluoroacetate (1:1)<br>LC-MS 366.7 [M − H]⁻, RT 0.80. |
| 205 | 6-(4-{(3aR,7aS)-3a-[(dimethylamino)methyl]octahydro-2H-isoindol-2-yl}phenyl)-5-ethyl-2-oxo-1,2-dihydropyridine-3-carboxylic acid trifluoroacetate (1:1)<br>¹H NMR (500 MHz, DMSO-d₆) δ ppm 8.27 (s, 1H) 7.30 (d, J = 8.67 Hz, 2H) 6.60 (d, J = 8.75 Hz, 2H) 3.35 (d, J = 8.35 Hz, 1H) 3.22-3.32 (m, 2H) 3.16 (d, J = 9.69 Hz, 1H) 2.74 (d, J = 13.71 Hz, 1H) 2.43-2.57 (m, 2H) 2.30 (s, 6 H) 2.19 (d, J = 13.71 Hz, 1H) 2.05-2.13 (m, 1H) 1.58-1.75 (m, 2H) 1.24-1.55 (m, 6 H) 1.06 (t, J = 7.49 Hz, 3H). LC-MS 425.3 [M + H]⁺, RT 0.65. |
| 206 | 6-{4-[(3aR,6aS)-5-benzylhexahydropyrrolo[3,4-c]pyrrol-2(1H)-yl]phenyl}-5-ethyl-2-oxo-1,2-dihydropyridine-3-carboxylic acid hydrochloride (1:1)<br>¹H NMR (500 MHz, DMSO-d₆) δ ppm 1.00-1.07 (m, 3H) 2.42-2.48 (m, 4H) 2.98 (q, J = 9.0 Hz, 1H) 3.12 (br. s., 1H) 3.28-3.39 (m, 1H) 3.40-3.50 (m, 2H) 3.57 (d, J = 10.1 Hz, 1H) 3.69 (br. s., 1H) 4.32-4.45 (m, 2H) 6.58-6.84 (m, 2H) 7.30-7.39 (m, 2H) 7.43-7.52 (m, 3H) 7.54-7.65 (m, 2H) 8.32 (s, 1H) 10.89 (br. s., 1H) 13.08 (br. s., 1H). LC-MS 442.3 [M − H]⁻, 444.6 [M + H]⁺, RT 0.87 min. |
| 207 | 5-ethyl-6-{4-[(3aR,6aS)-hexahydropyrrolo[3,4-c]pyrrol-2(1H)-yl]phenyl}-2-oxo-1,2-dihydropyridine-3-carboxylic acid hydrochloride (1:1)<br>¹H NMR (500 MHz, MeOH-d₄) δ ppm 1.12 (t, J = 7.6 Hz, 3H) 2.55 (q, J = 7.6 Hz, 2H) 3.26-3.34 (m, 4H) 3.43-3.57 (m, 4H) 3.58-3.69 (m, 2H) 6.87 (d, J = 8.8 Hz, 2H) 7.38 (d, J = 8.8 Hz, 2H) 8.45 (s, 1H). LC-MS 352.2 [M − H]⁻, 354.2 [M + H]⁺, RT 0.87 min. |
| 208 | 5-ethyl-6-{4-[(3aR,6aS)-5-methylhexahydropyrrolo[3,4-c]pyrrol-2(1H)-yl]phenyl}-2-oxo-1,2-dihydropyridine-3-carboxylic acid hydrochloride (1:1)<br>¹H NMR (500 MHz, DMSO-d₆) δ ppm 1.04 (t, J = 7.6 Hz, 3H) 2.46 (q, J = 7.6 Hz, 2H) 2.76-2.93 (m, 4H) 3.14 (br. s., 1H) 3.21-3.28 (m, 1H) 3.29-3.37 (m, 2H) 3.40-3.50 (m, 2H) 3.50-3.59 (m, 2H) 3.86 (br. s., 1H) 6.62-6.84 (m, 2H) 7.35 (d, J = 8.5 Hz, 2H) 8.32 (s, 1H) 9.91-10.53 (m, 1H) 13.08 (br. s., 1H) 15.02 (br. s., 1H). LC-MS 366.3 [M − H]⁻, 368.0 [M + H]⁺, RT 1.16 min. |
| 209 | 6-[4-(3,6-diazabicyclo[3.1.0]hex-3-yl)phenyl]-5-ethyl-2-oxo-1,2-dihydropyridine-3-carboxylic acid<br>¹H NMR (500 MHz, DMSO-d₆) δ ppm 1.03 (t, J = 7.6 Hz, 3H) 2.40 (q, J = 7.6 Hz, 2H) 3.25 (d, J = 12.0 Hz, 2H) 3.44 (s, 2H) 3.59 (d, J = 12.0 Hz, 2H) 7.21 (d, J = 8.5 Hz, 2H) 7.40 (d, J = 8.5 Hz, 2H) 8.31 (s, 1H) 15.20 (br. s., 1H). LC-MS 324.2 [M − H]⁻, 326.5 [M + H]⁺, RT 0.61 min. |
| 210 | 5-ethyl-6-{4-[(1S,5R,6R)-6-(methylamino)-3-azabicyclo[3.2.0]hept-3-yl]phenyl}-2-oxo-1,2-dihydropyridine-3-carboxylic acid hydrochloride (1:1)<br>¹H NMR (500 MHz, MeOH-d₄) δ ppm 1.12 (t, J = 7.6 Hz, 3H) 1.89-2.01 (m, 1H) 2.55 (q, J = 7.6 Hz, 2H) 2.64 (s, 3H) 2.69-2.78 (m, 1H) 3.07 (d, J = 9.1 Hz, 1H) 3.23 (dd, J = 11.3, 8.2 Hz, 1H) 3.39-3.48 (m, 1H) 3.66 (d, J = 9.1 Hz, 1H) 3.74-3.94 (m, 3H) 6.97 (d, J = 8.2 Hz, 2H) 7.38 (d, J = 8.2 Hz, 2H) 8.41 (s, 1H). LC-MS 366.1 [M − H]⁻, 368.5 [M + H]⁺, RT 0.81 min. |
| 211 | 6-{4-[(1S,5R,6R)-6-amino-3-azabicyclo[3.2.0]hept-3-yl]phenyl}-5-ethyl-2-oxo-1,2-dihydropyridine-3-carboxylic acid<br>¹H NMR (500 MHz, DMSO-d₆) δ ppm 1.05 (t, J = 7.3 Hz, 3H) 1.75-1.95 (m, 1H) 2.47 (q, J = 7.3 Hz, 2H) 2.88-2.97 (m, 1H) 3.03 (dd, J = 8.8, 5.7 Hz, 3H) 3.12-3.20 (m, 1H) 3.21-3.30 (m, 1H) 3.52 (d, J = 9.8 Hz, 1H) 3.80 (br. s., 1H) 3.93 (d, J = 9.8 Hz, 1H) 3.96-4.09 (m, 1H) 6.81 (d, J = 8.2 Hz, 2H) 7.37 (d, J = 8.2 Hz, 2H) 8.33 (br. s., 1H) 13.12 (br. s., 1H). LC-MS 352.3 [M − H]⁻, 354.3 [M + H]⁺, RT 0.80 min. |
| 212 | 6-{4-[(1S,5R,6S)-6-amino-3-azabicyclo[3.2.0]hept-3-yl]phenyl}-5-ethyl-2-oxo-1,2-dihydropyridine-3-carboxylic acid hydrochloride (1:1)<br>¹H NMR (500 MHz, DMSO-d₆) δ ppm 1.05 (t, J = 7.6 Hz, 3H) 2.08 (ddd, J = 12.6, 8.8, 3.5 Hz, 1H) 2.26-2.37 (m, 1H) 2.47 (q, J = 7.6 Hz, 2H) 3.00-3.16 (m, 4H) 3.52-3.55 (m, 1H) 3.62 (d, J = 9.8 Hz, 1H) 3.66 (d, J = 10.4 Hz, 1H) 6.84 (d, J = 8.8 Hz, 2H) 7.36 (d, J = 8.8 Hz, 2H) 8.24 (br. s., 3H) 8.33 (s, 1H) 13.10 (br. s., 1H). LC-MS 352.3 [M − H]⁻, 354.3 [M + H]⁺, RT 0.82 min. |
| 213 | 5-ethyl-6-[4-(octahydro-6H-pyrrolo[3,4-b]pyridin-6-yl)phenyl]-2-oxo-1,2-dihydropyridine-3-carboxylic acid hydrochloride (1:1)<br>LC-MS: 368.5 [M + H]⁺, RT 1.20 min. |
| 214 | 6-[4-(7-amino-5-azaspiro[2.4]hept-5-yl)phenyl]-5-ethyl-2-oxo-1,2-dihydropyridine-3-carboxylic acid trifluoroacetate (1:1)<br>LC-MS: 354.6 [M + H]⁺, RT 0.53 min. |
| 215 | 5-ethyl-6-{4-[(3aR,5r,6aS)-5-(methylamino)hexahydrocyclopenta[c]pyrrol-2(1H)-yl]phenyl}-2-oxo-1,2-dihydropyridine-3-carboxylic acid trifluoroacetate (1:1)<br>LC-MS: 382.4 [M + H]⁺, RT 0.55 min. |
| 216 | 6-{4-[(3S,4R)-3-(aminomethyl)-4-methylpyrrolidin-1-yl]phenyl}-5-ethyl-2-oxo-1,2-dihydropyridine-3-carboxylic acid<br>LC-MS: 356.3 [M + H]⁺, RT 0.55 min. |
| 217 | 6-(4-{3-[1-(benzylamino)cyclopropyl]pyrrolidin-1-yl}phenyl)-5-ethyl-2-oxo-1,2-dihydropyridine-3-carboxylic acid trifluoroacetate (1:1)<br>¹H NMR (500 MHz, DMSO-d₆) δ ppm 0.90-1.12 (m, 7 H) 1.56-1.67 (m, 1H) 2.12-2.23 (m, 4H) 2.87-2.98 (m, 2H) 3.44 (d, J = 8.12 Hz, 2H) 3.66 (s, 1H) 4.37 (br. s., 2H) 6.66 (d, J = 8.83 Hz, 2H) 7.34 (d, J = 8.67 Hz, 2H) 7.42-7.51 (m, 3H) 7.56 (d, J = 6.94 Hz, 2H) 8.31 (s, 1H). |

| Cpd | Name |
|---|---|
| 218 | 6-{4-[3-(1-aminocyclobutyl)pyrrolidin-1-yl]phenyl}-5-ethyl-2-oxo-1,2-dihydropyridine-3-carboxylic acid trifluoroacetate (1:1)<br>$^1$H NMR (500 MHz, DMSO-$d_6$) δ ppm 1.05 (t, J = 7.49 Hz, 3H) 1.77-1.95 (m, 2H) 1.97-2.09 (m, 1H) 2.12-2.31 (m, 5H) 2.44-2.49 (m, 2H) 2.66-2.76 (m, 1H) 3.19 (t, J = 9.73 Hz, 1H) 3.32 (td, J = 9.65, 6.94 Hz, 1H) 3.46-3.56 (m, 2H) 6.66 (d, J = 8.83 Hz, 2H) 7.34 (d, J = 8.75 Hz, 2H) 8.31 (s, 1H). |
| 219 | 6-[4-(3a-cyanooctahydro-2H-isoindol-2-yl)phenyl]-5-ethyl-2-oxo-1,2-dihydropyridine-3-carboxylic acid<br>$^1$H NMR (500 MHz, DMSO-$d_6$) δ ppm 1.07 (t, J = 7.57 Hz, 3H) 1.44-1.56 (m, 3H) 1.57-1.67 (m, 4H) 1.67-1.79 (m, 2H) 1.86-1.95 (m, 1H) 2.56 (q, J = 7.25 Hz, 2H) 2.73 (t, J = 5.04 Hz, 1H) 3.33 (t, J = 8.67 Hz, 1H) 3.47 (t, J = 8.67 Hz, 1H) 3.56-3.66 (m, 2H) 6.58 (d, J = 8.83 Hz, 2H) 7.33 (d, J = 8.51 Hz, 2H) 7.88 (s, 1H). LCMS 392.7 [M + H]$^+$, RT 1.28 min. |
| 220 | (3aR,6aR)-2-[4-(5-carboxy-3-ethyl-6-oxo-1,6-dihydropyridin-2-yl)phenyl]hexahydrocyclopenta[c]pyrrole-3a(1H)-carboxylic acid trifluoroacetate (1:1)<br>$^1$H NMR (500 MHz, CHCl$_3$-d) δ ppm 1.22 (t, J = 7.57 Hz, 3H) 1.65-2.49 (m, 7 H) 2.59-2.71 (m, 2H) 3.03-3.28 (m, 3H) 3.56-3.74 (m, 1H) 4.20 (m, 1H) 6.82-7.17 (m, 2H) 7.36-7.58 (m, 2H) 8.56-8.62 (m, 1H) 12.88 (br. s., 1H). LCMS 397.3 [M + H]$^+$, RT 1.18 min. |
| 221 | 6-{4-[3-(dimethylamino)pyrrolidin-1-yl]-2-fluorophenyl}-5-ethyl-2-oxo-1,2-dihydropyridine-3-carboxylic acid<br>LC-MS: 374.5 [M + H]$^+$, RT 0.54 min. |
| 222 | 5-ethyl-6-[4-(4-hydroxypiperidin-1-yl)phenyl]-2-oxo-1,2-dihydropyridine-3-carboxylic acid<br>LC-MS: 343.4 [M + H]$^+$, RT 0.65 min. |
| 223 | 6-{4-[4-(dimethylamino)piperidin-1-yl]phenyl}-5-ethyl-2-oxo-1,2-dihydropyridine-3-carboxylic acid<br>LC-MS: 370.5 [M + H]$^+$, RT 0.76 min. |
| 224 | 5-ethyl-6-[4-(4-methoxypiperidin-1-yl)phenyl]-2-oxo-1,2-dihydropyridine-3-carboxylic acid<br>LC-MS: 357.4 [M + H]$^+$, RT 0.89 min. |
| 225 | 5-ethyl-6-{2-fluoro-4-[(3R)-3-hydroxypyrrolidin-1-yl]phenyl}-2-oxo-1,2-dihydropyridine-3-carboxylic acid<br>LC-MS: 347.4 [M + H]$^+$, RT 0.95 min. |
| 226 | 5-ethyl-2-oxo-6-{4-[3-(pyridin-4-yl)pyrrolidin-1-yl]phenyl}-1,2-dihydropyridine-3-carboxylic acid<br>LC-MS: 390.3 [M + H]$^+$, RT 0.70 min. |
| 227 | 5-ethyl-2-oxo-6-{4-[3-(pyridin-2-yl)pyrrolidin-1-yl]phenyl}-1,2-dihydropyridine-3-carboxylic acid<br>LC-MS: 390.3 [M + H]$^+$, RT 1.09 min. |
| 228 | 6-[4-(4-aminopiperidin-1-yl)phenyl]-5-ethyl-2-oxo-1,2-dihydropyridine-3-carboxylic acid<br>LC-MS: 342.3 [M + H]$^+$, RT 0.83 min. |
| 230 | 5-ethyl-2-oxo-6-{4-[3-(1H-1,2,3-triazol-1-yl)pyrrolidin-1-yl]phenyl}-1,2-dihydropyridine-3-carboxylic acid<br>LC-MS: 380.3 [M + H$^+$, RT 1.02 min. |
| 231 | 6-{4-[(1R,5S,6s)-6-amino-3-azabicyclo[3.1.0]hex-3-yl]-2-fluorophenyl}-5-ethyl-2-oxo-1,2-dihydropyridine-3-carboxylic acid trifluoroacetate (1:1)<br>LC-MS: 358.3 [M + H]$^+$, RT 0.79 min. |
| 232 | 5-ethyl-6-[4-(3-ethyl-3-hydroxypyrrolidin-1-yl)phenyl]-2-oxo-1,2-dihydropyridine-3-carboxylic acid<br>LC-MS: 357.3 [M + H]$^+$, RT 0.98 min. |
| 233 | 5-ethyl-6-[4-(3-hydroxy-3-methylpyrrolidin-1-yl)phenyl]-2-oxo-1,2-dihydropyridine-3-carboxylic acid<br>LC-MS: 343.3 [M + H]$^+$, RT 1.04 min. |
| 234 | 6-[4-(3-{[(2-chlorobenzyl)amino]methyl}pyrrolidin-1-yl)phenyl]-5-ethyl-2-oxo-1,2-dihydropyridine-3-carboxylic acid<br>LC-MS: 468.3 [M + H]$^+$, RT 1.33 min. |
| 235 | 6-{4-[3-(aminomethyl)-3-methylpyrrolidin-1-yl]phenyl}-5-ethyl-2-oxo-1,2-dihydropyridine-3-carboxylic acid<br>LC-MS: 356.3 [M + H]$^+$, RT 0.93 min. |
| 236 | 6-[4-(3-{[(3-chlorobenzyl)amino]methyl}pyrrolidin-1-yl)phenyl]-5-ethyl-2-oxo-1,2-dihydropyridine-3-carboxylic acid<br>LC-MS: 466.3 [M + H]$^+$, RT 0.84 min. |
| 237 | 6-[4-(3-{[(4-chlorobenzyl)amino]methyl}pyrrolidin-1-yl)phenyl]-5-ethyl-2-oxo-1,2-dihydropyridine-3-carboxylic acid<br>LC-MS: 466.4 [M + H]$^+$, RT 1.24 min. |
| 238 | 5-ethyl-6-[4-(3-{[(3-fluorobenzyl)amino]methyl}pyrrolidin-1-yl)phenyl]-2-oxo-1,2-dihydropyridine-3-carboxylic acid<br>LC-MS: 450.4 [M + H]$^+$, RT 1.18 min. |
| 239 | 5-ethyl-6-[4-(3-{[(4-fluorobenzyl)amino]methyl}pyrrolidin-1-yl)phenyl]-2-oxo-1,2-dihydropyridine-3-carboxylic acid<br>LC-MS: 450.4 [M + H]$^+$, RT 1.12 min. |
| 240 | 5-ethyl-6-[4-(3-{[(2-fluorobenzyl)amino]methyl}pyrrolidin-1-yl)phenyl]-2-oxo-1,2-dihydropyridine-3-carboxylic acid<br>LC-MS: 450.4 [M + H]$^+$, RT 1.17 min. |

| Cpd | Name |
|---|---|
| 241 | 5-ethyl-2-oxo-6-[4-(3-{[(pyridin-3-ylmethyl)amino]methyl}pyrrolidin-1-yl)phenyl]-1,2-dihydropyridine-3-carboxylic acid<br>LC-MS: 433.4 [M + H]$^+$, RT 0.95 min. |
| 242 | 5-ethyl-2-oxo-6-[4-(3-{[(pyridin-4-ylmethyl)amino]methyl}pyrrolidin-1-yl)phenyl]-1,2-dihydropyridine-3-carboxylic acid<br>LC-MS: 433.4 [M + H]$^+$, RT 0.99 min. |
| 243 | 5-ethyl-2-oxo-6-[4-(3-{[(pyridin-2-ylmethyl)amino]methyl}pyrrolidin-1-yl)phenyl]-1,2-dihydropyridine-3-carboxylic acid<br>LC-MS: 433.4 [M + H]$^+$, RT 1.07 min. |
| 244 | 6-{4-[(3aR,4S,7aS)-4-azidooctahydro-2H-isoindol-2-yl]phenyl}-5-ethyl-2-oxo-1,2-dihydropyridine-3-carboxylic acid trifluoroacetate (1:1)<br>LC-MS 408.3 [M + H]$^+$, RT 1.45. |
| 245 | 6-{4-[(3aR,4S,6aS)-4-azidohexahydrocyclopenta[c]pyrrol-2(1H)-yl]phenyl}-5-ethyl-2-oxo-1,2-dihydropyridine-3-carboxylic acid trifluoroacetate (1:1)<br>LC-MS 394.8 [M + H]$^+$, RT 1.36. |

EXAMPLE 17

5-ethyl-6-{4-[(3aR,6aR)-hexahydropyrrolo[3,4-b]pyrrol-5(1H)-yl]phenyl}-4-hydroxy-2-oxo-1,2-dihydropyridine-3-carboxylic acid hydrochloride (1:1) (Cpd 246)

Step 1

A solution of 1-(4-chlorophenyl)butan-1-one (5.00 g, 27.37 mmol) and t-butyl amine (11.60 mL, 109.90 mmol) in DCM (30 mL) was cooled to 0° C. A solution of TiCl$_4$ (1M DCM, 18.00 mL, 18.00 mmol) was added dropwise via syringe pump over 30 min. The reaction mixture was allowed to warm to room temperature and stirred overnight. The mixture was diluted with DCM (200 mL) and then the reaction was quenched with NaHCO$_3$ (aqueous saturated, 60 mL). After vigorous shaking, the organic phase was separated using a PTFE phase separator, then dried over Na$_2$SO$_4$. The solvent was removed to afford a colorless oil (5.30 g, 81), which was used directly in the next step without further purification.

The oil (2.14 g, 8.99 mmol) and triethylmethane tricarboxylate (2.20 mL, 10.46 mmol) in diglyme (9 mL) were heated at 160° C. for 2 h. After the mixture was cooled to room temperature, a white solid was collected by filtration and washed with Et$_2$O. The resulting product (1.54 g, 53%) was obtained as a colorless crystalline material.

$^1$H NMR (500 MHz, DMSO-d$_6$) δ ppm 0.95 (t, J=7.4 Hz, 3H) 1.30 (t, J=7.1 Hz, 3H) 2.18 (d, J=7.4 Hz, 2H) 4.34 (q, J=7.1 Hz, 2H) 7.44 (d, J=8.2 Hz, 2H) 7.57 (d, J=8.2 Hz, 2H) 11.43 (br. s., 1H) 13.57 (s, 1H). LC-MS 322.2/324.2 [M+H]$^+$, RT 1.30 min.

Step 2

To a solution of ethyl 6-(4-chlorophenyl)-5-ethyl-4-hydroxy-2-oxo-1,2-dihydropyridine-3-carboxylate (1.00 g, 3.11 mmol), PPh$_3$ (2.00 g, 7.63 mmol) and BnOH (0.80 mL, 7.72 mmol) in THF (20 mL) at 0° C. was added DIAD (1.50 mL, 7.57 mmol) dropwise. The reaction mixture was stirred at 0° C. for 15 min and allowed to warm to room temperature, then stirred for 30 min. The THF was concentrated and the residue was purified by column chromatography (EtOAc/hexanes, 0-20% gradient) to afford ethyl 2,4-bis(benzyloxy)-6-(4-chlorophenyl)-5-ethylnicotinate (1.00 g, 64%) as a white solid.

$^1$H NMR (500 MHz, CHCl$_3$-d) δ ppm 1.03 (t, J=7.4 Hz, 3H) 1.32 (t, J=7.1 Hz, 3H) 2.55 (q, J=7.4 Hz, 2H) 4.38 (q, J=7.1 Hz, 2H) 5.15 (s, 2H) 5.42 (s, 2H) 7.27-7.48 (m, 14H). LC-MS 502.1 [M+H]$^+$, RT 1.83 min.

A mixture of ethyl 2,4-bis(benzyloxy)-6-(4-chlorophenyl)-5-ethylnicotinate (0.94 g, 1.87 mmol) and TMSOK (90%, 0.60 g, 4.21 mmol) in THF (7.5 mL) was heated at 70° C. in a sealed vial overnight. The THF was removed under reduced pressure and H$_2$O (2 mL) was added to the residue. The mixture was acidified with 1M HCl to pH~1 and the product was extracted with DCM (4×10 mL). After drying the organic phase over Na$_2$SO$_4$, the solvents were removed and the residue was triturated with hexanes. The resulting solid was filtered and washed with hexanes, affording the product (0.726 g, 82%) as a colorless solid $^1$H NMR (500 MHz, CHCl$_3$-d) δ ppm 1.03 (t, J=7.4 Hz, 3H) 2.56 (q, J=7.4 Hz, 2H) 5.17 (s, 2H) 5.50 (s, 2H) 7.28-7.49 (m, 14H). LC-MS 474.2/476.4 [M+H]$^+$, RT 1.67 min.

Step 3

2,4-bis(benzyloxy)-6-(4-chlorophenyl)-5-ethylnicotinic acid (0.2 g, 0.4 mmol), (3aR,6aR)-1-benzyloctahydropyrrolo[3,4-b]pyrrole (0.16 g, 0.8 mmol), NaOtBu (0.12 g, 1.2 mmol) and 2-(2'-di-tert-butylphosphine)biphenylpalladium (II) acetate (3 mg, 3 mol %) were weighed into a vial. The vial was evacuated and then back filled with Argon. Toluene (2 mL) was added and the vial was sealed and heated to 100° C. for 16 hrs. The reaction mixture was cooled to room temperature, then poured into 1M HCl and extracted with DCM. The combined organic phase was dried over Na$_2$SO$_4$, then filtered and concentrated. The crude residue was dissolved in MeOH (5 mL) and 10% Pd(OH)$_2$/C was added. Under H$_2$, the reaction mixture was stirred at room temperature for 2 hrs. The mixture was then filtered through Celite and concentrated. The crude residue was dissolved in CH$_2$Cl$_2$ and 2M HCl/Et$_2$O (1 mL) was added. The yellow precipitate was filtered and rinsed with Et$_2$O to afford the title compound (58 mg, 40%).

$^1$H NMR (500 MHz, DMSO-d$_6$) δ 1.03 (t, J=7.41 Hz, 3H) 1.88-1.96 (m, 1H) 2.13-2.23 (m, 1H) 2.37 (q, J=7.30 Hz, 2H) 3.14-3.28 (m, 3H) 3.34-3.53 (m, 3H) 3.82-3.89 (m, 1H) 4.31-4.38 (m, 1H) 6.77 (d, J=8.83 Hz, 2H) 7.34 (d, J=8.67 Hz, 2H). LC-MS 370.4 [M+H]$^+$, RT 0.51.

Using the procedure described above, additional compounds described herein may be prepared by substituting the appropriate starting materials, reagents and reaction conditions and include compounds selected from:

| Cpd | Name |
|---|---|
| 247 | 6-(4-{3-[1-(dimethylamino)cyclopropyl]pyrrolidin-1-yl}phenyl)-5-ethyl-4-hydroxy-2-oxo-1,2-dihydropyridine-3-carboxylic acid<br>$^1$H NMR (500 MHz, DMSO-d$_6$) δ ppm 0.92-1.11 (m, 7 H) 2.06 (s, 4H) 2.37 (s, 2H) 2.70-2.85 (m, 8 H) 2.88-2.99 (m, 1H) 3.10-3.28 (m, 2H) 3.58-3.71 (m, 2H) 6.60-6.73 (m, 2H) 7.23-7.35 (m, 2H) 13.83 (br. s., 1H). |
| 248 | 6-{4-[(3aR,5r,6aS)-5-aminohexahydrocyclopenta[c]pyrrol-2(1H)-yl]phenyl}-5-ethyl-4-hydroxy-2-oxo-1,2-dihydropyridine-3-carboxylic acid<br>LC-MS: 384.3 [M + H]$^+$, RT 0.68 min. |
| 249 | 6-(4-{(3S,4R)-3-[(dibenzylamino)methyl]-4-methylpyrrolidin-1-yl}phenyl)-5-ethyl-4-hydroxy-2-oxo-1,2-dihydropyridine-3-carboxylic acid<br>LC-MS: 552.5 [M + H]$^+$, RT 0.93 min. |
| 250 | 6-{4-[(3aR,5r,6aS)-5-(benzylamino)hexahydrocyclopenta[c]pyrrol-2(1H)-yl]phenyl}-5-ethyl-4-hydroxy-2-oxo-1,2-dihydropyridine-3-carboxylic acid<br>LC-MS: 474.4 [M + H]$^+$, RT 0.71 min. |
| 251 | 6-{4-[(3aR,5r,6aS)-5-(dibenzylamino)hexahydrocyclopenta[c]pyrrol-2(1H)-yl]phenyl}-5-ethyl-4-hydroxy-2-oxo-1,2-dihydropyridine-3-carboxylic acid<br>LC-MS: 565.0 [M + H]$^+$, RT 0.89 min. |
| 252 | 6-[4-(7-amino-5-azaspiro[2.4]hept-5-yl)phenyl]-5-ethyl-4-hydroxy-2-oxo-1,2-dihydropyridine-3-carboxylic acid trifluoroacetate (1:1)<br>LC-MS: 368.3 [M + H]$^+$, RT 0.68 min. |
| 253 | 6-{4-[1-(tert-butoxycarbonyl)octahydro-6H-pyrrolo[3,4-b]pyridin-6-yl]phenyl}-5-ethyl-4-hydroxy-2-oxo-1,2-dihydropyridine-3-carboxylic acid<br>LC-MS: 484.6 [M + H]$^+$, RT 1.00 min. |
| 254 | 5-ethyl-4-hydroxy-6-(4-{3-[(methylamino)methyl]pyrrolidin-1-yl}phenyl)-2-oxo-1,2-dihydropyridine-3-carboxylic acid hydrochloride (1:1)<br>$^1$H NMR (500 MHz, DMSO-d$_6$) δ 1.04 (s, 3H) 1.81-1.91 (m, 1H) 2.16-2.27 (m, 1H) 2.34-2.43 (m, 2H) 2.58 (s, 3H) 2.69-2.78 (m, 1H) 2.99-3.08 (m, 2H) 3.14-3.21 (m, 1H) 3.28-3.37 (m, 1H) 3.40 (s, 2H) 3.50-3.57 (m, 1H) 6.59-6.66 (m, 2H) 7.28-7.35 (m, 2H) 9.10 (br. s, 1H) 12.57 (br. s, 1H) 13.86 (br. s, 1H). LC-MS 372.3 [M + H]$^+$, RT 0.55. |
| 255 | 6-[4-(3-{[benzyl(methyl)amino]methyl}pyrrolidin-1-yl)phenyl]-5-ethyl-4-hydroxy-2-oxo-1,2-dihydropyridine-3-carboxylic acid<br>$^1$H NMR (500 MHz, DMSO-d$_6$) δ 0.91 (t, J = 7.37 Hz, 3H) 1.78-1.88 (m, 1H) 2.18 (s, 3H) 2.53-2.57 (m, 4H) 2.67-2.76 (m, 1H) 2.95-3.05 (m, 2H) 3.09-3.15 (m, 1H) 3.22-3.30 (m, 1H) 3.38 (s, 1H) 3.43-3.50 (m, 1H) 6.48-6.57 (m, 2H) 6.88-6.93 (m, 2H) 6.99-7.05 (m, 2H) 7.18-7.28 (m, 3H) 9.10-9.24 (m, 1H) 13.80-13.87 (m, 1H). |
| 256 | 5-ethyl-4-hydroxy-6-{4-[(3aR,4R,6aS)-4-(methylamino)hexahydrocyclopenta[c]pyrrol-2(1H)-yl]phenyl}-2-oxo-1,2-dihydropyridine-3-carboxylic acid hydrochloride (1:1)<br>$^1$H NMR (500 MHz, MeOH-d$_4$) δ 1.12 (t, J = 7.37 Hz, 3H) 1.71-1.80 (m, 1H) 1.83-1.94 (m, 1H) 2.06-2.16 (m, 1H) 2.18-2.26 (m, 1H) 2.46-2.54 (m, 2H) 2.83 (s, 3H) 3.02-3.10 (m, 1H) 3.20-3.27 (m, 1H) 3.35-3.40 (m, 1H) 3.51 (m, J = 7.00 Hz, 2H) 3.55-3.61 (m, 1H) 3.67-3.75 (m, 1H) 6.86-6.92 (m, 2H) 7.35-7.41 (m, 2H). LC-MS 398.3 [M + H]$^+$, RT 0.89. |
| 257 | 6-[4-(1,3'-bipyrrolidin-1'-yl)phenyl]-5-ethyl-4-hydroxy-2-oxo-1,2-dihydropyridine-3-carboxylic acid hydrochloride (1:1)<br>$^1$H NMR (500 MHz, MeOH-d$_4$) δ 0.98 (t, J = 7.41 Hz, 1H) 1.92-2.00 (m, 1H) 2.06-2.16 (m, 1H) 2.19-2.28 (m, 1H) 2.36 (q, J = 7.40 Hz, 2H) 2.45-2.54 (m, 1H) 3.11-3.18 (m, 1H) 3.30-3.37 (m, 1H) 3.50-3.61 (m, 2H) 3.61-3.67 (m, 2H) 3.67-3.73 (m, 1H) 3.95-4.03 (m, 1H) 6.66-6.73 (m, 2H) 7.21-7.27 (m, 2H). LC-MS 396.1 [M − H]$^−$, RT 0.52. |
| 258 | 6-{4-[(3aR,4S,7aS)-4-aminooctahydro-2H-isoindol-2-yl]phenyl}-5-ethyl-4-hydroxy-2-oxo-1,2-dihydropyridine-3-carboxylic acid hydrochloride (1:1)<br>$^1$H NMR (500 MHz, MeOH-d$_4$) δ 1.13 (t, J = 7.41 Hz, 3H) 1.51-1.61 (m, 1H) 1.67-1.86 (m, 4H) 2.02-2.10 (m, 1H) 2.34-2.41 (m, 1H) 2.52 (m, 2H) 2.75-2.86 (m, 1H) 3.15-3.23 (m, 1H) 3.36-3.45 (m, 2H) 3.47-3.53 (m, 1H) 3.64-3.69 (m, 1H) 6.75 (m, J = 8.91 Hz, 2H) 7.35 (m, J = 8.83 Hz, 2H). LC-MS 398.3 [M + H]$^+$, RT 0.90. |
| 259 | 6-{4-[(1R,5S,6s)-6-amino-3-azabicyclo[3.1.0]hex-3-yl]phenyl}-4-hydroxy-5-methyl-2-oxo-1,2-dihydropyridine-3-carboxylic acid hydrochloride (1:1)<br>$^1$H NMR (500 MHz, MeOH-d$_4$) δ 1.24-1.35 (m, 1H), 1.47-1.57 (m, 1H), 1.92-2.01 (m, 1H), 2.03-2.11 (m, 1H), 2.45-2.55 (m, 1H), 2.83 (s, 3H), 3.52-3.59 (m, 1H), 6.70-6.76 (m, 2H), 7.34-7.41 (m, 2H). LC-MS 342.3 [M + H]$^+$, RT 0.51. |
| 260 | 4-hydroxy-5-methyl-6-{4-[(3aR,4R,7aS)-4-(methylamino)octahydro-2H-isoindol-2-yl]phenyl}-2-oxo-1,2-dihydropyridine-3-carboxylic acid hydrochloride (1:1)<br>$^1$H NMR (500 MHz, MeOH-d$_4$) δ 1.13 (t, J = 7.41 Hz, 3H), 1.51-1.61 (m, 1H), 1.67-1.86 (m, 4H), 2.02-2.10 (m, 1H), 2.34-2.41 (m, 1H), 2.52 (m, 2H), 2.75-2.86 (m, 4H), 3.15-3.23 (m, 1H), 3.36-3.45 (m, 2H), 3.47-3.53 (m, 1H), 3.64-3.69 (m, 1H), 6.75 (m, J = 8.9 Hz, 2H), 7.35 (m, J = 8.8 Hz, 2H). LC-MS 398.3 [M + H]$^+$, RT 0.84. |
| 261 | 6-{4-[(3aR,4R,7aS)-4-(dimethylamino)octahydro-2H-isoindol-2-yl]phenyl}-5-ethyl-4-hydroxy-2-oxo-1,2-dihydropyridine-3-carboxylic acid hydrochloride (1:1)<br>$^1$H NMR (500 MHz, CHCl$_3$-d) δ ppm 7.30 (d, J = 8.35 Hz, 2H) 6.66 (d, J = 9.38 Hz, 2H) 4.12 (d, J = 6.62 Hz, 2H) 3.22 (s, 1H) 2.92 (s, 1H) 2.90 (br. s., 1H) 2.54 (br. s., 6 H) 2.05 (br. s., 4H) 2.02-2.02 (m, 4H) 1.26 (br. s., 4H) 1.17 (br. s., 5H). LC-MS 426.8 [M + H]$^+$, RT 0.99. |

-continued

| Cpd | Name |
|---|---|
| 262 | 6-{4-[(3aR,4R,7aS)-4-aminooctahydro-2H-isoindol-2-yl]phenyl}-5-ethyl-4-hydroxy-2-oxo-1,2-dihydropyridine-3-carboxylic acid trifluoroacetate (1:1)<br>$^1$H NMR (500 MHz, DMSO-d$_6$) δ ppm 8.02 (br. s., 2H) 7.31 (d, J = 8.83 Hz, 3H) 6.57 (d, J = 8.83 Hz, 2H) 3.21-3.28 (m, 1H) 3.16 (s, 1H) 2.28-2.42 (m, 5H) 1.70-1.80 (m, 2H) 1.47-1.64 (m, 2H) 1.29-1.37 (m, 1H) 0.96-1.10 (m, 6 H). LC-MS 396.7 [M − H]$^-$, RT 0.99. |
| 263 | 6-{4-[(3aR,4R,6aS)-4-(dimethylamino)hexahydrocyclopenta[c]pyrrol-2(1H)-yl]phenyl}-5-ethyl-4-hydroxy-2-oxo-1,2-dihydropyridine-3-carboxylic acid hydrochloride (1:1)<br>$^1$H NMR (500 MHz, CHCl$_3$-d) δ ppm 7.30 (d, J = 8.59 Hz, 2H) 6.69-6.69 (m, 2H) 6.72 (d, J = 8.67 Hz, 2H) 3.83-3.93 (m, 1H) 3.57 (dd, J = 9.73, 6.42 Hz, 1H) 3.41-3.53 (m, 3H) 3.33 (d, J = 9.30 Hz, 1H) 3.14 (br. s., 1H) 2.95 (d, J = 18.76 Hz, 6 H) 2.54 (q, J = 7.36 Hz, 2H) 2.06-2.21 (m, 2H) 1.71-1.84 (m, 1H) 1.19-1.24 (m, 1H) 1.16 (t, J = 7.37 Hz, 3H). LC-MS 412.7 [M + H]$^+$, RT 0.93. |
| 264 | 6-{4-[(3aR,4R,6aS)-4-aminohexahydrocyclopenta[c]pyrrol-2(1H)-yl]phenyl}-5-ethyl-4-hydroxy-2-oxo-1,2-dihydropyridine-3-carboxylic acid hydrochloride (1:1)<br>$^1$H NMR (500 MHz, DMSO-d$_6$) δ ppm 7.33 (d, J = 8.75 Hz, 2H) 6.71 (d, J = 8.67 Hz, 2H) 3.42-3.53 (m, 1H) 3.20-3.29 (m, 2H) 2.97-3.06 (m, 2H) 2.84-2.92 (m, 1H) 2.61-2.68 (m, 1H) 2.36 (s, 2H) 1.85-2.00 (m, 2H) 1.68-1.76 (m, 1H) 1.53-1.61 (m, 1H) 0.98-1.09 (m, 3H). LC-MS 384.3 [M + H]$^+$, RT 0.94. |
| 265 | 6-{4-[(3aR,4S,6aS)-4-aminohexahydrocyclopenta[c]pyrrol-2(1H)-yl]phenyl}-5-ethyl-4-hydroxy-2-oxo-1,2-dihydropyridine-3-carboxylic acid trifluoroacetate (1:1)<br>$^1$H NMR (500 MHz, DMSO-d$_6$) δ ppm 8.15 (s, 1H) 7.25 (d, J = 8.75 Hz, 2H) 6.65 (d, J = 8.75 Hz, 2H) 3.27-3.45 (m, 4H) 3.13-3.20 (m, 1H) 2.88-2.97 (m, 1H) 2.71 (br. s., 1H) 2.32-2.41 (m, 2H) 2.03-2.14 (m, 2H) 1.62-1.72 (m, 1H) 1.49 (s, 1H) 0.97-1.06 (m, 3H). LC-MS 384.7 [M + H]$^+$, RT 0.93. |
| 266 | 6-(4-{(3aR,7aS)-3a-[(dimethylamino)methyl]octahydro-2H-isoindol-2-yl}phenyl)-5-ethyl-4-hydroxy-2-oxo-1,2-dihydropyridine-3-carboxylic acid hydrochloride (1:1)<br>$^1$H NMR (500 MHz, DMSO-d$_6$) δ ppm 13.84 (br. s., 1H) 7.29 (br. s., 3H) 6.65 (br. s., 3H) 3.33 (br. s., 1H) 2.74-2.92 (m, 10 H) 1.48 (br. s., 6H) 1.04 (br. s., 9H). LC-MS 438.8 [M − H]$^-$, RT 1.07. |
| 267 | 5-ethyl-4-hydroxy-6-{4-[(3aR,4S,6aS)-4-(methylamino)hexahydrocyclopenta[c]pyrrol-2(1H)-yl]phenyl}-2-oxo-1,2-dihydropyridine-3-carboxylic acid hydrochloride (1:1)<br>$^1$H NMR (500 MHz, DMSO-d$_6$) δ ppm 7.31 (d, J = 8.43 Hz, 2H) 6.71 (d, J = 8.20 Hz, 2H) 3.43 (br. s., 2H) 3.32-3.39 (m, 2H) 3.15-3.24 (m, 1H) 2.62 (br. s., 3H) 2.37 (d, J = 7.01 Hz, 2H) 2.03-2.19 (m, 1H) 1.68-1.77 (m, 1H) 1.46-1.54 (m, 1H) 1.32-1.38 (m, 1H) 1.14-1.18 (m, 1H) 0.99-1.08 (m, 3H) 0.78-0.85 (m, 1H). LC-MS 398.8 [M + H]$^+$, RT 0.96. |
| 268 | 5-ethyl-4-hydroxy-6-{4-[(3aR,4S,7aS)-4-(methylamino)octahydro-2H-isoindol-2-yl]phenyl}-2-oxo-1,2-dihydropyridine-3-carboxylic acid hydrochloride (1:1)<br>$^1$H NMR (500 MHz, DMSO-d$_6$) δ ppm 7.30 (d, J = 8.75 Hz, 2H) 6.61 (d, J = 8.83 Hz, 2H) 3.61-3.68 (m, 1H) 3.28-3.42 (m, 4H) 3.15-3.24 (m, 1H) 2.53-2.72 (m, 5H) 2.38 (d, J = 7.57 Hz, 3H) 1.92-2.01 (m, 1H) 1.31-1.68 (m, 4H) 1.01-1.08 (m, 3H). LC-MS 412.7 [M + H]$^+$, RT 0.99. |
| 269 | 6-{4-[(1R,5S,6s)-6-amino-3-azabicyclo[3.1.0]hex-3-yl]phenyl}-5-ethyl-4-hydroxy-2-oxo-1,2-dihydropyridine-3-carboxylic acid hydrochloride (1:1)<br>(1R,5S,6s)-N,N-dibenzyl-3-azabicyclo[3.1.0]hexan-6-amine was prepared according to literature procedure *Chem. Eur. J.* 2002, 8, 3789-3801.<br>$^1$H NMR (500 MHz, MeOH-d$_4$) δ ppm 1.09 (t, J = 7.41 Hz, 3H) 2.12-2.21 (m, 2H) 2.47 (q, J = 7.41 Hz, 2H) 2.53 (t, J = 2.13 Hz, 1H) 3.39 (d, J = 9.38 Hz, 2H) 3.76 (d, J = 9.62 Hz, 2H) 6.75 (d, J = 8.75 Hz, 2H) 7.31 (d, J = 8.75 Hz, 2H). LC-MS: 354.3 [M − H]$^-$, 356.3 [M + H]$^+$, RT 0.85 min. |
| 270 | 5-ethyl-4-hydroxy-6-{4-[(1R,5S,6s)-6-(methylamino)-3-azabicyclo[3.1.0]hex-3-yl]phenyl}-2-oxo-1,2-dihydropyridine-3-carboxylic acid hydrochloride (1:1)<br>$^1$H NMR (500 MHz, DMSO-d$_6$) δ ppm 1.02 (t, J = 7.29 Hz, 3H) 2.29 (br. s., 2H) 2.35 (q, J = 7.29 Hz, 2H) 2.59-2.68 (m, 4H) 3.33 (d, J = 9.30 Hz, 2H) 3.64 (d, J = 9.77 Hz, 2H) 6.68 (d, J = 8.51 Hz, 2H) 7.28 (d, J = 8.51 Hz, 2H) 9.29 (br. s., 1H) 12.58 (s, 1H) 13.84 (br. s., 1H). LC-MS 368.3 [M − H]$^-$, 370.3 [M + H]$^+$, RT 0.85 min. |
| 271 | 6-{4-[(1R,5S,6s)-6-(dimethylamino)-3-azabicyclo[3.1.0]hex-3-yl]phenyl}-5-ethyl-4-hydroxy-2-oxo-1,2-dihydropyridine-3-carboxylic acid hydrochloride (1:1)<br>$^1$H NMR (500 MHz, DMSO-d$_6$) δ ppm 1.02 (t, J = 7.29 Hz, 3H) 2.35 (q, J = 7.29 Hz, 2H) 2.37-2.44 (m, 2H) 2.52-2.54 (m, 1H) 2.88 (s, 6 H) 3.29-3.33 (m, 2H) 3.66 (d, J = 9.85 Hz, 2H) 6.68 (d, J = 8.75 Hz, 2H) 7.29 (d, J = 8.75 Hz, 2H) 12.60 (s, 1H) 13.84 (s, 1H). LC-MS 382.3 [M − H]$^-$, 384.3 [M + H]$^+$, RT 0.84 min. |
| 272 | 5-ethyl-4-hydroxy-6-[4-(octahydro-6H-pyrrolo[3,4-b]pyridin-6-yl)phenyl]-2-oxo-1,2-dihydropyridine-3-carboxylic acid hydrochloride (1:1)<br>$^1$H NMR (500 MHz, MeOH-d$_4$) δ ppm 1.09 (t, J = 7.3 Hz, 3H) 1.79-2.03 (m, 4H) 2.48 (q, J = 7.3 Hz, 2H) 2.85-2.95 (m, 1H) 3.09 (td, J = 11.7, 3.0 Hz, 1H) 3.31-3.36 (m, 1H) 3.42-3.52 (m, 1H) 3.57 (t, J = 9.5 Hz, 1H) 3.61 (d, J = 11.7 Hz, 1H) 3.74 (dd, J = 11.7, 4.4 Hz, 1H) 3.99 (t, J = 4.4 Hz, 1H) 6.79 (d, J = 8.8 Hz, 2H) 7.37 (d, J = 8.8 Hz, 2H). LC-MS 382.1 [M − H]$^-$, 384.3 [M + H]$^+$, RT 0.85 min. |
| 273 | 5-ethyl-4-hydroxy-6-{4-[(3aR,6aS)-5-methylhexahydropyrrolo[3,4-c]pyrrol-2(1H)-yl]phenyl}-2-oxo-1,2-dihydropyridine-3-carboxylic acid hydrochloride (1:1)<br>$^1$H NMR (500 MHz, DMSO-d$_6$) δ ppm 1.01 (t, J = 7.4 Hz, 3H) 2.34 (q, J = 7.4 Hz, 2H) 2.77 (s, 3H) 3.02-3.27 (m, 4H) 3.28-3.42 (m, 2H) 3.47 (d, J = 9.1 Hz, 2H) 3.54 (br. s., 2H) 6.75 (d, J = 8.5 Hz, 2H) 7.29 (d, J = 8.5 Hz, 2H). LC-MS 382.3 [M − H]$^-$, 383.9 [M + H]$^+$, RT 1.25 min. |

| Cpd | Name |
|---|---|
| 274 | 5-ethyl-6-{4-[(3aR,6aS)-hexahydropyrrolo[3,4-c]pyrrol-2(1H)-yl]phenyl}-4-hydroxy-2-oxo-1,2-dihydropyridine-3-carboxylic acid hydrochloride (1:1)<br>$^1$H NMR (500 MHz, DMSO-d$_6$) δ ppm 1.02 (t, J = 7.4 Hz, 3H) 2.36 (q, J = 7.4 Hz, 2H) 3.00-3.20 (m, 4H) 3.21-3.34 (m, 1H) 3.35-3.51 (m, 5H) 6.71 (d, J = 8.8 Hz, 2H) 7.31 (d, J = 8.8 Hz, 2H) 9.76 (br. s, 2H) 12.59 (s, 1H) 13.85 (br. s., 1H). LC-MS 368.2 [M − H]$^−$, 370.0 [M + H]$^+$, RT 1.08 min. |
| 275 | 6-{4-[3-(dimethylamino)pyrrolidin-1-yl]phenyl}-5-ethyl-4-hydroxy-2-oxo-1,2-dihydropyridine-3-carboxylic acid hydrochloride (1:1)<br>$^1$H NMR (500 MHz, MeOH-d$_4$) δ ppm 1.09 (t, J = 7.4 Hz, 3H) 2.26-2.39 (m, 1H) 2.47 (d, J = 7.4 Hz, 2H) 2.57-2.69 (m, 1H) 3.00 (s, 6 H) 3.39-3.48 (m, 1H) 3.58-3.64 (m, 1H) 3.69 (td, J = 8.7, 3.5 Hz, 1H) 3.81 (t, J = 8.7 Hz, 1H) 4.05-4.13 (m, 1H) 6.81 (d, J = 8.5 Hz, 2H) 7.36 (d, J = 8.5 Hz, 2H). LC-MS 370.1 [M − H]$^−$, 372.9 [M + H]$^+$, RT 0.82 min. |
| 276 | 6-[4-(3a-cyanooctahydro-2H-isoindol-2-yl)phenyl]-5-ethyl-4-hydroxy-2-oxo-1,2-dihydropyridine-3-carboxylic acid trifluoroacetate (1:1)<br>$^1$H NMR (500 MHz, DMSO-d$_6$) δ ppm 1.03 (t, J = 7.41 Hz, 3H) 1.50 (d, J = 4.41 Hz, 3H) 1.62 (br. s., 2H) 1.72 (dd, J = 9.93, 4.26 Hz, 2H) 2.34-2.41 (m, 2H) 2.74 (s, 1H) 3.32-3.37 (m, 2H) 3.49 (dd, J = 9.77, 7.88 Hz, 2H) 3.60-3.68 (m, 2H) 6.66 (d, J = 8.83 Hz, 2H) 7.31 (d, J = 8.83 Hz, 2H) 12.59 (br. s., 1H) 13.84 (s, 1H). LCMS 408.3 [M + H]$^+$, RT 1.49 min. |
| 277 | 6-[4-(1-amino-3-azabicyclo[3.1.0]hex-3-yl)phenyl]-5-ethyl-4-hydroxy-2-oxo-1,2-dihydropyridine-3-carboxylic acid hydrochloride (1:1)<br>$^1$H NMR (500 MHz, DMSO-d$_6$): d 13.86 (1H, br), 12.60 (1H, br), 9.44 (1H, br), 9.05 (2H, br), 8.53 (1H, br), 7.31 (2H, d, J = 8.7 Hz), 6.70 (2H, d, J = 8.7 Hz), 2.95-2.90 (1H, m), 2.88-2.83 (1H, m), 2.36 (2H, q, J = 7.4 Hz), 2.18-1.39 (5H, m). |
| 278 | 6-(4-(2,8-diazaspiro[4.5]dec-2-yl)phenyl]-5-ethyl-4-hydroxy-2-oxo-1,2-dihydropyridine-3-carboxylic acid hydrochloride (1:1)<br>$^1$H NMR (500 MHz, DMSO-d$_6$): d 13.84 (1H, br), 12.57 (1H, br), 9.00 (1H, br), 8.94 (1H, br), 7.29 (2H, d, J = 8.7 Hz), 6.65 (2H, d, J = 8.7 Hz), 4.30 (4H, br), 3.20-3.05 (4H, m), 2.38 (2H, q, J = 7.4 Hz), 2.06-1.75 (6H, m), 1.10 (3H, t, J = 7.4 Hz). |
| 279 | 6-{4-[3-(2-aminopropan-2-yl)pyrrolidin-1-yl]phenyl}-5-ethyl-4-hydroxy-2-oxo-1,2-dihydropyridine-3-carboxylic acid hydrochloride (1:1)<br>$^1$H NMR (500 MHz, MeOH-d$_4$) δ ppm 1.11 (t, J = 7.41 Hz, 3H) 1.39-1.47 (m, 6 H) 1.92-2.03 (m, 1H) 2.14-2.25 (m, 1H) 2.34-2.46 (m, 1H) 2.49 (q, J = 7.25 Hz, 2H) 2.62-2.70 (m, 1H) 3.37-3.44 (m, 1H) 3.47-3.54 (m, 1H) 3.59 (t, J = 8.83 Hz, 1H) 6.74 (d, J = 8.83 Hz, 2H) 7.33 (d, J = 8.20 Hz, 2H). LC-MS: 384.4 [M − H]$^−$, 386.3 [M + H]$^+$, RT 0.84 min. |
| 280 | 5-ethyl-4-hydroxy-6-[4-(4-hydroxypiperidin-1-yl)phenyl]-2-oxo-1,2-dihydropyridine-3-carboxylic acid<br>LC-MS: 359.5 [M + H]$^+$, RT 0.87 min. |
| 281 | 6-{4-[4-(benzyloxy)piperidin-1-yl]phenyl}-5-ethyl-4-hydroxy-2-oxo-1,2-dihydropyridine-3-carboxylic acid<br>LC-MS: 449.5 [M + H]$^+$, RT 1.45 min. |
| 282 | 5-ethyl-4-hydroxy-6-[4-(4-methoxypiperidin-1-yl)phenyl]-2-oxo-1,2-dihydropyridine-3-carboxylic acid<br>LC-MS: 373.5 [M + H]$^+$, RT 1.14 min. |
| 283 | 6-{4-[4-(dibenzylamino)piperidin-1-yl]phenyl}-5-ethyl-4-hydroxy-2-oxo-1,2-dihydropyridine-3-carboxylic acid<br>LC-MS: 538.7 [M + H]$^+$, RT 1.00 min. |
| 284 | 6-[4-(4-aminopiperidin-1-yl)phenyl]-5-ethyl-4-hydroxy-2-oxo-1,2-dihydropyridine-3-carboxylic acid<br>LC-MS: 358.5 [M + H]$^+$, RT 0.68 min. |
| 285 | 6-{4-[(1R,5S,6s)-6-amino-3-azabicyclo[3.1.0]hex-3-yl]phenyl}-5-ethyl-4-hydroxy-2-oxo-1,2-dihydropyridine-3-carboxylic acid<br>LC-MS: 356.3 [M + H]$^+$, RT 0.73 min. |
| 286 | 5-ethyl-4-hydroxy-2-oxo-6-{4-[3-(pyridin-2-yl)pyrrolidin-1-yl]phenyl}-1,2-dihydropyridine-3-carboxylic acid<br>LC-MS: 406.3 [M + H]$^+$, RT 1.30 min. |
| 287 | 5-ethyl-4-hydroxy-2-oxo-6-{4-[3-(1H-1,2,3-triazol-1-yl)pyrrolidin-1-yl]phenyl}-1,2-dihydropyridine-3-carboxylic acid<br>LC-MS: 396.3 [M + H]$^+$, RT 1.50 min. |
| 288 | 5-ethyl-6-[4-(3-ethyl-3-hydroxypyrrolidin-1-yl)phenyl]-4-hydroxy-2-oxo-1,2-dihydropyridine-3-carboxylic acid<br>LC-MS: 373.3 [M + H]$^+$, RT 1.47 min. |
| 289 | 5-ethyl-4-hydroxy-6-[4-(3-hydroxy-3-methylpyrrolidin-1-yl)phenyl]-2-oxo-1,2-dihydropyridine-3-carboxylic acid<br>LC-MS: 357.3 [M − H]$^−$, RT 1.08 min. |
| 290 | 6-{4-[3-(aminomethyl)-3-methylpyrrolidin-1-yl]phenyl}-5-ethyl-4-hydroxy-2-oxo-1,2-dihydropyridine-3-carboxylic acid<br>LC-MS: 372.4 [M + H]$^+$, RT 0.88 min. |
| 291 | 6-{4-[3-(dimethylamino)pyrrolidin-1-yl]-2-fluorophenyl}-5-ethyl-4-hydroxy-2-oxo-1,2-dihydropyridine-3-carboxylic acid<br>LC-MS: 390.4 [M + H]$^+$, RT 0.73 min. |
| 292 | 5-ethyl-6-{2-fluoro-4-[(3R)-3-hydroxypyrrolidin-1-yl]phenyl}-4-hydroxy-2-oxo-1,2-dihydropyridine-3-carboxylic acid<br>LC-MS: 363.4 [M + H]$^+$, RT 0.97 min. |

| Cpd | Name |
|---|---|
| 293 | 5-ethyl-6-{2-fluoro-4-[(3R)-3-fluoropyrrolidin-1-yl]phenyl}-4-hydroxy-2-oxo-1,2-dihydropyridine-3-carboxylic acid<br>LC-MS: 365.3 [M + H]$^+$, RT 1.50 min. |
| 294 | 6-{4-[5-(tert-butoxycarbonyl)-2,5-diazabicyclo[2.2.1]hept-2-yl]phenyl}-5-ethyl-4-hydroxy-2-oxo-1,2-dihydropyridine-3-carboxylic acid<br>LC-MS 456.8 [M + H]$^+$, RT 1.42. |
| 295 | 6-[4-(2,5-diazabicyclo[2.2.1]hept-2-yl)phenyl]-5-ethyl-4-hydroxy-2-oxo-1,2-dihydropyridine-3-carboxylic acid trifluoroacetate (1:1)<br>LC-MS 356.4 [M + H]$^+$, RT 0.81. |
| 296 | 5-ethyl-4-hydroxy-6-{4-[(3aR,4R,7aS)-4-(methylamino)octahydro-2H-isoindol-2-yl]phenyl}-2-oxo-1,2-dihydropyridine-3-carboxylic acid hydrochloride (1:1)<br>$^1$H NMR (500 MHz, DMSO-d$_6$) δ ppm 8.18 (s, 1H) 7.24 (d, J = 8.51 Hz, 2H) 6.49 (d, J = 8.67 Hz, 2H) 3.22-3.44 (m, 5H) 3.06-3.14 (m, 1H) 2.74-2.87 (m, 1H) 2.63 (s, 3H) 2.27-2.43 (m, 3H) 1.84-1.94 (m, 1H) 1.71-1.81 (m, 1H) 1.56-1.65 (m, 1H) 1.43-1.55 (m, 1H) 1.23-1.36 (m, 1H) 1.05-1.23 (m, 1H) 1.00 (t, J = 7.33 Hz, 3H). LC-MS 412.5 [M + H]$^+$, RT 1.02. |
| 297 | 5-ethyl-6-{4-[(3aS)-1,3,3a,4,5,6-hexahydro-2H-isoindol-2-yl]phenyl}-4-hydroxy-2-oxo-1,2-dihydropyridine-3-carboxylic acid hydrochloride (1:1)<br>LC-MS 381.7 [M + H]$^+$, RT 1.66. |
| 315 | 4-hydroxy-5-methyl-2-oxo-6-(5-(pyrrolidin-1-yl)pyridin-2-yl)-1,2-dihydropyridine-3-carboxylic acid<br>$^1$H NMR (500 MHz, DMSO-d$_6$) δ ppm 2.04 (s, 3 H) 2.10-2.21 (m, 4 H) 3.63-3.78 (m, 4 H) 7.03-7.12 (m, 1 H) 7.51-7.62 (m, 1 H) 8.09-8.17 (m, 1 H) 12.59 (br. s, 1 H) 13.97 (br. s, 1 H). LC-MS: 316.2 [M + H]$^+$, RT 0.69 min. |
| 316 | 6-(5-(3-(dimethylamino)pyrrolidin-1-yl)pyridin-2-yl)-4-hydroxy-5-methyl-2-oxo-1,2-dihydropyridine-3-carboxylic acid<br>$^1$H NMR (500 MHz, DMSO-d$_6$) δ ppm 2.04 (s, 3 H) 2.11-2.19 (m, 2 H) 3.41 (s, 6 H) 3.61-3.83 (m, 5 H) 7.05-7.12 (m, 1 H) 7.55-7.60 (m, 1 H) 8.10-8.16 (m, 1 H) 12.41-12.67 (m, 1 H) 13.82-14.09 (m, 1 H). LC-MS: 359.2 [M + H]$^+$, RT 0.58 min. |
| 317 | 6-(5-((1R,5S,6s)-6-amino-3-azabicyclo[3.1.0]hexan-3-yl)pyridin-2-yl)-4-hydroxy-5-methyl-2-oxo-1,2-dihydropyridine-3-carboxylic acid<br>$^1$H NMR (500 MHz, DMSO-d$_6$) δ ppm 2.05 (s, 3 H) 2.44 (1H, s) 3.29 (2H, d, J = 10 Hz) 3.62 (2H, d, J = 10 Hz) 3.63-3.78 (m, 4 H) 7.09-7.17 (m, 1 H) 7.60-7.65 (m, 1 H) 8.16-8.21 (m, 1 H) 8.98-9.22 (m, 1 H) 9.93-10.06 (m, 1 H) 12.44-12.61 (m, 1 H) 13.83-13.97 (m, 1 H), 2.15 (2H, s). LC-MS: 343.2 [M + H]$^+$, RT 0.60 min. |
| 318 | 6-(4-((1R,5S,6s)-6-amino-3-azabicyclo[3.1.0]hexan-3-yl)-2-methylphenyl)-4-hydroxy-5-methyl-2-oxo-1,2-dihydropyridine-3-carboxylic acid<br>NMR: (DMSO-d$^6$, 500 MHz): δ 1.72 (3H, s), 2.09 (3H, s), 2.15 (2H, s), 2.44 (1H, s), 3.29 (2H, d, J = 10 Hz), 3.62 (2H, d, J = 10 Hz), 6.52 (1H, dd, J = 8 Hz, 2.5 Hz), 6.54 (1H, s), 7.05 (1H, d, J = 8 Hz), 8.41 (3H, m), 12.63 (1H, s), 13.83 (1H, s). LC-MS: 356.2 [M + H]$^+$, RT 1.17 min. |
| 319 | 5-ethyl-4-hydroxy-6-(4-(7-methyl-2,7-diazaspiro[3.5]nonan-2-yl)phenyl)-2-oxo-1,2-dihydropyridine-3-carboxylic acid<br>$^1$H NMR (500 MHz, MeOD-d$_6$) δ 1.11 (t, J = 5 Hz, 3H), 2.02-2.09 (m, 2H), 2.26-2.30 (m, 2H), 2.48 (q, J = 1 Hz, 2H), 2.92 (s, 3H), 3.10-3.15 (m, 2H), 3.52-3.55 (m, 2H), 3.77 (s, 2H), 3.86 (s, 2H), 6.63 (d, J = 8 Hz, 2H), 7.33 (d, J = 8 Hz, 2H). LC-MS 398.3 [M + H]$^+$, RT 0.55 min. |
| 320 | 6-(4-(2,7-diazaspiro[3.5]nonan-2-yl)phenyl)-5-ethyl-4-hydroxy-2-oxo-1,2-dihydropyridine-3-carboxylic acid<br>$^1$H NMR (500 MHz, MeOD-d$_6$) δ 1.11 (t, J = 7 Hz, 3H), 2.11-2.13 (m, 4H), 2.48 (q, J = 7 Hz, 2H), 3.25-3.27 (m, 4H), 3.82 (s, 4H), 6.63 (d, J = 8 Hz, 2H), 7.33 (d, J = 8 Hz, 2H). LC-MS 384.3 [M + H]$^+$, RT 0.54 min. |
| 321 | 6-(4-(2,7-diazaspiro[4.4]nonan-2-yl)phenyl)-5-ethyl-4-hydroxy-2-oxo-1,2-dihydropyridine-3-carboxylic acid<br>$^1$H NMR (500 MHz, MeOD-d$_6$) δ 1.12 (t, J = 7 Hz, 3H), 2.13-2.21 (m, 4H), 2.51 (q, J = 1 Hz, 2H), 3.42-3.56 (m, 8H), 6.75 (d, J = 8 Hz, 2H), 7.34 (d, J = 8 Hz, 2H). LC-MS 384.5 [M + H]$^+$, RT 0.55 min. |
| 322 | 5-ethyl-4-hydroxy-6-(4-(7-methyl-2,7-diazaspiro[4.4]nonan-2-yl)phenyl)-2-oxo-1,2-dihydropyridine-3-carboxylic acid<br>$^1$H NMR (500 MHz, MeOD-d$_6$) δ 1.12 (t, J = 7 Hz, 3H), 2.13-2.35 (m, 4H), 2.51 (q, J = 1 Hz, 2H), 3.03 (s, 3H), 3.19-3.29 (m, 2H), 3.47-3.55 (m, 4H), 3.73-3.76 (m, 2H), 6.75 (d, J = 8 Hz, 2H), 7.34 (d, J = 8 Hz, 2H). LC-MS 398.3 [M + H]$^+$, RT 0.55 min. |
| 323 | 6-(4-(2,5-diazaspiro[3.4]octan-2-yl)phenyl)-5-ethyl-4-hydroxy-2-oxo-1,2-dihydropyridine-3-carboxylic acid<br>$^1$H NMR (500 MHz, MeOD-d$_6$) δ 1.12 (t, J = 7 Hz, 3H), 2.13-2.34 (m, 4H), 2.51 (q, J = 7 Hz, 2H), 3.41-3.50 (m, 3H), 3.60-3.65 (m, 1H), 4.09-4.12 (m, 1H), 4.25-4.27 (m, 1H), 6.75 (d, J = 8 Hz, 2H), 7.34 (d, J = 8 Hz, 2H). LC-MS 370.3 [M + H]$^+$, RT 0.51 min. |
| 324 | 6-(4-(2,6-diazaspiro[3.3]heptan-2-yl)phenyl)-5-ethyl-4-hydroxy-2-oxo-1,2-dihydropyridine-3-carboxylic acid<br>$^1$H NMR (500 MHz, MeOD-d$_6$) δ 1.10 (t, J = 7 Hz, 3H), 2.46 (q, J = 1 Hz, 2H), 4.17 (s, 4H), 4.34 (s, 4H), 6.63 (d, J = 8 Hz, 2H), 7.33 (d, J = 8 Hz, 2H). LC-MS 356.3 [M + H]$^+$, RT 0.51 min. |
| 325 | 5-ethyl-6-(4-(ethylamino)phenyl)-4-hydroxy-2-oxo-1,2-dihydropyridine-3-carboxylic acid<br>$^1$H NMR (500 MHz, MeOD-d$_6$) δ 1.10 (t, J = 7 Hz, 3H), 1.40 (t, J = 7 Hz, 3H), 2.43 (q, J = 7 Hz, 2H), 3.49 (q, J = 7 Hz, 2H), 7.52 (d, J = 8 Hz, 2H), 7.65 (d, J = 8 Hz, 2H). LC-MS 303.3 [M + H]$^+$, RT 1.21 min. |

| Cpd | Name |
|---|---|
| 326 | 5-ethyl-4-hydroxy-6-(4-(methylamino)phenyl)-2-oxo-1,2-dihydropyridine-3-carboxylic acid<br>$^1$H NMR (500 MHz, MeOD-d$_6$) δ 1.10 (t, J = 7 Hz, 3H), 2.44 (q, J = 7 Hz, 2H), 3.07 (s, 3H), 7.39 (d, J = 8 Hz, 2H), 7.58 (d, J = 8 Hz, 2H). LC-MS 289.3 [M + H]$^+$, RT 1.14 min. |

EXAMPLE 18

6-[4-(dimethylamino)phenyl]-5-ethyl-4-methoxy-2-oxo-1,2-dihydropyridine-3-carboxylic acid (Cpd 298)

Step 1

To a solution of 1-(4-(dimethylamino)phenyl)butan-1-one (5.65 g, 29.54 mmol) in DCM (35 mL) was added benzylamine (3.50 mL, 32.01 mmol) and NEt$_3$ (10.0 mL, 71.74 mmol). The mixture was cooled to 0° C., then a TiCl$_4$ solution (1M DCM, 17.0 mL, 17.0 mmol) was added dropwise via syringe pump over 30 min. The reaction mixture was allowed to warm to room temperature and stirred overnight. The mixture was diluted with DCM (100 mL) and then the reaction was quenched with NaHCO$_3$ (aqueous saturated, 30 mL). After vigorous shaking, the organic phase was separated using a PTFE phase separator, then dried over Na$_2$SO$_4$. Removal of the solvent afforded the title product (7.37 g, 89%) as a yellow oil, which was used directly in the next step without further purification.

Step 2

Crude 4-(1-(benzylimino)butyl)-N,N-dimethylaniline (7.37 g, 26.28 mmol) and triethyl methanetricarboxylate (6.40 mL, 30.42 mmol) were mixed together in diglyme (30 mL). The mixture was heated at 160° C. overnight and the diglyme was removed. The residue was purified by column chromatography using EtOAc/hexanes (gradient 0-50%). After concentration of the desired fractions, the residue was triturated with hexanes and the solid was filtered to afford ethyl 1-benzyl-6-(4-(dimethylamino)phenyl)-5-ethyl-4-hydroxy-2-oxo-1,2-dihydropyridine-3-carboxylate (4.34 g, 35%) over 2 steps.

$^1$H NMR (500 MHz, CHCl$_3$-d) δ ppm 0.94 (t, J=7.4 Hz, 3H) 1.47 (t, J=7.1 Hz, 3H) 2.18 (q, J=7.4 Hz, 2H) 2.99 (s, 6H) 4.49 (q, J=7.1 Hz, 2H) 5.04 (br. s., 2H) 6.61 (d, J=8.5 Hz, 2H) 6.81 (d, J=8.5 Hz, 2H) 6.85-6.90 (m, 2H) 7.09-7.22 (m, 3H) 13.83 (s, 1H). LC-MS 419.2 [M−H]$^-$, 421.4 [M+H]$^+$, RT 1.62 min.

Step 3

The product ethyl 1-benzyl-6-(4-(dimethylamino)phenyl)-5-ethyl-4-hydroxy-2-oxo-1,2-dihydropyridine-3-carboxylate (0.50 g, 1.19 mmol) obtained above was dissolved in THF (8 mL). A mixture of MeOH (80 μL, 1.98 mmol) and PPh$_3$ (0.47 g, 1.79 mmol) were added. The mixture was cooled to 0° C., then DIAD (0.35 mL, 1.77 mmol) was added dropwise. The reaction was stirred at 0° C. for 15 min and slowly allowed to warm to room temperature. After 30 min, the starting material was no longer detected by LC/MS. The THF was concentrated and the residue was purified by column chromatography using EtOAc/hexanes (gradient 0-50%). The product was obtained as an oil (~0.74 g) contaminated with an inseparable DIAD by-product.

The obtained product was dissolved in MeOH (6 mL) and treated with a LiOH solution (1M H$_2$O, 6.0 mL, 6.0 mmol). The mixture was microwaved for 60 min at 120° C., then cooled to room temperature and a solid was filtered off. The MeOH from the mother liquor was removed under reduced pressure, then the aqueous phase was diluted with H$_2$O (15 mL) and extracted with EtOAc (10 mL). The organic phase was discarded and the aqueous phase was acidified with 1M HCl to pH~3. A yellow solid was filtered off, then washed with H$_2$O and dried to afford 1-benzyl-6-(4-(dimethylamino)phenyl)-5-ethyl-4-methoxy-2-oxo-1,2-dihydropyridine-3-carboxylic acid (0.25 g, 52%) over 2 steps.

$^1$H NMR (500 MHz, CHCl$_3$-d) δ ppm 0.93 (t, J=7.4 Hz, 3H) 2.22 (q, J=7.4 Hz, 2H) 3.01 (s, 6H) 4.16 (s, 3H) 5.13 (br. s., 2H) 6.64 (d, J=8.8 Hz, 2H) 6.84 (d, J=8.8 Hz, 2H) 6.87-6.91 (m, 2H) 7.20-7.26 (m, 3H). LC-MS 405.3 [M−H]$^-$, 407.4 [M+H]$^+$, RT 1.48 min.

Step 4

A suspension of 1-benzyl-6-(4-(dimethylamino)phenyl)-5-ethyl-4-methoxy-2-oxo-1,2-dihydropyridine-3-carboxylic acid (71.2 mg, 0.18 mmol) in a mixture of MeOH (1.5 mL) and AcOH (1.5 mL) was hydrogenated in a Paar shaker under 65 psi of H$_2$ for 6 h. After complete consumption of starting material was observed, DCM was added to the mixture, then the catalyst was filtered off and the filtrate was washed with DCM. The mother liquor was concentrated and the residue was triturated with Et$_2$O to afford 6-(4-(dimethylamino)phenyl)-5-ethyl-4-methoxy-2-oxo-1,2-dihydropyridine-3-carboxylic acid (33 mg, 60%) as yellow solid.

$^1$H NMR (500 MHz, CHCl$_3$-d) δ ppm 1.15 (t, J=7.4 Hz, 3H) 2.55 (q, J=7.4 Hz, 2H) 4.13 (s, 3H) 6.82 (d, J=8.5 Hz, 2H) 7.34 (d, J=8.5 Hz, 2H) 11.55 (br. s., 1H) 14.42 (br. s., 1H). LC-MS 315.3 [M−H]$^-$, 317.2 [M+H]$^+$, RT 1.10 min.

Using the procedure described above, additional compounds described herein may be prepared by substituting the appropriate starting materials, reagents and reaction conditions and include compounds selected from:

| Cpd | Name |
|---|---|
| 299 | 6-{4-[di(prop-2-en-1-yl)amino]phenyl}-5-ethyl-2-oxo-1,2-dihydropyridine-3-carboxylic acid<br>$^1$H NMR (500 MHz, CHCl$_3$-d) δ ppm 1.22 (t, J = 7.6 Hz, 3H) 2.64 (q, J = 7.6 Hz, 2H) 4.03 (br. s., 4H) 5.17-5.29 (m, 4H) 5.82-5.95 (m, 2H) 6.80 (d, J = 8.8 Hz, 2H) 7.33 (d, J = 8.8 Hz, 2H) 8.52 (s, 1H) 11.86 (br. s., 1H) 13.41 (br. s, 1H). LC-MS 337.9 [M − H]$^-$, 339.9 [M + H]$^+$, RT 1.33 min. |

| Cpd | Name |
|---|---|
| 300 | 6-{4-[di(prop-2-en-1-yl)amino]phenyl}-5-ethyl-4-hydroxy-2-oxo-1,2-dihydropyridine-3-carboxylic acid<br>$^1$H NMR (500 MHz, DMSO-d$_6$) δ ppm 1.04 (t, J = 7.4 Hz, 3H) 2.36 (q, J = 7.4 Hz, 2H) 4.01 (d, J = 4.9 Hz, 4H) 5.12-5.21 (m, 4H) 5.87 (ddd, J = 12.5, 10.1, 4.9 Hz, 2H) 6.77 (d, J = 8.8 Hz, 2H) 7.26 (d, J = 8.8 Hz, 2H) 12.51 (br. s., 1H) 13.85 (br. s., 1H). LC-MS 352.6 [M − H]$^−$, 354.9 [M + H]$^+$, RT 1.49 min. |

EXAMPLE 19

6-[4-(2,5-dihydro-1H-pyrrol-1-yl)phenyl]-5-ethyl-2-oxo-1,2-dihydropyridine-3-carboxylic acid (Cpd 301)

Step 1

To a solution of methyl 6-(4-(diallylamino)phenyl)-5-ethyl-2-oxo-1,2-dihydropyridine-3-carboxylate (0.116 g, 0.33 mmol) in DCM (3 mL) was added a Grubbs-II catalyst (14 mg, 5 mol %). The reaction mixture was stirred at room temperature overnight and then diluted with Et$_2$O (~5 ml). The resulting yellow precipitate was filtered and washed with Et$_2$O to afford methyl 6-(4-(2,5-dihydro-1H-pyrrol-1-yl)phenyl)-5-ethyl-2-oxo-1,2-dihydropyridine-3-carboxylate (0.075 g, 71%).

$^1$H NMR (500 MHz, CHCl$_3$-d) δ ppm 1.17 (t, J=7.6 Hz, 3H) 2.54 (q, J=7.6 Hz, 2H) 3.94 (s, 3H) 4.18 (s, 4H) 6.00 (s, 2H) 6.60 (d, J=8.8 Hz, 2H) 7.33 (d, J=8.8 Hz, 2H) 8.24 (s, 1H) 9.02 (br. s., 1H). LC-MS 325.0 [M+H]$^+$, RT 1.22 min.

Step 2

A mixture of methyl 6-(4-(2,5-dihydro-1H-pyrrol-1-yl)phenyl)-5-ethyl-2-oxo-1,2-dihydropyridine-3-carboxylate (37.4 mg, 0.12 mmol) and LiOH (1M aqueous, 0.40 mL, 0.40 mmol) in THF (0.80 mL) was heated at 50° C. for 2 h. The reaction mixture was cooled to room temperature and acidified with 1M HCl to pH~2. A bright yellow precipitate was filtered off, then washed with H$_2$O and Et$_2$O and dried to afford 6-(4-(2,5-dihydro-1H-pyrrol-1-yl)phenyl)-5-ethyl-2-oxo-1,2-dihydropyridine-3-carboxylic acid (25.0 mg, 70%).

$^1$H NMR (500 MHz, DMSO-d$_6$) δ ppm 1.06 (t, J=7.3 Hz, 3H) 2.48 (q, J=7.3 Hz, 2H) 4.13 (s, 4H) 6.06 (s, 2H) 6.64 (d, J=8.5 Hz, 2H) 7.35 (d, J=8.5 Hz, 2H) 8.31 (s, 1H) 13.05 (br. s., 1H) 15.04 (s, 1H). LC-MS 308.7 [M−H]$^−$, 311.0 [M+H]$^+$, RT 1.22 min.

EXAMPLE 20

6-[4-(2,5-dihydro-1H-pyrrol-1-yl)phenyl]-5-ethyl-4-hydroxy-2-oxo-1,2-dihydropyridine-3-carboxylic acid (Cpd 302)

Step 1

To a solution of methyl 6-(4-(diallylamino)phenyl)-5-ethyl-4-hydroxy-2-oxo-1,2-dihydropyridine-3-carboxylate (0.188 g, 0.51 mmol) in DCM (6 mL) was added a Grubbs-II catalyst (22 mg, 5 mol %). The reaction mixture was stirred at room temperature overnight. A yellow precipitate was filtered and washed with Et$_2$O to afford methyl 6-(4-(2,5-dihydro-1H-pyrrol-1-yl)phenyl)-5-ethyl-4-hydroxy-2-oxo-1,2-dihydropyridine-3-carboxylate (0.137 g, 79%).

$^1$H NMR (500 MHz, DMSO-d$_6$) δ ppm 1.02 (t, J=7.3 Hz, 3H) 2.31 (q, J=7.3 Hz, 2H) 3.84 (s, 3H) 4.11 (s, 4H) 6.05 (s, 2H) 6.59 (d, J=8.5 Hz, 2H) 7.26 (d, J=8.5 Hz, 2H) 11.23 (s, 1H) 13.56 (s, 1H). LC-MS 341.1 [M+H]$^+$, RT 1.41 min.

Step 2

A mixture of methyl 6-(4-(2,5-dihydro-1H-pyrrol-1-yl)phenyl)-5-ethyl-4-hydroxy-2-oxo-1,2-dihydropyridine-3-carboxylate (41.6 mg, 0.12 mmol) and LiI (41.0 mg, 0.31 mmol) in EtOAc (1.5 mL) was heated at 65° C. for 2 h. After the mixture was cooled to room temperature, Et$_2$O (5 mL) and 1 M HCl (2 mL) were added. A yellow precipitate was filtered off and then washed with H$_2$O and Et$_2$O. After drying, the product 6-(4-(2,5-dihydro-1H-pyrrol-1-yl)phenyl)-5-ethyl-4-hydroxy-2-oxo-1,2-dihydropyridine-3-carboxylic acid (25.8 mg, 66%) was obtained.

$^1$H NMR (500 MHz, DMSO-d$_6$) δ ppm 1.04 (t, J=7.3 Hz, 3H) 2.38 (q, J=7.3 Hz, 2H) 4.13 (s, 4H) 6.06 (s, 2H) 6.64 (d, J=8.8 Hz, 2H) 7.32 (d, J=8.8 Hz, 2H) 12.58 (br. s., 1H) 13.84 (br. s., 1H). LC-MS 324.7 [M−H]$^−$, 326.9 [M+H]$^+$, RT 1.41 min.

EXAMPLE 21

6-{4-[(3R,4S)-3,4-dihydroxypyrrolidin-1-yl]phenyl}-5-ethyl-2-oxo-1,2-dihydropyridine-3-carboxylic acid (Cpd 303)

Step 1

To a suspension of methyl 6-(4-(2,5-dihydro-1H-pyrrol-1-yl)phenyl)-5-ethyl-4-hydroxy-2-oxo-1,2-dihydropyridine-3-carboxylate (0.112 mg, 0.35 mmol) in THF was added NMO (40 mg, 0.14 mmol) followed by an OsO$_4$ solution (4% aqueous, 50 µL, 2.5 mol %). The reaction mixture was stirred at room temperature and monitored by LC/MS. After complete conversion to the product (~10 h), the precipitate was filtered off, washed with 10% aqueous Na$_2$S$_2$O$_3$ and H$_2$O then Et$_2$O. After drying, the product methyl 6-(4-((3R,4S)-3,4-dihydroxypyrrolidin-1-yl)phenyl)-5-ethyl-2-oxo-1,2-dihydropyridine-3-carboxylate (0.099 g, 80%) was obtained.

$^1$H NMR (500 MHz, DMSO-d$_6$) δ ppm 1.01 (t, J=7.4 Hz, 3H) 2.37 (q, J=7.4 Hz, 2H) 3.15 (dd, J=9.6, 3.9 Hz, 2H) 3.45 (dd, J=9.6, 5.0 Hz, 2H) 3.74 (s, 3H) 4.16 (br. s., 2H) 4.96 (br. s., 2H) 6.54 (d, J=8.5 Hz, 2H) 7.23 (d, J=8.5 Hz, 2H) 8.02 (s, 1H) 11.76 (br. s., 1H). LC-MS 359.2 [M+H]$^+$, RT 0.86 min.

Step 2

The product 6-(4-((3R,4S)-3,4-dihydroxypyrrolidin-1-yl)phenyl)-5-ethyl-2-oxo-1,2-dihydropyridine-3-carboxylate (52.3 mg, 0.15 mmol) obtained above was dissolved in THF (1.0 mL) and treated with a LiOH solution (1M aqueous, 0.50 mL, 0.50 mmol) at 50° C. for 4 h. The mixture was cooled to room temperature and acidified with 1 M HCl to pH~2. A yellow precipitate was filtered off and washed with H$_2$O and Et$_2$O. After drying, the product 6-(4-((3R,4S)-3,4-dihydroxypyrrolidin-1-yl)phenyl)-5-ethyl-2-oxo-1,2-dihydropyridine-3-carboxylic acid (37.2 mg, 74%) was obtained.

$^1$H NMR (500 MHz, CHCl$_3$-d) δ ppm 1.18 (t, J=7.4 Hz, 3H) 2.05-2.33 (m, 3H) 2.44-2.55 (m, 1H) 2.58 (q, J=7.4 Hz, 2H) 3.46 (dd, J=9.5, 7.2 Hz, 0H) 3.83 (t, J=9.5 Hz, 0H) 5.18 (d, J=7.2 Hz, 1H) 6.72 (d, J=8.8 Hz, 2H) 7.26 (d, J=3.5 Hz, 1H) 7.33 (d, J=8.8 Hz, 2H) 7.80 (d, J=3.5 Hz, 1H) 8.49 (s, 1H) 12.29 (br. s., 1H) 13.74 (s, 1H). LC-MS 342.8 [M−H]$^−$, 345.1 [M+H]$^+$, RT 0.86 min.

EXAMPLE 22

6-{4-[(3R,4S)-3,4-dihydroxypyrrolidin-1-yl]phenyl}-5-ethyl-4-hydroxy-2-oxo-1,2-dihydropyridine-3-carboxylic acid (Cpd 304)

To a suspension of methyl 6-(4-(2,5-dihydro-1H-pyrrol-1-yl)phenyl)-5-ethyl-4-hydroxy-2-oxo-1,2-dihydropyridine-3-carboxylate (52.8 mg, 0.16 mmol) in THF was added NMO (20 mg, 0.17 mmol), followed by an OsO$_4$ solution (4% aqueous, 50 μL, 5 mol %). The reaction mixture was stirred at room temperature and reaction completion was monitored by LC/MS. After complete conversion to the product (~4 days), the precipitate was filtered off, then washed with 10% aqueous Na$_2$S$_2$O$_3$, H$_2$O and Et$_2$O. After drying, the product (~40 mg) was suspended in EtOAc (1.5 mL) and treated with LiI (36.0 mg, 0.27 mmol) at 75° C. for 2 h. After the reaction mixture was cooled to room temperature, Et$_2$O (5 mL) and 1 M HCl (2 mL) were added. The resulting yellow precipitate was filtered off, then washed with H$_2$O and Et$_2$O and dried to afford 6-(4-((3R,4S)-3,4-dihydroxypyrrolidin-1-yl)phenyl)-5-ethyl-4-hydroxy-2-oxo-1,2-dihydropyridine-3-carboxylic acid (21.9 mg, 39%).

$^1$H NMR (500 MHz, DMSO-d$_6$) δ ppm 1.03 (t, J=7.3 Hz, 3H) 2.38 (q, J=7.3 Hz, 2H) 3.16 (dd, J=9.6, 3.9 Hz, 2H) 3.46 (dd, J=9.6, 5.4 Hz, 2H) 4.14-4.20 (m, 2H) 6.58 (d, J=8.5 Hz, 2H) 7.27 (d, J=8.5 Hz, 2H) 12.57 (s, 1H) 13.83 (s, 1H). LC-MS 359.1 [M−H]$^−$, 361.1 [M+H]$^+$, RT 1.00 min.

EXAMPLE 23

6-[5-(dimethylamino)thiophen-2-yl]-5-ethyl-2-oxo-1,2-dihydropyridine-3-carboxylic acid (Cpd 305)

Step 1:
1-(5-(dimethylamino)thiophen-2-yl)butan-1-one

A mixture of 1-(5-bromothiophen-2-yl)butan-1-one (2.50 g, 10.72 mmol) and a solution of Me$_2$NH (40% aqueous, 6.0 mL) was heated at 100° C. in a sealed vial over 48 hrs. After the mixture was cooled to room temperature, the mixture was diluted with H$_2$O and the product was extracted with DCM (3×40 mL). The organic phase was dried over Na$_2$SO$_4$, then the solvent was removed and the residue was purified by column chromatography using EtOAc/hexanes (gradient 0-50%) to afford the product 1-(5-(dimethylamino)thiophen-2-yl)butan-1-one (2.00 g, 94%).

$^1$H NMR (500 MHz, CHCl$_3$-d) δ ppm 0.98 (t, J=7.4 Hz, 3H) 1.75 (sxt, J=7.4 Hz, 2H) 2.70 (t, J=7.4 Hz, 2H) 3.05 (s, 6H) 5.83 (d, J=4.4 Hz, 1H) 7.46 (d, J=4.4 Hz, 1H). LC-MS 198.0 [M+H]$^+$, RT 1.11 min.

Step 2

To a solution of methyl 1-(2,4-dimethoxybenzyl)-6-(5-(dimethylamino)thiophen-2-yl)-5-ethyl-2-oxo-1,2-dihydropyridine-3-carboxylate (0.916 g, 2.00 mmol) in DCM (6 mL) was added anisole (0.50 mL) followed by TFA (1.0 mL). The reaction mixture was stirred at room temperature for 1 h until complete consumption of the starting material was observed. The solvents were removed and the residue was purified by column chromatography using EtOAc/hexanes (gradient 50-100%) to afford methyl 6-(5-(dimethylamino)thiophen-2-yl)-5-ethyl-2-oxo-1,2-dihydropyridine-3-carboxylate (0.188 g, 31%) as a solid.

$^1$H NMR (500 MHz, CHCl$_3$-d) δ ppm 1.32 (t, J=7.5 Hz, 3H) 2.82 (q, J=7.5 Hz, 2H) 3.05 (s, 6H) 3.95 (s, 3H) 5.90 (d, J=4.4 Hz, 1H) 7.39 (d, J=4.4 Hz, 1H) 7.93 (s, 1H) 11.05 (br. s., 1H). LC-MS 307.1 [M+H]$^+$, RT 1.21 min.

Step 3

To a suspension of methyl 6-(5-(dimethylamino)thiophen-2-yl)-5-ethyl-2-oxo-1,2-dihydropyridine-3-carboxylate (0.188 g, 0.61 mmol) in THF (3.5 mL) was added a LiOH solution (1M aqueous, 1.8 mL, 1.8 mmol). The reaction was heated at 65° C. for 4 h. After the mixture was cooled to room temperature, the mixture was acidified with 1M HCl to pH~2. A solid was filtered off, then washed with H$_2$O and Et$_2$O and dried to afford 6-(5-(dimethylamino) thiophen-2-yl)-5-ethyl-2-oxo-1,2-dihydropyridine-3-carboxylic acid (0.123 g, 69%).

$^1$H NMR (500 MHz, DMSO-d$_6$) δ ppm 1.16 (t, J=7.4 Hz, 3H) 2.73 (q, J=7.4 Hz, 2H) 3.01 (s, 6H) 6.11 (d, J=4.4 Hz, 1H) 7.57 (d, J=4.4 Hz, 1H) 8.13 (s, 1H) 12.57 (br. s., 1H) 14.75 (br. s., 1H). LC-MS 291.0 [M−H]$^−$, 293.0 [M+H]$^+$, RT 1.06 min.

EXAMPLE 24

6-[5-(dimethylamino)thiophen-2-yl]-5-ethyl-4-hydroxy-2-oxo-1,2-dihydropyridine-3-carboxylic acid (Cpd 306)

Step 1

To a solution of methyl 1-(2,4-dimethoxybenzyl)-6-(5-(dimethylamino)thiophen-2-yl)-5-ethyl-4-hydroxy-2-oxo-1,2-dihydropyridine-3-carboxylate (0.224 g, 0.47 mmol) in DCM (2 mL) was added anisole (0.50 mL) followed by TFA (0.50 mL). The reaction mixture was stirred at room temperature for 2 h until complete consumption of the starting material was observed. The solvents were removed and the residue was partitioned between DCM and NaHCO$_3$ (aqueous saturated). The organic phase was dried over Na$_2$SO$_4$ and the solvents were removed. The residue was triturated with Et$_2$O, then the solid was filtered and washed with Et$_2$O to provide methyl 6-(5-(dimethylamino)thiophen-2-yl)-5-ethyl-4-hydroxy-2-oxo-1,2-dihydropyridine-3-carboxylate (0.075 g, 49%). LC-MS 322.8 [M+H]$^+$, RT 1.20 min.

Step 2

Methyl 6-(5-(dimethylamino)thiophen-2-yl)-5-ethyl-4-hydroxy-2-oxo-1,2-dihydropyridine-3-carboxylate (70 mg, 0.22 mmol) was suspended in EtOAc (1.5 mL) and treated with LiI (73.0 mg, 0.54 mmol) at 65° C. for 2 h. After the mixture was cooled to room temperature, Et$_2$O (5 mL) and 1 M HCl (2 mL) were added. The resulting yellow precipitate was filtered, then washed with H₂O and Et₂O and dried to afford 6-(5-(dimethylamino)thiophen-2-yl)-5-ethyl-4-hydroxy-2-oxo-1,2-dihydropyridine-3-carboxylic acid (48.5 mg, 72%).

¹H NMR (500 MHz, DMSO-d₆) δ ppm 1.12 (t, J=7.4 Hz, 3H) 2.67 (d, J=7.4 Hz, 2H) 3.00 (s, 6H) 6.09 (d, J=4.4 Hz, 1H) 7.46 (d, J=4.4 Hz, 1H) 12.19 (br. s., 1H) 13.78 (br. s., 1H). LC-MS 307.1 [M−H]⁻, 309.0 [M+H]⁺, RT 1.26 min.

Using the procedure described above, additional compounds described herein may be prepared by substituting the appropriate starting materials, reagents and reaction conditions and include compounds selected from:

| Cpd | Name |
|---|---|
| 307 | 5-ethyl-4-hydroxy-2-oxo-6-[5-(pyrrolidin-1-yl)thiophen-2-yl]-1,2-dihydropyridine-3-carboxylic acid<br>¹H NMR (500 MHz, CHCl₃-d) δ ppm 1.23 (t, J = 7.4 Hz, 3H) 2.09-2.13 (m, 4H) 2.78 (q, J = 7.4 Hz, 2H) 3.28-3.41 (m, 4H) 5.87 (d, J = 4.4 Hz, 1H) 7.30 (d, J = 4.4 Hz, 1H) 10.37 (br. s., 1H) 13.67 (s, 1H) 14.85 (s, 1H). LC-MS 333.1 [M − H]⁻, 335.0 [M + H]⁺, RT 1.38 mm. |
| 308 | 5-ethyl-2-oxo-6-[5-(piperidin-1-yl)thiophen-2-yl]-1,2-dihydropyridine-3-carboxylic acid<br>¹H NMR (500 MHz, DMSO-d₆) δ ppm 1.15 (t, J = 7.4 Hz, 3H) 1.52-1.60 (m, 2H) 1.60-1.68 (m, 4H) 2.72 (q, J = 7.4 Hz, 2H) 3.22-3.28 (m, 4H) 6.31 (d, J = 4.1 Hz, 1H) 7.53 (d, J = 4.1 Hz, 1H) 8.17 (s, 1H) 12.63 (br. s., 1H) 14.75 (br. s., 1H). LC-MS 331.0 [M − H]⁻, 333.0 [M + H]⁺, RT 1.25 min. |
| 309 | 5-ethyl-4-hydroxy-2-oxo-6-[5-(piperidin-1-yl)thiophen-2-yl]-1,2-dihydropyridine-3-carboxylic acid<br>¹H NMR (500 MHz, CHCl₃-d) δ ppm 1.22 (t, J = 7.4 Hz, 3H) 1.62-1.69 (m, 2H) 1.76-1.86 (m, 4H) 2.75 (q, J = 7.4 Hz, 2H) 3.28-3.35 (m, 4H) 6.28 (d, J = 4.4 Hz, 1H) 7.24 (d, J = 4.4 Hz, 1H) 10.22 (br. s., 1H) 13.75 (s, 1H) 14.64 (br. s., 1H). LC-MS 347.1 [M − H]⁻, 349.1 [M + H]⁺, RT 1.44 min. |

EXAMPLE 25

6-(4-(dimethylamino)phenyl)-2-oxo-1,2-dihydropyridine-3-carboxylic acid (Cpd 310)

Step 1

A mixture of 6-1-(4-(dimethylamino)phenyl)ethanone (1.059 g, 6.49 mmol) and DMF-DMA (3.50 mL, 26.31 mmol) was microwaved at 200° C. for 40 min. The mixture was cooled to room temperature. A precipitate was formed, collected by filtration and washed with Et₂O to provide 3-(dimethylamino)-1-(4-(dimethylamino)phenyl)prop-2-en-1-one (1.180 g, 83%).

¹H NMR (500 MHz, DMSO-d₆) δ ppm 3.33 (s, 12H) 5.77 (d, J=12.6 Hz, 1H) 6.68 (d, J=9.1 Hz, 2H) 7.58 (d, J=12.6 Hz, 1H) 7.77 (d, J=9.1 Hz, 2H).

Step 2

To a suspension of NaH (60% oil, 0.54 g, 13.50 mmol) in DMF (10 mL) was added a solution of 3-(dimethylamino)-1-(4-(dimethylamino)phenyl)prop-2-en-1-one (1.18 g, 5.41 mmol), cyanoacetamide (0.50 g, 5.94 mmol) and MeOH (0.55 mL, 13.60 mmol) in DMF (10 mL). The reaction mixture was stirred at room temperature for 15 min and then heated to 95° C. overnight. The mixture was cooled to room temperature and the reaction was quenched with NH₄Cl (aqueous saturated). The resulting orange precipitate was filtered off, then washed several times with H₂O, dried in an N₂-flow and washed with Et₂O. The product 6-(4-(dimethylamino)phenyl)-2-oxo-1,2-dihydropyridine-3-carbonitrile (1.05 g, 81%) was obtained.

¹H NMR (500 MHz, DMSO-d₆) δ ppm 3.00 (s, 6H) 6.65 (d, J=7.9 Hz, 1H) 6.77 (d, J=8.8 Hz, 2H) 7.73 (d, J=8.8 Hz, 2H) 8.02 (d, J=7.9 Hz, 1H) 12.25 (br. s., 1H). LC-MS 240.1 [M+H]⁺, RT 1.12 min.

Step 3

6-(4-(dimethylamino)phenyl)-2-oxo-1,2-dihydropyridine-3-carbonitrile (0.304 g, 1.17 mmol) was heated with 6M HCl (10 mL) at 100° C. overnight. The HCl was concentrated under reduced pressure and 1M NaOH was added to the residue. The insoluble material was filtered off by vigorous shaking of the mixture. The mother liquor was acidified with 1M HCl to pH~1. After the mixture was cooled to room temperature, a precipitate formed that was collected by filtration and washed with water. After drying, the product (0.195 g, 60%) was obtained in 91% purity.

¹H NMR (500 MHz, DMSO-d₆) δ ppm 3.02 (s, 6H) 6.80 (d, J=9.1 Hz, 2H) 6.96 (d, J=7.9 Hz, 1H) 7.79 (d, J=9.1 Hz, 2H) 8.27 (d, J=7.9 Hz, 1H) 13.02 (br. s., 1H) 14.75 (br. s., 1H). LC-MS 256.9 [M−H]⁻, 259.2 [IVI+H]⁺, RT 1.12 min.

EXAMPLE 26

6-(4-(tert-butoxy)phenyl)-5-ethyl-2-oxo-1,2-dihydropyridine-3-carboxylic acid (Cpd 311)

Methyl 6-(4-bromophenyl)-5-ethyl-2-oxo-1,2-dihydropyridine-3-carboxylate (0.106 g, 0.31 mmol), Pd-catalyst (7.3 mg, 5 mol %) and t-BuONa (0.160 g, 1.66 mmol) were mixed under Argon in a heat-gun dried vial. Anhydrous toluene (1.0 mL) was added and the reaction mixture was heated under Argon at 80° C. for 1 h. The reaction was cooled to room temperature and THF (1.5 mL) and LiOH (1M aqueous, 1 mL) were added. The mixture was heated overnight at 50° C., then cooled to room temperature and acidified with 1M HCl to pH~2. The product was extracted with DCM (3×7 mL) and the organic phase was dried over Na₂SO₄. The solvents were concentrated and the residue was purified by preparative HPLC to afford the product (0.012 g, 12%) as a white solid.

¹H NMR (500 MHz, CHCl₃-d) δ ppm 1.18 (t, J=7.6 Hz, 3H) 1.47 (s, 9H) 2.57 (q, J=7.6 Hz, 2H) 7.17 (d, J=8.5 Hz, 2H) 7.39 (d, J=8.5 Hz, 2H) 8.55 (s, 1H) 12.28 (br. s., 1H) 13.62 (br. s., 1H). LC-MS 314.0 [M−H]⁻, 316.2 [IVI+H]⁺, RT 1.49 min.

EXAMPLE 27

6-(4-(dimethylamino)phenyl)-4-hydroxy-2-oxo-5-(2-oxoethyl)-1,2-dihydropyridine-3-carboxylic acid (Cpd 327)

Step 1: benzyl 5-allyl-6-(4-(dimethylamino)phenyl)-4-hydroxy-2-oxo-1,2-dihydropyridine-3-carboxylate A mixture of methyl 5-allyl-6-(4-(dimethylamino)phenyl)-4-hydroxy-2-oxo-1,2-dihydropyridine-3-carboxylate (0.656 g, 2.0 mmol), prepared according to the procedure in Example 2, in benzyl alcohol (2.1 mL, 20 mmol) was heated at 150° C. After 1 h, the mixture was diluted with ether, then filtered and washed with ether to give the title compound as a yellow solid (0.83 g, 98%). LC-MS 405.2 [M+H]$^+$, RT 1.55 min.

Step 2: benzyl 6-(4-(dimethylamino)phenyl)-4-hydroxy-2-oxo-5-(2-oxoethyl)-1,2-dihydropyridine-3-carboxylate To a suspension of benzyl 5-allyl-6-(4-(dimethylamino)phenyl)-4-hydroxy-2-oxo-1,2-dihydropyridine-3-carboxylate (404 mg, 1.0 mmol) in dioxane/water (20 mL, 3/1 v/v) were added a solution of $OSO_4$ (0.32 mL, 0.05 mmol, 4% in water), 2,6-lutidine (0.23 mL, 2.0 mmol) and $NaIO_4$ (0.62 g, 3.0 mmol). After 5 h, the mixture was diluted with EtOAc, then filtered and washed with EtOAc. The filtrate was concentrated and chromatographed with 0-2.5% MeOH/$CH_2Cl_2$ to give the title compound as a yellow foam (220 mg, 50%). LC-MS 407.2 [M+H]$^+$, RT 1.23 min.

Step 3: 6-(4-(dimethylamino)phenyl)-4-hydroxy-2-oxo-5-(2-oxoethyl)-1,2-dihydropyridine-3-carboxylic acid A mixture of benzyl 6-(4-(dimethylamino)phenyl)-4-hydroxy-2-oxo-5-(2-oxoethyl)-1,2-dihydropyridine-3-carboxylate (40 mg, 0.1 mmol) and 10% Pd/C (10 mg) in THF (1 mL) and MeOH (3 mL) was stirred vigorously under $H_2$ (1 atm). After 1 h, the mixture was filtered through Celite, then washed with 20% MeOH/$CH_2Cl_2$. The filtrate was concentrated and washed with $CH_3CN$ to give the title compound as a yellow solid (20 mg, 63%).
$^1$H NMR (500 MHz, DMSO-$d_6$) δ ppm 2.98 (s, 6H), 3.15 (s, 2H), 6.79 (d, J=9.1 Hz, 2H), 7.48 (d, J=9.1 Hz, 2H), 12.39-12.65 (m, 1H), 13.77-14.08 (br s, 1H), 16.02-16.34 (br s, 1H). LC-MS 317.2 [M+H]$^+$, RT 1.13 min.

EXAMPLE 28

6-(4-(dimethylamino)phenyl)-4-hydroxy-5-(2-hydroxyethyl)-2-oxo-1,2-dihydropyridine-3-carboxylic acid (Cpd 328)

Step 1: benzyl 6-(4-(dimethylamino)phenyl)-4-hydroxy-5-(2-hydroxyethyl)-2-oxo-1,2-dihydropyridine-3-carboxylate To a suspension of benzyl 6-(4-(dimethylamino)phenyl)-4-hydroxy-2-oxo-5-(2-oxoethyl)-1,2-dihydropyridine-3-carboxylate (83 mg, 0.2 mmol) in THF (1 mL) and EtOH (1 mL) was added $NaBH_4$. After 10 min, the reaction was quenched with 6 N HCl (0.2 mL), then concentrated and chromatographed with 0-10% MeOH/$CH_2Cl_2$ to give the title compound as a yellow foam (35 mg, 38%). LC-MS 409.3 [M+H]$^+$, RT 1.24 min.

Step 2: 6-(4-(dimethylamino)phenyl)-4-hydroxy-5-(2-hydroxyethyl)-2-oxo-1,2-dihydropyridine-3-carboxylic acid Following the procedure in Example 27, Step 3, benzyl 6-(4-(dimethylamino)phenyl)-4-hydroxy-5-(2-hydroxyethyl)-2-oxo-1,2-dihydropyridine-3-carboxylate (35 mg, 0.085 mmol), 10% Pd/C (10 mg) in THF (1 mL) and MeOH (2 mL) were reacted under $H_2$ (1 atm) to afford the title compound as a yellow foam (22 mg, 81%).
$^1$H NMR (500 MHz, DMSO-$d_6$) δ ppm 2.56 (t, J=7.3 Hz, 2H), 2.99 (s, 6H), 3.44-3.51 (m, 2H), 6.80 (d, J=8.8 Hz, 2H), 7.39 (d, J=9.1 Hz, 2H), 12.53-12.61 (br s, 1H), 13.83-13.89 (br s, 1H), 16.26-16.35 (br s, 1H). LC-MS 319.1 [M+H]$^+$, RT 1.03 min.

EXAMPLE 29

5-(2,3-dihydroxypropyl)-6-(4-(dimethylamino)phenyl)-4-hydroxy-2-oxo-1,2-dihydropyridine-3-carboxylic acid (Cpd 329)

Step 1: benzyl 5-(2,3-dihydroxypropyl)-6-(4-(dimethylamino)phenyl)-4-hydroxy-2-oxo-1,2-dihydropyridine-3-carboxylate To a solution of benzyl 5-allyl-6-(4-(dimethylamino)phenyl)-4-hydroxy-2-oxo-1,2-dihydropyridine-3-carboxylate (81 mg, 0.2 mmol) in THF/t-BuOH (2 mL, 7/1 v/v) was added a solution of $0SO_4$ (95 mt, 0.015 mmol, 4% in water) and NMO (70 mg, 0.6 mmol). The mixture was stirred at room temperature for 15 h, then concentrated and chromatographed with 0-5% MeOH/$CH_2Cl_2$ to give the title compound as a yellow foam (86 mg, 99%). LC-MS 439.2 [M+H]$^+$, RT 1.13 min.

Step 2: 5-(2,3-dihydroxypropyl)-6-(4-(dimethylamino)phenyl)-4-hydroxy-2-oxo-1,2-dihydropyridine-3-carboxylic acid Following the procedure in Example 27, Step 3, benzyl 5-(2,3-dihydroxypropyl)-6-(4-(dimethylamino)phenyl)-4-hydroxy-2-oxo-1,2-dihydropyridine-3-carboxylate (70 mg, 0.16 mmol), 10% Pd/C (20 mg) in THF (2 mL) under $H_2$ (1 atm) were reacted to afford the title compound as a yellow foam (53 mg, 95%).
$^1$H NMR (500 MHz, DMSO-$d_6$) δ ppm 2.37-2.47 (m, 2H), 2.97 (s, 6H), 3.15-3.21 (m, 2H), 3.72-3.80 (m, 1H), 4.40-4.47 (m, 1H), 4.60-4.69 (m, 1H), 6.76 (d, J=7.9 Hz, 2H), 7.46 (d, J=8.5 Hz, 2H). LC-MS 349.2 [M+H]$^+$, RT 0.97 min.

EXAMPLE 30

E)-6-(4-(dimethylamino)phenyl)-4-hydroxy-2-oxo-5-(prop-1-enyl)-1,2-dihydropyridine-3-carboxylic acid (Cpd 330)

Step 1: (E)-methyl 6-(4-(dimethylamino)phenyl)-4-hydroxy-2-oxo-5-(prop-1-enyl)-1,2-dihydropyridine-3-carboxylate A mixture of methyl 5-allyl-6-(4-(dimethylamino)phenyl)-4-hydroxy-2-oxo-1,2-dihydropyridine-3-carboxylate (492 mg, 1.5 mmol), prepared according to the procedure of Example 2, and PdCl$_2$(CH$_3$CN)$_2$ (39 mg, 0.15 mmol) in CH$_2$Cl$_2$ was refluxed for 30 min. The mixture was filtered through Celite. The filtrate was concentrated and chromatographed with 0-2% MeOH/CH$_2$Cl$_2$ to give the title compound as an orange solid (0.31 g, 63%). LC-MS 329.2 [M+H]$^+$, RT 1.23 min.

Step 2: (E)-6-(4-(dimethylamino)phenyl)-4-hydroxy-2-oxo-5-(prop-1-enyl)-1,2-dihydropyridine-3-carboxylic acid A mixture of (E)-methyl 6-(4-(dimethylamino)phenyl)-4-hydroxy-2-oxo-5-(prop-1-enyl)-1,2-dihydropyridine-3-carboxylate (66 mg, 0.2 mmol) and LiI (134 mg, 1.0 mmol) in EtOAc (2 mL) was heated at 65° C. After 3 h, the mixture was treated with 1 N HCl (1 mL). The resulting solid was filtered, then washed with water and CH$_3$CN, and dried to give the title compound as a yellow solid (37 mg, 60%).
$^1$H NMR (500 MHz, DMSO-d$_6$) δ ppm 1.72 (dd, J=6.6, 1.6 Hz, 3H), 3.00 (s, 6H), 5.84-5.92 (m, 1H), 6.19-6.28 (m, 1H), 6.80 (d, J=8.8 Hz, 2H), 7.32 (d, J=9.1 Hz, 2H), 12.61-12.70 (br s, 1H), 14.29-14.35 (br s, 1H), 16.25-16.40 (br s, 1H). LC-MS 315.1 [M+H]$^+$, RT 1.29 min.

EXAMPLE 31

6-(4-(dimethylamino)phenyl)-4-hydroxy-5-(hydroxymethyl)-2-oxo-1,2-dihydropyridine-3-carboxylic acid (Cpd 331)

Step 1: (E)-benzyl 6-(4-(dimethylamino)phenyl)-4-hydroxy-2-oxo-5-(prop-1-enyl)-1,2-dihydropyridine-3-carboxylate Following the procedure of Example 30, Step 1, benzyl 5-allyl-6-(4-(dimethylamino)phenyl)-4-hydroxy-2-oxo-1,2-dihydropyridine-3-carboxylate (0.97 g, 2.5 mmol) and PdCl$_2$(CH$_3$CN)$_2$ (90 mg, 0.25 mmol) in CH$_2$Cl$_2$ (25 mL) were reacted to give the title compound as a yellow solid (0.80 g, 80%). LC-MS 405.3 [M+H]$^+$, RT 0.90 min.

Step 2: benzyl 6-(4-(dimethylamino)phenyl)-5-formyl-4-hydroxy-2-oxo-1,2-dihydropyridine-3-carboxylate Following the procedure of Example 27, Step 2, (E)-benzyl 6-(4-(dimethylamino)phenyl)-4 hydroxy-2-oxo-5-(prop-1-enyl)-1,2-dihydropyridine-3-carboxylate (0.30 g, 0.74 mmol), OSO$_4$ (0.74 mL, 0.074 mmol, 2.5% in t-BuOH), 2,6-lutidine (0.19 mL, 1.6 mmol) and NaIO$_4$ (0.35 g, 1.6 mmol) in dioxane/water (20 mL, 3/1 v/v) were reacted to give the title compound as a yellow solid (0.243 g, 83%). LC-MS 393.2 [M+H]$^+$, RT 0.74 min.

Step 3: benzyl 6-(4-(dimethylamino)phenyl)-4-hydroxy-5-(hydroxymethyl)-2-oxo-1,2-dihydropyridine-3-carboxylate Following the procedure in Example 28, Step 1, benzyl 6-(4-(dimethylamino)phenyl)-5-formyl-4-hydroxy-2-oxo-1,2-dihydropyridine-3-carboxylate (60 mg, 0.15 mmol) and NaBH$_4$ (7.6 mg, 0.2 mmol) in EtOH (2 mL) and THF (2 mL) were reacted to give the title compound as a yellow solid (39 mg, 67%). LC-MS 395.2 [M+H]$^+$, RT 0.67 min.

Step 4: 6-(4-(dimethylamino)phenyl)-4-hydroxy-5-(hydroxymethyl)-2-oxo-1,2-dihydropyridine-3-carboxylic acid Following the procedure in Example 2, Step 3, benzyl 6-(4-(dimethylamino)phenyl)-4-hydroxy-5-(hydroxymethyl)-2-oxo-1,2-dihydropyridine-3-carboxylate (39 mg, 0.1 mmol), 10% Pd/C (8 mg) in 10% MeOH/CH$_2$Cl$_2$ (2 mL) under H$_2$ (1 atm) were reacted to give the title compound as a yellow solid (26 mg, 86%). LC-MS 305.1 [M+H]$^+$, RT 0.56 min.

EXAMPLE 32

6-(4-(dimethylamino)phenyl)-4-hydroxy-5-(methoxymethyl)-2-oxo-1,2-dihydropyridine-3-carboxylic acid (Cpd 332)

Step 1: benzyl 2,4-bis(benzyloxy)-6-(4-(dimethylamino)phenyl)-5-formylnicotinate To a mixture of benzyl 6-(4-(dimethylamino)phenyl)-5-formyl-4-hydroxy-2-oxo-1,2-dihydropyridine-3-carboxylate (627 mg, 1.6 mmol), benzyl alcohol (0.36 mL, 3.52 mmol) and triphenyl phosphine (0.92 g, 3.52 mmol) in THF (16 mL) at 0° C. was added DIAD dropwise. After the addition, the mixture was stirred at room temperature for 15 h. The mixture was then concentrated and chromatographed with 0-30% EtOAc in hexanes to give the title compound as a yellow oil (0.19 g, 21%). LC-MS 573.3 [M+H]$^+$, RT 0.95 min.

Step 2: benzyl 2,4-bis(benzyloxy)-6-(4-(dimethylamino)phenyl)-5-(hydroxymethyl)nicotinate Following the procedure in Example 28, Step 1, 2,4-bis(benzyloxy)-6-(4-(dimethylamino)phenyl)-5-formylnicotinate (0.19 g, 0.33 mmol) and NaBH$_4$ (25 mg, 0.66 mmol) in EtOH (1 mL) and THF (1 mL) were reacted to give the title compound as a light yellow oil (0.172 g, 90%). LC-MS 575.4 [M+H]$^+$, RT 1.00 min Step 3: benzyl 2,4-bis(benzyloxy)-6-(4-(dimethylamino)phenyl)-5-(methoxymethyl)nicotinate To a solution of benzyl 2,4-bis(benzyloxy)-6-(4-(dimethylamino)phenyl)-5-(hydroxymethyl) nicotinate (0.172 g, 0.3 mmol) and MeI (0.5 mL, 8 mmol) in THF (5 mL) at room temperature was added a NaH solution (24 mg, 0.6 mmol, 60% in mineral oil). After 15 h, the reaction was quenched with water and extracted with EtOAc. The organics were concentrated and chromatographed with 0-10% EtOAc in hexanes to give the title compound as a yellow oil (60 mg, 30%). LC-MS 589.3 [M+H]$^+$, RT 1.08 min.

Step 4: 6-(4-(dimethylamino)phenyl)-4-hydroxy-5-(methoxymethyl)-2-oxo-1,2-dihydropyridine-3-carboxylic acid Following the procedure in Example 27, Step 3, benzyl 2,4-bis(benzyloxy)-6-(4-(dimethylamino)phenyl)-5-(methoxymethyl)nicotinate (60 mg, 0.1 mmol), 10% Pd/C (8 mg) in 10% MeOH/CH$_2$Cl$_2$ (2 mL) under H$_2$ (1 atm) were reacted to give the title compound as a yellow solid (17 mg, 53%).
$^1$H NMR (500 MHz, DMSO-d$_6$) δ ppm 3.01 (s, 6H), 3.28 (s, 3H), 4.05-4.09 (s, 2H), 6.82 (d, J=9.2 Hz, 2H), 7.48 (d, J=8.8 Hz, 2H), 12.59-12.67 (br s, 1H), 13.76-13.86 (br s, 1H), 15.87-15.98 (br s, 1H). LC-MS 317.2 [M+H]$^+$, RT 0.70 min.

EXAMPLE 33

6-(4-(dimethylamino)phenyl)-4-hydroxy-2-oxo-5-(prop-1-ynyl)-1,2-dihydropyridine-3-carboxylic acid (Cpd 333)

Step 1: 1-(2,4-dimethoxybenzyl)-6-(4-(dimethylamino)phenyl)-4-hydroxy-2-oxo-5-(prop-1-ynyl)-1,2-dihydropyridine-3-carboxylic acid To a solution of 1-(2,4-dimethoxybenzyl)-6-(4-(dimethylamino)phenyl)-4-hydroxy-2-oxo-5-((trimethylsilyl)ethynyl)-1,2-dihydropyridine-3-carboxylic acid (27 mg, 0.05 mmol), prepared according to the procedures in Example 2, in dioxane (0.5 mL) was added TMSOK (28 mg, 0.2 mmol). After heating at 50° C. for 4 h, the reaction mixture was acidified with 1N HCl to pH 3-4 and concentrated. The residue was chromatographed with 0-3% MeOH/CH$_2$Cl$_2$ to give the title compound as a yellow solid (13 mg, 56%). LC-MS 463.2 [M+H]$^+$, RT 0.81 min.

Step 2: 6-(4-(dimethylamino)phenyl)-4-hydroxy-2-oxo-5-(prop-1-ynyl)-1,2-dihydropyridine-3-carboxylic acid To the product 1-(2,4-dimethoxybenzyl)-6-(4-(dimethylamino)phenyl)-4-hydroxy-2-oxo-5-(prop-1-ynyl)-1,2-dihydropyridine-3-carboxylic acid (12 mg, 0.026 mmol) obtained above was added i-Pr$_3$SiH (0.30 mL) followed by TFA (0.60 mL). The mixture was heated at 50° C. for 15 min until complete consumption of starting material was observed. The TFA was removed under reduced pressure, followed by treatment with 1 N HCl in ether (1 mL) to give the title compound as a yellow solid (9 mg, 77%, HCl salt).
$^1$H NMR (500 MHz, DMSO-d$_6$) δ ppm 2.42 (s, 3H), 3.04 (s, 6H), 6.74 (s, 1H), 6.86 (d, J=9.1 Hz, 2H), 7.67 (d, J=9.1 Hz, 2H), 13.02-13.11 (br s, 1H). LC-MS 313.2 [M+H]$^+$, RT 0.62 min.

EXAMPLE 34

5-ethyl-4-hydroxy-6-(4-hydroxyphenyl)-2-oxo-1,2-dihydropyridine-3-carboxylic acid (Cpd 334)

Step 1: 6-chloro-5-ethyl-4-hydroxypyridin-2(1H)-one

A mixture of butyronitrile (30 mL) and malonyl dichloride (25.0 g, 177 mmol) was stirred at room temperature under N$_2$ for 3 days. The reaction mixture was diluted with dioxane (100 mL) and filtered. The precipitate was washed with dioxane (20 mL), then ethyl ether (2×30 mL) and dried in air to provide 6-chloro-5-ethyl-4-hydroxypyridin-2(1H)-one (12.7 g, 67% pure, containing 33% of a 6-chloro-2-propyl-1,2-dihydropyrimidin-4-ol by-product, based on $^1$HNMR) which was used directly in the next step without further purification.
$^1$H NMR (500 MHz, MeOH-d$_4$) δ ppm 6.43 (1H, s), 2.72 (2H, q, J=7.36 Hz), 1.09-1.19 (3H, m).

Step 2: 4,6-bis(benzyloxy)-2-chloro-3-ethylpyridine

The intermediate obtained in Step 1 (12.7 g) was dissolved in THF (250 mL) followed by the addition of Ph$_3$P (54.0 g, 210 mmol). The mixture was cooled in an ice-water bath and DIAD (42 mL, 211 mmol) was added dropwise. After the addition, the reaction mixture was stirred for 5 min, followed by the addition of benzyl alcohol (23.6 mL, 228 mmol) dropwise. The cooling bath was removed and the mixture was stirred for another 4 hr. The solvents were removed on a rotovap. The residue was treated with a 1:1 mixture of hexanes and ethyl ether (600 mL) and stirred for 0.5 hr. The precipitate was filtered and washed with the 1:1 mixture of hexanes and ethyl ether until the desired product was not found in the wash. All the filtrates were combined, then concentrated and chromatographed (silica gel, ethyl acetate in hexanes 0-3% gradient) to furnish an intermediate, 4,6-bis(benzyloxy)-2-chloro-3-ethylpyridine, as a colorless oil (7.7 g, yield: 12.3%, two steps).
$^1$H NMR (500 MHz, CHCl$_3$-d) δ ppm 7.28-7.56 (10H, m), 6.27 (1H, s), 5.30-5.39 (2H, m), 5.08 (2H, s), 2.75 (2H, q, J=7.25 Hz), 1.08-1.19 (3H, m).

Step 3: benzyl 2,4-bis(benzyloxy)-6-chloro-5-ethylnicotinate

To a solution of the intermediate obtained in Step 2 (7.7 g, 21.8 mmol) in THF (80 mL), at −78° C., was added n-BuLi (21.8 mL, 54.4 mmol) dropwise. The mixture was stirred for an additional 15 min at −78° C. Benzyl chloroformate (4.7 mL, 32.6 mmol) was then added and the resulting mixture was stirred for 10 min before the cooling bath was removed. The mixture was allowed to warm to room temperature while stirring. The reaction was quenched with a solution of NH$_4$Cl (5 mL), diluted with ethyl ether (150 mL), then washed with water (2×30 mL) and brine (30 mL). After drying with Na$_2$SO$_4$, the solvent was removed and the residue was chromatographed (silica gel, ethyl acetate in hexanes, 0-5%) to provide the product as a white crystalline material (6.9 g, 65%).
$^1$H NMR (500 MHz, CHCl$_3$-d) δ ppm 7.24-7.43 (15H, m), 5.39 (2H, s), 5.30 (2H, s), 4.97 (2H, s), 2.66 (2H, q, J=7.57 Hz), 1.10 (3H, t, J=7.41 Hz).

Step 4: benzyl 2,4-bis(benzyloxy)-5-ethyl-6-(4-hydroxyphenyl)nicotinate

A mixture of benzyl 2,4-bis(benzyloxy)-6-chloro-5-ethylnicotinate (83 mg, 0.17 mmol), 4-hydroxyphenylboronic acid (35 mg, 0.26 mmol), Pd$_2$(dba)$_3$ (7.8 mg, 0.0085 mmol), tri-tert-butylphosphonium tetrafluoroborate (4.9 mg, 0.017 mmol) and KF (100 mg, 1.7 mmol) in THF (2.0 mL) was stirred at 60° C. overnight under an Argon atmosphere, then filtered through Celite. The solvent was evaporated and the residue purified with silica column chromatography using ethyl acetate in hexanes (2-30%) to give the product benzyl 2,4-bis(benzyloxy)-5-ethyl-6-(4-hydroxyphenyl)nicotinate (69 mg, 74%).
$^1$H NMR (500 MHz, CHCl$_3$-d) δ ppm 1.03 (d, J=7.3 Hz, 3H), 2.57 (d, J=7.6 Hz, 2H), 4.86-5.02 (br s, 1H), 5.03 (s, 2H), 5.34 (s, 2H), 5.43 (s, 2H), 6.86-6.91 (m, 2H), 7.27-7.42 (m, 17H). LC-MS 546.3 [M+H]$^+$, RT 1.69 min.

Step 5: 5-ethyl-4-hydroxy-6-(4-hydroxyphenyl)-2-oxo-1,2-dihydropyridine-3-carboxylic acid A solution of benzyl 2,4-bis(benzyloxy)-5-ethyl-6-(4-hydroxyphenyl)nicotinate (69 mg, 0.13 mmol) in a 3:1 mixture of ethyl acetate/methanol (2.0 mL) was hydrogenated with 10% Pd/C (20 mg) under H$_2$ for 1 h at room temperature. The mixture was filtered through Celite, the solvents were evaporated and the solid was triturated with ether to give the title compound (27 mg, 77%).

¹H NMR (500 MHz, DMSO-d₆) δ ppm 1.00 (t, J=7.4 Hz, 3H), 2.32 (d, J=7.3 Hz, 2H), 6.87-6.92 (m, 2H), 7.27-7.32 (m, 2H), 9.99 (s, 1H), 12.48-12.75 (m, 1H), 13.77-14.03 (m, 1H), 16.13-16.43 (m, 1H). LC-MS 274.2 [M−H]⁻, 276.1 [M+H]⁺, RT 1.11 min.

Using the procedure described above, additional compounds described herein may be prepared by substituting the appropriate starting materials, reagents and reaction conditions and include compounds selected from:

| Cpd | Name |
|---|---|
| 335 | 6-(6-(3-(dimethylamino)pyrrolidin-1-yl)pyridin-3-yl)-5-ethyl-4-hydroxy-2-oxo-1,2-dihydropyridine-3-carboxylic acid<br>¹H NMR (500 MHz, DMSO-d₆) δ ppm 1.04 (3 H, t, J = 7.41 Hz), 1.92-2.04 (1 H, m), 2.24-2.34 (1 H, m), 2.34-2.42 (2 H, m), 3.33 (6 H, s, obscured by water), 3.36-3.45 (2 H, m), 3.63-3.70 (1 H, m), 3.77-3.86 (1 H, m), 4.05-4.13 (1 H, m), 6.58 (1 H, d, J = 8.51 Hz), 7.62 (1 H, dd, J = 8.83, 2.52 Hz), 8.14-8.20 (1 H, m). LC-MS 373.2 [M + H]⁺, RT 0.47 min. |
| 336 | 5-ethyl-4-hydroxy-2-oxo-6-(6-(pyrrolidin-1-yl)pyridin-3-yl)-1,2-dihydropyridine-3-carboxylic acid<br>¹H NMR (500 MHz, DMSO-d₆) δ ppm 1.04 (3 H, t, J = 7.41 Hz), 1.94-1.99 (4 H, m), 2.38 (2 H, d, J = 7.57 Hz), 3.44 (4 H, t, J = 6.46 Hz), 6.54 (1 H, d, J = 8.51 Hz), 7.58 (1 H, dd, J = 8.83, 2.52 Hz), 8.16 (1 H, dd, J = 2.52, 0.63 Hz). LC-MS 330.2 [M + H]⁺, RT 0.55 min. |
| 337 | 6-(6-(3-(dimethylamino)pyrrolidin-1-yl)pyridin-3-yl)-4-hydroxy-5-methyl-2-oxo-1,2-dihydropyridine-3-carboxylic acid<br>¹H NMR (500 MHz, MeOH-d₄) δ ppm 1.95-2.06 (m, 1 H), 2.33-2.42 (m, 1 H), 2.46 (s, 6 H), 2.49 (s, 3 H), 3.07-3.21 (m, 1 H), 3.33-3.41 (m, 1 H), 3.45-3.56 (m, 1 H), 3.69-3.80 (m, 1 H), 3.82-3.93 (m, 1 H), 6.63 (d, J = 8.8 Hz, 1 H), 7.59 (dd, J = 8.8, 2.5 Hz, 1 H), 8.09 (d, J = 2.5 Hz, 1 H). LC-MS 359.2 [M + H]⁺, RT 0.43 min. |

EXAMPLE 35

5-ethyl-4-hydroxy-6-(4-(1-methylpiperidin-4-yl)phenyl)-2-oxo-1,2-dihydropyridine-3-carboxylic acid (Cpd 338)

Step 1: methyl 6-(4-chlorophenyl)-1-(2,4-dimethoxybenzyl)-5-ethyl-4-(methoxymethoxy)-2-oxo-1,2-dihydropyridine-3-carboxylate Methyl 6-(4-chlorophenyl)-1-(2,4-dimethoxybenzyl)-5-ethyl-4-hydroxy-2-oxo-1,2-dihydropyridine-3-carboxylate, prepared according to Example 2 (1.70 g, 3.7 mmol), was dissolved in DMF (7 mL) and cooled to 0° C. A solution of sodium hydride (60% dispersion in mineral oil, 178 mg, 4.5 mmol) was added to the mixture. After 10 min of vigorous stirring at 0° C., a solution of chloro(methoxy)methane (0.36 g, 4.5 mmol) in DMF (7 mL) was added dropwise to the mixture. The mixture was stirred for an additional 10 min at 0° C., then was warmed to room temperature. After LC/MS showed complete consumption of the starting material, the reaction was quenched by the addition of an aqueous saturated NaHCO₃ solution (10 mL). The product was extracted with EtOAc and the combined organics were dried and concentrated. The residue was chromatographed on silica gel (0-50% EtOAc in hexanes) to afford the product as a yellow solid (1.6 g, 88% yield).

¹H NMR (500 MHz, Acetone-d) δ ppm 0.91 (t, J=7 Hz, 3H), 2.12 (q, J=7 Hz, 2H), 3.54 (s, 3H), 3.55 (s, 3H), 3.78 (s, 3H), 3.85 (s, 3H), 4.86 (s, 2H), 5.25 (s, 2H), 6.37 (d, J=3 Hz, 1H), 6.46 (dd, J=8, 2 Hz, 1H), 6.78 (d, J=8 Hz, 1H), 7.12 (d, J=8 Hz, 2H), 7.43 (d, J=8 Hz, 2H). LC-MS 502.2/504.2 [M+H]⁺, RT 1.42 min.

Step 2: methyl 6-(4-(1-(tert-butoxycarbonyl)-1,2,3,6-tetrahydropyridin-4-yl)phenyl)-1-(2,4-dimethoxybenzyl)-5-ethyl-4-(methoxymethoxy)-2-oxo-1,2-dihydropyridine-3-carboxylate The intermediate from Step 1 (0.26 g, 0.5 mmol) was mixed with tert-butyl 4-(4,4,5,5-tetramethyl-1,3,2-dioxaborolan-2-yl)-5,6-dihydropyridine-1(2H)-carboxylate (0.31 g, 1.0 mmol), Pd(OAc)₂ (0.0056 g, 5 mol %), S-Phos (0.0205 g, 10 mol %) and K₃PO₄ (0.32 g, 1.5 mmol) in a mixture of toluene/water (1 mL/0.1 mL). The mixture was degassed by purging the reaction flask under vacuum and then backfilling with Argon (3×). The reaction mixture was heated at 100° C. with vigorous magnetic stirring for 2 hr until LC/MS showed complete consumption of starting material. After cooling to room temperature, the mixture was filtered and the solids were washed with EtOAc. The filtrate was concentrated and purified by chromatography on silica gel (0-100% EtOAc in hexanes) to afford the product as a yellow solid (0.26 g, 80% yield). LC-MS 649.4 [M+H]⁺, RT 1.52 min.

Step 3: methyl 6-(4-(1-(tert-butoxycarbonyl)piperidin-4-yl)phenyl)-1-(2,4-dimethoxybenzyl)-5-ethyl-4-hydroxy-2-oxo-1,2-dihydropyridine-3-carboxylate The intermediate from Step 2 (0.26 mg, 0.40 mmol) was mixed with Pd/C (10%, 26 mg) in a mixture of ethyl acetate/methanol (1/1, 5 mL) and stirred under H₂ (1 atm) overnight. The mixture was filtered through Celite, then concentrated and purified by column chromatography, eluting with 0-100% EtOAc in hexanes, to afford the product as a colorless oil (0.24 g, 92% yield). LC-MS 651.5 [M+H]⁺, RT 1.59 min.

Step 4

To a solution of the compound prepared from Step 3 (0.13 mg, 0.20 mmol) in dichloromethane (1 mL) was added trifluoroacetic acid (1 mL). The mixture was stirred at room temperature until LC/MS showed complete consumption of the starting material. The solvent was removed and the residue was triturated with aqueous NaHCO₃. The solid was collected by filtration, then washed with H₂O and Et₂O and dried to afford the title compound (0.06 g, 84%) as a white solid. LC-MS 355.3 [M−H]⁻, RT 0.86 min.

Step 5: methyl 5-ethyl-4-hydroxy-6-(4-(1-methylpiperidin-4-yl)phenyl)-2-oxo-1,2-dihydropyridine-3-carboxylate To a solution of the compound prepared from Step 4 (60 mg, 0.17 mmol) in dichloromethane/methanol (10/1, 1 mL) was added formaldehyde (0.05 mL, 37%, 0.8 mmol) and sodium triacetoxyborohydride (107 mg, 0.51 mmol). The mixture was stirred at room temperature for 1 hr and the reaction was quenched by the addition of water (a few drops). The solvents were removed and the dried residue was used in the next step without further purification. LC-MS 371.2 [M+H]$^+$, RT 0.96 min.

Step 6: 5-ethyl-4-hydroxy-6-(4-(1-methylpiperidin-4-yl)phenyl)-2-oxo-1,2-dihydropyridine-3-carboxylic acid To a solution of the crude material from Step 5 in EtOAc (2 mL) was added lithium iodide (100 mg, 0.75 mmol). The reaction mixture was heated to 65° C. and stirred for 1 hr. After cooling, the mixture was filtered and the solids were washed with EtOAc. The solids were stirred in 1N HCl (1 mL) for 10 minutes and then filtered. The residue was washed with water and diethyl ether to provide the title compound as an off-white solid (25 mg, 42%) over two steps.
$^1$H NMR (500 MHz, DMSO-d$_6$) δ 1.01 (t, J=7 Hz, 3H), 1.86-1.91 (m, 2H), 2.07-2.10 (m, 2H), 2.28 (q, J=7 Hz, 2H), 2.80 (s, 3H), 2.89-2.91 (m, 1H), 3.08-3.11 (m, 2H), 3.52-3.56 (m, 2H), 7.43 (d, J=8 Hz, 2H), 7.48 (d, J=8 Hz, 2H), 8.89 (bs, 1H), 12.75 (bs, 1H), 13.93 (bs, 1H). LC-MS 357.2 [M+H]$^+$, RT 0.51 min.

Using the procedure described above, additional compounds described herein may be prepared by substituting the appropriate starting materials, reagents and reaction conditions and includes compounds selected from:

| Cpd | Name |
|---|---|
| 339 | 5-ethyl-6-(4-(1-ethylpiperidin-4-yl)phenyl)-4-hydroxy-2-oxo-1,2-dihydropyridine-3-carboxylic acid<br>$^1$H NMR (500 MHz, DMSO-d$_6$) δ 1.01 (t, J = 7 Hz, 3H), 1.27 (t, J = 5 Hz, 3H), 1.83-1.90 (m, 2H), 2.09-2.12 (m, 2H), 2.29 (q, J = 7 Hz, 2H), 2.82-2.95 (m, 1H), 3.03-3.08 (m, 2H), 3.17 (q, J = 7 Hz, 2H), 3.59-3.63 (m, 2H), 7.43 (d, J = 8 Hz, 2H), 7.48 (d, J = 8 Hz, 2H), 8.89 (bs, 1H), 12.81 (bs, 1H), 13.94 (bs, 1H). LC-MS 371.2 [M + H]$^+$, RT 0.99*. |

EXAMPLE 36

5-ethyl-4-hydroxy-2-oxo-6-(4-(1,2,3,6-tetrahydropyridin-4-yl)phenyl)-1,2-dihydropyridine-3-carboxylic acid (Cpd 340)

Step 1: methyl 5-ethyl-4-hydroxy-2-oxo-6-(4-(1,2,3,6-tetrahydropyridin-4-yl)phenyl)-1,2-dihydropyridine-3-carboxylate To a solution of the compound prepared from Scheme 1, Step 2 (0.26 mg, 0.4 mmol) in dichloromethane (1 mL) was added trifluoroacetic acid (1 mL). The mixture was stirred at room temperature until LC/MS showed complete consumption of the starting material. The solvent was removed under reduced pressure and the crude product was used in the next step without further purification. LC-MS 353.3 [M−H]$^−$, RT 0.96 min.

Step 2: 5-ethyl-4-hydroxy-2-oxo-6-(4-(1,2,3,6-tetrahydropyridin-4-yl)phenyl)-1,2-dihydropyridine-3-carboxylic acid To a solution of the crude material from Step 1 in EtOAc (5 mL) was added lithium iodide (266 mg, 2.0 mmol). The reaction mixture was heated to 65° C. and stirred for 1 hr. After cooling, the mixture was filtered and the solids were washed with EtOAc. The solids were stirred in 1N HCl (1 mL) for 10 min and then filtered. The residue was washed with water and diethyl ether to provide the title compound as an off-white solid (50 mg, 30%) over two steps.
$^1$H NMR (500 MHz, DMSO-d$_6$) δ 1.00 (t, J=7 Hz 3H), 2.30 (q, J=7 Hz 2H), 2.70-2.75 (m, 2H), 3.34-3.37 (m, 2H), 3.80-3.85 (m, 2H), 6.37 (bs, 1H), 7.52 (d, J=13 Hz, 2H), 7.66 (d, J=13 Hz, 2H), 8.79 (bs, 1H), 12.81 (bs, 1H), 13.94 (bs, 1H). LC-MS 343.2 [M+H]$^+$, RT 0.97 min.

EXAMPLE 37

5-ethyl-6-(4-(1-ethyl-1,2,3,6-tetrahydropyridin-4-yl)phenyl)-4-hydroxy-2-oxo-1,2-dihydropyridine-3-carboxylic acid (Cpd 341)

Step 1: methyl 5-ethyl-6-(4-(1-ethyl-1,2,3,6-tetrahydropyridin-4-yl)phenyl)-4-hydroxy-2-oxo-1,2-dihydropyridine-3-carboxylate Following the procedure in Example 35, Step 5, to methyl 5-ethyl-4-hydroxy-2-oxo-6-(4-(1,2,3,6-tetrahydropyridin-4-yl)phenyl)-1,2-dihydropyridine-3-carboxylate (60 mg, 0.17 mmol) was added acetaldehyde (0.05 mL, 0.8 mmol) and sodium triacetoxyborohydride (107 mg, 0.51 mmol) in a mixture of dichloromethane/methanol (10/1, 1 mL) to give the title compound which was used without further purification in the following step. LC-MS 383.5 [M+H]$^+$, RT 0.88 min.

Step 2: -ethyl-6-(4-(1-ethyl-1,2,3,6-tetrahydropyridin-4-yl)phenyl)-4-hydroxy-2-oxo-1,2-dihydropyridine-3-carboxylic acid Following the procedure in Example 35, Step 6, methyl 5-ethyl-6-(4-(1-ethyl-1,2,3,6-tetrahydropyridin-4-yl)phenyl)-4-hydroxy-2-oxo-1,2-dihydropyridine-3-carboxylate (crude) and lithium iodide (266 mg, 2.0 mmol) in EtOAc (2 mL) were reacted to give the title compound (23 mg, 40%) over two steps.
$^1$H NMR (500 MHz, MeOD-d$_6$) δ 1.08 (t, J=7 Hz, 3H), 1.40 (t, J=8 Hz, 3H), 2.43 (q, J=7 Hz, 2H), 2.90-2.95 (m, 2H), 3.19-3.21 (m, 2H), 3.41-3.47 (m, 2H), 3.80-3.84 (m, 2H), 6.37 (bs, 1H), 7.48 (d, J=8 Hz, 2H), 7.66 (d, J=8 Hz, 2H). LC-MS 369.2 [M+H]$^+$, RT 0.98 min.

Using the procedure described above, additional compounds described herein may be prepared by substituting the appropriate starting materials, reagents and reaction conditions and includes compounds selected from:

| Cpd | Name |
|---|---|
| 342 | 5-ethyl-4-hydroxy-6-(4-(1-methyl-1,2,3,6-tetrahydropyridin-4-yl)phenyl)-2-oxo-1,2-dihydropyridine-3-carboxylic acid<br>$^1$H NMR (500 MHz, MeOD-$d_6$) δ 1.11 (t, J = 7 Hz, 3H), 2.43 (q, J = 7 Hz, 2H), 2.97-23.03 (m, 2H), 3.05 (s, 3H), 3.59-3.62 (m, 2H), 3.97-4.00 (m, 2H), 6.33 (bs, 1H), 7.53 (d, J = 8 Hz, 2H), 7.72 (d, J = 8 Hz, 2H). LC-MS 355.2 [M + H]$^+$, RT 0.98 min. |

EXAMPLE 38

6-(4-(2-(dimethylamino)ethyl)phenyl)-5-ethyl-4-hydroxy-2-oxo-1,2-dihydropyridine-3-carboxylic acid (Cpd 343)

Step 1. (E)-methyl 1-(2,4-dimethoxybenzyl)-6-(4-(2-ethoxyvinyl)phenyl)-5-ethyl-4-hydroxy-2-oxo-1,2-dihydropyridine-3-carboxylate Methyl 6-(4-chlorophenyl)-1-(2,4-dimethoxybenzyl)-5-ethyl-4-(methoxymethoxy)-2-oxo-1,2-dihydropyridine-3-carboxylate from Example 35, Step 1 (0.26 g, 0.5 mmol) was mixed with (E)-2-(2-ethoxyvinyl)-4,4,5,5-tetramethyl-1,3,2-dioxaborolane (0.2 g, 1.0 mmol), Pd(OAc)$_2$ (0.0067 g, 6 mol %), S-Phos (0.031 g, 15 mol %) and KOH (0.11 g, 1.0 mmol) in acetonitrile (5 mL). The mixture was degassed by purging the reaction flask under vacuum, then backfilling with Argon (3×). The reaction mixture was heated at 80° C. with vigorous magnetic stirring overnight. After cooling to room temperature, the mixture was filtered and the solids were washed with EtOAc. The filtrate was concentrated and purified by chromatography on silica gel (0-100% EtOAc in hexanes) to afford the product as a yellow solid (0.21 g, 77%).
$^1$H NMR (500 MHz, Acetone-d) δ ppm 0.91 (t, J=7 Hz, 3H), 1.31 (t, J=7 Hz, 3H), 2.14 (q, J=7 Hz, 2H), 3.56 (s, 3H), 3.77 (s, 3H), 3.92 (s, 3H), 3.96 (q, J=7 Hz, 2H), 4.86 (s, 2H), 5.91 (d, J=13 Hz, 1H), 6.38 (d, J=3 Hz, 1H), 6.46 (dd, J=8, 3 Hz, 1H), 6.75 (d, J=8 Hz, 1H), 6.97 (d, J=8 Hz, 2H), 7.27-7.31 (m, 3H). LC-MS 494.3 [M+H]$^+$, RT 1.62 min.

Step 2. methyl 1-(2,4-dimethoxybenzyl)-6-(4-(2-(dimethylamino)ethyl)phenyl)-5-ethyl-4-hydroxy-2-oxo-1,2-dihydropyridine-3-carboxylate The intermediate from Step 1 (0.1 g, 0.2 mmol) was mixed with HCl/dioxane (4M, 3 mL) and stirred at room temperature for 1 hr. The mixture was diluted with cold water and extracted with ethyl acetate. The organics were washed with water, then dried and concentrated to give the crude aldehyde which was used in the next step without further purification. The crude material was mixed with dimethylamine (2.0 M in THF, 0.1 mL, 0.2 mmol) and NaBH(OAc)$_3$ (0.085 g, 0.4 mmol) in dichloromethane (1 mL). The mixture was stirred overnight, and then water (a few drops) was added. The solvents were removed under reduced pressure and the residue was purified by chromatography on silica gel (eluting with 10% methanol in CH$_2$Cl$_2$) to provide the desired product as a yellow oil (0.03 g, 30% yield).
LC-MS 495.3 [M+H]$^+$, RT 1.62 min.

Step 3. 6-(4-(2-(dimethylamino)ethyl)phenyl)-5-ethyl-4-hydroxy-2-oxo-1,2-dihydropyridine-3-carboxylic acid To a suspension of methyl 1-(2,4-dimethoxybenzyl)-6-(4-(2-(dimethylamino)ethyl)phenyl)-5-ethyl-4-hydroxy-2-oxo-1,2-dihydropyridine-3-carboxylate (0.03 g, 0.06 mmol) in CH$_2$Cl$_2$ (1.0 mL) was added TFA (1.0 mL) at room temperature. The mixture was stirred at temperature for 2 h and monitored for completion by LC-MS. The solvent was then removed under reduced pressure and the crude product was used directly in the next step without further purification.

To a solution of the crude material in EtOAc (1 mL) was added lithium iodide (50 mg, 0.38 mmol). The reaction mixture was heated to 65° C. and stirred for 1 hr. After cooling, the mixture was filtered and the solids were washed with EtOAc. The solids were stirred in 1N HCl (1 mL) for 10 min and then filtered. The residue was washed with water and diethyl ether to provide the title compound as an off-white solid (5 mg, 22%) over two steps.
$^1$H NMR (500 MHz, MeOD-$d_6$) δ 1.08 (t, J=7 Hz, 3H), 2.42 (q, J=7 Hz, 2H), 3.02 (s, 6H), 3.16-3.20 (m, 2H), 3.46-3.49 (m, 2H), 7.50 (d, J=6 Hz, 2H), 7.55 (d, J=6 Hz, 2H). LC-MS 331.2 [M+H]$^+$, RT 0.49 min.

EXAMPLE 39

5-ethyl-6-(1-methyl-5-(pyrrolidin-1-ylmethyl)-1H-pyrrol-3-yl)-2-oxo-1,2-dihydropyridine-3-carboxylic acid (Cpd 348)

Step 1: methyl 6-chloro-5-ethyl-2-methoxynicotinate

To a solution of 3,5-dichloro-6-ethyl-2H-1,4-oxazin-2-one (10.0 g, 52.0 mmol) in DCM (10 mL) was added dry MeOH (10.4 mL, 257 mmol). The reaction was stirred overnight at room temperature. The mixture was purified by column chromatography, eluting with EtOAc/hexanes (gradient 0-10%) to afford 5-chloro-6-ethyl-3-methoxy-2H-1,4-oxazin-2-one (4.54 g, 55%) as an oil.

The product 5-chloro-6-ethyl-3-methoxy-2H-1,4-oxazin-2-one (4.54 g, 28.10 mmol) obtained above was mixed with methyl propiolate (6.0 mL, 71.80 mmol) and BF$_3$-etherate (0.26 mL, 2.81 mmol). The mixture was heated at 40° C. for 72 h, then cooled to room temperature and purified via silica gel column eluting with EtOAc/hexanes (gradient 0-15%) to afford methyl 6-chloro-5-ethyl-2-methoxynicotinate (4.84 g, 75%) as an off-white solid.
$^1$H NMR (500 MHz, CHCl$_3$-d) δ ppm 1.24 (t, J=7.6 Hz, 3H) 2.70 (q, J=7.6 Hz, 2H) 3.91 (s, 3H) 4.04 (s, 3H) 8.05 (s, 1H).

Step 2

6-chloro-5-ethyl-2-methoxynicotinate (0.575 g, 2.50 mmol), bis(pinacolato)diborate (0.762 g, 300 mmol), Pd(dppf)Cl$_2$ (91.0 mg, 0.1 mmol, 4 mol %), and KOAc (0.740 g, 7.50 mmol) were mixed together in a heat-gun dried vial. The vial was placed under vacuum, then back filled with Argon and dioxane (10 mL) was added. The mixture was heated at 100° C. for 12 hrs and cooled to room temperature, then 5-bromo-1-methyl-1H-pyrrole-2-carbaldehyde (0.800 g, 4.3 mmol), fresh Pd(dppf)Cl$_2$ (73.0 mg, 0.1 mmol, 4 mol %), K$_2$CO$_3$ (1.00 g, 7.60 mmol) and H$_2$O (2.50 mL) were added. The reaction vial was resealed under Argon and heated at 100° C. for 2 h. The mixture was cooled to room temperature, diluted with H$_2$O (15 mL) and extracted with DCM (3×20 mL). The combined organic phases were washed with NaCl (aqueous saturated, 15 mL), dried over Na$_2$SO$_4$, then filtered and concentrated. The residue was purified by column chromatography (EtOAc/hexanes, 0-15% gradient) to afford the product methyl 5-ethyl-6-(5-formyl-1-methyl-1H-pyrrol-2-yl)-2-methoxynicotinate (0.51 g, 68%).

$^1$H NMR (500 MHz, CHCl$_3$-d) δ ppm 1.19 (t, J=7.57 Hz, 3H) 2.68 (q, J=7.57 Hz, 2H) 3.96 (s, 3H) 3.97 (s, 3H) 4.02-4.06 (m, 3H) 6.41 (d, J=4.10 Hz, 1H) 7.02 (d, J=4.10 Hz, 1H) 8.17 (s, 1H) 9.67 (s, 1H).

Step 3

To a solution of methyl 5-ethyl-6-(5-formyl-1-methyl-1H-pyrrol-2-yl)-2-methoxynicotinate (0.12 g, 0.4 mmol) in DCE (4 mL) was added AcOH (50 μL) and pyrrolidine (100 μL, 1.2 mmol). The mixture was stirred at room temperature for 30 min, then NaBH(OAc)$_3$ (0.17 g, 0.8 mmol) was added. The reaction mixture was stirred at room temperature for one additional hour, then diluted with DCM and washed with water. The organic phase was dried over Na$_2$SO$_4$, then filtered and concentrated. The residue was dissolved in 4M HCl (2 mL) and the resulting solution was heated to 80° C. for 1 hr. The mixture was cooled to room temperature and a precipitate was collected by filtration to afford the title compound (34 mg, 25% over 2 steps).

$^1$H NMR (500 MHz, MeOH-d$_4$) δ ppm 1.24 (t, J=7.53 Hz, 3H) 2.05-2.15 (m, 2H) 2.18-2.28 (m, 2H) 2.73 (q, J=7.57 Hz, 2H) 3.23-3.31 (m, 2H) 3.59-3.68 (m, 2H) 3.88 (s, 3H) 4.55 (s, 2H) 6.81 (d, J=1.97 Hz, 1H) 7.40 (d, J=1.97 Hz, 1H) 8.42 (s, 1H). LC-MS 330.2 [M+H]$^+$, RT 0.62 min.

Using the procedures described above, additional compounds described herein may be prepared by substituting the appropriate starting materials, reagents and reaction conditions and includes compounds selected from:

BIOLOGICAL EXAMPLES

The following biological examples demonstrate the usefulness of the compounds described herein for treating bacterial infections.

Example 1

The antibacterial activity from a microbroth dilution method may be presented as the minimum inhibitory concentration (MIC in mg/mL). The MIC value is the lowest concentration of a drug which prevents macroscopically visible bacterial growth under test conditions.

In the following tables, an MIC value between >12.5 μg/mL and ≤150 μg/mL is indicated by a single star (*), an MIC value between >3.5 μg/mL and ≤12.5 μg/mL is indicated by two stars (), an MIC value between >1.0 μg/mL and ≤3.5 μg/mL is indicated by three stars (*) and an MIC value of ≤1.0 μg/mL is indicated by four stars (****). The term ND indicates that the MIC value was Not Determined.

Antibacterial activity of test compounds against the super sensitive Gram-negative *Escherichia coli* (*E. coli*) BAS849 bacterium, the control Gram-negative *E. coli* 25922 strain and the Gram-positive *Staphylococcus aureus* (*S. aureus*) 29213 bacterium are shown in Table 1.

TABLE 1

| Cpd | BAS849 | 25922 | 29213 |
|---|---|---|---|
| 1 | * | ND | * |
| 2 | * | * | ** |
| 3 | **** | ** | * |
| 4 | **** | * | * |
| 5 | **** | * | * |
| 6 | ** | * | * |
| 7 | ** | * | *** |
| 8 | **** | ** | * |
| 9 | **** | * | *** |
| 10 | * | * | * |
| 11 | * | * | * |
| 12 | **** | ** | * |

| Cpd | Name |
|---|---|
| 349 | 5-ethyl-6-(1-methyl-5-(piperidin-1-ylmethyl)-1H-pyrrol-3-yl)-2-oxo-1,2-dihydropyridine-3-carboxylic acid<br>$^1$H NMR (500 MHz, MeOH-d$_4$) δ ppm 1.25 (s, 3 H) 1.95-2.05 (m, 2 H) 2.70-2.77 (m, 2 H) 3.01-3.11 (m, 4 H) 3.57-3.64 (m, 4 H) 3.87 (s, 3 H) 4.41-4.46 (m, 2 H) 6.79-6.84 (m, 1 H) 7.40-7.45 (m, 1 H) 8.40-8.45 (m, 1 H). LC-MS 344.2 [M + H]$^+$, RT 0.64 min. |
| 350 | 5-ethyl-6-(1-methyl-5-(pyrrolidin-1-ylmethyl)-1H-pyrrol-2-yl)-2-oxo-1,2-dihydropyridine-3-carboxylic acid<br>$^1$H NMR (500 MHz, DMSO-d$_6$) δ ppm 1.02 (t, J = 7.49 Hz, 3 H) 1.84-2.09 (m, 4 H) 2.35-2.46 (m, 2 H) 3.03-3.15 (m, 2 H) 3.41-3.48 (m, 2 H) 3.55 (s, 3 H) 4.42-4.51 (m, 2 H) 6.41 (s, 1 H) 6.51 (d, J = 3.78 Hz, 1 H) 8.41 (s, 1 H). LC-MS 328.3 [M – H]$^-$, RT 0.64 min. |
| 351 | 6-(5-((dimethylamino)methyl)-1-methyl-1H-pyrrol-2-yl)-5-ethyl-2-oxo-1,2-dihydropyridine-3-carboxylic acid<br>$^1$H NMR (500 MHz, MeOH-d$_4$) δ ppm 1.12 (t, J = 7.57 Hz, 3 H) 2.46 (q, J = 7.57 Hz, 2 H) 2.95 (s, 6 H) 3.60 (s, 3 H) 4.51 (s, 2 H) 6.50 (d, J = 3.86 Hz, 1 H) 6.61 (d, J = 3.86 Hz, 1 H) 8.53 (s, 1 H). LC-MS 302.3 [M – H]$^-$, RT 0.60 min. |
| 352 | 5-ethyl-6-(1-methyl-5-(piperidin-1-ylmethyl)-1H-pyrrol-2-yl)-2-oxo-1,2-dihydropyridine-3-carboxylic acid<br>$^1$H NMR (500 MHz, MeOH-d$_4$) δ ppm 1.13 (t, J = 7.61 Hz, 3 H) 1.50-1.62 (m, 1 H) 1.72-1.95 (m, 3 H) 1.97-2.07 (m, 2 H) 2.42-2.53 (m, 2 H) 3.00-3.11 (m, 2 H) 3.59 (s, 5 H) 4.47 (s, 2 H) 6.51 (d, J = 3.78 Hz, 1 H) 6.60 (d, J = 3.78 Hz, 1 H) 8.53 (s, 1 H). LC-MS 342.3 [M – H]$^-$, RT 0.69 min. |
| 353 | 6-(5-((3-(dimethylamino)pyrrolidin-1-yl)methyl)-1-methyl-1H-pyrrol-2-yl)-5-ethyl-2-oxo-1,2-dihydropyridine-3-carboxylic acid<br>LC-MS: 373.4 [M + H]$^+$, RT 0.56 min. |

TABLE 1-continued

| Cpd | BAS849 | 25922 | 29213 |
|---|---|---|---|
| 13 | *** | * | ** |
| 14 | * | * | * |
| 15 | * | * | * |
| 16 | **** | ** | * |
| 17 | **** | ** | * |
| 18 | **** | ** | ** |
| 19 | * | * | * |
| 20 | * | * | * |
| 21 | ** | * | ** |
| 22 | * | * | * |
| 23 | * | * | * |
| 24 | **** | ** | * |
| 25 | **** | ** | * |
| 26 | * | * | * |
| 27 | **** | * | * |
| 28 | **** | * | ** |
| 29 | *** | * | *** |
| 30 | *** | * | * |
| 31 | * | * | * |
| 32 | ** | * | ** |
| 33 | * | * | * |
| 34 | * | * | * |
| 35 | * | * | * |
| 36 | ** | * | * |
| 37 | * | * | * |
| 38 | **** | *** | ** |
| 39 | ** | * | *** |
| 40 | * | * | * |
| 41 | * | * | * |
| 42 | **** | * | *** |
| 43 | **** | * | * |
| 44 | *** | * | *** |
| 45 | ** | * | ** |
| 46 | * | * | * |
| 47 | *** | * | ** |
| 48 | ** | * | ** |
| 49 | ** | * | ** |
| 50 | * | * | * |
| 51 | ** | * | ** |
| 52 | * | * | * |
| 53 | **** | *** | * |
| 54 | * | * | * |
| 55 | **** | * | ** |
| 56 | ** | * | ** |
| 57 | * | * | * |
| 58 | ** | * | ** |
| 59 | * | * | * |
| 60 | ** | * | ** |
| 61 | ** | * | ** |
| 62 | * | * | * |
| 63 | *** | * | ** |
| 64 | ** | * | * |
| 65 | ** | * | * |
| 66 | ** | * | * |
| 67 | ** | * | *** |
| 68 | * | * | * |
| 69 | ** | * | ** |
| 70 | **** | * | * |
| 71 | *** | * | ** |
| 72 | ** | * | * |
| 73 | ** | * | ** |
| 74 | ** | * | * |
| 75 | *** | * | * |
| 76 | * | * | * |
| 77 | *** | * | ** |
| 78 | ** | * | * |
| 79 | **** | * | ** |
| 80 | ** | * | * |
| 81 | *** | * | ** |
| 82 | ** | * | *** |
| 83 | **** | ** | ** |
| 84 | ** | * | * |
| 85 | **** | * | ** |
| 86 | *** | * | * |
| 87 | **** | * | * |
| 88 | **** | **** | ** |
| 89 | * | * | * |
| 90 | **** | *** | ** |
| 91 | * | * | * |
| 92 | * | * | * |
| 93 | **** | * | * |
| 94 | **** | * | * |
| 95 | **** | ** | * |
| 96 | **** | ** | ** |
| 97 | **** | ** | * |
| 98 | **** | * | ** |
| 99 | **** | **** | *** |
| 100 | **** | ** | *** |
| 101 | **** | * | * |
| 102 | *** | * | * |
| 103 | ** | * | * |
| 105 | *** | ** | * |
| 106 | * | * | * |
| 107 | *** | * | * |
| 108 | **** | * | * |
| 109 | **** | * | ** |
| 110 | **** | ** | * |
| 111 | **** | *** | * |
| 112 | **** | * | * |
| 113 | ** | ** | * |
| 114 | *** | * | * |
| 115 | **** | ** | * |
| 116 | * | * | * |
| 117 | * | * | * |
| 118 | ** | * | * |
| 119 | *** | * | * |
| 120 | **** | * | * |
| 121 | **** | ** | * |
| 122 | **** | ** | * |
| 123 | **** | **** | ** |
| 124 | **** | **** | *** |
| 125 | **** | ** | * |
| 126 | **** | **** | *** |
| 127 | * | * | * |
| 128 | **** | * | *** |
| 129 | **** | *** | ** |
| 130 | **** | *** | ** |
| 131 | **** | ** | * |
| 132 | **** | *** | ** |
| 133 | *** | * | * |
| 134 | **** | ** | * |
| 135 | **** | * | * |
| 136 | *** | * | * |
| 137 | **** | * | * |
| 138 | * | * | * |
| 139 | **** | ** | ** |
| 140 | **** | ** | * |
| 141 | **** | * | ** |
| 142 | *** | * | * |
| 143 | ** | * | * |
| 144 | **** | *** | ** |
| 145 | **** | * | *** |
| 146 | **** | * | * |
| 147 | **** | ** | ** |
| 148 | ** | * | * |
| 149 | **** | *** | * |
| 150 | **** | *** | * |
| 151 | **** | *** | * |
| 152 | **** | *** | ** |
| 153 | **** | **** | *** |
| 154 | **** | *** | ** |
| 155 | **** | *** | ** |
| 156 | **** | * | * |
| 157 | **** | ** | * |
| 158 | **** | ** | ** |
| 159 | *** | * | * |
| 160 | **** | *** | * |
| 161 | **** | *** | * |
| 162 | ** | * | * |
| 163 | **** | ** | * |
| 164 | **** | *** | ** |
| 165 | *** | * | * |
| 166 | **** | ** | * |
| 167 | *** | * | * |
| 168 | **** | * | * |
| 169 | **** | *** | * |

TABLE 1-continued

| Cpd | BAS849 | 25922 | 29213 |
|---|---|---|---|
| 170 | * | * | * |
| 171 | ** | * | * |
| 172 | **** | ** | * |
| 173 | **** | *** | * |
| 174 | **** | **** | * |
| 175 | **** | *** | * |
| 176 | * | * | * |
| 177 | **** | **** | * |
| 178 | **** | **** | * |
| 179 | *** | ** | * |
| 180 | *** | * | * |
| 181 | ** | * | * |
| 182 | **** | **** | * |
| 183 | **** | ** | * |
| 184 | *** | * | * |
| 185 | **** | ** | * |
| 186 | * | * | * |
| 187 | **** | ** | * |
| 188 | **** | ** | * |
| 189 | **** | ** | * |
| 190 | *** | * | * |
| 191 | **** | *** | * |
| 192 | **** | ** | ** |
| 193 | *** | * | * |
| 194 | *** | * | ** |
| 195 | *** | ** | * |
| 196 | * | * | * |
| 197 | ** | * | * |
| 198 | **** | ** | * |
| 199 | **** | ** | ** |
| 200 | *** | ** | * |
| 201 | ** | * | * |
| 202 | *** | * | * |
| 203 | *** | * | * |
| 204 | *** | * | * |
| 205 | *** | * | * |
| 206 | *** | ** | * |
| 207 | ** | * | * |
| 208 | *** | ** | * |
| 209 | ** | * | * |
| 210 | *** | * | * |
| 211 | **** | ** | * |
| 212 | **** | ** | * |
| 213 | *** | * | * |
| 214 | *** | * | * |
| 215 | *** | ** | * |
| 216 | * | * | * |
| 217 | **** | ** | ** |
| 218 | *** | ** | * |
| 219 | **** | * | * |
| 220 | ** | * | * |
| 221 | *** | ** | * |
| 222 | *** | * | * |
| 223 | * | * | * |
| 224 | **** | * | * |
| 225 | **** | ** | * |
| 226 | **** | *** | ** |
| 227 | **** | *** | *** |
| 228 | * | * | * |
| 230 | **** | *** | ** |
| 231 | **** | *** | * |
| 232 | **** | *** | ** |
| 233 | **** | ** | * |
| 234 | **** | *** | * |
| 235 | *** | * | * |
| 236 | **** | *** | ** |
| 237 | **** | **** | ** |
| 238 | **** | *** | * |
| 239 | **** | **** | * |
| 240 | **** | *** | * |
| 241 | **** | **** | * |
| 242 | **** | *** | * |
| 243 | **** | *** | * |
| 244 | **** | * | *** |
| 245 | **** | ** | ** |
| 246 | **** | *** | * |
| 247 | **** | ** | ** |
| 248 | *** | * | * |
| 249 | * | * | * |
| 250 | ** | * | * |
| 251 | * | * | * |
| 252 | **** | *** | * |
| 253 | **** | * | ** |
| 254 | **** | *** | * |
| 255 | ** | * | ** |
| 256 | **** | *** | ** |
| 257 | **** | **** | * |
| 258 | **** | *** | ** |
| 259 | **** | *** | * |
| 260 | ** | ** | *** |
| 261 | **** | ** | ** |
| 262 | **** | *** | ** |
| 263 | **** | *** | * |
| 264 | **** | *** | ** |
| 265 | *** | ** | * |
| 266 | *** | * | ** |
| 267 | *** | ** | * |
| 268 | *** | ** | ** |
| 269 | **** | **** | ** |
| 270 | **** | **** | ** |
| 271 | **** | ** | * |
| 272 | **** | **** | ** |
| 273 | **** | *** | * |
| 274 | *** | * | * |
| 275 | **** | **** | * |
| 276 | **** | * | *** |
| 277 | **** | *** | ** |
| 278 | **** | ** | ** |
| 279 | **** | *** | * |
| 280 | **** | * | * |
| 281 | ** | * | * |
| 282 | **** | * | * |
| 283 | ** | * | * |
| 284 | ** | * | * |
| 285 | **** | **** | ** |
| 286 | **** | *** | *** |
| 287 | **** | *** | ** |
| 288 | **** | *** | *** |
| 289 | **** | *** | *** |
| 290 | **** | *** | * |
| 291 | *** | ** | * |
| 292 | **** | *** | * |
| 293 | **** | ** | ** |
| 294 | **** | * | *** |
| 295 | *** | * | * |
| 296 | **** | *** | *** |
| 297 | **** | * | ** |
| 298 | ** | * | * |
| 299 | *** | * | * |
| 300 | *** | * | *** |
| 301 | **** | **** | **** |
| 302 | **** | *** | **** |
| 303 | **** | * | * |
| 304 | **** | ** | ** |
| 305 | **** | * | * |
| 306 | **** | ** | ** |
| 307 | **** | * | ** |
| 308 | *** | * | * |
| 309 | **** | * | ** |
| 310 | * | * | * |
| 311 | ** | * | * |
| 312 | **** | * | * |
| 313 | **** | * | * |
| 314 | ** | * | * |
| 315 | *** | * | * |
| 316 | * | * | * |
| 317 | ** | ** | * |
| 318 | ** | * | * |
| 319 | **** | ** | * |
| 320 | ** | * | * |
| 321 | *** | * | * |
| 322 | **** | **** | ** |
| 323 | *** | ** | * |
| 324 | ** | * | * |
| 325 | **** | ** | * |
| 326 | **** | ** | * |

TABLE 1-continued

| Cpd | BAS849 | 25922 | 29213 |
| --- | --- | --- | --- |
| 327 | ** | * | * |
| 328 | **** | ** | * |
| 329 | * | * | * |
| 330 | *** | * | * |
| 331 | *** | * | * |
| 332 | * | * | * |
| 333 | *** | * | * |
| 334 | ** | * | * |
| 335 | ** | * | * |
| 336 | *** | * | * |
| 337 | * | * | * |
| 338 | * | * | * |
| 339 | ** | * | * |
| 340 | ** | * | * |
| 341 | *** | * | * |
| 342 | *** | ** | * |
| 343 | ** | * | * |
| 343 | ** | * | * |
| 344 | * | * | * |
| 345 | * | * | * |
| 346 | * | * | * |
| 347 | *** | ** | * |
| 348 | ** | * | * |
| 349 | * | * | * |
| 350 | * | * | * |
| 351 | * | * | * |
| 352 | * | * | * |
| 353 | * | * | * |

Example 2

Antibacterial activity of test compounds against the quinolone resistant *E. coli* LZ3111 bacterium is shown in Table 2. The *E. coli* LZ3111 strain is genetically engineered and possesses double mutations in both the gyrase A and par C regions of the topoisomerase subunits. Mutations in these regions are known to confer a high level resistance to the quinolone class of antibiotics.

TABLE 2

| Cpd | LZ3111 |
| --- | --- |
| 3 | * |
| 4 | * |
| 5 | *** |
| 8 | * |
| 12 | * |
| 16 | * |
| 17 | * |
| 18 | * |
| 20 | ** |
| 24 | * |
| 25 | * |
| 30 | * |
| 38 | * |
| 41 | * |
| 42 | * |
| 44 | * |
| 45 | * |
| 49 | * |
| 50 | * |
| 55 | * |
| 68 | * |
| 75 | * |
| 83 | * |
| 84 | * |
| 85 | * |
| 86 | * |
| 87 | *** |
| 88 | * |
| 90 | * |
| 92 | * |
| 93 | * |
| 94 | * |
| 95 | * |
| 96 | * |
| 97 | * |
| 99 | * |
| 100 | * |
| 101 | * |
| 105 | * |
| 107 | * |
| 108 | * |
| 110 | * |
| 111 | * |
| 112 | * |
| 113 | * |
| 115 | * |
| 116 | * |
| 117 | * |
| 121 | * |
| 123 | * |
| 124 | * |
| 126 | * |
| 128 | * |
| 129 | * |
| 130 | * |
| 131 | * |
| 132 | * |
| 134 | * |
| 135 | * |
| 136 | * |
| 139 | * |
| 140 | * |
| 141 | * |
| 144 | * |
| 147 | * |
| 149 | * |
| 150 | * |
| 151 | * |
| 152 | * |
| 153 | * |
| 154 | * |
| 155 | * |
| 157 | * |
| 158 | * |
| 159 | * |
| 160 | * |
| 161 | * |
| 163 | * |
| 164 | * |
| 165 | * |
| 166 | * |
| 167 | * |
| 168 | * |
| 169 | * |
| 173 | * |
| 174 | * |
| 175 | * |
| 177 | * |
| 178 | * |
| 179 | * |
| 182 | * |
| 183 | * |
| 184 | * |
| 185 | * |
| 187 | * |
| 188 | * |
| 190 | * |
| 191 | * |
| 192 | * |
| 193 | * |
| 194 | * |
| 195 | * |
| 196 | * |
| 197 | * |
| 198 | * |
| 199 | * |
| 200 | * |
| 201 | * |

TABLE 2-continued

| Cpd | LZ3111 |
|---|---|
| 202 | * |
| 203 | * |
| 204 | * |
| 205 | * |
| 206 | * |
| 207 | * |
| 208 | * |
| 209 | * |
| 210 | * |
| 211 | * |
| 212 | * |
| 213 | * |
| 214 | * |
| 215 | * |
| 216 | * |
| 218 | * |
| 219 | * |
| 220 | * |
| 221 | * |
| 222 | * |
| 223 | * |
| 224 | * |
| 225 | * |
| 226 | * |
| 227 | * |
| 228 | * |
| 230 | * |
| 231 | * |
| 232 | * |
| 233 | * |
| 234 | * |
| 235 | * |
| 236 | * |
| 237 | * |
| 238 | * |
| 239 | * |
| 240 | * |
| 241 | * |
| 242 | * |
| 243 | * |
| 244 | * |
| 245 | * |
| 247 | * |
| 248 | * |
| 249 | * |
| 250 | * |
| 251 | * |
| 252 | ** |
| 253 | * |
| 254 | ** |
| 255 | * |
| 256 | *** |
| 257 | ** |
| 258 | **** |
| 259 | *** |
| 260 | **** |
| 261 | *** |
| 262 | **** |
| 263 | ** |
| 264 | *** |
| 265 | ** |
| 266 | ** |
| 267 | ** |
| 268 | *** |
| 269 | ** |
| 270 | *** |
| 271 | ** |
| 272 | **** |
| 273 | * |
| 274 | * |
| 275 | *** |
| 276 | * |
| 277 | ** |
| 278 | * |
| 279 | **** |
| 280 | * |
| 281 | * |
| 282 | * |

TABLE 2-continued

| Cpd | LZ3111 |
|---|---|
| 283 | * |
| 284 | * |
| 285 | ** |
| 286 | * |
| 287 | * |
| 288 | ** |
| 289 | * |
| 290 | ** |
| 291 | * |
| 292 | * |
| 293 | * |
| 294 | * |
| 295 | * |
| 296 | **** |
| 297 | * |
| 300 | * |
| 301 | * |
| 302 | * |
| 304 | * |
| 306 | * |
| 310 | * |
| 312 | * |
| 313 | * |
| 314 | ** |
| 315 | * |
| 316 | * |
| 317 | * |
| 318 | * |
| 319 | * |
| 320 | * |
| 321 | * |
| 322 | * |
| 323 | ** |
| 324 | * |
| 325 | * |
| 326 | * |
| 327 | * |
| 328 | ** |
| 329 | ** |
| 330 | * |
| 331 | ** |
| 332 | * |
| 333 | * |
| 334 | * |
| 335 | **** |
| 336 | ** |
| 337 | **** |
| 338 | * |
| 339 | * |
| 340 | * |
| 341 | ** |
| 342 | ** |
| 343 | * |
| 348 | * |
| 349 | * |
| 350 | * |
| 351 | * |
| 352 | * |
| 353 | * |

Example 3

Antibacterial activity of test compounds against MDR *E. coli* strains is shown in Table 3. The *E. coli* ELZ4000 and *E. coli* ELZ4251 strains are MDR clinical isolates.

TABLE 3

| Cpd | ELZ4251 | ELZ4000 |
|---|---|---|
| 3 | * | * |
| 4 | * | * |
| 5 | *** | ** |
| 8 | * | * |

TABLE 3-continued

| Cpd | ELZ4251 | ELZ4000 |
|---|---|---|
| 12 | * | * |
| 16 | * | * |
| 17 | * | * |
| 18 | * | * |
| 24 | * | * |
| 25 | * | * |
| 38 | * | * |
| 75 | * | * |
| 83 | * | * |
| 84 | * | * |
| 85 | * | * |
| 87 | *** | *** |
| 88 | * | * |
| 90 | * | * |
| 92 | * | * |
| 93 | * | * |
| 94 | * | * |
| 95 | * | * |
| 96 | * | * |
| 97 | * | * |
| 99 | * | * |
| 100 | * | * |
| 101 | * | * |
| 105 | * | * |
| 107 | * | * |
| 108 | * | * |
| 110 | * | * |
| 111 | * | * |
| 115 | * | * |
| 121 | * | * |
| 123 | * | * |
| 124 | * | * |
| 126 | * | * |
| 128 | * | * |
| 129 | * | * |
| 130 | * | * |
| 131 | * | * |
| 132 | * | * |
| 134 | * | * |
| 139 | * | * |
| 140 | * | * |
| 141 | * | * |
| 144 | * | * |
| 147 | * | * |
| 149 | * | * |
| 150 | * | * |
| 151 | * | * |
| 152 | * | * |
| 153 | * | * |
| 154 | * | * |
| 155 | * | * |
| 157 | * | * |
| 158 | * | * |
| 160 | * | * |
| 161 | * | * |
| 163 | * | * |
| 164 | * | * |
| 174 | * | * |
| 177 | * | * |
| 178 | * | * |
| 179 | * | * |
| 182 | * | * |
| 183 | * | * |
| 185 | * | * |
| 187 | * | * |
| 202 | * | * |
| 203 | * | * |
| 206 | * | * |
| 208 | * | * |
| 216 | * | * |
| 244 | * | * |
| 246 | ** | * |
| 252 | * | * |
| 254 | ** | * |
| 256 | ** | * |
| 257 | *** | ** |
| 258 | ** | * |
| 259 | ** | ** |
| 260 | *** | ** |
| 261 | ** | * |
| 262 | *** | *** |
| 263 | * | * |
| 264 | ** | * |
| 265 | ** | * |
| 266 | * | * |
| 268 | ** | * |
| 269 | * | * |
| 270 | ** | * |
| 271 | ** | * |
| 272 | *** | ** |
| 273 | * | * |
| 275 | *** | ** |
| 277 | * | * |
| 279 | *** | ** |
| 285 | ** | * |
| 290 | ** | * |
| 296 | ** | * |
| 300 | * | * |
| 301 | * | * |
| 302 | * | * |
| 304 | * | * |
| 306 | * | * |
| 310 | * | * |

Example 4

Antibacterial activity of test compounds against the Gram-negative *Acinetobacter baumannii* (*A. baumannii*) BAA747 and *Klebsiella pneumoniae* (*K. pneumoniae*) 35657 bacterium and the resistant *A. baumannii* MXX2240 and *K. pneumoniae* MXX1232 strains are shown in Table 4. The MMX strains are MDR clinical isolates.

TABLE 4

| Cpd | BAA747 | MMX2240 | 35657 | MMX1232 |
|---|---|---|---|---|
| 4 | ND | ND | ** | ND |
| 5 | ** | **** | * | * |
| 20 | * | ** | * | * |
| 25 | ** | *** | ND | * |
| 75 | * | ND | ND | ND |
| 84 | * | ND | ND | ND |
| 86 | * | * | * | * |
| 87 | ** | **** | * | * |
| 88 | **** | * | **** | * |
| 90 | *** | ** | ** | * |
| 92 | * | ND | ND | ND |
| 93 | * | ND | * | ND |
| 94 | * | ND | * | ND |
| 95 | ND | ND | * | ND |
| 97 | ND | ND | ** | ND |
| 99 | ND | ND | ** | ND |
| 100 | ND | ND | * | ND |
| 101 | ND | ND | ** | ND |
| 124 | **** | * | ND | * |
| 126 | **** | * | ND | * |
| 173 | ** | * | *** | * |
| 177 | *** | * | **** | * |
| 178 | *** | * | **** | * |
| 192 | * | ND | * | ND |
| 217 | * | ND | ** | ND |
| 219 | * | ND | * | ND |
| 225 | * | ND | *** | ND |
| 226 | *** | * | ** | * |
| 227 | *** | * | ** | * |
| 231 | * | ND | *** | ND |
| 232 | *** | * | *** | * |
| 246 | * | * | *** | * |
| 247 | * | ND | ** | ND |
| 254 | ** | * | ** | * |
| 256 | * | * | *** | * |

TABLE 4-continued

| Cpd | BAA747 | MMX2240 | 35657 | MMX1232 |
|---|---|---|---|---|
| 257 | *** | * | *** | * |
| 258 | * | ** | *** | * |
| 259 | ** | * | *** | * |
| 260 | * | ND | ** | ND |
| 261 | * | * | * | * |
| 262 | ** | *** | *** | * |
| 263 | ** | * | ** | * |
| 264 | * | * | ** | * |
| 265 | * | * | ** | * |
| 266 | * | ND | * | ND |
| 267 | * | ND | ** | ND |
| 268 | * | * | * | * |
| 269 | **** | ** | **** | * |
| 270 | **** | * | **** | * |
| 271 | * | ND | ND | ND |
| 272 | *** | ** | **** | * |
| 275 | *** | *** | *** | * |
| 276 | * | ND | * | ND |
| 277 | ** | * | *** | * |
| 279 | * | ** | ** | * |
| 285 | **** | * | *** | * |
| 286 | ** | * | * | * |
| 288 | *** | *** | ** | * |
| 292 | ** | ND | *** | ND |
| 293 | * | ND | * | ND |
| 296 | * | ** | *** | * |
| 310 | * | ND | ND | ND |
| 312 | ** | * | ** | * |
| 313 | ** | * | ** | * |
| 314 | * | * | * | * |
| 315 | * | * | * | * |
| 316 | * | * | * | * |
| 317 | * | * | ** | * |
| 318 | * | * | * | * |
| 319 | * | * | ** | * |
| 320 | * | * | ** | * |
| 321 | * | * | ** | * |
| 322 | *** | * | *** | * |
| 323 | * | * | * | * |
| 324 | * | * | * | * |
| 325 | ** | * | ** | * |
| 326 | *** | ** | ** | * |
| 327 | * | * | * | * |
| 328 | * | ** | ** | * |
| 329 | * | * | * | * |
| 330 | * | * | * | * |
| 331 | * | * | * | * |
| 332 | * | * | * | * |
| 333 | * | * | * | * |
| 334 | * | * | * | * |
| 335 | * | * | * | * |
| 336 | * | * | * | * |
| 337 | * | * | * | * |
| 338 | * | * | * | * |
| 339 | * | * | * | * |
| 340 | * | * | ** | * |
| 341 | * | * | ** | * |
| 342 | * | * | ** | * |
| 343 | * | * | * | * |

Example 5

Antibacterial activity of test compounds against the Gram-negative bacterium *Pseudomonas aeruginosa* (*P. aeruginosa*) 27853 is shown in Table 5.

TABLE 5

| Cpd | 27853 |
|---|---|
| 4 | * |
| 5 | * |
| 8 | * |
| 12 | * |
| 20 | * |
| 75 | * |
| 83 | * |
| 84 | * |
| 85 | * |
| 86 | * |
| 87 | * |
| 88 | ** |
| 90 | * |
| 92 | * |
| 93 | * |
| 94 | * |
| 95 | * |
| 96 | * |
| 97 | * |
| 99 | ** |
| 100 | * |
| 101 | * |
| 107 | * |
| 108 | * |
| 110 | * |
| 111 | * |
| 115 | * |
| 123 | ** |
| 126 | ** |
| 128 | * |
| 129 | * |
| 131 | * |
| 139 | * |
| 140 | * |
| 141 | * |
| 144 | * |
| 147 | * |
| 149 | * |
| 150 | * |
| 151 | * |
| 152 | ** |
| 153 | ** |
| 154 | * |
| 155 | * |
| 157 | * |
| 158 | * |
| 173 | * |
| 174 | * |
| 177 | *** |
| 178 | * |
| 192 | * |
| 202 | * |
| 203 | * |
| 216 | * |
| 217 | * |
| 219 | * |
| 225 | * |
| 226 | * |
| 227 | ** |
| 231 | * |
| 232 | * |
| 244 | * |
| 246 | * |
| 247 | * |
| 252 | * |
| 254 | ** |
| 256 | * |
| 257 | * |
| 258 | * |
| 259 | * |
| 260 | * |
| 261 | * |
| 262 | * |
| 263 | * |
| 264 | * |
| 265 | * |
| 266 | * |
| 267 | * |
| 268 | * |
| 269 | *** |
| 270 | *** |
| 271 | * |

TABLE 5-continued

| Cpd | 27853 |
|---|---|
| 272 | ** |
| 275 | ** |
| 276 | * |
| 277 | * |
| 279 | * |
| 285 | ** |
| 286 | * |
| 288 | ** |
| 290 | * |
| 292 | ** |
| 293 | * |
| 296 | * |
| 301 | ** |
| 302 | ** |
| 304 | * |
| 310 | * |
| 312 | * |
| 313 | * |
| 314 | * |
| 315 | * |
| 316 | * |
| 317 | * |
| 318 | * |
| 319 | * |
| 320 | * |
| 321 | * |
| 322 | ** |
| 323 | * |
| 324 | * |
| 325 | * |
| 326 | * |
| 327 | * |
| 328 | * |
| 329 | * |
| 330 | * |
| 331 | * |
| 332 | * |
| 333 | * |
| 334 | * |
| 335 | * |
| 336 | * |
| 337 | * |
| 338 | * |
| 339 | * |
| 340 | * |
| 341 | * |
| 342 | * |
| 343 | * |

Example 6

Antibacterial activity of test compounds against the Gram-negative bacteria *Haemophilus influenzae* (*H. influenzae*) 49247, *Moraxella catarrhalis* (*M. catarrhalis*) 25238 and *Neisseria meningitidis* (*N. meningitidis*) 13090 is shown in Table 6.

TABLE 6

| Cpd | 49247 | 25238 | 13090 |
|---|---|---|---|
| 1 | **** | ** | ** |
| 2 | **** | **** | **** |
| 3 | ND | **** | **** |
| 5 | *** | *** | **** |
| 6 | **** | ** | **** |
| 7 | **** | **** | *** |
| 8 | **** | **** | **** |
| 9 | **** | **** | **** |
| 11 | **** | * | * |
| 12 | **** | **** | **** |
| 13 | **** | **** | **** |
| 14 | **** | * | * |
| 16 | **** | **** | ND |
| 17 | **** | **** | **** |
| 18 | **** | **** | ND |
| 22 | * | * | ** |
| 38 | ND | **** | ND |
| 53 | ND | **** | ND |
| 75 | ND | * | ND |
| 82 | **** | **** | **** |
| 83 | **** | **** | **** |
| 84 | **** | ** | *** |
| 86 | **** | *** | **** |
| 87 | *** | *** | **** |
| 88 | ** | **** | **** |
| 89 | **** | * | * |
| 90 | ND | **** | **** |
| 91 | *** | **** | ** |
| 92 | *** | * | ** |
| 93 | **** | **** | **** |
| 94 | **** | **** | **** |
| 95 | **** | **** | **** |
| 96 | **** | **** | **** |
| 97 | **** | **** | **** |
| 98 | *** | ** | **** |
| 99 | **** | **** | **** |
| 100 | **** | **** | **** |
| 101 | **** | **** | **** |
| 102 | *** | **** | *** |
| 103 | **** | * | ** |
| 105 | ** | ** | *** |
| 106 | **** | * | ** |
| 107 | **** | **** | **** |
| 108 | **** | **** | **** |
| 109 | **** | **** | **** |
| 110 | **** | **** | **** |
| 111 | **** | **** | **** |
| 114 | **** | **** | **** |
| 115 | **** | **** | **** |
| 121 | **** | **** | **** |
| 123 | **** | **** | **** |
| 124 | **** | **** | **** |
| 126 | **** | **** | **** |
| 128 | *** | **** | **** |
| 132 | **** | **** | **** |
| 134 | **** | ** | **** |
| 138 | * | **** | * |
| 140 | **** | **** | **** |
| 141 | **** | **** | **** |
| 142 | ** | *** | **** |
| 144 | **** | **** | **** |
| 145 | **** | **** | **** |
| 146 | *** | **** | **** |
| 147 | **** | **** | **** |
| 148 | * | * | ** |
| 150 | **** | **** | **** |
| 151 | **** | **** | **** |
| 154 | **** | **** | **** |
| 155 | **** | **** | **** |
| 156 | **** | **** | **** |
| 157 | **** | **** | **** |
| 160 | **** | **** | ND |
| 177 | ND | **** | **** |
| 182 | ND | **** | **** |
| 185 | ND | *** | **** |
| 187 | ND | *** | **** |
| 246 | *** | ** | *** |
| 254 | * | * | *** |
| 256 | ** | *** | **** |
| 257 | *** | *** | **** |
| 258 | ** | *** | **** |
| 259 | *** | ** | **** |
| 260 | * | ** | *** |
| 261 | * | ** | **** |
| 262 | ** | ** | *** |
| 263 | ** | *** | *** |
| 264 | ** | *** | **** |
| 265 | * | ** | *** |
| 268 | * | ** | ** |
| 269 | **** | **** | **** |
| 270 | **** | **** | **** |

TABLE 6-continued

| Cpd | 49247 | 25238 | 13090 |
|---|---|---|---|
| 272 | **** | **** | **** |
| 273 | ND | *** | *** |
| 275 | **** | **** | **** |
| 277 | *** | *** | **** |
| 279 | ** | ** | * |
| 285 | **** | *** | **** |
| 296 | ** | ** | **** |
| 298 | ** | * | ** |
| 300 | * | **** | **** |
| 302 | **** | **** | **** |
| 304 | **** | **** | **** |
| 306 | **** | **** | **** |
| 310 | ND | * | ND |

Example 7

Combinations with Antibacterial Agents

The in vitro effects of Compound 269 in combination with ciprofloxacin were investigated in various organisms using the microdilution checkerboard method for the measurement of antibiotic synergy. Assays can be performed in a 96-well checkerboard titration format, with serial dilutions of each compound to identify the lowest MIC value (μg/mL) for each drug where the bacterial culture is completely inhibited. The ability of compounds to either act synergistically, additively, indifferently or antagonistically can be determined. Synergy is defined such that when the elements A and B are combined, the result is greater than the expected arithmetic sum A+B.

The calculated fractional inhibitory concentration (FIC) is a quantitative measure of drug interactions: where values ≤0.5=synergy, values between >0.5 and <2=additive, values between ≥2 and ≤4=indifference, and values >4=antagonism. Table 7 shows the MIC (μg/mL) for ciprofloxacin (Cipro), Compound 269 (Cpd 269), and the combination product (Cipro: 269). The FIC was calculated using the checkerboard method in a 96-well microtiter plate. Combinations that demonstrated no difference (Indiff) in the resulting activity and those that demonstrated synergistic (Syn) or additive (Add) activity are indicated.

TABLE 7

| Strain | Cipro MIC | Cpd 269 MIC | Cipro:269 MIC | FIC | Result |
|---|---|---|---|---|---|
| E. coli 25922 | 0.013 | 0.19 | 0.003:0.049 | 0.49 | Syn |
| E. coli 3111 | 125 | 3.1 | 125:3.1 | 2 | Indiff |
| A. baumannii BAA747 | 0.098 | 0.39 | 0.012:0.098 | 0.28 | Syn |
| A. baumannii (MDR) | 125 | 12.5 | 31.2:3.12 | 0.5 | Syn |
| K. pneumoniae 35657 | 0.01 | 0.39 | 0.0008:0.098 | 0.31 | Syn |
| P. aeruginosa 27853 | 0.2 | 1.6 | 0.012:0.78 | 0.56 | Add |
| S. aureus 29213 | 0.39 | 3.12 | 0.098:0.78 | 0.5 | Syn |
| S. aureus (MDR) | 31.2 | 6.2 | 7.8:3.1 | 0.75 | Add |

Results:

The results shown in Table 7 suggest that development of a combination therapy is an option to treat certain infections.

Combination therapy can be applied with any quinolone antibiotic including, without limitation, one or more of Ciprofloxacin, Enoxacin, Gatifloxacin, Levofloxacin, Lomefloxacin, Moxifloxacin, Nalidixic acid, Norfloxacin or Ofloxacin.

In addition, combination therapy can be applied with any non-quinolone antibiotic including, without limitation, one or more of Amikacin, Amoxicillin, Ampicillin, Arsphenamine, Azithromycin, Azlocillin, Aztreonam, Bacitracin, Capreomycin, Carbenicillin, Cefaclor, Cefadroxil, Cefalexin, Cefalotin (Cefalothin), Cefamandole, Cefazolin, Cefdinir, Cefditoren, Cefixime, Cefoperazone, Cefotaxime, Cefoxitin, Cefpodoxime, Cefprozil, Ceftazidime, Ceftibuten, Ceftizoxime, Ceftriaxone, Cefuroxime, Chloramphenicol, Cilastatin, Clarithromycin, Clavulanate, Clindamycin, Clofazimine, Cloxacillin, Colistin, Cycloserine, Dalfopristin, Dapsone, Daptomycin, Dicloxacillin, Dirithromycin, Doripenem, Doxycycline, Erythromycin, Ethambutol, Ethionamide, Flucloxacillin, Fosfomycin, Furazolidone, Fusidic acid, Gentamicin, Imipenem, Isoniazid, Kanamycin, Lincomycin, Linezolid, Loracarbef, Mafenide, Meropenem, Methicillin, Metronidazole, Mezlocillin, Minocycline, Mupirocin, Nafcillin, Neomycin, Netilmicin, Nitrofurantoin, Oxacillin, Oxytetracycline, Paromomycin, Penicillin G, Penicillin V, Piperacillin, Platensimycin, Polymyxin B, Pyrazinamide, Quinupristin, Rapamycin, Rifabutin, Rifampicin, Rifampin, Rifapentine, Rifaximin, Roxithromycin, Silver sulfadiazine, Spectinomycin, Streptomycin, Sulbactam, Sulfacetamide, Sulfadiazine, Sulfamethizole, Sulfamethoxazole, Sulfanilimide, Sulfasalazine, Sulfisoxazole, Tazobactam, Teicoplanin, Telavancin, Telithromycin, Temocillin, Tetracycline, Thiamphenicol, Ticarcillin, Tigecycline, Tinidazole, Tobramycin, Trimethoprim, Troleandomycin or Vancomycin.

Without regard to whether a document cited herein was specifically and individually indicated as being incorporated by reference, all documents referred to herein are incorporated by reference into the present application for any and all purposes to the same extent as if each individual reference was fully set forth herein.

Although certain embodiments have been described in detail above, those having ordinary skill in the art will clearly understand that many modifications are possible in the embodiments without departing from the teachings thereof. All such modifications are intended to be encompassed within the claims included herein.

What is claimed is:
1. A compound of Formula (I):

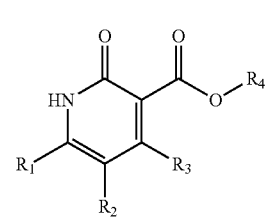

or a form thereof, wherein
$R_1$ is phenyl, optionally substituted with one, two or three substituents each selected from $R_5$ and one additional substituent selected from $R_6$;
$R_2$ is halogen, cyano, $C_{1-8}$alkyl, halo-$C_{1-8}$alkyl, hydroxyl-$C_{1-8}$alkyl, formyl-$C_{1-8}$alkyl, $C_{1-8}$alkoxy-$C_{1-8}$alkyl, $C_{2-8}$alkenyl, $C_{2-8}$alkynl, carboxyl, amino, $C_{1-8}$alkyl-amino, $(C_{1-8}$alkyl$)_2$-amino, amino-$C_{1-8}$alkyl, $C_{1-8}$alkyl-amino-$C_{1-8}$alkyl, $(C_{1-8}$alkyl$)_2$-amino-$C_{1-8}$alkyl, $C_{3-14}$cycloalkyl, $C_{3-8}$cycloalkyl-oxy, aryl or aryl-$C_{1-8}$alkyl, wherein each instance of aryl is optionally substituted with one halogen substituent;
$R_3$ is hydroxyl;
$R_4$ is hydrogen;

$R_5$ is halogen, hydroxyl, oxo, cyano, nitro, $C_{1-8}$alkyl, hydroxyl-$C_{1-8}$alkyl, halo-$C_{1-8}$alkyl, $C_{1-8}$alkoxy, halo-$C_{1-8}$alkoxy, $C_{1-8}$alkyl-thio, carboxyl, $C_{1-8}$alkyl-carbonyl, $C_{1-8}$alkoxy-carbonyl, amino-carbonyl, amino, $C_{1-8}$alkyl-amino, ($C_{1-8}$alkyl)$_2$-amino, $C_{2-8}$alkenyl-amino, ($C_{2-8}$alkenyl)$_2$-amino, $C_{2-8}$alkynyl-amino, ($C_{2-8}$alkynyl)$_2$-amino, amino-$C_{1-8}$alkyl, $C_{1-10}$alkyl-amino-$C_{1-8}$alkyl, ($C_{1-8}$alkyl)$_2$-amino-$C_{1-8}$alkyl, $C_{2-8}$alkenyl-amino-$C_{1-8}$alkyl, ($C_{2-8}$alkenyl)$_2$-amino-$C_{1-8}$alkyl, $C_{2-8}$alkynyl-amino-$C_{1-8}$alkyl, ($C_{2-8}$alkynyl)$_2$-amino-$C_{1-8}$alkyl, halo-$C_{1-8}$alkyl-amino, (halo-$C_{1-8}$alkyl)$_2$-amino, halo-$C_{1-8}$alkyl-amino-$C_{1-8}$alkyl, (halo-$C_{1-8}$alkyl)$_2$-amino-$C_{1-8}$alkyl, $C_{1-8}$alkoxy-$C_{1-8}$alkyl-amino, ($C_{1-8}$alkoxy-$C_{1-8}$alkyl,$C_{1-8}$alkyl)-amino, ($C_{1-8}$alkoxy-$C_{1-8}$alkyl)$_2$-amino, $C_{1-8}$alkoxy-$C_{1-8}$alkyl-amino-$C_{1-8}$alkyl, ($C_{1-8}$alkoxy-$C_{1-8}$alkyl,$C_{1-8}$alkyl)-amino-$C_{1-8}$alkyl, ($C_{1-8}$alkoxy-$C_{1-8}$alkyl)$_2$-amino-$C_{1-8}$alkyl, amino-$C_{1-8}$alkyl-amino, (amino-$C_{1-8}$alkyl,$C_{1-8}$alkyl)amino, $C_{1-8}$alkyl-amino-$C_{1-8}$alkyl-amino, ($C_{1-8}$alkyl-amino-$C_{1-8}$alkyl,$C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl,$C_{1-8}$alkyl]amino, amino-$C_{1-8}$alkyl-amino-$C_{1-8}$alkyl, (amino-$C_{1-8}$alkyl,$C_{1-8}$alkyl)amino-$C_{1-8}$alkyl, $C_{1-8}$alkyl-amino-$C_{1-8}$alkyl-amino-$C_{1-8}$alkyl, ($C_{1-8}$alkyl-amino-$C_{1-8}$alkyl,$C_{1-8}$alkyl)amino-$C_{1-8}$alkyl, ($C_{1-8}$alkyl)$_2$-amino-$C_{1-8}$alkyl-amino-$C_{1-8}$alkyl, [($C_{1-8}$alkyl)$_2$-amino-$C_{1-8}$alkyl,$C_{1-8}$alkyl]amino-$C_{1-8}$alkyl, hydroxyl-amino, hydroxyl-$C_{1-8}$alkyl-amino, (hydroxyl-$C_{1-8}$alkyl,$C_{1-8}$alkyl)amino, (hydroxyl-$C_{1-8}$alkyl)$_2$-amino, hydroxyl-$C_{1-8}$alkyl-amino-$C_{1-8}$alkyl, (hydroxyl-$C_{1-8}$alkyl,$C_{1-8}$alkyl)amino-$C_{1-8}$alkyl, hydroxyl-$C_{1-8}$alkyl-amino-$C_{1-8}$alkyl-amino, (hydroxyl-$C_{1-8}$alkyl-amino-$C_{1-8}$alkyl,$C_{1-8}$alkyl)amino, (hydroxyl-$C_{1-8}$alkyl,$C_{1-8}$alkyl)amino-$C_{1-8}$alkyl-amino, [(hydroxyl-$C_{1-8}$alkyl,$C_{1-8}$alkyl)amino-$C_{1-8}$alkyl,$C_{1-8}$alkyl]amino, ($C_{1-8}$alkyl-carbonyl,$C_{1-8}$alkyl)amino-$C_{1-8}$alkyl, $C_{1-8}$alkyl-amino-carbonyl, ($C_{1-8}$alkyl)$_2$-amino-carbonyl or ($C_{1-8}$alkyl)$_2$-amino-carbonyl-$C_{1-8}$alkyl-amino-$C_{1-8}$alkyl;

$R_6$ is $C_{3-14}$cycloalkyl, $C_{3-14}$cycloalkyl-$C_{1-8}$alkyl, $C_{3-14}$cycloalkyl-oxy, $C_{3-14}$cycloalkyl-$C_{1-8}$alkoxy, $C_{3-14}$cycloalkyl-amino, $C_{3-14}$cycloalkyl-amino-$C_{1-8}$alkyl, ($C_{3-14}$cycloalkyl,$C_{1-8}$alkyl)amino-$C_{1-8}$alkyl, ($C_{3-14}$cycloalkyl)$_2$-amino-$C_{1-8}$alkyl, $C_{3-14}$cycloalkyl-$C_{1-8}$alkyl-amino-$C_{1-8}$alkyl, ($C_{3-14}$cycloalkyl-$C_{1-8}$alkyl,$C_{1-8}$alkyl) amino-$C_{1-8}$alkyl, ($C_{3-14}$cycloalkyl-$C_{1-8}$alkyl)$_2$-amino-$C_{1-8}$alkyl, aryl, aryl-$C_{1-8}$alkyl, aryl-$C_{1-8}$alkoxy, aryl-amino, (aryl,$C_{1-8}$alkyl)amino, (aryl)$_2$-amino, aryl-amino-$C_{1-8}$alkyl, (aryl,$C_{1-8}$alkyl)amino-$C_{1-8}$alkyl, (aryl)$_2$-amino-$C_{1-8}$alkyl, aryl-$C_{1-8}$alkyl-amino, (aryl-$C_{1-8}$alkyl,$C_{1-8}$alkyl)amino, (aryl-$C_{1-8}$alkyl)$_2$-amino, aryl-$C_{1-8}$alkyl-amino-$C_{1-8}$alkyl, (aryl-$C_{1-8}$alkyl,$C_{1-8}$alkyl)amino-$C_{1-8}$alkyl, (aryl-$C_{1-8}$alkyl)$_2$-amino-$C_{1-8}$alkyl, heteroaryl, heteroaryl-$C_{1-8}$alkyl, heteroaryl-amino, heteroaryl-$C_{1-8}$alkyl-amino, (heteroaryl-$C_{1-8}$alkyl,$C_{1-8}$alkyl)amino, (heteroaryl-$C_{1-8}$alkyl)$_2$-amino, heteroaryl-$C_{1-8}$alkyl-amino-$C_{1-8}$alkyl, (heteroaryl-$C_{1-8}$alkyl,$C_{1-8}$alkyl)amino-$C_{1-8}$alkyl, heterocyclyl, heterocyclyl-$C_{1-8}$alkyl, heterocyclyl-oxy, heterocyclyl-$C_{1-8}$ alkoxy, heterocyclyl-amino, (heterocyclyl,$C_{1-8}$alkyl)amino, (heterocyclyl)$_2$-amino, heterocyclyl-amino-$C_{1-8}$alkyl, (heterocyclyl,$C_{1-8}$alkyl)amino-$C_{1-8}$alkyl, (heterocyclyl)$_2$-amino-$C_{1-8}$alkyl, (heterocyclyl,$C_{3-14}$cycloalkyl-$C_{1-8}$alkyl)amino-$C_{1-8}$alkyl, heterocyclyl-$C_{1-8}$alkyl-amino-$C_{1-8}$alkyl, (heterocyclyl-$C_{1-8}$alkyl,$C_{1-8}$alkyl)amino-$C_{1-8}$alkyl, (heterocyclyl-$C_{1-8}$alkyl)$_2$-amino-$C_{1-8}$alkyl, heterocyclyl-oxy-amino, (heterocyclyl-oxy,$C_{1-8}$alkyl)amino, (heterocyclyl-oxy)$_2$-amino, (heterocyclyl-oxy-$C_{1-8}$alkyl,$C_{1-8}$alkyl)amino, heterocyclyl-carbonyl or heterocyclyl-carbonyl-oxy;

wherein each instance of heterocyclyl is optionally substituted with one, two or three substituents each selected from $R_7$; and, wherein each instance of $C_{3-14}$cycloalkyl, aryl and heteroaryl is optionally substituted with one, two or three substituents each selected from $R_8$;

$R_7$ is azido, halogen, hydroxyl, oxo, cyano, nitro, $C_{1-8}$alkyl, halo-$C_{1-8}$alkyl, hydroxyl-$C_{1-8}$alkyl, $C_{1-8}$alkoxy-$C_{1-8}$alkyl, $C_{1-8}$ alkoxy, halo-$C_{1-8}$ alkoxy, hydroxyl-$C_{1-8}$alkoxy, carboxyl, $C_{1-8}$alkyl-carbonyl, $C_{1-8}$alkoxy-carbonyl, amino, $C_{1-8}$alkyl-amino, ($C_{1-8}$alkyl)$_2$-amino, halo-$C_{1-8}$alkyl-amino, (halo-$C_{1-8}$alkyl)$_2$-amino, halo-$C_{1-8}$alkyl-amino-$C_{1-8}$alkyl, (halo-$C_{1-8}$alkyl)$_2$-amino-$C_{1-8}$alkyl, amino-$C_{1-8}$alkyl, $C_{1-8}$alkyl-amino-$C_{1-8}$alkyl, ($C_{1-8}$alkyl)$_2$-amino-$C_{1-8}$alkyl, [($C_{1-8}$alkyl)$_2$-amino-$C_{1-8}$alkyl,$C_{1-8}$alkyl]amino-$C_{1-8}$alkyl $C_{1-8}$alkyl-thio, amino-carbonyl, $C_{1-8}$alkyl-amino-carbonyl, ($C_{1-8}$alkyl)$_2$-amino-carbonyl, $C_{1-8}$alkyl-carbonyl-amino, (carboxyl-$C_{1-8}$alkyl,$C_{1-8}$alkyl)amino-carbonyl-amino, $C_{3-14}$cycloalkyl, $C_{3-14}$cycloalkyl-amino, aryl, aryl-$C_{1-8}$alkyl, aryl-amino, (aryl,$C_{1-8}$alkyl)amino, (aryl)$_2$-amino, aryl-$C_{1-8}$alkyl-amino, (aryl-$C_{1-8}$alkyl,$C_{1-8}$alkyl)amino, (aryl-$C_{1-8}$alkyl)$_2$-amino, aryl-$C_{1-8}$alkyl-amino-$C_{1-8}$alkyl, (aryl-$C_{1-8}$alkyl,$C_{1-8}$alkyl)amino-$C_{1-8}$alkyl, (aryl-$C_{1-8}$alkyl)$_2$-amino-$C_{1-8}$alkyl, aryl-amino-$C_{1-8}$alkyl, (aryl,$C_{1-8}$alkyl)amino-$C_{1-8}$alkyl, (aryl)$_2$-amino-$C_{1-8}$alkyl, aryl-amino-carbonyl, aryl-$C_{1-8}$ alkoxy, aryl-$C_{1-8}$ alkoxy-carbonyl-amino, heteroaryl, heteroaryl-$C_{1-8}$alkyl, heteroaryl-amino, (heteroaryl)$_2$-amino, heteroaryl-$C_{1-8}$alkyl-amino, (heteroaryl-$C_{1-8}$alkyl,$C_{1-8}$alkyl)amino, (heteroaryl-$C_{1-8}$alkyl)$_2$-amino, heteroaryl-$C_{1-8}$alkyl-amino-$C_{1-8}$alkyl, (heteroaryl-$C_{1-8}$alkyl,$C_{1-8}$alkyl)amino-$C_{1-8}$alkyl, (heteroaryl-$C_{1-8}$alkyl)$_2$-amino-$C_{1-8}$alkyl, heterocyclyl, heterocyclyl-$C_{1-8}$alkyl, heterocyclyl-amino-$C_{1-8}$alkyl or heterocyclyl-oxy;

wherein each instance of $C_{3-14}$cycloalkyl is optionally substituted with one substituent selected from $R_9$;

wherein each instance of aryl is optionally substituted with one substituent selected from $R_{10}$; and, wherein each instance of heterocyclyl and heteroaryl is optionally substituted with one substituent selected from $R_{11}$;

$R_8$ is azido, halogen, hydroxyl, cyano, nitro, $C_{1-8}$alkyl, halo-$C_{1-8}$alkyl, $C_{1-8}$alkoxy, $C_{1-8}$alkoxy-$C_{1-8}$alkyl, halo-$C_{1-8}$alkoxy, carboxyl, $C_{1-8}$alkoxy-carbonyl, amino, $C_{1-8}$alkyl-amino, ($C_{1-8}$alkyl)$_2$-amino, $C_{1-8}$alkyl-thio, aryl, aryl-$C_{1-8}$alkoxy, heteroaryl, heterocyclyl, heterocyclyl-$C_{1-8}$alkyl or heterocyclyl-oxy;

$R_9$ is amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl or aryl-$C_{1-8}$alkyl-amino;

$R_{10}$ is halogen; and, $R_{11}$ is halogen, hydroxyl, $C_{1-8}$alkyl, halo-$C_{1-8}$alkyl, $C_{1-8}$alkoxy, $C_{1-8}$alkoxy-$C_{1-8}$alkyl, halo-$C_{1-8}$alkoxy, amino, $C_{1-8}$alkyl-amino or ($C_{1-8}$alkyl)$_2$-amino;

wherein the form of the compound is selected from a free acid, free base, hydrate, solvate, clathrate, isotopologue, racemate, enantiomer, diastereomer, stereoisomer, polymorph or tautomer form thereof.

2. The compound of claim 1, wherein

R$_2$ is cyano, C$_{1-8}$alkyl, halo-C$_{1-8}$alkyl, hydroxyl-C$_{1-8}$alkyl, formyl-C$_{1-8}$alkyl, C$_{1-8}$alkoxy-C$_{1-8}$alkyl, C$_{2-8}$alkenyl, C$_{2-8}$alkynl, carboxyl, C$_{3-14}$cycloalkyl, aryl or aryl-C$_{1-8}$alkyl, wherein each instance of aryl is optionally substituted with one halogen substituent;

R$_5$ is halogen, oxo, cyano, C$_{1-8}$alkyl, hydroxyl-C$_{1-8}$alkyl, C$_{1-8}$alkoxy, carboxyl, amino-carbonyl, amino, C$_{1-8}$alkyl-amino, (C$_{1-8}$alkyl)$_2$-amino, (C$_{2-8}$alkenyl)$_2$-amino, amino-C$_{1-8}$alkyl, C$_{1-10}$alkyl-amino-C$_{1-8}$alkyl, (C$_{1-8}$alkyl)$_2$-amino-C$_{1-8}$alkyl, C$_{2-8}$ alkenyl-amino-C$_{1-8}$alkyl, C$_{2-8}$alkynyl-amino-C$_{1-8}$alkyl, halo-C$_{1-8}$alkyl-amino, halo-C$_{1-8}$alkyl-amino-C$_{1-8}$alkyl, (hydroxyl-C$_{1-8}$alkyl,C$_{1-8}$alkyl)amino, (C$_{1-8}$alkoxy-C$_{1-8}$alkyl,C$_{1-8}$alkyl)-amino-C$_{1-8}$alkyl, (C$_{1-8}$alkyl)$_2$-amino-C$_{1-8}$alkyl-amino, [(C$_{1-8}$alkyl)$_2$-amino-C$_{1-8}$alkyl,C$_{1-8}$alkyl]amino, amino-C$_{1-8}$alkyl-amino-C$_{1-8}$alkyl, C$_{1-8}$alkyl-amino-C$_{1-8}$alkyl-amino-C$_{1-8}$alkyl, (C$_{1-8}$alkyl)$_2$-amino-C$_{1-8}$alkyl-amino-C$_{1-8}$alkyl, [(C$_{1-8}$alkyl)$_2$-amino-C$_{1-8}$alkyl,C$_{1-8}$alkyl]amino-C$_{1-8}$alkyl, (C$_{1-8}$alkyl-carbonyl,C$_{1-8}$alkyl)amino-C$_{1-8}$alkyl or (C$_{1-8}$alkyl)$_2$-amino-carbonyl-C$_{1-8}$alkyl-amino-C$_{1-8}$alkyl;

R$_6$ is C$_{3-14}$cycloalkyl-amino-C$_{1-8}$alkyl, (C$_{3-14}$cycloalkyl,C$_{1-8}$alkyl)amino-C$_{1-8}$alkyl, C$_{3-14}$cycloalkyl-C$_{1-8}$alkyl-amino-C$_{1-8}$alkyl, aryl, aryl-amino, (aryl,C$_{1-8}$alkyl) amino, aryl-amino-C$_{1-8}$alkyl, aryl-C$_{1-8}$alkyl-amino-C$_{1-8}$alkyl, (aryl-C$_{1-8}$alkyl,C$_{1-8}$alkyl)amino-C$_{1-8}$alkyl, (aryl-C$_{1-8}$alkyl)$_2$-amino-C$_{1-8}$alkyl, heteroaryl, heteroaryl-C$_{1-8}$alkyl-amino-C$_{1-8}$alkyl, (heteroaryl-C$_{1-8}$alkyl,C$_{1-8}$alkyl)amino-C$_{1-8}$alkyl, heterocyclyl, heterocyclyl-C$_{1-8}$alkyl, heterocyclyl-amino-C$_{1-8}$alkyl, (heterocyclyl,C$_{1-8}$alkyl)amino-C$_{1-8}$alkyl, (heterocyclyl,C$_{3-14}$cycloalkyl-C$_{1-8}$alkyl)amino-C$_{1-8}$alkyl, heterocyclyl-C$_{1-8}$alkyl-amino-C$_{1-8}$alkyl or (heterocyclyl-oxy-C$_{1-8}$alkyl,C$_{1-8}$alkyl)amino;

wherein each instance of heterocyclyl is optionally substituted with one, two or three substituents each selected from R$_7$; and, wherein each instance of heteroaryl is optionally substituted with one, two or three substituents each selected from R$_8$;

R$_7$ is azido, halogen, hydroxyl, oxo, cyano, C$_{1-8}$alkyl, halo-C$_{1-8}$alkyl, hydroxyl-C$_{1-8}$alkyl, C$_{1-8}$alkoxy-C$_{1-8}$alkyl, C$_{1-8}$alkoxy, carboxyl, C$_{1-8}$alkyl-carbonyl, C$_{1-8}$alkoxy-carbonyl, amino, C$_{1-8}$alkyl-amino, (C$_{1-8}$alkyl)$_2$-amino, amino-C$_{1-8}$alkyl, C$_{1-8}$alkyl-amino-C$_{1-8}$alkyl, (C$_{1-8}$alkyl)$_2$-amino-C$_{1-8}$alkyl, [(C$_{1-8}$alkyl)$_2$-amino-C$_{1-8}$alkyl,C$_{1-8}$alkyl]amino-C$_{1-8}$alkyl (C$_{1-8}$alkyl)$_2$-amino-carbonyl, C$_{1-8}$alkyl-carbonyl-amino, (carboxyl-C$_{1-8}$alkyl,C$_{1-8}$alkyl)amino-carbonyl-amino, C$_{3-14}$cycloalkyl, C$_{3-14}$cycloalkyl-amino, aryl, aryl-C$_{1-8}$alkyl, aryl-amino, (aryl,C$_{1-8}$alkyl)amino, aryl-C$_{1-8}$alkyl-amino, (aryl-C$_{1-8}$alkyl,C$_{1-8}$alkyl)amino, (aryl-C$_{1-8}$alkyl)$_2$-amino, aryl-C$_{1-8}$alkyl-amino-C$_{1-8}$alkyl, (aryl-C$_{1-8}$alkyl,C$_{1-8}$alkyl)amino-C$_{1-8}$alkyl, (aryl-C$_{1-8}$alkyl)$_2$-amino-C$_{1-8}$alkyl, aryl-amino-C$_{1-8}$alkyl, aryl-C$_{1-8}$alkoxy, aryl-C$_{1-8}$alkoxy-carbonyl-amino, heteroaryl, heteroaryl-C$_{1-8}$alkyl-amino-C$_{1-8}$alkyl, heterocyclyl, heterocyclyl-C$_{1-8}$alkyl, heterocyclyl-amino-C$_{1-8}$alkyl or heterocyclyl-oxy;

wherein each instance of C$_{3-14}$cycloalkyl is optionally substituted with one substituent selected from R$_9$;

wherein each instance of aryl is optionally substituted with one substituent selected from R$_{10}$; and, wherein each instance of heterocyclyl and heteroaryl is optionally substituted with one substituent selected from R$_{11}$;

R$_8$ is C$_{1-8}$alkyl;
R$_9$ is amino, (C$_{1-8}$alkyl)$_2$-amino or aryl-C$_{1-8}$alkyl-amino;
R$_{10}$ is halogen; and,
R$_{11}$ is C$_{1-8}$alkyl.

3. The compound of claim 1, wherein

R$_2$ is C$_{1-8}$alkyl selected from the group consisting of methyl, ethyl, propyl and isopropyl; hydroxyl-C$_{1-8}$alkyl selected from the group consisting of hydroxyl-methyl, hydroxyl-ethyl and hydroxyl-propyl; formyl-C$_{1-8}$alkyl selected from the group consisting of formylmethyl, formylethyl and formylpropyl; C$_{3-14}$cycloalkyl selected from the group consisting of cyclopropyl, cyclobutyl, cyclopentyl and cyclohexyl; aryl selected from phenyl; or, aryl-C$_{1-8}$alkyl selected from benzyl.

4. The compound of claim 1, wherein R$_6$ is

C$_{3-14}$cycloalkyl-amino-C$_{1-8}$alkyl, wherein C$_{3-14}$cycloalkyl is selected from the group consisting of cyclopropyl, cyclobutyl, cyclopentyl and cyclohexyl;

(C$_{3-14}$cycloalkyl,C$_{1-8}$alkyl)amino-C$_{1-8}$alkyl, wherein C$_{3-14}$cycloalkyl is selected from the group consisting of cyclopropyl, cyclobutyl and cyclopentyl;

C$_{3-14}$cycloalkyl-C$_{1-8}$alkyl-amino-C$_{1-8}$alkyl, wherein C$_{3-14}$cycloalkyl is selected from the group consisting of cyclopropyl, cyclobutyl, cyclopentyl, cyclohexyl and cycloheptyl;

aryl, wherein aryl is selected from phenyl;
aryl-C$_{1-8}$alkoxy, wherein aryl is selected from phenyl;
aryl-amino, wherein aryl is selected from phenyl;
(aryl,C$_{1-8}$alkyl)amino, wherein aryl is selected from phenyl;
aryl-amino-C$_{1-8}$alkyl, wherein aryl is selected from phenyl;
aryl-C$_{1-8}$alkyl-amino-C$_{1-8}$alkyl, wherein aryl is selected from phenyl;
(aryl-C$_{1-8}$alkyl,C$_{1-8}$alkyl)amino-C$_{1-8}$alkyl, wherein aryl is selected from phenyl;
(aryl-C$_{1-8}$alkyl)$_2$-amino-C$_{1-8}$alkyl, wherein aryl is selected from phenyl;
heteroaryl, wherein heteroaryl is selected from the group consisting of pyrrolyl, thiazolyl, 1H-1,2,3-triazolyl, 1H-tetrazolyl, 2H-tetrazolyl, imidazolyl and pyridinyl;
heteroaryl-C$_{1-8}$alkyl-amino-C$_{1-8}$alkyl, wherein heteroaryl is selected from the group consisting of pyridin-2-yl, pyridin-3-yl and pyridin-4-yl;
(heteroaryl-C$_{1-8}$alkyl,C$_{1-8}$alkyl)amino-C$_{1-8}$alkyl, wherein heteroaryl is selected from the group consisting of pyridin-3-yl and pyridin-4-yl;
heterocyclyl, wherein heterocyclyl is selected from the group consisting of azetidinyl, pyrrolidinyl, tetrahydrofuranyl, piperidinyl, piperazinyl, morpholinyl, 1,4-diazepanyl, 1,3-dioxolanyl, 2,5-dihydro-1H-pyrrolyl, dihydro-1H-imidazolyl, 1,4,5,6-tetrahydropyrimidinyl, 1,2,3,6-tetrahydropyridinyl, tetrahydro-2H-pyranyl, 3,4-dihydroisoquinolin-(1H)-yl, 1,2,3,4-tetrahydroisoquinolinyl, hexahydropyrrolo[3,4-b][1,4]oxazin-(2H)-yl, (4aR,7aS)-hexahydropyrrolo[3,4-b][1,4]oxazin-(4aH)-yl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, (3aR,6aR)-hexahydrocyclopenta[c]pyrrol- (1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-2(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, (1R,5S,6s)-3-azabicyclo[3.1.0]hexanyl, (cis,cis)-3-azabicyclo[3.1.0]hexanyl, 3,6-diazabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl and 2,8-diazaspiro[4.5]decanyl;

heterocyclyl-$C_{1-8}$alkyl, wherein heterocyclyl is selected from the group consisting of azetidinyl, pyrrolidinyl, tetrahydrofuranyl, piperidinyl, piperazinyl, morpholinyl, 1,4-diazepanyl, 1,3-dioxolanyl, 2,5-dihydro-1H-pyrrolyl, dihydro-1H-imidazolyl, 1,4,5,6-tetrahydropyrimidinyl, 1,2,3,6-tetrahydropyridinyl, tetrahydro-2H-pyranyl, 3,4-dihydroisoquinolin-(1H)-yl, 1,2,3,4-tetrahydroisoquinolinyl, hexahydropyrrolo[3,4-b][1,4]oxazin-(2H)-yl, (4aR,7aS)-hexahydropyrrolo[3,4-b][1,4]oxazin-(4aH)-yl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-2(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, (1R,5S,6s)-3-azabicyclo[3.1.0]hexanyl, (cis,cis)-3-azabicyclo[3.1.0]hexanyl, 3,6-diazabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl and 2,8-diazaspiro[4.5]decanyl;

heterocyclyl-amino-$C_{1-8}$alkyl, wherein heterocyclyl is selected from the group consisting of azetidin-1-yl and piperidin-4-yl;

(heterocyclyl,$C_{1-8}$alkyl)amino-$C_{1-8}$alkyl, wherein heterocyclyl is selected from the group consisting of piperidin-3-yl and piperidin-4-yl;

(heterocyclyl,$C_{3-14}$cycloalkyl-$C_{1-8}$alkyl)amino-$C_{1-8}$alkyl, wherein heterocyclyl is selected from the group consisting of piperidin-3-yl and piperidin-4-yl;

heterocyclyl-$C_{1-8}$alkyl-amino-$C_{1-8}$alkyl, wherein heterocyclyl is selected from the group consisting of pyrrolidin-2-yl, piperidin-2-yl, piperidin-3-yl, piperidin-4-yl and tetrahydro-2H-pyran-4-yl; or (heterocyclyl-oxy-$C_{1-8}$alkyl,$C_{1-8}$alkyl)amino selected from tetrahydro-2H-pyran-2-yl-oxy-$C_{1-8}$alkyl,$C_{1-8}$alkyl)amino.

5. The compound of claim 1, wherein $R_6$ is heteroaryl, wherein heteroaryl is selected from the group consisting of 1H-tetrazolyl, imidazolyl, pyrrolyl and 2H-tetrazolyl; or, heterocyclyl, wherein heterocyclyl is selected from the group consisting of azetidinyl, pyrrolidinyl, tetrahydrofuranyl, piperidinyl, piperazinyl, morpholinyl, 2,5-dihydro-1H-pyrrolyl, 1,2,3,6-tetrahydropyridinyl, hexahydropyrrolo[3,4-b][1,4]oxazin-(2H)-yl, (4aR,7aS)-hexahydropyrrolo[3,4-b][1,4]oxazin-(4aH)-yl, (3aR,6aR)-hexahydropyrrolo[3,4-b]pyrrol-(1H)-yl, (3aR,6aS)-hexahydropyrrolo[3,4-c]pyrrol-(1H)-yl, 5,7-dihydro-6H-pyrrolo[3,4-b]pyridinyl, octahydro-6H-pyrrolo[3,4-b]pyridinyl, (3aR,6aR)-hexahydrocyclopenta[c]pyrrol-3a(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-(1H)-yl, 1,3-dihydro-2H-isoindolyl, octahydro-2H-isoindolyl, (3aS)-1,3,3a,4,5,6-hexahydro-2H-isoindolyl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]hept-5-enyl, 3-azabicyclo[3.1.0]hexanyl, 3,6-diazabicyclo[3.1.0]hexanyl, (1R,5S,6s)-3-azabicyclo[3.1.0]hexanyl, (1S,5R,6R)-3-azabicyclo[3.2.0]heptanyl, (1S,5R,6S)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl and 2,8-diazaspiro[4.5]decanyl.

6. The compound of claim 1, wherein $R_6$ is heteroaryl, wherein heteroaryl is selected from the group consisting of 1H-tetrazol-5-yl, imidazol-1-yl, pyrrol-1-yl and 2H-tetrazol-2-yl; or, heterocyclyl, wherein heterocyclyl is selected from the group consisting of azetidin-1-yl, pyrrolidin-1-yl, tetrahydrofuran-2-yl, piperidin-1-yl, piperazin-1-yl, morpholin-4-yl, 2,5-dihydro-1H-pyrrol-1-yl, 1,2,3,6-tetrahydropyridin-4-yl, hexahydropyrrolo[3,4-b][1,4]oxazin-6(2H)-yl, (4aR,7aS)-hexahydropyrrolo[3,4-b][1,4]oxazin-4(4aH)-yl, (3aR,6aR)-hexahydropyrrolo[3,4-b]pyrrol-5(1H)-yl, (3aR,6aS)-hexahydropyrrolo[3,4-c]pyrrol-2(1H)-yl, 5,7-dihydro-6H-pyrrolo[3,4-b]pyridin-6-yl, octahydro-6H-pyrrolo[3,4-b]pyridin-6-yl, (3aR,6aR)-hexahydrocyclopenta[c]pyrrol-3a(1H)-yl, (3aR,4R,6aS)-hexahydrocyclopenta[c]pyrrol-2(1H)-yl, (3aR,4S,6aS)-hexahydrocyclopenta[c]pyrrol-2(1H)-yl, (3aR,5r,6aS)-hexahydrocyclopenta[c]pyrrol-2(1H)-yl, 1,3-dihydro-2H-isoindol-2-yl, octahydro-2H-isoindol-2-yl, (3aS)-1,3,3a,4,5,6-hexahydro-2H-isoindol-2-yl, (3aR,7aS)-octahydro-2H-isoindol-2-yl, (3aR,4R,7aS)-octahydro-2H-isoindol-2-yl, (3aR,4S,7aS)-octahydro-2H-isoindol-2-yl, 2,5-diazabicyclo[2.2.1]heptan-2-yl, 2-azabicyclo[2.2.1]hept-5-en-2-yl, 3-azabicyclo[3.1.0]hexan-3-yl, 3,6-diazabicyclo[3.1.0]hexan-3-yl, (1R,5S,6s)-3-azabicyclo[3.1.0]hexan-6-yl, (1R,5S,6s)-3-azabicyclo[3.1.0]hexan-6-yl, (1S,5R,6R)-3-azabicyclo[3.2.0]heptan-3-yl, (1S,5R,6S)-3-azabicyclo[3.2.0]

heptan-3-yl, 5-azaspiro[2.4]heptan-5-yl, 2,6-diazaspiro[3.3]heptan-2-yl, 2,5-diazaspiro[3.4]octan-2-yl, 2,6-diazaspiro[3.4]octan-6-yl, 2,7-diazaspiro[3.5]nonan-2-yl, 2,7-diazaspiro[4.4]nonan-2-yl, 2-azaspiro[4.5]decan-2-yl and 2,8-diazaspiro[4.5]decan-2-yl.

7. The compound of claim 1, wherein $R_7$ is
$C_{3-14}$cycloalkyl, wherein $C_{3-14}$cycloalkyl is selected from the group consisting of cyclopropyl and cyclobutyl;
$C_{3-14}$cycloalkyl-amino, wherein $C_{3-14}$cycloalkyl is selected from cyclopropyl;
aryl, wherein aryl is selected from phenyl;
aryl-$C_{1-8}$alkyl, wherein aryl is selected from phenyl;
aryl-amino, wherein aryl is selected from phenyl;
(aryl,$C_{1-8}$alkyl)amino, wherein aryl is selected from phenyl;
aryl-$C_{1-8}$alkyl-amino, wherein aryl is selected from phenyl;
(aryl-$C_{1-8}$alkyl,$C_{1-8}$alkyl)amino, wherein aryl is selected from phenyl;
(aryl-$C_{1-8}$alkyl)$_2$-amino, wherein aryl is selected from phenyl;
aryl-$C_{1-8}$alkyl-amino-$C_{1-8}$alkyl, wherein aryl is selected from phenyl;
(aryl-$C_{1-8}$alkyl,$C_{1-8}$alkyl)amino-$C_{1-8}$alkyl, wherein aryl is selected from phenyl;
(aryl-$C_{1-8}$alkyl)$_2$-amino-$C_{1-8}$alkyl, wherein aryl is selected from phenyl;
aryl-$C_{1-8}$alkoxy, wherein aryl is selected from phenyl;
aryl-$C_{1-8}$alkoxy-carbonyl-amino, wherein aryl is selected from phenyl;
heteroaryl, wherein heteroaryl is selected from the group consisting of pyridin-2-yl, pyridin-4-yl, thiazol-2-yl and 1H-1,2,3-triazol-1-yl;
heteroaryl-$C_{1-8}$alkyl-amino-$C_{1-8}$alkyl, wherein heteroaryl is selected from the group consisting of pyridin-2-yl, pyridin-3-yl and pyridin-4-yl;
heterocyclyl, wherein heterocyclyl is selected from the group consisting of pyrrolidin-1-yl and morpholin-4-yl;
heterocyclyl-$C_{1-8}$alkyl, wherein heterocyclyl is selected from pyrrolidin-1-yl; or, heterocyclyl-oxy, wherein heterocyclyl is selected from tetrahydro-2H-pyran-2-yloxy.

8. The compound of claim 1, wherein the compound of Formula (I) is a compound of Formula (Ia):

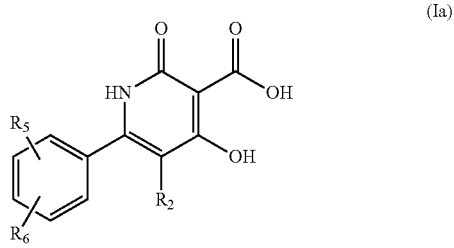

(Ia)

or a form thereof; wherein the form of the compound is selected from a free acid, free base, hydrate, solvate, clathrate, isotopologue, racemate, enantiomer, diastereomer, stereoisomer, polymorph or tautomer form thereof.

9. The compound of claim 1, wherein the compound or a form thereof is selected from the group consisting of:
5-benzyl-6-[4-(dimethylamino)phenyl]-4-hydroxy-2-oxo-1,2-dihydropyridine-3-carboxylic acid
6-[4-(dimethylamino)phenyl]-4-hydroxy-5-methyl-2-oxo-1,2-dihydropyridine-3-carboxylic acid
5-cyclohexyl-6-[4-(dimethylamino)phenyl]-4-hydroxy-2-oxo-1,2-dihydropyridine-3-carboxylic acid
6-[4-(dimethylamino)phenyl]-4-hydroxy-2-oxo-5-propyl-1,2-dihydropyridine-3-carboxylic acid
5-cyclopropyl-6-[4-(dimethylamino)phenyl]-4-hydroxy-2-oxo-1,2-dihydropyridine-3-carboxylic acid
5-ethyl-4-hydroxy-6-{4-[(2-hydroxyethyl)(methyl)amino]phenyl}-2-oxo-1,2-dihydropyridine-3-carboxylic acid
5-ethyl-4-hydroxy-6-(4-methylphenyl)-2-oxo-1,2-dihydropyridine-3-carboxylic acid
5-ethyl-4-hydroxy-2-oxo-6-[2-(piperidin-1-yl)phenyl]-1,2-dihydropyridine-3-carboxylic acid
5-ethyl-4-hydroxy-6-(4-methoxy-2-methylphenyl)-2-oxo-1,2-dihydropyridine-3-carboxylic acid
6-(2,4-dimethoxyphenyl)-5-ethyl-4-hydroxy-2-oxo-1,2-dihydropyridine-3-carboxylic acid
5-ethyl-4-hydroxy-6-[2-methyl-4-(pyrrolidin-1-yl)phenyl]-2-oxo-1,2-dihydropyridine-3-carboxylic acid
5-ethyl-4-hydroxy-2-oxo-6-(2,4,6-trimethoxyphenyl)-1,2-dihydropyridine-3-carboxylic acid
5-ethyl-4-hydroxy-2-oxo-6-(2,3,4-trimethoxyphenyl)-1,2-dihydropyridine-3-carboxylic acid
5-ethyl-6-[2-fluoro-4-(piperidin-1-yl)phenyl]-4-hydroxy-2-oxo-1,2-dihydropyridine-3-carboxylic acid
5-ethyl-4-hydroxy-6-[2-methoxy-4-(pyrrolidin-1-yl)phenyl]-2-oxo-1,2-dihydropyridine-3-carboxylic acid
5-ethyl-4-hydroxy-2-oxo-6-[2-(pyrrolidin-1-yl)phenyl]-1,2-dihydropyridine-3-carboxylic acid
5-ethyl-4-hydroxy-6-[4-methoxy-2-(pyrrolidin-1-yl)phenyl]-2-oxo-1,2-dihydropyridine-3-carboxylic acid
5-ethyl-4-hydroxy-6-[2-methoxy-4-(piperidin-1-yl)phenyl]-2-oxo-1,2-dihydropyridine-3-carboxylic acid
5-ethyl-4-hydroxy-6-[2-methyl-4-(piperidin-1-yl)phenyl]-2-oxo-1,2-dihydropyridine-3-carboxylic acid
6-[4-(dimethylamino)-2-fluorophenyl]-5-ethyl-4-hydroxy-2-oxo-1,2-dihydropyridine-3-carboxylic acid
6-[4-(dimethylamino)-2-methylphenyl]-5-ethyl-4-hydroxy-2-oxo-1,2-dihydropyridine-3-carboxylic acid
6-[2-(dimethylamino)phenyl]-5-ethyl-4-hydroxy-2-oxo-1,2-dihydropyridine-3-carboxylic acid
6-[2-(dimethylamino)-4-methoxyphenyl]-5-ethyl-4-hydroxy-2-oxo-1,2-dihydropyridine-3-carboxylic acid
6-[4-(dimethylamino)-2-methoxyphenyl]-5-ethyl-4-hydroxy-2-oxo-1,2-dihydropyridine-3-carboxylic acid
6-[4-(dimethylamino)-3-methylphenyl]-5-ethyl-4-hydroxy-2-oxo-1,2-dihydropyridine-3-carboxylic acid
6-[4-(dimethylamino)-3-methoxyphenyl]-5-ethyl-4-hydroxy-2-oxo-1,2-dihydropyridine-3-carboxylic acid
5-ethyl-4-hydroxy-6-[3-methoxy-4-(pyrrolidin-1-yl)phenyl]-2-oxo-1,2-dihydropyridine-3-carboxylic acid
5-ethyl-4-hydroxy-6-[3-methoxy-4-(piperidin-1-yl)phenyl]-2-oxo-1,2-dihydropyridine-3-carboxylic acid
5-ethyl-4-hydroxy-6-[3-methyl-4-(pyrrolidin-1-yl)phenyl]-2-oxo-1,2-dihydropyridine-3-carboxylic acid
5-ethyl-4-hydroxy-6-[3-methyl-4-(piperidin-1-yl)phenyl]-2-oxo-1,2-dihydropyridine-3-carboxylic acid
5-ethyl-6-(4-fluorophenyl)-4-hydroxy-2-oxo-1,2-dihydropyridine-3-carboxylic acid
6-(4-chlorophenyl)-5-ethyl-4-hydroxy-2-oxo-1,2-dihydropyridine-3-carboxylic acid
6-(4-bromophenyl)-5-ethyl-4-hydroxy-2-oxo-1,2-dihydropyridine-3-carboxylic acid
5-ethyl-4-hydroxy-6-(4-iodophenyl)-2-oxo-1,2-dihydropyridine-3-carboxylic acid 5-ethyl-4-hydroxy-6-{4-[(3-iodopropyl)amino]phenyl}-2-oxo-1,2-dihydropyridine-3-carboxylic acid
6-[4-(azetidin-1-yl)phenyl]-5-ethyl-4-hydroxy-2-oxo-1,2-dihydropyridine-3-carboxylic acid
5-ethyl-6-{4-[(3 S)-3-fluoropyrrolidin-1-yl]phenyl}-4-hydroxy-2-oxo-1,2-dihydropyridine-3-carboxylic acid
6-[4-(dimethylamino)phenyl]-5-ethyl-4-hydroxy-2-oxo-1,2-dihydropyridine-3-carboxylic acid
6-[4-(dimethylamino)-3-fluorophenyl]-5-ethyl-4-hydroxy-2-oxo-1,2-dihydropyridine-3-carboxylic acid
6-[4-(dimethylamino)phenyl]-4-hydroxy-2-oxo-5-(propan-2-yl)-1,2-dihydropyridine-3-carboxylic acid
6-[4-(diethylamino)phenyl]-5-ethyl-4-hydroxy-2-oxo-1,2-dihydropyridine-3-carboxylic acid
5-ethyl-4-hydroxy-2-oxo-6-[4-(pyrrolidin-1-yl)phenyl]-1,2-dihydropyridine-3-carboxylic acid
6-{4-[4-(tert-butoxycarbonyl)piperazin-1-yl]phenyl}-5-ethyl-4-hydroxy-2-oxo-1,2-dihydropyridine-3-carboxylic acid
5-ethyl-4-hydroxy-6-[4-(1H-imidazol-1-yl)phenyl]-2-oxo-1,2-dihydropyridine-3-carboxylic acid
5-ethyl-4-hydroxy-2-oxo-6-[4-(piperidin-1-yl)phenyl]-1,2-dihydropyridine-3-carboxylic acid
5-ethyl-4-hydroxy-2-oxo-6-[4-(2-oxopyrrolidin-1-yl)phenyl]-1,2-dihydropyridine-3-carboxylic acid
5-ethyl-4-hydroxy-6-{4-[(3R)-3-hydroxypyrrolidin-1-yl]phenyl}-2-oxo-1,2-dihydropyridine-3-carboxylic acid
5-ethyl-4-hydroxy-6-{4-[(3R)-3-hydroxypiperidin-1-yl]phenyl}-2-oxo-1,2-dihydropyridine-3-carboxylic acid
5-ethyl-4-hydroxy-6-[4-(3-hydroxypyrrolidin-1-yl)phenyl]-2-oxo-1,2-dihydropyridine-3-carboxylic acid
6-(4-{3-[1-(dimethylamino)cyclopropyl]pyrrolidin-1-yl}phenyl)-5-ethyl-4-hydroxy-2-oxo-1,2-dihydropyridine-3-carboxylic acid
6-{4-[(3aR,5r,6aS)-5-aminohexahydrocyclopenta[c]pyrrol-2(1H)-yl]phenyl}-5-ethyl-4-hydroxy-2-oxo-1,2-dihydropyridine-3-carboxylic acid
6-(4-{(3S,4R)-3-[(dibenzylamino)methyl]-4-methylpyrrolidin-1-yl}phenyl)-5-ethyl-4-hydroxy-2-oxo-1,2-dihydropyridine-3-carboxylic acid
6-{4-[(3aR,5r,6aS)-5-(benzylamino)hexahydrocyclopenta[c]pyrrol-2(1H)-yl]phenyl}-5-ethyl-4-hydroxy-2-oxo-1,2-dihydropyridine-3-carboxylic acid
6-{4-[(3aR,5r,6aS)-5-(dibenzylamino)hexahydrocyclopenta[c]pyrrol-2(1H)-yl]phenyl}-5-ethyl-4-hydroxy-2-oxo-1,2-dihydropyridine-3-carboxylic acid
6-{4-[1-(tert-butoxycarbonyl)octahydro-6H-pyrrolo[3,4-b]pyridin-6-yl]phenyl}-5-ethyl-4-hydroxy-2-oxo-1,2-dihydropyridine-3-carboxylic acid
6-[4-(3-{[benzyl(methyl)amino]methyl}pyrrolidin-1-yl)phenyl]-5-ethyl-4-hydroxy-2-oxo-1,2-dihydropyridine-3-carboxylic acid
5-ethyl-4-hydroxy-6-[4-(4-hydroxypiperidin-1-yl)phenyl]-2-oxo-1,2-dihydropyridine-3-carboxylic acid
6-{4-[4-(benzyloxy)piperidin-1-yl]phenyl}-5-ethyl-4-hydroxy-2-oxo-1,2-dihydropyridine-3-carboxylic acid
5-ethyl-4-hydroxy-6-[4-(4-methoxypiperidin-1-yl)phenyl]-2-oxo-1,2-dihydropyridine-3-carboxylic acid
6-{4-[4-(dibenzylamino)piperidin-1-yl]phenyl}-5-ethyl-4-hydroxy-2-oxo-1,2-dihydropyridine-3-carboxylic acid
6-[4-(4-aminopiperidin-1-yl)phenyl]-5-ethyl-4-hydroxy-2-oxo-1,2-dihydropyridine-3-carboxylic acid
6-{4-[(1R,5S,6s)-6-amino-3-azabicyclo[3.1.0]hex-3-yl]phenyl}-5-ethyl-4-hydroxy-2-oxo-1,2-dihydropyridine-3-carboxylic acid
5-ethyl-4-hydroxy-2-oxo-6-{4-[3-(pyridin-2-yl)pyrrolidin-1-yl]phenyl}-1,2-dihydropyridine-3-carboxylic acid
5-ethyl-4-hydroxy-2-oxo-6-{4-[3-(1H-1,2,3-triazol-1-yl)pyrrolidin-1-yl]phenyl}-1,2-dihydropyridine-3-carboxylic acid
5-ethyl-6-[4-(3-ethyl-3-hydroxypyrrolidin-1-yl)phenyl]-4-hydroxy-2-oxo-1,2-dihydropyridine-3-carboxylic acid
5-ethyl-4-hydroxy-6-[4-(3-hydroxy-3-methylpyrrolidin-1-yl)phenyl]-2-oxo-1,2-dihydropyridine-3-carboxylic acid
6-{4-[3-(aminomethyl)-3-methylpyrrolidin-1-yl]phenyl}-5-ethyl-4-hydroxy-2-oxo-1,2-dihydropyridine-3-carboxylic acid
6-{4-[3-(dimethylamino)pyrrolidin-1-yl]-2-fluorophenyl}-5-ethyl-4-hydroxy-2-oxo-1,2-dihydropyridine-3-carboxylic acid
5-ethyl-6-{2-fluoro-4-[(3R)-3-hydroxypyrrolidin-1-yl]phenyl}-4-hydroxy-2-oxo-1,2-dihydropyridine-3-carboxylic acid
5-ethyl-6-{2-fluoro-4-[(3R)-3-fluoropyrrolidin-1-yl]phenyl}-4-hydroxy-2-oxo-1,2-dihydropyridine-3-carboxylic acid
6-{4-[5-(tert-butoxycarbonyl)-2,5-diazabicyclo[2.2.1]hept-2-yl]phenyl}-5-ethyl-4-hydroxy-2-oxo-1,2-dihydropyridine-3-carboxylic acid
6-{4-[di(prop-2-en-1-yl)amino]phenyl}-5-ethyl-4-hydroxy-2-oxo-1,2-dihydropyridine-3-carboxylic acid
6-[4-(2,5-dihydro-1H-pyrrol-1-yl)phenyl]-5-ethyl-4-hydroxy-2-oxo-1,2-dihydropyridine-3-carboxylic acid
6-{4-[(3R,4S)-3,4-dihydroxypyrrolidin-1-yl]phenyl}-5-ethyl-4-hydroxy-2-oxo-1,2-dihydropyridine-3-carboxylic acid
6-(4-((1R,5S,6s)-6-amino-3-azabicyclo[3.1.0]hexan-3-yl)-2-methylphenyl)-4-hydroxy-5-methyl-2-oxo-1,2-dihydropyridine-3-carboxylic acid
5-ethyl-4-hydroxy-6-(4-(7-methyl-2,7-diazaspiro[3.5]nonan-2-yl)phenyl)-2-oxo-1,2-dihydropyridine-3-carboxylic acid
6-(4-(2,7-diazaspiro[3.5]nonan-2-yl)phenyl)-5-ethyl-4-hydroxy-2-oxo-1,2-dihydropyridine-3-carboxylic acid
6-(4-(2,7-diazaspiro[4.4]nonan-2-yl)phenyl)-5-ethyl-4-hydroxy-2-oxo-1,2-dihydropyridine-3-carboxylic acid
5-ethyl-4-hydroxy-6-(4-(7-methyl-2,7-diazaspiro[4.4]nonan-2-yl)phenyl)-2-oxo-1,2-dihydropyridine-3-carboxylic acid
6-(4-(2,5-diazaspiro[3.4]octan-2-yl)phenyl)-5-ethyl-4-hydroxy-2-oxo-1,2-dihydropyridine-3-carboxylic acid
6-(4-(2,6-diazaspiro[3.3]heptan-2-yl)phenyl)-5-ethyl-4-hydroxy-2-oxo-1,2-dihydropyridine-3-carboxylic acid
5-ethyl-6-(4-(ethylamino)phenyl)-4-hydroxy-2-oxo-1,2-dihydropyridine-3-carboxylic acid
5-ethyl-4-hydroxy-6-(4-(methylamino)phenyl)-2-oxo-1,2-dihydropyridine-3-carboxylic acid
6-(4-(dimethylamino)phenyl)-4-hydroxy-2-oxo-5-(2-oxoethyl)-1,2-dihydropyridine-3-carboxylic acid
6-(4-(dimethylamino)phenyl)-4-hydroxy-5-(2-hydroxyethyl)-2-oxo-1,2-dihydropyridine-3-carboxylic acid
5-(2,3-dihydroxypropyl)-6-(4-(dimethylamino)phenyl)-4-hydroxy-2-oxo-1,2-dihydropyridine-3-carboxylic acid
(E)-6-(4-(dimethylamino)phenyl)-4-hydroxy-2-oxo-5-(prop-1-enyl)-1,2-dihydropyridine-3-carboxylic acid
6-(4-(dimethylamino)phenyl)-4-hydroxy-5-(hydroxymethyl)-2-oxo-1,2-dihydropyridine-3-carboxylic acid 6-(4-(dimethylamino)phenyl)-4-hydroxy-5-(methoxymethyl)-2-oxo-1,2-dihydropyridine-3-carboxylic acid 6-(4-(dimethylamino)phenyl)-4-hydroxy-2-oxo-5-(prop-1-ynyl)-1,2-dihydropyridine-3-carboxylic acid 5-ethyl-4-hydroxy-6-(4-hydroxyphenyl)-2-oxo-1,2-dihydropyridine-3-carboxylic acid 5-ethyl-4-hydroxy-6-(4-(1-methylpiperidin-4-yl)phenyl)-2-oxo-1,2-dihydropyridine-3-carboxylic acid 5-ethyl-6-(4-(1-ethylpiperidin-4-yl)phenyl)-4-hydroxy-2-oxo-1,2-dihydropyridine-3-carboxylic acid 5-ethyl-4-hydroxy-2-oxo-6-(4-(1,2,3,6-tetrahydropyridin-4-yl)phenyl)-1,2-dihydropyridine-3-carboxylic acid 5-ethyl-6-(4-(1-ethyl-1,2,3,6-tetrahydropyridin-4-yl)phenyl)-4-hydroxy-2-oxo-1,2-dihydropyridine-3-carboxylic acid 5-ethyl-4-hydroxy-6-(4-(1-methyl-1,2,3,6-tetrahydropyridin-4-yl)phenyl)-2-oxo-1,2-dihydropyridine-3-carboxylic acid, and 6-(4-(2-(dimethylamino)ethyl)phenyl)-5-ethyl-4-hydroxy-2-oxo-1,2-dihydropyridine-3-carboxylic acid wherein the form of the compound is selected from a free acid, free base, salt, hydrate, solvate, clathrate, isotopologue, racemate, enantiomer, diastereomer, stereoisomer, polymorph or tautomer form thereof.

10. The compound of claim 1, wherein the compound or a form thereof is selected from the group consisting of:

5-ethyl-4-hydroxy-2-oxo-6-[4-(piperazin-1-yl)phenyl]-1,2-dihydropyridine-3-carboxylic acid trifluoroacetate 5-ethyl-6-{4-[(3aR,6aR)-hexahydropyrrolo[3,4-b]pyrrol-5(1H)-yl]phenyl}-4-hydroxy-2-oxo-1,2-dihydropyridine-3-carboxylic acid hydrochloride 6-[4-(7-amino-5-azaspiro[2.4]hept-5-yl)phenyl]-5-ethyl-4-hydroxy-2-oxo-1,2-dihydropyridine-3-carboxylic acid trifluoroacetate 5-ethyl-4-hydroxy-6-(4-{3-[(methylamino)methyl]pyrrolidin-1-yl}phenyl)-2-oxo-1,2-dihydropyridine-3-carboxylic acid hydrochloride 5-ethyl-4-hydroxy-6-{4-[(3aR,4R,6aS)-4-(methylamino)hexahydrocyclopenta[c]pyrrol-2(1H)-yl]phenyl}-2-oxo-1,2-dihydropyridine-3-carboxylic acid hydrochloride 6-[4-(1,3'-bipyrrolidin-1'-yl)phenyl]-5-ethyl-4-hydroxy-2-oxo-1,2-dihydropyridine-3-carboxylic acid hydrochloride 6-{4-[(3aR,4S,7aS)-4-aminooctahydro-2H-isoindol-2-yl]phenyl}-5-ethyl-4-hydroxy-2-oxo-1,2-dihydropyridine-3-carboxylic acid hydrochloride 6-{4-[(1R,5S,6s)-6-amino-3-azabicyclo[3.1.0]hex-3-yl]phenyl}-4-hydroxy-5-methyl-2-oxo-1,2-dihydropyridine-3-carboxylic acid hydrochloride 4-hydroxy-5-methyl-6-{4-[(3aR,4R,7aS)-4-(methylamino)octahydro-2H-isoindol-2-yl]phenyl}-2-oxo-1,2-dihydropyridine-3-carboxylic acid hydrochloride 6-{4-[(3aR,4R,7aS)-4-(dimethylamino)octahydro-2H-isoindol-2-yl]phenyl}-5-ethyl-4-hydroxy-2-oxo-1,2-dihydropyridine-3-carboxylic acid hydrochloride 6-{4-[(3aR,4R,7aS)-4-aminooctahydro-2H-isoindol-2-yl]phenyl}-5-ethyl-4-hydroxy-2-oxo-1,2-dihydropyridine-3-carboxylic acid trifluoroacetate 6-{4-[(3aR,4R,6aS)-4-(dimethylamino)hexahydrocyclopenta[c]pyrrol-2(1H)-yl]phenyl}-5-ethyl-4-hydroxy-2-oxo-1,2-dihydropyridine-3-carboxylic acid hydrochloride 6-{4-[(3aR,4R,6aS)-4-aminohexahydrocyclopenta[c]pyrrol-2(1H)-yl]phenyl}-5-ethyl-4-hydroxy-2-oxo-1,2-dihydropyridine-3-carboxylic acid trifluoroacetate 6-{4-[(3aR,4S,6aS)-4-aminohexahydrocyclopenta[c]pyrrol-2(1H)-yl]phenyl}-5-ethyl-4-hydroxy-2-oxo-1,2-dihydropyridine-3-carboxylic acid trifluoroacetate 6-{4-{(3aR,7aS)-3a-[(dimethylamino)methyl]octahydro-2H-isoindol-2-yl}phenyl)-5-ethyl-4-hydroxy-2-oxo-1,2-dihydropyridine-3-carboxylic acid hydrochloride 5-ethyl-4-hydroxy-6-{4-[(3aR,4S,6aS)-4-(methylamino)hexahydrocyclopenta[c]pyrrol-2(1H)-yl]phenyl}-2-oxo-1,2-dihydropyridine-3-carboxylic acid hydrochloride 5-ethyl-4-hydroxy-6-{4-[(3aR,4S,7aS)-4-(methylamino)octahydro-2H-isoindol-2-yl]phenyl}-2-oxo-1,2-dihydropyridine-3-carboxylic acid hydrochloride 6-{4-[(1R,5S,6s)-6-amino-3-azabicyclo[3.1.0]hex-3-yl]phenyl}-5-ethyl-4-hydroxy-2-oxo-1,2-dihydropyridine-3-carboxylic acid hydrochloride 5-ethyl-4-hydroxy-6-{4-[(1R,5S,6s)-6-(methylamino)-3-azabicyclo[3.1.0]hex-3-yl]phenyl}-2-oxo-1,2-dihydropyridine-3-carboxylic acid hydrochloride 6-{4-[(1R,5S,6s)-6-(dimethylamino)-3-azabicyclo[3.1.0]hex-3-yl]phenyl}-5-ethyl-4-hydroxy-2-oxo-1,2-dihydropyridine-3-carboxylic acid hydrochloride 5-ethyl-4-hydroxy-6-[4-(octahydro-6H-pyrrolo[3,4-b]pyridin-6-yl)phenyl]-2-oxo-1,2-dihydropyridine-3-carboxylic acid hydrochloride 5-ethyl-4-hydroxy-6-{4-[(3aR,6aS)-5-methylhexahydropyrrolo[3,4-c]pyrrol-2(1H)-yl]phenyl}-2-oxo-1,2-dihydropyridine-3-carboxylic acid hydrochloride 5-ethyl-6-{4-[(3aR,6aS)-hexahydropyrrolo[3,4-c]pyrrol-2(1H)-yl]phenyl}-4-hydroxy-2-oxo-1,2-dihydropyridine-3-carboxylic acid hydrochloride 6-{4-[3-(dimethylamino)pyrrolidin-1-yl]phenyl}-5-ethyl-4-hydroxy-2-oxo-1,2-dihydropyridine-3-carboxylic acid hydrochloride 6-[4-(3a-cyanooctahydro-2H-isoindol-2-yl)phenyl]-5-ethyl-4-hydroxy-2-oxo-1,2-dihydropyridine-3-carboxylic acid trifluoroacetate 6-[4-(1-amino-3-azabicyclo[3.1.0]hex-3-yl)phenyl]-5-ethyl-4-hydroxy-2-oxo-1,2-dihydropyridine-3-carboxylic acid hydrochloride 6-[4-(2,8-diazaspiro[4.5]dec-2-yl)phenyl]-5-ethyl-4-hydroxy-2-oxo-1,2-dihydropyridine-3-carboxylic acid hydrochloride 6-{4-[3-(2-aminopropan-2-yl)pyrrolidin-1-yl]phenyl}-5-ethyl-4-hydroxy-2-oxo-1,2-dihydropyridine-3-carboxylic acid hydrochloride 6-[4-(2,5-diazabicyclo[2.2.1]hept-2-yl)phenyl]-5-ethyl-4-hydroxy-2-oxo-1,2-dihydropyridine-3-carboxylic acid trifluoroacetate 5-ethyl-4-hydroxy-6-{4-[(3aR,4R,7aS)-4-(methylamino)octahydro-2H-isoindol-2-yl]phenyl}-2-oxo-1,2-dihydropyridine-3-carboxylic acid hydrochloride, and 5-ethyl-6-{4-[(3 aS)-1,3,3a,4,5,6-hexahydro-2H-isoindol-2-yl]phenyl}-4-hydroxy-2-oxo-1,2-dihydropyridine-3-carboxylic acid hydrochloride;

wherein the form of the compound is selected from a free acid, free base, hydrate, solvate, clathrate, isotopologue, racemate, enantiomer, diastereomer, stereoisomer, polymorph or tautomer form thereof.

11. A method of treating a bacterial infection in a subject in need thereof comprising administering an effective amount of a compound of claim 1 to the subject, wherein the bacterial infection results from a bacteria of the phyla selected from the group consisting of Acidobacteria; Actinobacteria; Aquificae; Bacteroidetes; Caldiserica; Chlamydiae; Chlorobi; Chloroflexi; Chrysiogenetes; Cyanobacteria; Deferribacteres; Deinococcus-Thermus; Dictyoglomi;

Elusimicrobia; Fibrobacteres; Firmicutes; Fusobacteria; Gemmatimonadetes; Lentisphaerae; Nitrospira; Planctomycetes; Proteobacteria; Spirochaetes; Synergistetes; Tenericutes; Thermodesulfobacteria; Thermomicrobia; Thermotogae; and Verrucomicrobia.

12. The method of claim 11, wherein the bacterial infection results from a bacteria of the phyla selected from the group consisting of Proteobacteria, Spirochaetes, Bacteriodetes, Chlamydiae, Firmicutes and Actinobacteria.

13. A method of treating a bacterial infection in a subject in need thereof, comprising administering an effective amount of a compound of claim 1 to the subject, wherein the bacterial infection results from a bacterial species selected from the group consisting of *Acinetobacter baumannii, Bacillus anthracis, Bacillus subtilis, Enterobacter* spp., *Enterococcus faecalis, Enterococcus faecium, Escherichia coli, Francisella tularensis, Haemophilus influenzae, Klebsiella pneumoniae, Moraxella catarrhalis, Mycobacterium tuberculosis, Neisseria* spp., *Pseudomonas aeruginosa, Shigella* spp., *Staphylococcus aureus, Streptococcus pyogenes, Streptococcus pneumoniae* and *Yersinia pestis*.

14. The method of claim 11, wherein the effective amount of the compound or a form thereof is in a range of from about 0.001 mg/Kg/day to about 500 mg/Kg/day.

15. A pharmaceutical composition comprising an effective amount of a compound of claim 1 or a form thereof in admixture with a pharmaceutically acceptable excipient; wherein the form of the compound is selected from a free acid, free base, hydrate, solvate, clathrate, isotopologue, racemate, enantiomer, diastereomer, stereoisomer, polymorph or tautomer form thereof.

16. A combination therapy comprising an effective amount of a compound of claim 1 or a form thereof and an effective amount of an antibiotic or antibacterial agent; wherein the form of the compound is selected from a free acid, free base, hydrate, solvate, clathrate, isotopologue, racemate, enantiomer, diastereomer, stereoisomer, polymorph or tautomer form thereof.

17. The combination therapy of claim 16, wherein the agent is one or more selected from the group consisting of Ciprofloxacin, Enoxacin, Gatifloxacin, Levofloxacin, Lomefloxacin, Moxifloxacin, Nalidixic acid, Norfloxacin and Ofloxacin.

18. The combination therapy of claim 16, wherein the agent is one or more selected from the group consisting of Amikacin, Amoxicillin, Ampicillin, Arsphenamine, Azithromycin, Azlocillin, Aztreonam, Bacitracin, Capreomycin, Carbenicillin, Cefaclor, Cefadroxil, Cefalexin, Cefalotin, Cefamandole, Cefazolin, Cefdinir, Cefditoren, Cefixime, Cefoperazone, Cefotaxime, Cefoxitin, Cefpodoxime, Cefprozil, Ceftazidime, Ceftibuten, Ceftizoxime, Ceftriaxone, Cefuroxime, Chloramphenicol, Cilastatin, Clarithromycin, Clavulanate, Clindamycin, Clofazimine, Cloxacillin, Colistin, Cycloserine, Dalfopristin, Dapsone, Daptomycin, Dicloxacillin, Dirithromycin, Doripenem, Doxycycline, Erythromycin, Ethambutol, Ethionamide, Flucloxacillin, Fosfomycin, Furazolidone, Fusidic acid, Gentamicin, Imipenem, Isoniazid, Kanamycin, Lincomycin, Linezolid, Loracarbef, Mafenide, Meropenem, Methicillin, Metronidazole, Mezlocillin, Minocycline, Mupirocin, Nafcillin, Neomycin, Netilmicin, Nitrofurantoin, Oxacillin, Oxytetracycline, Paromomycin, Penicillin G, Penicillin V, Piperacillin, Platensimycin, Polymyxin B, Pyrazinamide, Quinupristin, Rapamycin, Rifabutin, Rifampicin, Rifampin, Rifapentine, Rifaximin, Roxithromycin, Silver sulfadiazine, Spectinomycin, Streptomycin, Sulbactam, Sulfacetamide, Sulfadiazine, Sulfamethizole, Sulfamethoxazole, Sulfanilimide, Sulfasalazine, Sulfisoxazole, Tazobactam, Teicoplanin, Telavancin, Telithromycin, Temocillin, Tetracycline, Thiamphenicol, Ticarcillin, Tigecycline, Tinidazole, Tobramycin, Trimethoprim, Troleandomycin and Vancomycin.

19. The method of claim 13, wherein the effective amount of the compound or a form thereof is in a range of from about 0.001 mg/Kg/day to about 500 mg/Kg/day; wherein the form of the compound is selected from a free acid, free base, hydrate, solvate, clathrate, isotopologue, racemate, enantiomer, diastereomer, stereoisomer, polymorph or tautomer form thereof.

* * * * *